US012480162B2

(12) United States Patent
Shea et al.

(10) Patent No.: US 12,480,162 B2
(45) Date of Patent: Nov. 25, 2025

(54) DETECTION OF METASTATIC DISEASE AND RELATED METHODS

(71) Applicant: THE REGENTS OF THE UNIVERSITY OF MICHIGAN, Ann Arbor, MI (US)

(72) Inventors: Lonnie D. Shea, Ann Arbor, MI (US); Robert S. Oakes, College Park, MD (US); Grace Bushnell, Ann Arbor, MI (US); Jacqueline S. Jeruss, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1080 days.

(21) Appl. No.: 16/754,042

(22) PCT Filed: Oct. 8, 2018

(86) PCT No.: PCT/US2018/054859
§ 371 (c)(1),
(2) Date: Apr. 6, 2020

(87) PCT Pub. No.: WO2019/071257
PCT Pub. Date: Apr. 11, 2019

(65) Prior Publication Data

US 2020/0323893 A1 Oct. 15, 2020

Related U.S. Application Data

(60) Provisional application No. 62/571,702, filed on Oct. 12, 2017, provisional application No. 62/569,460, filed on Oct. 6, 2017.

(51) Int. Cl.
*C12Q 1/6886* (2018.01)

(52) U.S. Cl.
CPC .................................. *C12Q 1/6886* (2013.01)

(58) Field of Classification Search
None
See application file for complete search history.

(56) References Cited

U.S. PATENT DOCUMENTS 4,526,988 A 7/1985 Hertel
4,808,614 A 2/1989 Hertel
(Continued)

FOREIGN PATENT DOCUMENTS

EP 0184365 A2 6/1986
WO 2007/070660 A2 6/2007
(Continued)

OTHER PUBLICATIONS

Coleman, R. Drug Discovery Today. 2003. 8: 233-235 (Year: 2003).*

(Continued)

*Primary Examiner* — Carla J Myers
(74) *Attorney, Agent, or Firm* — Casimir Jones, S.C.; Rikki A. Hullinger

(57) ABSTRACT

Provided herein are methods of determining a subject's metastatic potential, comprising measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level. Related methods are also provided herein.

22 Claims, 31 Drawing Sheets

Specification includes a Sequence Listing.

(56) References Cited

U.S. PATENT DOCUMENTS

| | | | |
|---|---|---|---|
| 4,829,000 | A | 5/1989 | Kleinman et al. |
| 6,281,256 | B1 | 8/2001 | Harris et al. |
| 6,630,124 | B1 | 10/2003 | Gozes et al. |
| 7,427,602 | B1 | 9/2008 | Shea et al. |
| 7,611,728 | B2 | 11/2009 | Kidane et al. |
| 2004/0063206 | A1 | 4/2004 | Rowley et al. |
| 2010/0159008 | A1 | 6/2010 | Barron et al. |
| 2011/0296538 | A1 | 12/2011 | Segall et al. |
| 2014/0072510 | A1 | 3/2014 | Shea et al. |
| 2014/0227327 | A1 | 8/2014 | Bencherif et al. |
| 2014/0274769 | A1 | 9/2014 | Wang et al. |
| 2015/0190485 | A1 | 7/2015 | Shea et al. |
| 2015/0283073 | A1 | 10/2015 | Tang |
| 2015/0283218 | A1 | 10/2015 | Shea et al. |
| 2015/0285810 | A1 | 10/2015 | Lu et al. |
| 2017/0281798 | A1 | 10/2017 | Shea et al. |
| 2018/0050068 | A1 | 2/2018 | Correa et al. |
| 2018/0185550 | A1 | 7/2018 | Kasputis et al. |

FOREIGN PATENT DOCUMENTS

| | | | |
|---|---|---|---|
| WO | WO 2008/104543 | * | 2/2008 |
| WO | 2009/002401 | A2 | 12/2008 |
| WO | 2011/053940 | A2 | 5/2011 |
| WO | 2011/063336 | A2 | 5/2011 |
| WO | 2012/167230 | A1 | 12/2012 |
| WO | 2014/063128 | A1 | 4/2014 |
| WO | 2015/002707 | A1 | 1/2015 |
| WO | 2015/187925 | A2 | 12/2015 |
| WO | 2016/057702 | A2 | 4/2016 |
| WO | 2016/172710 | A2 | 10/2016 |
| WO | 2017/120486 | A1 | 7/2017 |
| WO | 2018/165432 | A1 | 9/2018 |
| WO | 2019/210209 | A1 | 10/2019 |
| WO | 2019/226718 | A1 | 11/2019 |
| WO | 2020/082090 | A1 | 4/2020 |

OTHER PUBLICATIONS

Liu et al Clinical Immunology. 2004. 112: 225-230 (Year: 2004).*

Pavlovic et al J Nat Cancer Inst. 2015: 107(12): djv256, pp. 1-12 (Year: 2015).*

Schmidt et al. Blood. 1998. 91: 22-29 (Year: 1998).*

Garber et al. PNAS. 2001. 98: 13784-13789 (Year: 2001).*

Aguado, BA. 2015. Development of a Biomaterial Implant for Early Detection of Cancer Metastasis. Dissertation, Northwestern University, available via URL: < proquest.com/openview/b01f3b4c44d80725addf6011dff9c06e/1?pq-origsite=gscholar&cbl=18750>). (Year: 2015).*

Bersani et al Cancer Research. 74(24): 7229-7238 and Supplementary Data, 24 pages total (Year: 2014).*

National Center for Biotechnology Information for CSF3. National Library of Medicine, National Institutes of Health, Bethesda MD, available via UR: <ncbi.nlm.nih.gov/gene/1440> (Year: 2025).*

Van 't Veer et al., Gene expression profiling predicts clinical outcome of breast cancer, Nature, 415:530-6 (2002).

Vassiliou et al., Miniaturized, biopsy-implantable chemical sensor with wireless, magnetic resonance readout, Lab. Chip., 15:3485-72 (2015).

Vegas et al., Combinatorial hydrogel library enables identification of materials that mitigate the foreign body response in primates, Nat. Biotechnol., 34(3):345-352 (2016).

Vijver et al., A gene-expression signature as a predictor of survival in breast cancer, N. Engl. J. Med., 347(25):1999-2009 (2002).

Vlieghere et al., Tumor-environment biomimetics delay peritoneal metastasis formation by deceiving and redirecting disseminated cancer cells, Biomaterials, 54:148-57 (2015).

Wang et al., Hepatocellular carcinoma cells induce regulatory T cells and lead to poor prognosis via production of transforming growth factor-beta1, Cell Physiol. Biochem., 38:306-18 (2016).

Weber et al., Human antimicrobial protein hCAP18/LL-37 promotes a metastatic phenotype in breast cancer, Breast Cancer Res., 11(1):R6 (2009).

Wirtz et al., The physics of cancer: the role of physical interactions and mechanical forces in metastasis, Nature Reviews Cancer, 11(7):512-522 (2011).

Xi et al., RNA Biomarkers: Frontier Precision Medicine for Cancer, Non-coding RNA., 3:1 (2017).

Xia et al., Bone metastasis in a novel breast cancer mouse model containing human breast and human bone, Breast Cancer Res. Treat., 132:471-86 (2012).

Xu et al., Circulating tumour DNA methylation markers for diagnosis and prognosis of hepatocellular carcinoma, Nat. Mater., 16:1155-61 (2017).

Youn et al., Characterization of the nature of granulocytic myeloid-derived suppressor cells in tumor-bearing mice, J. Leukoc. Biol., 91(1):167-181 (2012).

Zander et al., Blood-based gene expression signatures in non-small cell lung cancer, Clin. Cancer Res., 17:3360-7 (2011).

Zhou et al., Prognostic value of tumor-infiltrating Foxp3þ regulatory T cells in patients with breast cancer. a meta-analysis, J. Cancer, 8:4098-105 (2017).

Zhu et al., Progress and challenges of sequencing and analyzing circulating tumor cells, Cell Biol. Toxicol., 34:405-15 (2018).

Hodi et al., Immunemodified response evaluation criteria in solid tumors (imRECIST): refining guidelines to assess the clinical benefit of cancer immunotherapy, J. Clin. Oncol., 36:850-8 (2019).

Holzapfel et al., Species-specific homing mechanisms of human prostate cancer metastasis in tissue engineered bone, Biomaterials, 35:4108-15 (2014).

Hoshino et al., Tumour exosome integrins determine organotropic metastasis, Nature, 527:329-35 (2015).

Hu et al., Tumor-infiltrating FoxP3((þ)) Tregs predict favorable outcome in colorectal cancer patients: a meta-analysis, Oncotarget., 8:75361-71 (2017).

Ierano et al., CXCL12 loaded-dermal filler captures CXCR4 expressing melanoma circulating tumor cells, Cell Death Dis., 10:562 (2019).

International Application No. PCT/US17/12556, International Preliminary Report on Patentability, mailed Jul. 19, 2018.

International Application No. PCT/US17/12556, International Search Report and Written Opinion, mailed Mar. 14, 2017.

International Application No. PCT/US18/54859, International Preliminary Report on Patentability, mailed Apr. 16, 2020.

International Application No. PCT/US18/54859, International Search Report and Written Opinion, mailed Jan. 4, 2019.

Jain et al., Guiding intracortical brain tumour cells to an extracortical cytotoxic hydrogel using aligned polymeric nanofibres, Nat. Mater., 13:308-16 (2014).

Janes et al., A biological approach to computational models of proteomic networks, Curr. Opin. Chem. Biol., 10(1):73-80 (2006).

Jang et al., Plasmid delivery in vivo from porous tissueengineering scaffolds: transgene expression and cellular transfection, Mol. Ther., 12:475-83 (2005).

Kaplan et al., Bonemarrow cells in the "pre-metastatic niche": within bone and beyond, Cancer Metastasis Rev., 25:521-9 (2006).

Kaplan et al., Preparing the "soil": the premetastatic niche, Cancer Research, 66(23):11089-11093 (2006).

Kaplan et al., VEGFR1-positive haematopoietic bone marrow progenitors initiate the pre-metastatic niche, Nature, 438:820-827 (2005).

Karathanasis, Detecting Early onset of metastatic disease using MRI, imaging technology news, (2013).

Kievit et al., Chitosan-alginate 3D scaffolds as a mimic of the glioma tumor microenvironment, Biomaterials, 31(22):5903-5910 (2010).

Kim et al., Regulation of chitinase-3-like-1 in T cell elicits Th1 and cytotoxic responses to inhibit lung metastasis, Nat. Commun., 9(1):503 (2018).

Kirby et al., Gene expression assays, Adv. Clin. Chem., 44:247-292 (2007).

(56) References Cited

OTHER PUBLICATIONS

Ko et al., The use of chemokine-releasing tissue engineering scaffolds in a model of inflammatory response-mediated melanoma cancer metastasis, Biomaterials, 33:876-85 (2012).
Koo et al., Wireless bioresorbable electronic system enables sustained nonpharmacological neuroregenerative therapy, Nat. Med., 24:1830-6 (2018).
Kowanetz et al., Granulocyte-colony stimulating factor promotes lung metastasis through mobilization of Ly6Gþ Ly6Cþ granulocytes, Proc. Natl. Acad. Sci. USA., 107:21248-55 (2010).
Kurra et al., Pseudoprogression in cancer immunotherapy: rates, time course and patient outcomes, J. Clin. Oncol., 34(15 suppl ) (2016).
Kusuma et al., Integrindependent response to laminin-511 regulates breast tumor cell invasion and metastasis, Int. J. Cancer, 130:555-66 (2012).
Kusuma et al., Laminin a5-derived peptides modulate the properties of metastatic breast tumour cells, Clin. Exp. Metastasis., 28:909-21 (2011).
Kveler et al., Immune-centric network of cytokines and cells in disease context identified by computational mining of PubMed, Nat. Biotechnol., 36:651-9 (2018).
Kwa et al., Clinical utility of gene-expression signatures in early stage breast cancer, Nat. Rev. Clin. Oncol., 14:595-610 (2017).
Lee et al., Biomaterial platform to establish a hypoxic metastatic niche in vivo, ACS Appl. Bio. Mater., 2:1549-60 (2019).
Lee et al., Implantable microenvironments to attract hematopoietic stem/cancer cells, Proc. Natl. Acad. Sci. USA., 109:19638-43 (2012).
Li et al., Design of biodegradable, implantable devices towards clinical translation, Nat. RevMater., 5:61-81 (2020).
Lim et al., Tumor-infiltrating monocytes/macrophages promote tumor invasion and migration by upregulating S100A8 and S100A9 expression in cancer cells, Oncogene, 35: 5735-45 (2016).
Liu et al., Tumor exosomal RNAs promote lung pre-metastatic niche formation by activating alveolar epithelial TLR3 to recruit neutrophils article tumor Exosomal RNAs promote lung premetastatic niche formation by activating alveolar epithelial TLR3 to recruit neutrophils, Cancer Cell, 30:243-56 (2016).
Luzzi et al., Multistep nature of metastatic inefficiency: dormancy of solitary cells after successful extravasation and limited survival of early micrometastases, Am. J. Pathol., 153(3):865-873 (1998).
Ma et al., “Liquid biopsy”-ctDNA detection with great potential and challenges, Ann. Transl. Med., 3:235 (2015).
Ma et al., A two-gene expression ratio predicts clinical outcome in breast cancer patients treated with tamoxifen, Cancer Cell, 5:607-16 (2004).
Maiti et al., Vascular endothelial growth factor induces MEF2C and MEF2-dependent activity in endothelial cells, Investigative ophthalmology & visual science, 49(8):3640-3648 (2008).
Mandal et al., Cell and fluid samplingmicroneedle patches formonitoring skin-resident immunity, Sci. Transl. Med., 10(467):eaar2227 (2018).
Marland et al., Implantable microsystems for personalised anticancer therapy. In: Mitra S, Cumming DRS, editors. CMOS Circuits for Biological Sensing and Processing, Springer International Publishing, 259-86 (2018).
Martine et al., Engineering a humanized bone organ model in mice to study bone metastases, Nat. Protoc., 12:639-63 (2017).
Mcgovern et al., Animal models for bone tissue engineering and modelling disease, Dis Model Mech., 11(4):dmm033084 (2018).
Mei et al., Prognostic role of pretreatment blood neutrophil-to-lymphocyte ratio in advanced cancer survivors: A systematic review and meta-analysis of 66 cohort studies, Cancer Treat Rev., 58:1-13 (2017).
Miller et al., Significance of circulating tumor cells detected by the Cell Search system in patients with metastatic breast colorectal and prostate cancer, J. Oncol.,2010:617421 (2010).
Minn et al., Distinct organ-specific metastatic potential of individual breast cancer cells and primary tumors, J. Clin. Invest., 115(1):44-55 (2005).
Minn et al., Genes that mediate breast cancer metastasis to lung, Nature, 436:518-24 (2005).
Moreau et al., Tissue-engineered bone serves as a target for metastasis of human breast cancer in a mouse model, Cancer Research, 67(21):10304-10308 (2007).
Morris et al., Engineered niches to analyze mechanisms of metastasis and guide precision medicine, Cancer Research, 80(18):3786-94 (2020).
Muller et al., Involvement of chemokine receptors in breast cancer metastasis, Nature, 410:50-56 (2001).
Narod, Disappearing breast cancers, Curr. Oncol., 19:59-60 (2012).
Nemeth et al., Severe combined immunodeficient-hu model of human prostate cancer metastasis to human bone, Cancer Res., 59:1987-93 (1999).
Newman et al., An ultrasensitive method for quantitating circulating tumor DNA with broad patient coverage, Nat. Med., 20:548-54 (2014).
Oakes et al., Engineering biomaterials to direct innate immunity, Adv. Ther., 2(6):1800157 (2019).
Oakes et al., Metastatic conditioning of myeloid cells at subcutaneous synthetic niche reflects disease progression and predicts therapeutic outcomes, Cancer Research, 80(3):602-12 (2020).
Oliva et al., Regulation of dendrimer/dextran material performance by altered tissue microenvironment in inflammation and neoplasia, Sci. Trans. Med., 7:272ra211 (2015).
Onken et al., An accurate, clinically feasible multi-gene expression assay for predicting metastasis in uveal melanoma, J. Malec. Diag., 12(4):461-468 (2010).
Ouzounova et al., Monocytic and granulocytic myeloid derived suppressor cells differentially regulate spatiotemporal tumour plasticity during metastatic cascade, Nat. Commun., 8:14979 (2017).
Paget, The distribution of secondary growths in cancer of the breast, Lancet, 133:571-3 (1889).
Paik et al., A multigene assay to predict recurrence of tamoxifen-treated, node-negative breast cancer, N. Engl. J. Med., 351(27):2817-2826 (2004).
Pantel et al., Bone marrow as a reservoir for disseminated tumor cells: a special source for liquid biopsy in cancer patients, Bonekey Rep., 3:584 (2014).
Park et al., B1 integrin inhibitory antibody induces apoptosis of breast cancer cells, inhibits growth, and distinguishes malignant from normal phenotype in three dimensional cultures and in vivo, Cancer Res., 66:1526-35 (2006).
Parker et al., Supervised risk predictor of breast cancer based on intrinsic subtypes, J. Clin. Oncol., 27:1160-7 (2009).
Poudineh et al., Profiling circulating tumour cells and other biomarkers of invasive cancers, Nat. Biomed. Eng., 2:72-84 (2018).
Qiao et al., Engineering 3D approaches to model the dynamic microenvironments of cancer bone metastasis, Bone Res., 6:3 (2018).
Quent et al., A humanised tissue engineered bone model allows species specific breast cancer related bonemetastasis in vivo, J. Tissue Eng Regen Med., 12:494-504 (2018).
Rack et al., Prevalence of CA 27.29 in primary breast cancer patients before the start of systemic treatment, Anticancer Res., 30:1837-41 (2010).
Raimondi et al., Clinical utility of circulating tumor cell counting through CellSearch((R)): the dilemma of a concept suspended in Limbo, Onco Targets Ther., 7:619-25 (2014).
Raja et al., A new dignostic for cancer dynamics: status and initial test of the NANIVID, Proceedings of Spie, 7207:72070E (2009).
Rakha et al., Breast cancer prognostic classification in the molecular era: the role of histological grade, Breast Cancer Res., 12:207 (2010).
Ralston et al., Inverse scattering for optical coherence tomography, JOSA A, 23(5):1027-1037 (2006).
Rankin et al., Hypoxic control of metastasis, Science, 352:57-63 (2016).

(56) References Cited

OTHER PUBLICATIONS

Rao et al., Enhanced survival with implantable scaffolds that capture metastatic breast cancer cells in Vivo, Cancer Res., 76(18):5209-5218 (2016).
Riethdorf et al., Detection of circulating tumor cells in peripheral blood of patients with metastatic breast cancer: a validation study of the Cell Search system, Clin. Cancer Res., 13:920-8 (2007).
Robinson, The early detection of liver metastases, Cancer Imaging, 2(2):1-3 (2002).
Robson et al., Olaparib for metastatic breast cancer in patients with a germline BRCA mutation, N. Engl. J. Med., 377:523-33 (2017).
Rotunno et al., A gene expression signature from peripheral whole blood for stage I lung adenocarcinoma, Cancer Prev. Res., 4:1599-608 (2011).
Samant et al., Mechanisms of sampling interstitial fluid from skin using a microneedle patch, Proc. Natl. Acad. Sci. USA., 115:4583-8 (2018).
Schmid et al., IMpassion130: results from a global, randomised, double-blind, phase III study of atezolizumab (atezo) þ nab-paclitaxel (nab-P) vs. placebo þ nab-P in treatment-naive, locally advanced or metastatic triple-negative breast cancer (mTNBC), Ann. Oncol., 29:viii707-viii708 (2018).
Scholler, Urban N.CA125 in ovarian cancer, Biomark Med., 1:513-23 (2007).
Seib et al., Tissue engineering a surrogate niche for metastatic cancer cells, Biomaterials, 51:313-9 (2015).
Seyfried et al., On the origin of cancer metastasis, Crit. Rev. Oncog., 18:43-73 (2013).
Shafiee et al., Immune system augmentation via humanization using stem/progenitor cells and bioengineering in a breast cancer model study, Int. J. Cancer, 1482:1470-82 (2018).
Sharma et al., Early detection of breast cancer based on gene-expression patterns in peripheral blood cells, Breast Cancer Res., 7:R634-44 (2005).
Shepard et al., Hydrogel design for supporting neurite outgrowth and promoting gene delivery to maximize neurite extension, Biotechnol. Bioeng., 109(3):830-839 (2012).
Shin et al., Bioresorbable pressure sensors protected with thermally grown silicon dioxide for the monitoring of chronic diseases and healing processes, Nat. Biomed. Eng., 3:37-46 (2019).
Showe et al., Gene expression profiles in peripheral blood mononuclear cells can distinguish patients with non-small cell lung cancer from patients with nonmalignant lung disease, Cancer Res., 69:9202-10 (2009).
Siawaya et al., An evaluation of commercial fluorescent bead-based luminex cytokine assays, PLoS One, 3(7):e2535 (2008).
Siegel et al., Cancer statistics, 2019, CA Cancer J. Clin., 69:7-34 (2019).
Sieh et al., Paracrine interactions between LNCaP prostate cancer cells and bioengineered bone in 3D in vitro culture reflect molecular changes during bone metastasis, Bone., 63:121-31 (2014).
Simpson et al., Monoclonal antibodies for the therapy of cancer, BMC Proceedings, 8:06 (2014).
Sinha et al., Proinflammatory S100 proteins regulate the accumulation of myeloid-derived suppressor cells, J. Immunology, 181(7):4666-4675 (2008).
Skardal et al., A Reductionist metastasis-on-a-chip platform for in vitro tumor progression modeling and drug screening, Biotechnol. Bioeng., 113:2020-32 (2016).
Slomovic et al., Synthetic biology devices for in vitro and in vivo diagnostics, Proc. Natl. Acad. Sci. USA., 112:14429-35 (2015).
Socarras et al., Foreign body response to subcutaneous implants in diabetic rats, PLoS One, 9(11):e110945 (2014).
Soung et al., Exosomes in cancer diagnostics, Cancers, 9:8 (2017).
Spicer et al., Detection of extracellular matrix modification in cancer models with inverse spectroscopic optical coherence tomography Detection of extracellularmatrix modification in cancer models with inverse spectroscopic optical coherence tomography, Phys. Med. Biol., 61:6892-904 (2019).
Sulaiman et al., Hydrogel-coated microneedle arrays forminimally invasive sampling and sensing of specific circulating nucleic acids from skin interstitial fluid, ACS Nano., 13:9620-8 (2019).
Sylman et al., The predictive value of inflammation-related peripheral blood measurements in cancer staging and prognosis, Front. Oncol., 8:78 (2018).
Szajnik et al., Exosomes in plasma of patients with ovarian carcinoma: potential biomarkers of tumor progression and response to therapy, Gynecol. Obstet., Suppl 4:3 (2013).
Tastanova et al., Synthetic biology-based cellular biomedical tattoo for detection of hypercalcemia associated with cancer, Sci. Transl. Med., 10:1-12 (2018).
Thibaudeau et al., A tissue-engineered humanized xenograft model of human breast cancer metastasis to bone, Dis. Model Mech., 7:299-309 (2014).
Vaiselbuh et al., Ectopic human mesenchymal stem cell-coated scaffolds in NOD/SCID Mice: An in vivo model of the leukemia niche, Tissue Eng Part C Methods 16:1523-31 (2010).
Aalipour et al., Engineered immune cells as highly sensitive cancer diagnostics, Nat. Biotechnol., 37:531-9 (2019).
Aaroe et al., Gene expression profiling of peripheral blood cells for early detection of breast cancer, Breast Cancer Res., 12:R7 (2010).
Aguado et al., Biomaterial scaffolds as pre-metastatic nichemimics systemically alter the primary tumor and tumor microenvironment, Adv. Healthc Mater., 7(10):e1700903 (2018).
Aguado et al., Engineering the Pre-Metastatic Niche, Nat. Biom. Eng., 1:1-28 (2017).
Aguado et al., Extracellular matrix mediators of metastatic cell colonization characterized using scaffold mimics of the pre-metastatic niche, Acta. Biomaterialia, 33:13-24 (2016).
Aguado et al., Secretome identification of immune cell factors mediating metastatic cell homing, Sci. Rep., 5:17566 (2015).
Albeituni et al., Hampering immune suppressors: therapeutic targeting of myeloid-derived suppressor cells in cancer, Cancer J., 19(6):490-501 (2013).
Alter et al., Singular value decomposition for genome-wide expression data processing and modeling, Proc. Natl Acad. Sci. USA., 97(18):10101-10106 (2000).
Anderson et al., Foreign body reaction to biomaterials, Semin. Immunol., 20:86-100 (2008).
Anker et al., Detection of circulating tumour DNA in the blood (plasma/serum) of cancer patients, Cancer Metastasis Rev., 18:65-73 (1999).
Azarin et al., In vivo capture and label-free detection of early metastatic cells, Nat. Commun., 6:8094 (2015).
Becker et al., Optical in vivo imaging of the alarmin S100A9 in tumor lesions allows for estimation of the individual malignant potential by evaluation of tumor-host cell interaction, J. Nucl. Med., 56:450-6 (2015).
Bersani et al., Bioengineered implantable scaffolds as a tool to study stromal-derived factors in metastatic cancer models, Cancer Res., 74(24):7229-7238 (2014).
Breiman, Random forests, Machine learning, 45:5-32 (2001).
Bushnell et al. Biomaterial scaffolds recruit an aggressive population of metastatic tumor cells in vivo, Cancer Res., 79:2042-53 (2019).
Bushnell et al., High frequency spectral ultrasound imaging to detect metastasis in implanted biomaterial scaffolds, Ann. Biomed. Eng., 48:477-89 (2020).
Bushnell et al., Microporous scaffolds loaded with immunomodulatory lentivirus to study the contribution of immune cell populations to tumor cell recruitment in vivo, Biotechnol. Bioeng., 117:210-22 (2020).
Bushnell et al., Precision health for breast cancer metastasis: biomaterial scaffolds as an engineered metastatic niche to define, study, and monitor metastatic progression, Oncoscience, 6:380-2 (2019).
Carlsson et al., Molecular serumportraits in patients with primary breast cancer predict the development of distant metastases, Proc. Natl. Acad. Sci. USA., 108:14252-7 (2011).
Carpenter et al., Implantable pre-metastatic niches for the study of the microenvironmental regulation of disseminated human tumour cells, Nat. Biomed. Eng., 2:915-29 (2018).

(56) References Cited

OTHER PUBLICATIONS

Chafe et al., Carbonic anhydrase IX promotes myeloid-derived suppressor cell mobilization and establishment of a metastatic niche by stimulating G-CSF production, Cancer Res., 75:996-1009 (2015).
Chambers et al., Metastasis: dissemination and growth of cancer cells in metastatic sites, Nature Reviews Cancer, 2(8):563-72 (2002).
Chen et al., Mutation detection with a liquid biopsy 96 mutation assay in cancer patients and healthy donors, Cancer Transl Med., 3:39 (2017).
Cheng et al., Inhibition of dendritic cell differentiation and accumulation of myeloid-derived suppressor cells in cancer is regulated by S100A9 protein, J. Exp. Med., 205(10):2235-2249 (2008).
Ciriello et al., Comprehensive molecular portraits of invasive lobular breast cancer, Cell, 163:506-19 (2015).
Cox et al., The hypoxic cancer secretome induces pre-metastatic bone lesions through lysyl oxidase, Nature, 522:106-10 (2015).
Curiel et al., Specific recruitment of regulatory T cells in ovarian carcinoma fosters immune privilege and predicts reduced survival, Nat. Med., 10(9):942-949 (2004).
Curiel, Regulatory T cells and treatment of cancer, Curr. Opin. Immunol., 20:241-6 (2008).
Daniel et al., Implantable diagnostic device for cancer monitoring, Biosens Bioelectron., 24:3252-7 (2009).
Decker et al., Systems analysis of dynamic transcription factor activity identifies targets for treatment in Olaparib resistant cancer cells, Biotechnol Bioeng., 114(9):2085-2095 (2017).
Devarasetty et al., Bioengineered submucosal organoids for in vitro modeling of colorectal cancer, Tissue Eng2 Part A, 23:1026-41 (2017).
Downs-Canner et al., Suppressive IL-17A + Foxp3 + and ex-Th17 IL-17A neg Foxp3 + T reg cells are a source of tumour-associated T reg cells, Nat. Commun., 8:14649 (2017).
Dubsky et al., The EndoPredict score provides prognostic information on late distant metastases in ER+/HER2− breast cancer patients, Br. J. Cancer, 109:2959-64 (2013).
Egan, Monitoring patients undergoing cancer therapy, Lab. Med., 31:666-71 (2000).
Ehrchen et al., The endogenous Tolllike receptor 4 agonist S100A8/S100A9 (calprotectin) as innate amplifier of infection, autoimmunity, and cancer, J. Leukoc. Biol., 86:557-66 (2009).
Eom et al., Comparison of fine-needle aspiration and core needle biopsy under ultrasonographic guidance for detecting malignancy and for the tissue-specific diagnosis of salivary gland tumors, AJNR Am. J. Neuroradiol., 36(6):1188-1193 (2015).
Erler et al., Hypoxiainduced lysyl oxidase is a critical mediator of bone marrow cell recruitment to form the premetastatic niche, Cancer Cell, 15:35-44 (2009).
Erler et al., Lysyl oxidase is essential for hypoxia-induced metastasis, Nature, 440:1222-6 (2006).
European Application No. 17736443, European Search Report and Opinion, mailed Jul. 26, 2019.
European Application No. 18865283, European Search Report and Opinion, mailed Jun. 23, 2021.
Fiala et al., Utility of circulating tumor DNA in cancer diagnostics with emphasis on early detection, BMC Med., 16:1-10 (2018).
Fuente et al., M-Trap: exosome-based capture of tumor cells as a new technology in peritoneal metastasis, J. Natl. Cancer Inst., 107(9):djv184 (2015).
Giles et al., Activation of hematopoietic stem/progenitor cells promotes immunosuppression within the pre-metastatic niche, Cancer Res., 76(6):1335-1345 (2015).
Guo et al., Monoclonal antibodies in cancer therapy, Clin. Oncol. Cancer Res., 8:215-219 (2011).
Hapach et al., Engineered models to parse apart the metastatic cascade, NPJ Precis Oncol., 3:20 (2019).
Harris et al., Use of biomarkers to guide decisions on adjuvant systemic therapy for women with early-stage invasive breast cancer: American society of clinical oncology clinical practice guideline, J. Clin. Oncol., 34(10):1134-1150 (2016).
Heo et al., Towards smart tattoos: implantable biosensors for continuous glucose monitoring, Adv. Healthc Mater., 2:43-56 (2013).
Hiratsuka et al., Endothelial focal adhesion kinase mediates cancer cell homing to discrete regions of the lungs via E-selectin upregulation, Proc. Natl. Acad. Sci. USA., 108:3725-30 (2011).
Hiratsuka et al., The S100A8-serum amyloid A3-TLR4 paracrine cascade establishes a pre-metastatic phase, Nat. Cell Biol., 10(11):1349-1355 (2008).
Hiratsuka et al., Tumour-mediated upregulation of chemoattractants and recruitment of myeloid cells predetermines lung metastasis, Nat. Cell Biol., 8(12):1369-1375 (2006).

* cited by examiner

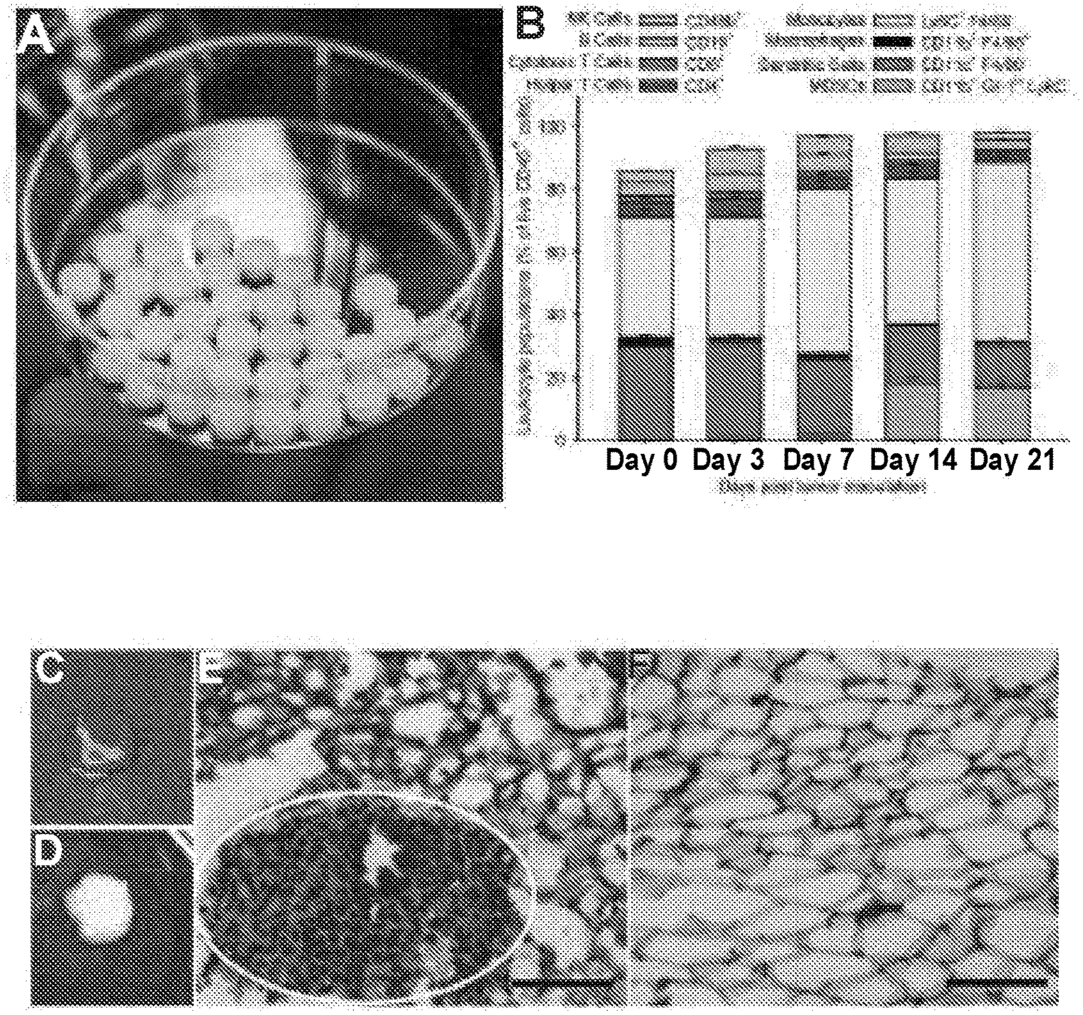

- Previously, we've synthetically created the pMN *in vivo* via microporous polymer (PLGA and PCL) scaffolds (A) that promote tissue ingrowth following implantation at various distal sites.
- Tissue ingrowth includes CD45+ leukocytes that undergo a dramatic population shift[1] (B) following the initiation of tumorigenesis, which leads to a notable upregulation of CD11b$^{+}$ Gr-1$^{hi}$ Ly6C- cells that have been associated with MDSC phenotype.
- Importantly, these implanted scaffolds capture CTCs as indicated by bioluminescence (C) and H&E labeled tumor cells (E), as compared with a lack of signal and cells in unimplanted fat[2] (D,F).

FIGURE 2

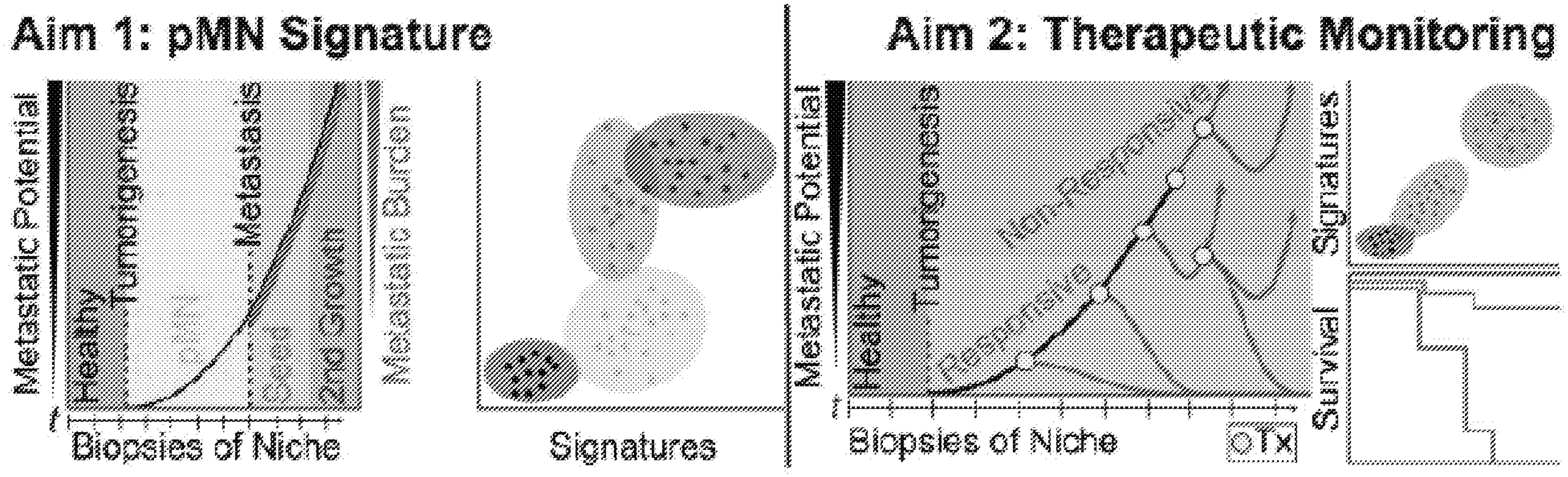

<u>Hypothesis</u>: The molecular composition of the implanted scaffold microenvironment changes as a result of primary tumor conditioning of distant sites. The alterations in molecular composition enable construction of a pMN signature for monitoring of metastatic potential. Additionally, this signature will be useful for characterizing the distal response to therapies and identify if distal conditioning and metastatic potential has been altered.

- Molecular profiling of primary tumors and combination of multiple variables into a single multivariate signature has proven to be a powerful clinical tool for predicting the risk of distant metastatic disease as well as illuminating mechanistic drivers of disease progression.

FIGURE 3

- Volcano plot of fold change and significance of OpenArray qRT-PCR for 635 gene panel (TaqMan OpenArray Mouse Inflammation Panel).
- Housekeeping gene (HKG) stability was analyzed to determine a subset of 5 HKG (Gapdh, Hmbs, Tbp, Ubc, Ywhaz) for normalization.

(to be continued)

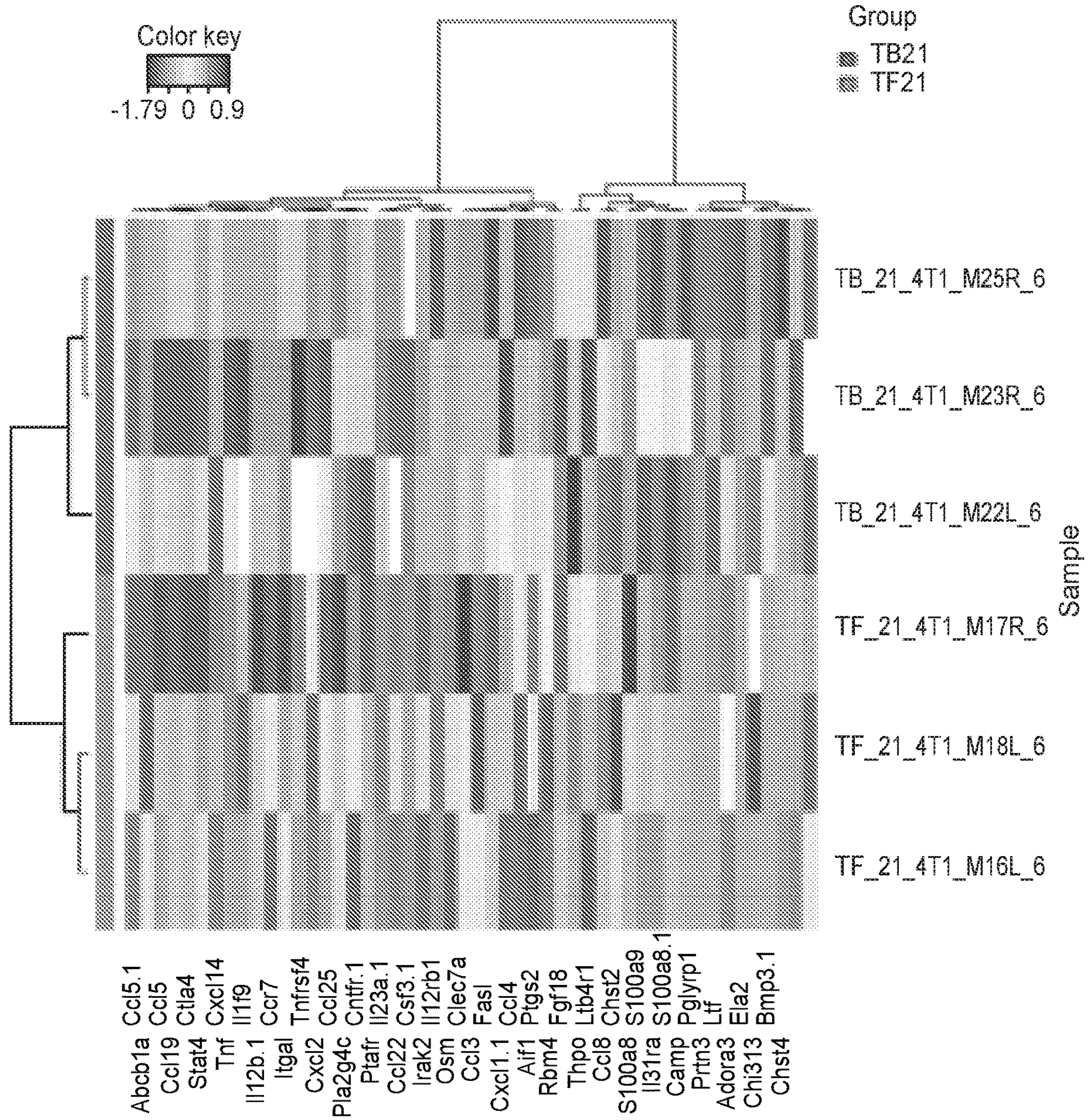

- Normalized OpenArray qRT-PCR data was analyzed with sparse partial least squares discriminant analysis (sPLS-DA) to identify the most discriminant factors for classification.
- Agreement in fold change magnitude, sPLS-DA discrimination, and an elastic net regularization were used to select for a subset of genes (expression changes listed below) for developing the signature.

Genes

Day 21 (n=3)

FIGURE 6
(continuation)

(to be continued)

(continuation)

DETECTION OF METASTATIC DISEASE AND RELATED METHODS

CROSS REFERENCE TO RELATED APPLICATIONS

This application is a U.S. National Phase of PCT/US2018/054859, filed Oct. 8, 2018, which claims priority to U.S. Provisional Application No. 62/569,460, filed on Oct. 6, 2017, and U.S. Provisional Application No. 62/571,702, filed on Oct. 12, 2017. The contents of each application are incorporated herein by reference.

GRANT FUNDING DISCLOSURE

This invention was made with government support under Contract No. CA173745 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 230,480 byte ASCII (Text) file named "52538_SeqListing.txt," created on Oct. 3, 2018.

BACKGROUND

Cancer is the second leading cause of death in the United States, claiming more than half a million American lives every year. Cancer's lethality is due to its ability to spread throughout the body, or its ability to become metastatic. Metastatic cancer does not always cause symptoms, and, even if symptoms do occur, the nature and frequency of the symptoms depend on the size and location of the metastatic tumors. Also, some metastatic cancer symptoms, such as pain, headache, dizziness, shortness of breath, and swelling of the belly, are common to other diseases and disorders and not unique to metastatic cancer. Once cancer becomes metastatic, it is often difficult to control and most metastatic cancers are not curable.

For these reasons and others, much effort has gone into developing methods for detecting metastatic cancer in the early stages. Current methodologies for metastatic cancer detection include blood tests to identify any metastases in the liver or bones, bone scans, X-rays, and computerized tomography (CT) scans. Improvements in these basic techniques include designing better imaging agents. For example, Karathanasis, Efstathios "Detecting Early Onset of Metastatic Disease Using MRI", Imaging Technology News, May 15, 2013, describes a detection method using an imaging agent that targets a specific biomarker (alpha(v) beta(3) integrin) expressed by metastatic cancer cells. As discussed in Robinson, "The Early Detection of Liver Metastases" *Cancer Imaging* 2(2): 1-3 (2002), certain methodologies are limited to the size of the metastatic lesions detected; some imaging techniques (e.g., CT, magnetic resonance imaging (MRI)), detect relatively larger lesions, while other techniques (e.g., radionuclide, or doppler perfusion) detect smaller lesions. Azarin et al., *Nat Commun* 6: 8094 (2015) describes biomaterial scaffolds that recruit or capture metastatic cells and the subsequent identification or detection of such metastatic cells in the scaffolds through alabel-free detection system using inverse spectroscopic optical coherence tomography. (IS-OCT). Common to all of these strategies is the reliance of the imaging, detection, identification or characterization of the metastatic cells.

For multiple reasons, it would be advantageous to detect metastatic cancer at even earlier stages than the stage(s) at which the above methodologies detect. It would be beneficial, for example, to detect metastatic cancer before cancer cell homing, migration, and/or colonization occur.

SUMMARY

The present disclosure is directed generally to synthetic scaffolds that form engineered pre-metastatic niches (pMN) and methods of use and diagnosis related thereto. The disclosure includes methods for identifying a subject's metastatic status, risk or predisposition via detection of changes in the expression profile of cells captured in the synthetic scaffolds.

Presented herein are data demonstrating that expression profiles, such as, for example, gene expression profiles, RNA expression profiles, protein expression profiles (e.g., cytokine and chemokine expression profiles) of cells captured in synthetic engineered pMN change over time after tumorigenesis and that such expression profiles of tumor-bearing animals differ from those of tumor-free animals. Also presented herein are data showing that such expression profiles of cells localized in the scaffolds change over time after treatment (e.g., surgical tumor resection) and that the expression profiles of treated animals differ from those of untreated animals.

Without being bound to any particular theory, these expression profiles of the cells of the scaffolds are representative of a subject's status with regard to metastatic disease and the potential, risk, or likelihood therefor, and therefore, such expression profiles allow for early diagnosis or detection of metastatic cancer. For example, such profiles may be used to monitor an animal with a tumor or cancer before, during or after the onset of metastatic disease or before, during or after the onset of tumor cell colonization at a metastatic site. Because the expression profiles represent the subject's status in this regard, the expression profiles may be used to determine a subject's therapy, e.g., determine a subject's need for therapy for metastatic disease. In related aspects, the expression profiles may also be useful for determining the efficacy of a treatment administered to or performed on a subject receiving such treatment. In yet other related aspects, the expression profiles may be used in methods of preventing or delaying the onset of metastatic disease or reducing metastatic potential.

Accordingly, provided herein are methods of determining a subject's status with regard to metastatic disease. In exemplary embodiments, the subject has a tumor or cancer. Provided herein are methods of determining a subject's metastatic potential. In exemplary aspects, the method comprises measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level.

Also provided herein are methods of detecting metastatic disease, or a predisposition thereto, in a subject in need thereof. In exemplary embodiments, the method comprises measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level.

The present disclosure provides methods of monitoring a subject's metastatic potential or metastatic disease. In exemplary embodiments, the methods comprise measuring a level of expression of a gene, an RNA, or a protein, or a combination thereof, in a sample obtained from a synthetically-engineered pMN implanted in the subject at a first time point and measuring the expression level of the gene, RNA, or protein in a sample obtained from the synthetically-engineered pMN at a second time point, wherein the expression level measured at the first time point is compared to the expression level measured at the second time point. In exemplary aspects, the first time point occurs before a treatment and the second time point occurs after a treatment and the method is a method of determining the efficacy of a treatment for metastatic disease.

Methods of determining treatment for a subject with a tumor or cancer are provided by the present disclosures. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level.

The present disclosure also provides a method for determining a subject's need for metastatic disease therapy. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level.

The present disclosure also provides methods of preventing or delaying the onset of metastatic disease. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA or protein in the sample is compared to a control level, and administering a metastatic disease therapy based on the measured level of expression.

Further provided herein are systems comprising: a processor; a memory device coupled to the processor, and machine readable instructions stored on the memory device. Computer-readable storage media having stored thereon machine-readable instructions executable by a processor and methods implemented by a processor in a computer are additionally provided herein.

BRIEF DESCRIPTION OF THE DRAWINGS

FIG. 2 demonstrates that microporous polymer scaffolds create a synthetic pMN in vivo.

FIG. 3 is an outline for a pMN signature and monitoring of metastatic potential. Metastatic potential as a diagnostic based on the magnitude of conditioning in distal pMN sites.

DETAILED DESCRIPTION

Metastatic Disease and Cancer

The present disclosure provides methods relating to a subject's status with regard to metastatic disease. As used herein, the term "metastatic disease" means "metastatic cancer". In the context of most cancer types, "metastatic cancer" is synonymous with "stage IV cancer". For purposes herein, the cancer may be any cancer known in the art, such as, for example, any of: acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, uterine cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma. In exemplary aspects, the metastatic cancer is triple-negative breast cancer, pancreatic cancer, prostate cancer, or melanoma.

During the process of metastasis, cancer cells localized at a vascularized primary tumor detach from the primary tumor and intravasate (or enter into the vasculature), thereby becoming a circulating tumor cell (CTC). A CTC can undergo homing and migration to a secondary site, which may be distant from the primary tumor. The CTC can subsequently adhere to the blood vessel wall near the secondary site and extravasate (or exit the vasculature) into the tissue at the secondary site. At the secondary site, the tumor cell may begin proliferating and begin the growth or colonization of a secondary tumor at this distant site. See, e.g., Wirtz et al., Nature Reviews Cancer 2011.

Figure 1:
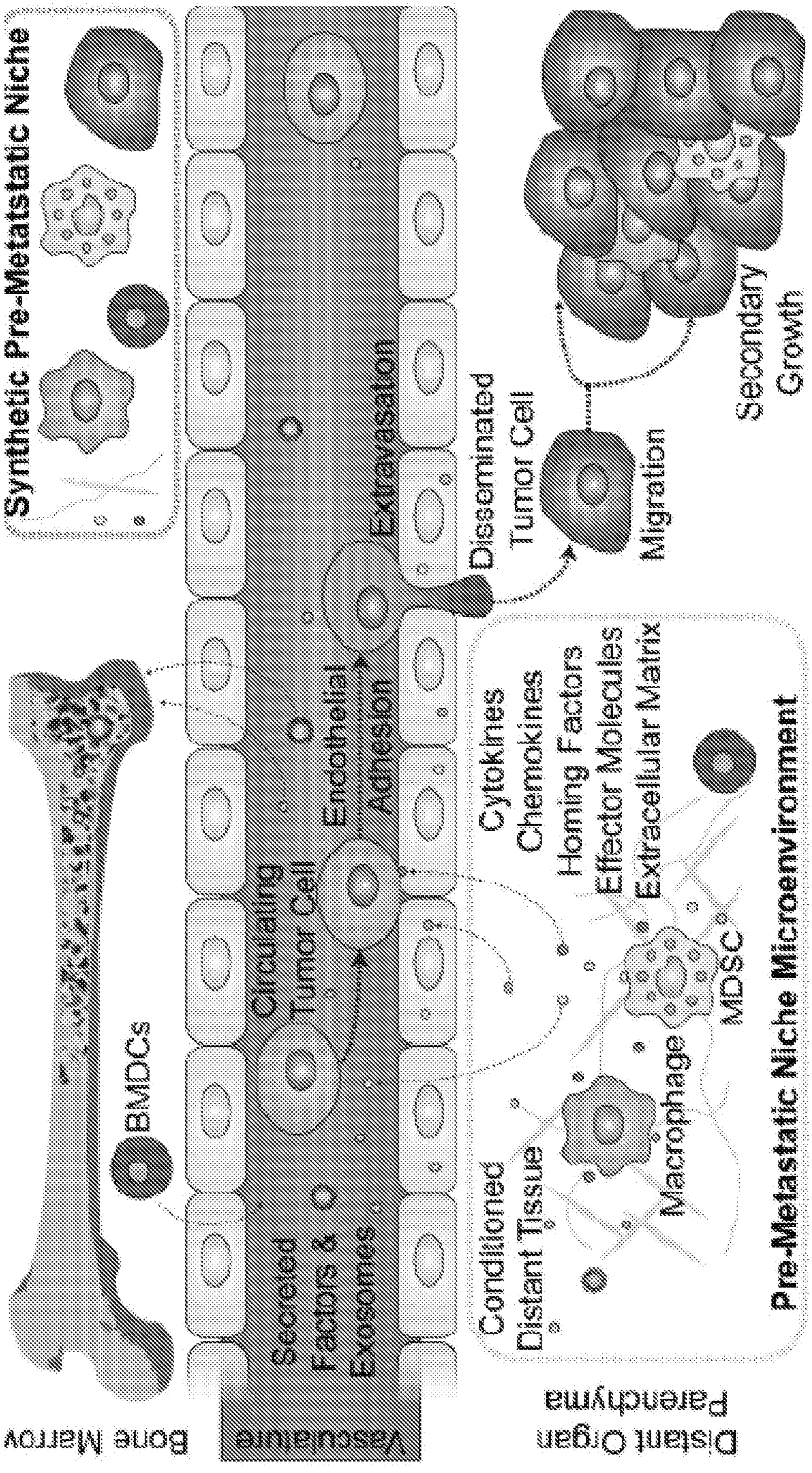
FIG. 1 is an illustration of the process of a circulating tumor cell (CTC) homing to and colonizing at a secondary site and the influence of the pMN immune microenvironment.

At each of these stages, tumor cells uniquely interact with their environment. CTCs exhibit a tropism for specific distal microenvironments, thus indicating that metastasis is predetermined. These primed distal microenvironments are termed pre-metastatic niches (pMN) and facilitate homing then colonization of CTCs. Development of the pMN is driven by systemic conditioning from the primary tumor and its secretion of factors and exosomes, which is amplified by simultaneous conditioning of the bone marrow. See, FIG. 1. Without being bound to any particular theory, the stage of metastasis is reflected by the expression profile of the cells of the pMN. The expression profile of the cells of the pMN serves as a molecular signature of the pMN, and data provided herein demonstrate that the molecular signature changes over the course of time after tumorigenesis and throughout the stages of metastasis. As supported by the data presented herein, the expression profile of the cells of the pMN are represented by the expression of the cells of engineered pMNs (also referred to herein and in the art as "biomaterial scaffolds" or "scaffolds"). Thus, the expression profiles of scaffolds are representative of the stage of metastatic disease and/or the potential, risk or likelihood therefor, and therefore, such profiles allow for early diagnosis, detection, and management (e.g., treatment) of metastatic cancer.

Metastatic Potential and Disease Detection

Provided herein are methods of determining a subject's status with regard to metastatic disease. In exemplary embodiments, the subject has a tumor or cancer. The present disclosure provides methods of determining a subject's metastatic potential. As used herein, the term "metastatic potential" means the potential, risk, chance, or likelihood that a cancer will become metastatic. "Metastatic potential" is a measure of the likelihood for onset of metastatic disease or metastatic cancer. In exemplary aspects, the method comprises measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level. In exemplary instances, the methods of determining a subject's metastatic potential achieves or is similar to, if not the same as, determining a tumor's or cancer's metastatic stage in a subject. In exemplary embodiments, such methods of determining a tumor's or cancer's metastatic stage comprises measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level.

Also provided herein are methods of detecting metastatic disease, or a predisposition thereto, in a subject in need thereof. In exemplary embodiments, the method comprises measuring a level of expression of a gene, an RNA or a protein, or a combination thereof, in a sample obtained from a synthetically-engineered pMN implanted in the subject, wherein the measured expression level of the gene, RNA or protein in the sample is compared to a control level.

In exemplary instances, the methods comprise measuring the expression level of at least 2, 3, 4, 5 or more genes, at least 2, 3, 4, 5 or more RNA, and/or at least 2, 3, 4, 5 or more proteins in the sample. In exemplary instances, the methods comprise measuring the expression level of at least 10, 15, 20 or more genes, at least 10, 15, 20 or more RNA, and/or at least 10, 15, 20 or more proteins in the sample. In exemplary instances, the methods comprise measuring the expression level of at least 50, 100, 200 or more genes, at least 50, 100, 200 or more RNA, and/or at least 50, 100, 200 or more proteins in the sample. In exemplary instances, the methods comprise measuring the expression level of a plurality of different genes, a plurality of RNA, and/or a plurality of proteins. In exemplary aspects, the expression levels of the genes, RNA, and/or proteins are processed through an algorithm to obtain a single metric or single score of gene expression, RNA expression, or protein expression. In exemplary aspects, the expression levels are normalized to housekeeping gene expression levels. In exemplary aspects, the expression levels are processed through singular value decomposition, dynamic mode decomposition, principle component analysis, fisher linear discriminant, or linear combination. In exemplary aspects, the expression levels of the genes, RNA, and/or proteins (optionally normalized to housekeeping gene expression levels) or the single metric or single score is processed through a machine learning algorithm to obtain a score of prediction of disease state, e.g., a % chance of attaining a diseased state (metastatic potential). In exemplary aspects, the metric of gene expression, RNA expression, or protein expression is combined with the prediction score to obtain a graphical or numerical output, which may be used as a control (or a panel of controls) against which the measured levels are compared.

Monitoring Metastatic Potential, Metastatic Disease, and Treatment Thereof

The present disclosure provides methods of monitoring a subject's metastatic potential or metastatic disease. In exemplary embodiments, the methods comprise measuring a level of expression of a gene, an RNA, or a protein, or a combination thereof, in a sample obtained from a synthetically-engineered pMN implanted in the subject at a first time point and measuring the expression level of the gene, RNA, or protein in a sample obtained from the synthetically-engineered pMN at a second time point, wherein the expression level measured at the first time point is compared to the expression level measured at the second time point. In exemplary aspects, the first time point occurs before a treatment and the second time point occurs after a treatment and the method is a method of determining the efficacy of a treatment for metastatic disease.

In exemplary instances, the methods comprise measuring the expression level of at least 2, 3, 4, 5 or more genes, at least 2, 3, 4, 5 or more RNA, and/or at least 2, 3, 4, 5 or more proteins in the sample. In exemplary instances, the methods comprise measuring the expression level of at least 10, 15, 20 or more genes, at least 10, 15, 20 or more RNA, and/or at least 10, 15, 20 or more proteins in the sample. In exemplary instances, the methods comprise measuring the expression level of at least 50, 100, 200 or more genes, at least 50, 100, 200 or more RNA, and/or at least 50, 100, 200 or more proteins in the sample. In exemplary instances, the methods comprise measuring the expression level of a plurality of different genes, a plurality of RNA, and/or a plurality of proteins. In exemplary instances, the methods comprise measuring the expression level of a plurality of different genes, a plurality of RNA, and/or a plurality of proteins. In exemplary aspects, the expression levels of the genes, RNA, and/or proteins are processed through an algorithm to obtain a single metric or single score of gene expression, RNA expression, or protein expression. In exemplary aspects, the expression levels are normalized to housekeeping gene expression levels. In exemplary aspects, the expression levels are processed through singular value decomposition, dynamic mode decomposition, principle component analysis, fisher linear discriminant, or linear combination. In exemplary aspects, the expression levels of the genes, RNA, and/or proteins (optionally normalized to housekeeping gene expression levels) or the single metric or single score is processed through a machine learning algorithm to obtain a score of prediction of disease state, e.g., a % chance of attaining a diseased state (metastatic potential). In exemplary aspects, the metric of gene expression, RNA expression, or protein expression is combined with the prediction score to obtain a graphical or numerical output, which may be used as a control (or a panel of controls) against which the measured levels are compared. Once metastatic potential is determined in this manner, a determination of whether or not the subject has metastatic disease may be made.

Methods of Determining a Subject's Treatment or Need Therefor

As the methods of the present disclosures determine metastatic potential and/or detect metastatic disease in a subject, methods of determining treatment for a subject or determining a subject's need for a metastatic disease therapy are provided.

Methods of determining treatment for a subject with a tumor or cancer are further provided by the present disclosure. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA or protein in the sample is compared to a control level.

The present disclosure also provides a method for determining a subject's need for metastatic disease therapy. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA or protein in the sample is compared to a control level.

In exemplary instances, the methods comprise measuring the expression level of at least 2, 3, 4, 5 or more genes, at least 2, 3, 4, 5 or more RNA, and/or at least 2, 3, 4, 5 or more proteins in the sample. In exemplary instances, the methods comprise measuring the expression level of at least 10, 15, 20 or more genes, at least 10, 15, 20 or more RNA, and/or at least 10, 15, 20 or more proteins in the sample. In exemplary instances, the methods comprise measuring the expression level of at least 50, 100, 200 or more genes, at least 50, 100, 200 or more RNA, and/or at least 50, 100, 200 or more proteins in the sample. In exemplary instances, the methods comprise measuring the expression level of a plurality of different genes, a plurality of RNA, and/or a plurality of proteins. In exemplary instances, the methods comprise measuring the expression level of a plurality of different genes, a plurality of RNA, and/or a plurality of proteins. In exemplary aspects, the expression levels of the genes, RNA, and/or proteins are processed through an algorithm to obtain a single metric or single score of gene expression, RNA expression, or protein expression. In exemplary aspects, the expression levels are normalized to housekeeping gene expression levels. In exemplary aspects, the expression levels are processed through singular value decomposition, dynamic mode decomposition, principle component analysis, fisher linear discriminant, or linear combination. In exemplary aspects, the expression levels of the genes, RNA, and/or proteins (optionally normalized to housekeeping gene expression levels) or the single metric or single score is processed through a machine learning algorithm to obtain a score of prediction of disease state, e.g., a % chance of attaining a diseased state (metastatic potential). In exemplary aspects, the metric of gene expression, RNA expression, or protein expression is combined with the prediction score to obtain a graphical or numerical output, which may be used as a control (or a panel of controls) against which the measured levels are compared. Once metastatic potential is determined, a physician may have sufficient information to decide the best course of treatment for the subject and whether or not the course includes treatment for metastatic disease therapy.

In exemplary aspects, the score is indicative of aberrant immunological events. In exemplary instances, the score is indicative of an immunosuppressive and tumor cell hospitable environment. In some aspects, such an outcome is reflected by increased expression of S100a8/9. In certain aspects, the score is indicative of the need for inhibition of MDSC suppressive function. In exemplary aspects, it is determined that anti-metastatic disease therapy is warranted. In certain instances, it is determined that a systemic anti-metastatic disease therapy (e.g., PARP inhibitor) is needed.

Treatment Methods

As the early detection or diagnosis of metastatic disease enables proper management of the disease, the present disclosure provides a method of treating metastatic disease in a subject or a method of treating a subject with a tumor or cancer. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level, and administering an anti-metastatic disease treatment to the subject or performing anti-metastatic disease therapy on the subject, based on the measured level of expression.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating cancer of the present disclosure can provide any amount or any level of treatment. Furthermore, the treatment provided by the method of the present disclosure can include treatment of one or more conditions or symptoms or signs of the cancer being treated. Also, the treatment provided by the methods of the present disclosure can encompass slowing the progression of the cancer. For example, the methods can treat cancer by virtue of enhancing the T cell activity or an immune response against the cancer, reducing tumor or cancer growth, reducing metastasis of tumor cells, increasing cell death of tumor or cancer cells, and the like. In exemplary aspects, the methods treat by way of delaying the onset or recurrence of the cancer by at least 1 day, 2 days, 4 days, 6 days, 8 days, 10 days, 15 days, 30 days, two months, 3 months, 4 months, 6 months, 1 year, 2 years, 3 years, 4 years, or more. In exemplary aspects, the methods treat by way increasing the survival of the subject.

The present disclosure provides methods of prophylactically treating (i.e., preventing) or delaying the onset of metastatic disease. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level, and administering an anti-metastatic disease treatment to the subject or performing anti-metastatic disease therapy on the subject, based on the measured level of expression.

Because cancer is lethal due to its nature of becoming metastatic cancer, delaying the onset of metastatic disease may effectively increase the survival of the subject. Accordingly, the present disclosure further provides methods of increasing the survival of a subject with a tumor or cancer. In exemplary embodiments, the methods comprise measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level, and administering an anti-metastatic disease treatment to the subject or performing anti-metastatic disease therapy on the subject, based on the measured level of expression.

In exemplary instances, the methods comprise measuring the expression level of at least 2, 3, 4, 5 or more genes, at least 2, 3, 4, 5 or more RNA, and/or at least 2, 3, 4, 5 or more proteins in the sample. In exemplary instances, the methods comprise measuring the expression level of at least 10, 15, 20 or more genes, at least 10, 15, 20 or more RNA, and/or at least 10, 15, 20 or more proteins in the sample. In exemplary instances, the methods comprise measuring the expression level of at least 50, 100, 200 or more genes, at least 50, 100, 200 or more RNA, and/or at least 50, 100, 200 or more proteins in the sample. In exemplary instances, the methods comprise measuring the expression level of a plurality of different genes, a plurality of RNA, and/or a plurality of proteins. In exemplary instances, the methods comprise measuring the expression level of a plurality of different genes, a plurality of RNA, and/or a plurality of proteins. In exemplary aspects, the expression levels of the genes, RNA, and/or proteins are processed through an algorithm to obtain a single metric or single score of gene expression, RNA expression, or protein expression. In exemplary aspects, the expression levels are normalized to housekeeping gene expression levels. In exemplary aspects, the expression levels are processed through singular value decomposition, dynamic mode decomposition, principle component analysis, fisher linear discriminant, or linear combination. In exemplary aspects, the expression levels of the genes, RNA, and/or proteins (optionally normalized to housekeeping gene expression levels) or the single metric or single score is processed through a machine learning algorithm to obtain a score of prediction of disease state, e.g., a % chance of attaining a diseased state (metastatic potential). In exemplary aspects, the metric of gene expression, RNA expression, or protein expression is combined with the prediction score to obtain a graphical or numerical output, which may be used as a control (or a panel of controls) against which the measured levels are compared. Once metastatic potential is determined, an appropriate course of treatment for the subject may be provided to the subject and the treatment may be provided to the subject. An exemplary method is described herein at Example 7.

As used herein "anti-metastatic disease treatment" refers to the administration of a systemic agent targeting mechanistic pathways specific to metastasis. As used herein, "anti-metastatic disease therapy" refers to a treatment program that may include multiple dosing regimen or combinations of agents indicated as anti-metastatic disease treatments. Examples of anti-metastatic disease treatment include for instance, a poly ADP ribose polymerase (PARP) inhibitor (e.g., Olaparib) that targets metastatic tumor cells or Gemcitabine that may deplete myeloid-derived suppressor cells. Examples of anti-metastatic disease therapy include for example multiple doses of Gemcitabine or a combination therapy that includes both Gemcitabine and Olaparib. In exemplary instances, the anti-metastatic disease treatment comprises a PARP inhibitor or Gemcitabine. In various aspects, the anti-metastatic disease treatment comprises a compound that targets MDSCs through inhibiting MDSC suppressive function, inhibiting MDSC expansion, inhibiting MDSC recruitment, and/or inducing MDSC differentiation. Such treatments are described in the art, e.g., Albeituni et al., Cancer J 19(6): 490-501 (2013). In exemplary aspects, the anti-metastatic disease treatment comprises an inhibitor of reactive nitrogen species (RNS), a nitroaspirin, triterpenoid, very small size proteoliposome (VSSP), a phosphodiesterase-5 (PDE-5) inhibitor, e.g., sildenafil, an exosome formation inhibitor (e.g., an amiloride), a combination of gemcitabine and 5-fluorouracil, a cyclooxygenase-2 (COX-2) inhibitor, prostaglandin E2 (PGE2) inhibitor, sunitinib, amino bisphosphonate (e.g., zoledronate, pamidronate), a combination of doxorubicin and a cyclophosphamide, vemurafenib, a CXCR2 or CXCR4 antagonist, vitamin D3, an anti-G-CSF antibody, an anti-Bv8 antibody, an anti-CSF-1 antibody, an anti-CCL2 antibody, a taxane (e.g., docetaxel, paclitaxel), an all trans-retinoic acid (ATRA), a TLR9 activator, curcumin, whole-glucan particles (WGP).

Samples

The samples of the methods of the present disclosure are samples obtained from a synthetically-engineered pMN. At some point in time relative to when the sample is obtained, the synthetically-engineered pMN was implanted in the subject. In exemplary aspects, the sample is obtained from a synthetically-engineered pMN that has been removed from the subject prior to the sample being taken. In exemplary aspects, the sample is obtained from a synthetically-engineered pMN while still implanted into a subject. In exemplary instances, the sample is a core-needle biopsy obtained from the synthetically-engineered pMN while still implanted into a subject. In exemplary aspects, the sample is a fine-needle aspiration obtained from the synthetically-engineered pMN while still implanted into a subject. Such methods of obtaining samples are known in the art. See, e.g., Eom et al., *AJNR Am J Neuroradiol.* 2015 June; 36(6):1188-93.

In exemplary aspects, the sample comprises immune cells, stromal cells, or a combination thereof. In exemplary aspects, the sample comprises immune cells, including, but not limited to, macrophages, dendritic cells, MDSCs, neutrophils, monocytes, helper T cells, cytotoxic T cells, B cells, NK cells, CD45+ cells, and the like. In exemplary aspects, the sample comprises a combination of two or more of the above immune cell types. In exemplary aspects, the sample comprises stromal cells, including, for example, fibroblasts, endothelial cells, pericytes, and the like. In exemplary aspects, the sample comprises a combination of two or more of the above stromal cell types. In exemplary aspects, the sample comprises a combination of immune cells and stromal cells. In exemplary aspects, the sample comprises CD45+ cells.

In exemplary aspects, the sample obtained from the synthetically-engineered pMN substantially lacks tumor cells or cancer cells. In exemplary aspects, less than 10% of the cells in the sample are tumor or cancer cells. In exemplary aspects, less than 5% of the cells in the sample are tumor or cancer cells. In exemplary aspects, less than 3% of the cells in the sample are tumor or cancer cells. In exemplary aspects, less than 2% of the cells in the sample are tumor or cancer cells. In exemplary aspects, less than 1% of the cells in the sample are tumor or cancer cells. In exemplary aspects, less than 0.5% of the cells in the sample are tumor or cancer cells. In exemplary aspects, less than 0.1% of the cells in the sample are tumor or cancer cells. The presently disclosed methods are advantageous, in part, because the methods are not based on the characterization of the metastatic cells. Rather, the methods are based (at least in part) on the non-cancer/non-tumor cells of the pMN (as represented by the scaffold).

Synthetically-Engineered pMN

With regard to the methods of the present disclosure, the samples are obtained from a synthetically-engineered pMN, which is also referred to herein as "synthetic pMN" or "engineered pMN" or "synthetic scaffold" or "biomaterial scaffold" or "scaffold". The scaffold may be any scaffold which mimics the cellular and molecular components of the pMN and is able to capture or recruit metastatic cells. In exemplary aspects, the scaffold maintains residence in tissue for several weeks to years and facilitates ingrowth of tissue and the retrieval of that tissue at later time points. Such scaffolds are known in the art. See, e.g., Azarin et al., Nat Commun 6: 8094 (2015); Aguado et al., Sci Rep 5: 17566 (2015); Aguado et al., Acta Biomaterialia (2016); and Rao et al., Cancer Res 76(18): 5209-5218 (2016); U.S. Patent Application Publication No. 2014/0072510 A1; International Patent Application Publication No. WO 2017/120486.

In exemplary embodiments, the scaffold is porous and/or permeable. In exemplary embodiments, the scaffold comprises a polymeric matrix and acts as a substrate permissible for metastasis, colonization, cell growth, etc. In exemplary embodiments, the scaffold provides an environment for attachment, incorporation, adhesion, encapsulation, etc. of agents (e.g., DNA, lentivirus, protein, cells, etc.) that create a metastatic capture site within the scaffold. In exemplary embodiments, agents are released (e.g., controlled or sustained release) to attract circulating tumor cells, metastatic cells, or pre-metastatic cells. With regard to agents (e.g., therapeutic agents) and sustained release, for long term therapy (e.g., days, weeks or months) and/or to maintain the highest possible drug concentration at a particular location in the body, the present disclosure in certain embodiments provides a sustained release depot formulation with the following non-limiting characteristics: (1) the process used to prepare the matrix does not chemically or physically damage the agent; (2) the matrix maintains the stability of the agent against denaturation or other metabolic conversion by protection within the matrix until release, which is important for very long sustained release; (3) the entrapped agent is released from the hydrogel composition at a substantially uniform rate, following a kinetic profile, and furthermore, a particular agent can be prepared with two or more kinetic profiles, for example, to provide in certain embodiments, a loading dose and then a sustained release dose; (4) the desired release profile can be selected by varying the components and the process by which the matrix is prepared; and (5) the matrix is nontoxic and degradable. PEG scaffolds as disclosed herein are also contemplated to function as a scaffold that achieves sustained release of a therapeutically active agent. Accordingly, in some embodiments an agent is configured for specific release rates. In further embodiments, multiple different agents are configured for different release rates. For example, a first agent may release over a period of hours while a second agent releases over a longer period of time (e.g., days, weeks, months, etc.). In some embodiments, and as described above, the scaffold or a portion thereof is configured for sustained release of agents. In some embodiments, the sustained release provides release of biologically active amounts of the agent over a period of at least 30 days (e.g., 40 days, 50 days, 60 days, 70 days, 80 days, 90 days, 100 days, 180 days, etc.).

In exemplary embodiments, the scaffold is partially or exclusively composed of a micro-porous poly(e-caprolactone) (PCL), forming a PCL scaffold. Such PCL scaffolds have a greater stability than the micro-porous poly(lactide-co-glycolide) (PLG) biomaterial scaffolds. In exemplary embodiments, the scaffold comprises PCL and/or PEG and/or alginate.

In some embodiments, the scaffold is a controlled release scaffold formed partially or exclusively of hydrogel, e.g., a poly(ethylene glycol) (PEG) hydrogel to form a PEG scaffold. Any PEG is contemplated for use in the compositions and methods of the disclosure. In general, the PEG has an average molecular weight of at least about 5,000 daltons. In further embodiments, the PEG has an average molecular weight of at least 10,000 daltons, 15,000 daltons, and is preferably between 5,000 and 20,000 daltons, or between 15,000 and 20,000 daltons. Also preferred is PEG having an average molecular weight of 5,000, of 6,000, of 7,000, of 8,000, of 9,000, of 10,000, of 11,000, of 12,000 of 13,000, of 14,000, or of 25,000 daltons. In further embodiments, the PEG is a four-arm PEG. In preferred embodiments, each arm of the four-arm PEG is terminated in an acrylate, a vinyl sulfone, or a maleimide. It is contemplated that use of vinyl sulfone or maleimide in the PEG scaffold renders the scaffold resistant to degradation. It is further contemplated that use of acrylate in the PEG scaffold renders the scaffold susceptible to degradation.

In some embodiments, one or more agents are associated with a scaffold to establish a hospitable environment for metastasis and/or to provide a therapeutic benefit to a subject. Agents may be associated with the scaffold by covalent or non-covalent interactions, adhesion, encapsulation, etc. In some embodiments, a scaffold comprises one or more agents adhered to, adsorbed on, encapsulated within, and/or contained throughout the scaffold. The present invention is not limited by the nature of the agents. Such agents include, but are not limited to, proteins, nucleic acid molecules, small molecule drugs, lipids, carbohydrates, cells, cell components, and the like. In various embodiments, the agent is a therapeutic agent. In some embodiments, two or more (e.g., 3, 4, 5, 6, 7, 8, 9, 10 . . . 20 . . . 30 . . . 40 . . . , 50, amounts therein, or more) different agents are included on or within the scaffold. In some embodiments, agents associated with a scaffold include metastatic markers, such as: CD133 (which generally defines all progenitors), VEGF-1 (hematopoietic progenitor cells (HPCs)), VEGFR-2 (endothelial progenitor cells (EPCs)), CDIIb and GR1 (myeloid-derived suppressor cells), F4/80 and CDIIb (macrophages), and CDIIb+CD115+Ly6c+(inflammatory monocytes). In some embodiments, agents associated with a scaffold include lentivirus encoding a gene that aids in establishing a hospitable environment for metastasis and/or providing a therapeutic benefit to a subject. In other embodiments, no agents are provided with the scaffold.

In further embodiments, it is contemplated that a scaffold of the disclosure recruits more and/or different cells relative to a scaffold that comprises, e.g., PLG. For example, in some embodiments a scaffold of the disclosure recruits more tumor cells than a scaffold that comprises, e.g., PLG. In various embodiments, a scaffold of the disclosure recruits and/or captures about 5, 10, 20, 50, 100, 200, 500, 1000 or more cells relative to a scaffold that comprises, e.g., PLG. In some embodiments, the types of cells that associate with a scaffold of the disclosure are different from a scaffold that comprises, e.g., PLG. For example and without limitation, a higher percentage of CD49b cells are found in association with a PCL scaffold relative to a PLG scaffold; further, there are about equal quantities of F4/80 and CDIIc cells in association with a PLG scaffold, whereas there are three times as many CDIIc cells as F4/80 cells in association with a PCL scaffold.

In certain embodiments, the scaffold comprises a polymeric matrix. In some embodiments, the matrix is prepared by a gas foaming/particulate leaching procedure, and includes a wet granulation step prior to gas foaming that allows for a homogeneous mixture of porogen and polymer and for sculpting the scaffold into the desired shape.

Thus, in some aspects, the scaffolds may be formed of a biodegradable polymer, e.g., PCL, that is fabricated by emulsifying and homogenizing a solution of polymer to create microspheres. Other methods of microsphere production are known in the art and are contemplated by the present disclosure. See, e.g., U.S. Patent Application Publication Numbers 2015/0190485 and 2015/0283218, each of which is incorporated herein in its entirety. The microspheres are then collected and mixed with a porogen (e.g., salt particles), and the mixture is then pressed under pressure. The resulting discs are heated, optionally followed by gas foaming. Finally, the salt particles are removed. The fabrication provides a mechanically stable scaffold which does not compress or collapse after in vivo implantation, thus providing proper conditions for cell growth.

In some aspects, the scaffolds are formed of a substantially non-degradable polymer, e.g., PEG. Degradable hydrogels encapsulating gelatin microspheres may be formed based on a previously described Michael-Type addition PEG hydrogel system with modifications [Shepard et al., Biotechnol Bioeng. 109(3): 830-9 (2012)]. Briefly, four-arm polyethylene glycol) vinyl sulfone (PEG-VS) (20 kDa) is dissolved in 0.3 M triethanolamine (TEA) pH 8.0 at a concentration of 0.5 mg^L to yield a final PEG concentration of 10%. The plasmin-degradable trifunctional (3 cysteine groups) peptide crosslinker (Ac-GCYKN CGYKN CG) is dissolved in 0.3 M TEA pH 10.0 to maintain reduction of the free thiols at a concentration that maintain a stoichiometrically balanced molar ratio of VS:SH. Prior to gelation, gelatin microspheres are hydrated with 10 μί sterile Millipore or lentivirus solution. Subsequently, the PEG and peptide crosslinking solutions are mixed well and immediately added to the hydrated gelatin microspheres for encapsulation. In some embodiments, and as described above, salt is used as the porogen instead of gelatin microspheres. In this case, the PEG solution is made in a saturated salt solution, so that the porogen does not significantly dissolve.

In some embodiments, UV crosslinking is used instead of peptide crosslinking. Ultraviolet crosslinking is contemplated for use with PEG-maleimide, PEG-VS, and PEG-acrylate.

Scaffolds of the present disclosure may comprise any of a large variety of structures including, but not limited to, particles, beads, polymers, surfaces, implants, matrices, etc.

Scaffolds may be of any suitable shape, for example, spherical, generally spherical (e.g., all dimensions within 25% of spherical), ellipsoidal, rod-shaped, globular, polyhedral, etc. The scaffold may also be of an irregular or branched shape.

In some embodiments, a scaffold comprises nanoparticles or microparticles (e.g., compressed or otherwise fashioned into a scaffold). In various embodiments, the largest cross-sectional diameters of a particle within a scaffold is less than about 1,000 μm, 500 μm, 200 μm, 100 μm, 50 μm, 20 μm, 10 μm, 5 μm, 2 μm, 1 μm, 500 nm, 400 nm, 300 nm, 200 nm or 100 nm. In some embodiments, a population of particles has an average diameter of: 200-1000 nm, 300-900 nm, 400-800 nm, 500-700 nm, etc. In some embodiments, the overall weights of the particles are less than about 10,000 kDa, less than about 5,000 kDa, or less than about 1,000 kDa, 500 kDa, 400 kDa, 300 kDa, 200 kDa, 100 kDa, 50 kDa, 20 kDa, 10 kDa.

In some embodiments, a scaffold comprises PCL. In further embodiments, a scaffold comprises PEG. In certain embodiments, PCL and/or PEG polymers and/or alginate polymers are terminated by a functional group of chemical moiety (e.g., ester-terminated, acid-terminated, etc.).

In some embodiments, the charge of a matrix material (e.g., positive, negative, neutral) is selected to impart application-specific benefits (e.g., physiological compatibility, beneficial interactions with chemical and/or biological agents, etc.). In certain embodiments scaffolds are capable of being conjugated, either directly or indirectly, to a chemical or biological agent). In some instances, a carrier has multiple binding sites (e.g., 2, 3, 4, 5, 6, 7, 8, 9, 10 . . . 20 . . . 50 . . . 100, 200, 500, 1000, 2000, 5000, 10,000, or more).

In exemplary embodiments, the life times of the scaffolds are well within the timeframe of clinical significance are demonstrated. For example, stability lifetimes of greater than 90 days are contemplated, with percent degradation profiles of less than about 50%, 45%, 40%, 35%, 30%, 25%, 20%, 15%, 10%, 5%, and 1% respectively, where the percent degradation refers to the scaffolds' ability to maintain its structure for sufficient cell capture as a comparison of its maximum capture ability. Such ability is measured, for example, as the change in porous scaffold volume over time, the change in scaffold mass over time, and/or the change in scaffold polymer molecular weight over time. These long life times mean that scaffolds can now be applied in patient-friendly conditions that allow subjects to wear the scaffold under normal daily living conditions, inside and outside the clinical environment.

Further still, with the present techniques scaffolds are provided that remain functionalized long enough to provide targeted treatment sites in vivo, that is, locations where metastatic cells are not merely just detected, but over time target, to provide a specific location for cell resection and possible removal of all metastatic cells.

The ability of the present scaffolds to remain functionalized over greater periods of time has, in some examples, provided for formation of a sustained or controllable release scaffold. These scaffolds, for example, may comprise protein responsive materials that are non-degradable when implanted and recruiting metastatic cells. When exposed to activating proteins (e.g., an enzyme), however, these scaffolds degrade to then release the captured metastatic cells. In some examples, such a property is contemplated for use in vitro to facilitate the recovery of the captured cells. For example and without limitation, in some examples the scaffold is an alginate scaffold and the activating protein is alginate lyase.

In some embodiments, the scaffold or a portion thereof is configured to be sufficiently porous to permit metastasis of cells into the pores. The size of the pores may be selected for particular cell types of interest and/or for the amount of ingrowth desired and are, for example without limitation, at least about 20 μm, 30 μm, 40 μm, 50 μm, 100 μm, 200 μm, 500 μm, 700 μm, or 1000 μm. In some embodiments, the PEG gel is not porous but is instead characterized by a mesh size that is, e.g., 10 nanometers (nm), 15 nm, 20 nm, 25 nm, 30 nm, 40 nm, or 50 nm.

The effectiveness of the longer lifetime scaffolds herein, especially for use as targeted treatment sites, relates to Paget's "seed and soil" paradigm which proposes that, prior to colonization by metastatic cells, supportive cells (e.g., fibroblasts, immune cells, endothelial cells), soluble factors, and extracellular matrix (ECM) components establish a microenvironment conducive to tumor cell homing and colonization. The importance of this paradigm is that metastasis to specific organs is not random, but rather is influenced by the properties of the local environment. The use of longer lifetime scaffolds, in vivo, provides sufficient time for these support cells to establish the microenvironment, at the scaffold, to which metastatic cells are attracted. The initial translation of these principals led to the development and implementation of micro-porous poly(lactide-co-glycolide) (PLG) biomaterial scaffolds, as described in U.S. application Ser. No. 13/838,800, which is hereby incorporated by reference in its entirety. There, the recruitment of metastatic breast cancer cells through the local immune response in vivo was demonstrated. However, PLG scaffolds were degradable over time scales considered too short for clinical translation.

Sites of Metastasis and Scaffold Implantation Sites

While metastatic cancer can spread to essentially any part of the body, different types of cancers tend to spread to particular body parts. Common sites of metastasis are shown in the table below.

| Cancer Type | Main Sites of Metastasis |
|---|---|
| Bladder | Bone, liver, lung |
| Breast | Bone, brain, liver, lung |
| Colon | Liver, lung, peritoneum |
| Kidney | Adrenal gland, bone, brain, liver, lung |
| Lung | Adrenal gland, bone, brain, liver, other lung |
| Melanoma | Bone, brain, liver, lung, skin, muscle |
| Ovary | Liver, lung, peritoneum |
| Pancreas | Liver, lung, peritoneum |
| Prostate | Adrenal gland, bone, liver, lung |
| Rectal | Liver, lung, peritoneum |
| Stomach | Liver, lung, peritoneum |
| Thyroid | Bone, liver, lung |
| Uterus | Bone, liver, lung, peritoneum, vagina |

Source: National Cancer Institute website at cancer.gov/types/metastatic-cancer.

The site at which the scaffold is implanted desirably is one of the above common sites of metastasis. In exemplary aspects, the site at which the scaffold is implanted in the subject is a lung, liver, brain, bone, peritoneum, omental fat, muscle, or lymph node of the subject. Additionally or alternatively, in some embodiments, the scaffold is implanted subcutaneously. In exemplary aspects, more than one scaffold is implanted in the subject. In exemplary aspects, the subject comprises more than one scaffold. In further examples, at least 1, at least 2, at least 3, at least 4, at least 5, at least 6, at least 7, at least 8, at least 9, or at least 10 scaffolds are implanted in a subject. In exemplary aspects, samples from each of the scaffolds implanted in the subject are obtained and expression profiles of each sample are measured.

Measuring Expression Levels

The methods of the present disclosure relate to measuring a level of expression of a gene, an RNA, e.g., a messenger RNA (mRNA), or a protein, in a sample obtained from a scaffold implanted in a subject. In exemplary embodiments, the methods comprise measuring a combination of at least two of an expression level of a gene, an RNA, and a protein. In exemplary embodiments, the methods comprise measuring the expression level of at least one gene, at least one RNA, and at least one protein. In exemplary instances, the methods comprise measuring the expression level of at least 2, 3, 4, 5 or more genes, at least 2, 3, 4, 5 or more RNA, and/or at least 2, 3, 4, 5 or more proteins in the sample. In exemplary instances, the methods comprise measuring the expression level of at least 10, 15, 20 or more genes, at least 10, 15, 20 or more RNA, and/or at least 10, 15, 20 or more proteins in the sample. In exemplary instances, the methods comprise measuring the expression level of at least 50, 100, 200 or more genes, at least 50, 100, 200 or more RNA, and/or at least 50, 100, 200 or more proteins in the sample. In exemplary instances, the methods comprise measuring the expression level of a plurality of different genes, a plurality of RNA, and/or a plurality of proteins.

In exemplary aspects, the methods comprise measuring the expression level of more than 10 different genes, more than 100 different genes, more than 1000 different genes, more than 5000-10,000 different genes, and the expression levels of the different genes constitute a gene signature.

In exemplary aspects, the methods comprise measuring the expression level of more than 10 different RNA, more than 100 different RNA, more than 1000 different RNA, more than 5000-10,000 different RNA, and the expression levels of the different RNA constitute an RNA signature, or a transcriptome.

In exemplary aspects, the methods comprise measuring the expression level of more than 10 different proteins, more than 100 different proteins, more than 1000 different proteins, more than 5000-10,000 different proteins, and the expression levels of the different proteins constitute a protein signature, or a proteome.

In exemplary aspects, the methods comprise measuring the expression level of the S100A8 gene or the S100A9 gene, or an expression product (e.g., an RNA or protein) encoded thereby. In exemplary aspects, the methods comprise measuring the expression level of the S100A8 gene or the S100A9 gene, the S100A8 RNA or the S100A9 RNA, or the S100A8 protein or the A100A9 protein. In exemplary aspects, the method comprises measuring a level of expression of both the S100A8 gene and the S100A9 gene or the expression products of both genes. In exemplary aspects, the method comprises measuring a level of expression of the RNA or protein encoded by the S100A8 gene or the S100A9 gene or both.

In exemplary aspects, the methods comprise measuring a level of expression of one or more of the following genes: Ccl22, Cxcl2, Ccr7, Csf3, Bmp15, IL-23a, S100A9, Chi3l3, Pglryp1, S100A8, Ltf, Ela2, and Camp. In exemplary aspects, the methods comprise measuring the level of expression at the gene level, the RNA level, or the protein level, or a combination thereof. In exemplary aspects, the method comprises measuring a level of expression of the RNA or protein encoded by one or more of the following genes: Ccl22, Cxcl2, Ccr7, Csf3, Bmp15, IL-23a, S100A9, Chi313, Pglryp1, S100A8, Ltf, Ela2, and Camp. In exemplary aspects, the method comprises measuring a level of expression of one or more of Csf3, IL-1a, IL-12p70, IL-6, Cxcl5, IL-15, Cxcl10, Ccl2, Cxcl9, and Ccl5 at the gene, RNA and/or protein level.

In exemplary aspects, the methods comprise measuring a level of expression of one or more of the following genes: Ccl22, Ccr7, Bmp15, S100A9, Chi3l3, Pglryp1, S100A8, Ltf, Ela2, and Camp. In exemplary aspects, the methods comprise measuring the level of expression at the gene level, the RNA level, or the protein level, or a combination thereof. In exemplary aspects, the method comprises measuring a level of expression of the RNA or protein encoded by one or more of the following genes: Ccl22, Ccr7, Bmp15, S100A9, Chi313, Pglryp1, S100A8, Ltf, Ela2, and Camp.

In exemplary aspects, the methods comprise measuring a level of expression of one or more of the following genes or the RNA or protein encoded by one or more of the following genes: Gapdh, Hmbs, Tbp, Ubc, Ywhaz, Bmp15, Camp, Ccl22, Ccr7, Chi3l3, Csf3, Cxcl2, Ela2, 1123a, Ltf, Pglyrp1, S100a8, S100a9. In additional or alternative exemplary aspects, the methods comprise measuring a level of expression of one or more of the following genes or the RNA or protein encoded by one or more of the following genes: Actb, B2m, Cdkn1a, Gusb, Hprt1, Ipo8, Pgk1, Polr2a, Ppia, Rplp2, Tfrc, 5730403B10Rik, A2m, Abcb1a, Abcf1, Acvr1, Acvr2b, Acvr11, Adipoq, Adora1, Adora2a, Adora3, Adrb2, Afap1l2, Aif1, Aimp1, Aimp1, Akt1, Alox15, Alox5, Alox5, Alox5, Alox5, Alox5, Alox5, Alox5ap, Anxa1, Aoah, Aoc3, Aox1, Apcs, Apoa1, Apoa1, Apoa4, Apoe, Areg, Atrn, Axl, B4galt1, Bad, Bcl10, Bcl6, Bdkrb1, Bdkrb2, Blnk, Bmp1, Bmp10, Bmp2, Bmp3, Bmp3, Bmp4, Bmp5, Bmp6, Bmp6, Bmp7, Bmp7, Bmp7, Bmp8a, Bmp8b, Bmpr1b, Bre, C1qa, C1qb, C1qc, C1r1, C1s, C2, C3, C3ar1, C3ar1, C6, C8a, C8b, C8g, C9, Casp1, Casp8, Cav1, Ccbp2, Ccl1, Ccl11, Ccl17, Ccl19, Ccl2, Ccl20, Ccl24, Ccl25, Ccl26, Ccl28, Ccl3, Ccl4, Ccl5, Ccl5, Ccl6, Ccl7, Ccl7, Ccl8, Ccr1, Ccr111, Ccr2, Ccr3, Ccr3, Ccr4, Ccr5, Ccr6, Ccr8, Ccr8, Ccr9, Ccr11, Ccrl2, Cd14, Cd163, Cd180, Cd1d1, Cd24a, Cd274, Cd28, Cd4, Cd40, Cd40lg, Cd44, Cd46, Cd55, Cd70, Cd74, Cd80, Cd86, Cd97, Cdk5, Cdo1, Cebpa, Cebpb, Cer1, Cfb, Cfd, Cfh, Cfhr1, Cfi, Cfp, Cftr, Chrna7, Chst1, Chst2, Chst4, Cklf, Clcf1, Clec7a, Clu, Cmklr1, Cmtm2a, Cmtm2b, Cmtm3, Cmtm4, Cmtm5, Cmtm6, Cmtm7, Cmtm8, Cntfr, Cntfr, Cntnap1, Cr11, Cr2, Crh, Crlf1, Crp, Csf1, Csf2, Csf2, Csf2ra, Csf2rb, Csf3, Ctf1, Ctla4, Cx3cl1, Cx3cr1, Cxcl1, Cxcl1, Cxcl10, Cxcl11, Cxcl12, Cxcl14, Cxcl16, Cxcl17, Cxcl3, Cxcl5, Cxcl9, Cxcr3, Cxcr3, Cxcr4, Cxcr6, Cxcr7, Cybb, Cyp26b1, Darc, Ddx58, Dnajc8, Ebi3, Eda2r, Egfr, Egfr, Ephx2, Epo, Erap1, Erbb2, Ereg, F11r, F2, F2r, F2rl1, F3, Fabp4, Fabp4, Fam3b, Fam3c, Fas, Fast, Fcer1a, Fcer1g, Fcgr2b, Fgf10, Fgf11, Fgf12, Fgf18, Fgf2, Fgf20, Fgf23, Figf, Flt31, Fn1, Fos, Fos, Foxp3, Fpr1, Fpr3, Gal, Gdf11, Gdf15, Gdf2, Gdf3, Gdf5, Gdf6, Gdf9, Gh, Ghrl, Ghsr, Glmn, Gpr17, Gpr68, Gpx1, Gpx4, Grem1, Grem2, Grn, Gsk3b, Gusb, Gusb, H2Q10, H47, Havcr2, Hc, Hdac4, Hdac4, Hdac4, Hdac5, Hdac5, Hdac5, Hdac7, Hdac7, Hdac9, Hgf, Hgf, Hgf, Hif1a, Hmgb1, Hmox1, Hprt1, Hprt1, Hprt1, Hpse, Hrh1, Hrh1, Hsp90ab1, Hspd1, Icos, Icos1, Ifih1, Ifna12, Ifna14, Ifna2, Ifna4, Ifnar1, Ifnar2, Ifnb1, Ifne, Ifng, Ifng, Ifngr1, Ifngr2, Ifnk, Igf1, Igfbp4, Ik, Il10, Il10ra, Il10rb, Il12a, Il12a, Il12b, Il12b, Il12rb1, Il12rb2, Il13, Il13, Il13ra1, Il13ra1, Il13ra2, Il15, Il15ra, Il16, Il17a, Il17c, Il17d, Il17f, Il17ra, Il17rb, Il18, Il18 bp, Il18rap, Il19, Il1a, Il1b, Il1b, Il1f10, Il1f5, Il1f6, Il1f9, Il10, Il1rap, Il1rap12, Il1rl1, Il1rl2, Il1rn, Il2, Il2, Il20, Il21, Il22; Iltifb, Il22ra1, Il22ra2, Il23a, Il23r, Il24, Il27, Il27ra, Il28b, Il28ra, Il28ra, IL2rg, Il3, Il31ra, Il33, Il3ra, Il4, Il4ra, Il5, Il5ra, Il6, Il6, Il6, Il6ra, Il6st, Il7r, Il8ra, Il8rb, Il9, Inha, Inhba, Inhbb, Ins2, Irak1, Irak2, Irak3, Irak4, Irf3, Irf3, Irf7, Itgal, Itgam, Itgb2, Itgb21, Itgb6, Jak1, Jak2, Jak3, Jun, Kit, Kitt, Klf6, Klkb1, Klrg1, Kng1, Krt1, Krt7, Krt8, Lbp, Lefty1; Lefty2, Lefty2, Lefty2, Lefty2, Lep, Lepr, Lif, Lifr, Lifr, Lilrb3, Lrp8, Lta4h, Ltb, Ltb4r1, Ltbp4, Ltbp4, Ltbr, Ly75, Ly86, Lyn, Malt1, Map2k3, Map2k6, Mapk14, Mapk8, Mapkapk2, Masp1, Masp2, Mbl2, Mefv, MgII, Mmp25, Mrc1, Mstn, Muc1, Muc4, Myd88, Ncam1, Ncf1, Ndst1, Nfam1, Nfatc3, Nfatc4, Nfe2I1, Nfkb1, Nfrkb, Nfx1, Nlrc4, NIrp3, Nmi, Nod1, Nod2, Nodal, Nono, Nos2, Nox4, Nr3c1, Nup85, Oit1, Olr1, Orm1, Osm, Oxgr1, P2rx1, P2rx7, P2ry1, Pdgfb, Pik3r1, Pla2g2d, Pla2g2e, Pla2g4c, Pla2g7, Plaa, Plp2, Pparg, Pparg, Ppbp, Ppia, Ppia; E030024N20Rik, Prdx5, Prg2, PrI7d1, Procr, Prok2, Prok2, Prtn3, Ptafr, Pten, Ptges, Ptgs1, Ptgs2, Ptn, Ptpn6, Ptprc, Ptx3, Ptx3, Pxdn, Pxmp2, Pycard, Rac1, Rbm4, Rcan1, Reg3a, Reg3g, Rela, Retn, Rhoa, Rhoa, Rhoa, Ripk2, Ryr1, S100a8, S100b, S1pr1, S1pr3, Saa1, Saa3, Scgb3a1, Scn9a, Scube1, Sdcbp, Sectm1b, Sele, Selp, Serpina1a, Serpina3c, Serpinf2, Serping1, Sftpa1, Sh2b2, Siglec1, Siva1, Slco1a4, Slurp1, Socs1, Socs2, Sod1, Sod1, Spp1, Spred1, Spred2, Stab1, Stat1, Stat3, Stat4, Stat5b, Stat6, Tacr1, Tgfb1, Tgfb2, Tgfbr1, Tgfbr1, Tgm2, Thpo, Timm50, Tirap, Tir1, Tir1, Tlr1; Tlr6, Tlr11, Tir12, Tlr13, Tlr2, Tlr3, Tlr4, Tlr5, Tlr6, Tlr7, Tlr9, Tnc, Tnf, Tnfaip3, Tnfaip6, Tnfrsf11b, Tnfrsf14, Tnfrsf18, Tnfrsf19, Tnfrsf1a, Tnfrsf1a, Tnfrsf1b, Tnfrsf25, Tnfrsf4, Tnfrsf8, Tnfrsf9, Tnfsf10, Tnfsf11, Tnfsf12; Tnfsf12-tnfsf13, Tnfsf13; Tnfsf12-tnfsf13, Tnfsf13b, Tnfsf14, Tnfsf15, Tnfsf18, Tnfsf4, Tnfsf8, Tnfsf9, Tollip, Tpst1, Trem1, Trf, Trip6, Trp53, Trpv1, Tslp, Twist1, Txlna, Unc13d, Vegfa, Vegfb, Vegfc, Vip, Vps45, Wnt16, Xcl1, Xcr1, Zfp36.

The above genes, as well as the RNA and proteins encoded by the genes, are known in the art. The sequences of each are available at the website for the National Center for Biotechnology Information (see Table A), some sequences of which are provided in the sequence listing submitted herewith.

TABLE A

| Gene name (abbreviation, full) | NCBI Gene ID No. | Gene accession number (assembly and range noted) | mRNA Accession | Protein Accession |
|---|---|---|---|---|
| Ccl22, C-C motif chemokine ligand 22 | 6367 | NC_000016.10 Reference GRCh38.p7 Primary Assembly Range: 57357909 . . . 57366190 | NM_002990.4 SEQ ID NO: 1 | NP_002981.2 SEQ ID NO: 2 |
| Cxcl2, C-X-C motif chemokine ligand 2 | 2920 | NC_000004.12 Reference GRCh38.p7 Primary Assembly Range 74097035 . . . 74099280 complement | NM_002089.3 SEQ ID NO: 3 | NP_002080.1 SEQ ID NO: 4 |
| Ccr7, C-C motif chemokine receptor 7 | 1236 | NC_000017.11 Reference GRCh38.p7 Primary Assembly Range 40553769 . . . 40565484 complement | NM_001301714.1 SEQ ID NO: 5 NM_001301716.1 SEQ ID NO: 7 NM_001301717.1 SEQ ID NO: 9 NM_001301718.1 SEQ ID NO: 11 NM_001838.3 SEQ ID NO: 13 | NP_001288643.1 SEQ ID NO: 6 NP_001288645.1 SEQ ID NO: 8 NP_001288646.1 SEQ ID NO: 10 NP_001288647.1 SEQ ID NO: 12 NP_001829.1 SEQ ID NO: 14 |
| Csf3, colony stimulating factor 3 | 1440 | NC_000017.11 Reference GRCh38.p7 Primary Assembly Range 40015361 . . . 40017813 | NM_000759.3 SEQ ID NO: 15 NM_001178147.1 SEQ ID NO: 17 NM_172219.2 SEQ ID NO: 19 NM_172220.2 SEQ ID NO: 21 | NP_000750.1 SEQ ID NO: 16 NP_001171618.1 SEQ ID NO: 18 NP_757373.1 SEQ ID NO: 20 NP_757374.2 SEQ ID NO: 22 |
| Bmp15, bone morphogenetic protein 15 | 9210 | NC_000023.11 Reference GRCh38.p7 Primary Assembly Range 50910735 . . . 50916641 | NM_005448.2 SEQ ID NO: 23 | NP_005439.2 SEQ ID NO: 24 |
| IL-23a, interleukin 23 subunit alpha | 51561 | NC_000012.12 Reference GRCh38.p7 Primary Assembly Range 56334159 . . . 56340410 | NM_016584.2 SEQ ID NO: 25 | NP_057668.1 SEQ ID NO: 26 |
| S100A9, S100 calcium binding protein A9 | 6280 | NC_000001.11 Reference GRCh38.p7 Primary Assembly Range 153357854 . . . 153361027 | NM_002965.3 SEQ ID NO: 27 | NP_002956.1 SEQ ID NO: 28 |

TABLE A-continued

| Gene name (abbreviation, full) | NCBI Gene ID No. | Gene accession number (assembly and range noted) | mRNA Accession | Protein Accession |
|---|---|---|---|---|
| Chi3l3, chitinase-like 3 | 12655 | NC_000069.6 Reference GRCm38.p4 057BL/6J Range 106147554 . . . 106167564 complement | NM_009892.3 SEQ ID NO: 29 | NP_034022.2 SEQ ID NO: 30 |
| Pglryp1, | 8993 | NC_000019.10 Reference GRCh38.p7 Primary Assembly Range 46019153 . . . 46023298 complement | NM_005091.2 SEQ ID NO: 53 | NP_005082.1 SEQ ID NO: 54 |
| S100A8, S100 calcium binding protein A8 | 6279 | Genomic NC_000001.11 Reference GRCh38.p7 Primary Assembly Range 153390032 . . . 153422583 complement | NM_001319196.1 SEQ ID NO: 31 NM_001319197.1 SEQ ID NO: 33 NM_001319198.1 SEQ ID NO: 35 NM_001319201.1 SEQ ID NO: 37 NM_002964.4 SEQ ID NO: 39 | NP_001306125.1 isoform a SEQ ID NO: 32 NP 001306126.1 isoform b SEQ ID NO: 34 NP_001306127.1 isoform c SEQ ID NO: 36 NP_001306130.1 isoform d SEQ ID NO: 38 NP_002955.2 isoform d with alt splice junction SEQ ID NO: 40 |
| Ltf, lactotransferrin | 4057 | NC_000003.12 Reference GRCh38.p7 Primary Assembly Range 46436005 . . . 46485234 complement | NM_001199149.1 SEQ ID NO: 41 NM_001321121.1 SEQ ID NO: 43 NM_001321122.1 SEQ ID NO: 45 NM_002343.5 SEQ ID NO: 47 | NP_001186078.1 SEQ ID NO: 42 NP_001308050.1 SEQ ID NO: 44 NP_001308051.1 SEQ ID NO: 46 NP_002334.2 SEQ ID NO: 48 |
| Ela2, ELANE, elastase neutrophil expressed | 1991 | NC_00019.10 Reference GRCh38.p7 Primary Assembly Range 850997 . . . 856250 | NM_001972.3 SEQ ID NO: 49 | NP_001963.1 SEQ ID NO: 50 |
| Camp, cathelicidin antimicrobial peptide | 820 | NC_000003.12 Reference GRCh38.p7 Primary Assembly Range 48223347 . . . 48225491 | NM_004345.4 SEQ ID NO: 51 | NP_004336.3 SEQ ID NO: 52 |

Suitable methods of determining expression levels of nucleic acids (e.g., mRNA) are known in the art and include quantitative polymerase chain reaction (qPCR), including, but not limited to, quantitative real-time PCR (qRT-PCR), RNAseq, Northern blotting and Southern blotting. Techniques for measuring gene expression include, for example, gene expression assays with or without the use of gene chips are described in Onken et al., J Molec Diag 12(4): 461-468 (2010); and Kirby et al., Adv Clin Chem 44:247-292 (2007). Affymetrix gene chips and RNA chips and gene expression assay kits (e.g., Applied Biosystems™ TaqMan® Gene Expression Assays) are also commercially available from companies, such as ThermoFisher Scientific (Waltham, MA). Suitable methods of determining expression levels of proteins are known in the art and include immunoassays (e.g., Western blotting, an enzyme-linked immunosorbent assay (ELISA), a radioimmunoassay (RIA), and immunohistochemical assay) or bead-based multiplex assays, e.g., those described in Djoba Siawaya J F, Roberts T, Babb C, Black G, Golakai H J, Stanley K, et al. (2008) An Evaluation of Commercial Fluorescent Bead-Based Luminex Cytokine Assays. PLOS ONE 3(7): e2535. Proteomic analysis which is the systematic identification and quantification of proteins of a particular biological system are known. Mass spectrometry is typically the technique used for these purposes. Protein expression Suitable methods of measuring expression are described herein. See the section entitled EXAMPLES.

Controls

In the methods described herein, the level that is measured may be the same as a control level or a cut off level or a threshold level, or may be increased or decreased relative to a control level or a cut off level or a threshold level. In some aspects, the control level is that of a control subject which may be a matched control of the same species, gender, ethnicity, age group, smoking status, BMI, current therapeutic regimen status, medical history, or a combination thereof, but differs from the subject being diagnosed in that the control does not suffer from the disease in question or is not at risk for the disease. Thus, in exemplary aspects, the control level(s) of the gene(s), RNA, or protein(s) is/are level(s) of a subject known to not have metastatic disease. In alternative aspects, the control level(s) of the gene(s), RNA, or protein(s) is/are level(s) of a subject known to have metastatic disease. In exemplary aspects, as further described herein, the measured level is compared to both a control level of a subject known to not have metastatic disease and a control level of a subject known to have metastatic disease. In exemplary aspects, as further described herein, the measured level is compared to multiple control levels: a control level of a subject known to not have metastatic disease and several control levels of subjects known to have metastatic disease but differ from one another by the stage of metastatic disease. For example, a panel of control levels may be used to compare the measured level and the panel of control levels include a control level of a subject who does not have a tumor or a cancer, a control level of a subject known to have a tumor that has not metastasized, a control level of a subject known to have advanced metastatic disease, a control level of a subject known to be in an early stage of metastatic disease, and a control level of a subject known to be in a mid-stage of metastatic disease. In exemplary aspects, the panel of control levels are graphically displayed as elliptical areas, wherein each elliptical area represents the average and standard deviation of the control level in regards to probability of metastatic disease (e.g., along the y-axis) and a score of metastatic potential (e.g., along the x-axis). In some instances, the measured level is plotted on this graphic and the distance from the nearest control elliptical area is indicative of the subject's metastatic potential.

In exemplary aspects, the method comprises measuring the level of expression of a gene, RNA, or protein at a first time point and at a second time point and the measured level of the first time point serves as a control level or establishes a baseline.

Relative to a control level, the level that is determined may an increased level. As used herein, the term "increased" with respect to level (e.g., expression level, biologicalactivity level) refers to any % increase above a control level. The increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., expression level, biologicalactivity level) refers to any % decrease below a control level. The decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

Housekeeping Genes

For purposes herein, the levels of expression are measured and the measured levels may be normalized or calibrated to a level of a housekeeping gene. The housekeeping gene in some aspects is GAPDH, Hmbs, Tbp, Ubc, Ywhaz. In exemplary aspects, the housekeeping gene is any one of those set forth in the Table B or any one of those comprising a sequence of SEQ ID NOs: 55-90.

TABLE B

| Gene Name | NCBI Accession No. |
|---|---|
| Actin, beta (ACTB) | NM_001101 |
| aldolase A, fructose-bisphosphate (ALDOA) | NM_000034 |
| Glyceraldehyde-3-phosphate dehydrogenase (GAPDH) | NM_002046 |
| Phosphoglycerate kinase 1 (PGK1) | NM_000291 |
| Lactate dehydrogenase A (LDHA), | NM_005566 |
| Ribosomal protein S27a (RPS27A) | NM_002954 |
| Ribosomal protein L19 (RPL19) | NM_000981 |
| Ribosomal protein L11 (RPL11) | NM_000975 |
| Non-POU domain containing, octamer-binding (NONO) | NM_007363 |
| Rho GDP dissociation inhibitor (GDI) alpha (ARHGDIA) | NM_004309 |
| Ribosomal protein L32 (RPL32) | NM_000994 |
| Ubiquitin C (UBC) | NM_021009 |
| HMBS | NM_000190.3 |
| | NM_001024382.1 |
| | NM_001258208.1 |
| | NM_001258209.1 |
| TBP | NM_001172085.1 |
| | NM_003194.4 |
| Ywhaz | NM_001135699.1 |
| | NM_001135700.1 |
| | NM_001135701.1 |
| | NM_001135702.1 |
| | NM_003406.3 |
| | NM_145690.2 |

Subjects

In exemplary aspects, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human. In some aspects, the human is an adult aged 18 years or older. In some aspects, the human is a child aged 17 years or less. In exemplary aspects, the subject has a tumor or cancer. The tumor or cancer may be any of those known in the art or described herein.

Additional Steps

With regard to the methods of the invention, the methods may include additional steps. For example, the method may include repeating one or more of the recited step(s) of the method. Accordingly, in exemplary aspects, the method comprises measuring a level of expression of a gene, an RNA, or a protein, in a sample obtained from a scaffold and re-measuring the level, e.g., at a different time point, for accuracy. In exemplary aspects, the method comprises implanting the scaffold into the subject. In exemplary aspects, the method comprises obtaining the sample from the subject. In exemplary embodiments, more than one sample is obtained from the scaffold. In exemplary embodiments, 2, 3, 4, 5, 6, 7, 8, 9, 10, or more samples are obtained from the scaffold, each sample obtained at a different point in time. In exemplary aspects, a sample is obtained from the scaffold once a day, 2× per day, 3× per day, 4× per day or more frequently. In exemplary aspects, a sample is obtained from the scaffold every 2, 3, 4, 5, or 6 days. In exemplary aspects, a sample is obtained from the scaffold once a week or once every 2 weeks, 3 weeks, 4 weeks, 5 weeks, 6 weeks, 7 weeks, or 8 weeks or less frequently. In exemplary aspects, a sample is obtained on a regular basis based on the analysis of a first sample. In exemplary aspects, a sample is obtained on a regular basis until a pre-determined goal is met. In exemplary aspects, the pre-determined goal is the determination of the subject as exhibiting a complete therapeutic response to a treatment, e.g., chemotherapy, immune therapy, gene therapy, radiation, surgical resection.

In exemplary aspects, the method comprises measuring an expression level for every sample obtained. In exemplary aspects, the expression level is measured within 1, 4, 6, 8, 12, 16, or 24 hours of obtaining the sample. In exemplary aspects, the sample is cryopreserved and expression of the sample is determined at a later time.

In exemplary aspects, the methods comprise processing the sample for measurement of expression. For example, the methods may comprise RNA isolation from cells of the scaffold. The methods may comprises homogenizing in a Trizol reagent for RNA isolation or in a detergent for protein isolation. In exemplary aspects, it is desirable to fractionate the cells of the sample into cell type specific sub-populations. In this regard, the methods comprise in exemplary instances a step for separating the cells of the scaffold into cell type specific sub-populations. In exemplary aspects, the cells of the scaffold are separated into subpopulations of immune cells and stromal cells. In exemplary instances, the cells of the scaffold are separated into fibroblasts, endothelial cells, dendritic cells, CD45+ cells, T-cells, B-cells, monocytes, macrophages, MDSCs, neutrophils, and natural killer cells. In exemplary aspects, the methods comprise measuring or quantifying the different cell populations in the sample and/or measuring tumor cell populations in the sample, in addition to or instead of measuring a level of expression of a gene, an RNA or a protein, in a sample obtained from a synthetically-engineered pre-metastatic niche (pMN) implanted in the subject. In exemplary aspects, the methods comprise determining the cell population profile of the sample. In exemplary aspects, the methods comprises determining the cell signature of the sample. Methods of measuring cell populations in a sample may be performed by known techniques, including, fluorescent-assisted cell sorting (FACS), magnetic-assisted cell sorting, histological techniques, e.g., fluorescent immunohistochemistry or multiplexed fluorescent imaging technologies. In exemplary aspects, the methods comprise monitoring the cell populations over time.

In exemplary aspects, the method comprises measuring an expression level of the sample in more than one way. In exemplary instances, the methods comprise measuring expression using a gene chip and an ELISA or other immunoassay. In exemplary instances, the methods comprise measuring expression levels of one or more housekeeping genes and comparing the measured levels of genes to housekeeping genes. In exemplary aspects, the methods comprises normalizing the expression level data to expression levels of one or more housekeeping genes.

In exemplary aspects, when the method comprises, e.g., measuring a level of expression of a plurality of genes, RNA, and/or proteins, the methods comprise constructing a matrix of expression levels, e.g., a matrix of gene expression levels, a matrix of RNA expression levels, a matrix of protein expression levels. The matrices can be further categorized into biological pathways or functions, e.g., a sub-matrix of genes, RNA, and/or proteins involved in cell cycle control, immune cell proliferation and activation, metastatic intravasation, extravasation, homing, migration, or colonization, or a sub-matrix for extracellular matrix (ECM) components. The matrices may be manipulated to remove data points or add data points from a second source of data, an ELISA vs. a multiplex bead-based assay. The expression levels of the matrices may be normalized to housekeeping genes and/or to total protein concentrations. In exemplary aspects, the methods comprise analyzing the expression level matrices for expression level changes, significance, false-detection rate of key variables, and for the identification of analytes of particular interest via regularization, supervised discriminate analysis (e.g., using Lasso or Elastic Net; Partial Least-Squares Discriminate Analysis (PLS-DA); feature selection).

In exemplary aspects, the matrices are compressed into a single metric or score. In exemplary aspects, such decompression of multiple variables into a single metric or score is accomplished via linear combination of multiple gene or protein expression levels, singular value decomposition (SVD), dynamic mode decomposition (DMD), principle component analysis (PCA), or Fisher linear discriminant. Methods of SVD for similar purposes are described in Alter et al., Proc Natl Acad Sci USA. 2000 Aug. 29; 97(18): 10101-10106.

In exemplary aspects, a machine learning algorithm is employed to attain a prediction of metastatic disease state or status. The algorithm may comprise one or more of logistic regression, discriminant analysis (linear or quadratic), random forest generation or other ensemble/decision tree classification, neural networks pattern recognition (hidden layers), support vector machines, nearest neighbor (fine-course weighted) and Bayesian networks.

In exemplary aspects, the method comprises providing to the subject a treatment or therapy purposed for treating metastatic disease. The treatment or therapy purposed for treating metastatic disease may be any of those known in the art or described herein. In exemplary instances, the therapy is surgical resection or radiation therapy. In exemplary aspects, the treatment comprises administration of one or more chemotherapeutic agents.

In exemplary aspects, the method further comprises combining multiple metrics into a multivariate signature. This step may comprise combining multiple scoring and prediction algorithms to a graphical or numerical output for identification of trends, correlations and outliers. Visual outputs for correlation include side by side box or bar plots for each algorithm or a combination thereof into a multidimensional output (e.g., multivariable plot of SVD score and RF prediction). Example figures show the SVD score plotted on the x-axis and the RF prediction plotted on the y-axis. This outline is flexible. The general concept is to establish a parameter space composed of these multivariate metrics with high and low end to aid categorization of test samples.

Further details relating to data processing are provided below.

Data Processing

The present techniques further include measuring levels of the genes, RNA, or proteins and determining a pMN expression signature for a subject using a processing system. For example, in exemplary embodiments, metastatic potential is determined or metastatic disease, or a predisposition thereto, is detected by measuring a level of expression of a gene, a RNA or a protein, or a combination thereof, in a sample obtained from a synthetically-engineered pMN implanted in a subject. In exemplary embodiments, a level of expression of a plurality of genes, RNA, and/or proteins, are measured. The measured expression level data are then provided to a processing system that compares the measured expression level data to control levels of the expression data. In some exemplary embodiments, the processing system compares measured expression level data of a first time instance to measured expression level data taken at a second time instance, or to a plurality of time instances. In exemplary aspects, the first time point occurs before a treatment and the second time point occurs after a treatment and the method is a method of determining the efficacy of a treatment for metastatic disease.

The processing system may compare measured expression level data using different algorithm-based analyses subsystems. In some examples, one type of subsystem employs a compression algorithm, such as a single value decomposition (SVD) algorithm that receives a plurality of different measured expression level data and compresses that data into a single scoring metric. In some examples, one type of subsystem employs a probability determination, such as a Random Forest algorithm, that indicates a probability of metastases for a pMN. In some examples, that probability indicates a subject's metastatic potential or metastatic disease.

An example implementation of the processing system to determine pMN expression signature for a subject is as follows.

At an initial processing stage, sample implantation is performed, followed by retrieval. An implant polymer scaffold, in accordance with the teachings herein and other example scaffolds including those described above is inserted into a subject, such as a predetermined high-risk subject, prior to disease onset. The implant is then used for early detection of metastatic potential or disease. In some examples, implantation occurs following therapeutic intervention and is used for monitoring therapeutic efficacy.

At the time point of interest, e.g., after a given number of days or after a therapeutic intervention, a biopsy is performed to remove the scaffold, either surgically removal of the entire scaffold or removal of only a portion thereof, such as performing a core-needle biopsy of the scaffold microenvironment.

With the scaffold removed or a scaffold microenvironment removed, the scaffold contents are processed for molecular content determination. In some examples, such processing includes isolate RNA and/or protein from scaffold biopsy (e.g., homogenize in Trizol reagent or detergent, respectively). Optionally, in some examples, fractionate cell populations within the scaffold for cell type specific analysis may be performed. While cell population analysis techniques will be understood, in some examples, separate cell populations based on fluorescent-assisted cell sorting or magnetic-assisted cell sorting may be performed. Analysis of gene or protein expression may be achieved, in some examples, using either qRT-PCR or RNAseq, for gene expression, and either ELISA or Luminex (bead-based multiplex assays), for protein expression. The result from this initial processing stage is measured expression level data that is provided to a processing system.

Figure 5:
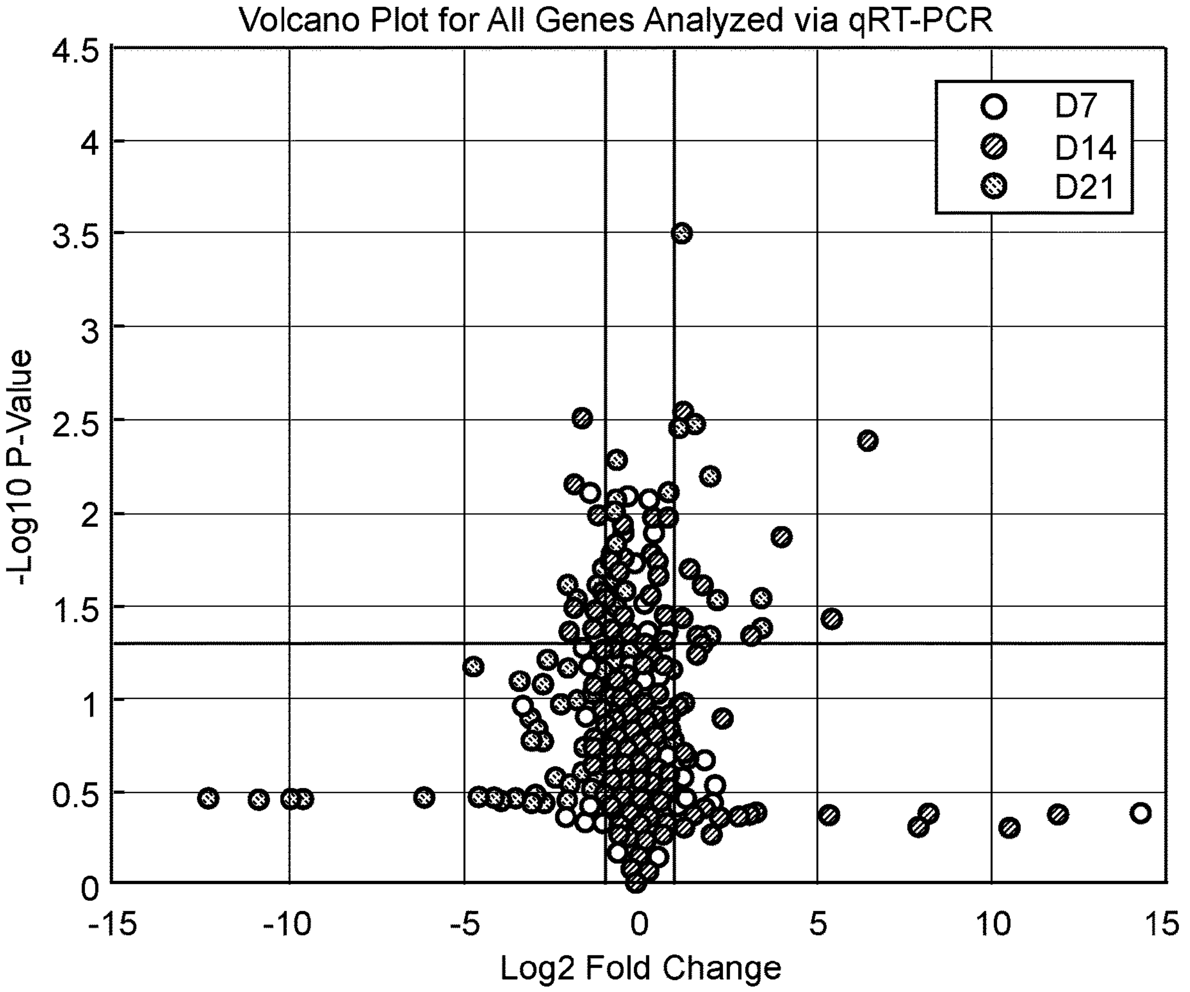
FIG. 5 is a volcano plot for all genes analyzed via qRT-PCR.

At a next stage, measured expression level data is pre-processed in the processing system. In exemplary embodiments, the processing system analyzes the measured expression level data and performs an alignment of various analytes into a format for either signature development or test sample characterization. The alignment may be in the form of a matrix with or without categorical indicators, for example. An example output of fold change from a significance from a compiled matrix is shown in FIG. 5.

The processing system may include numerous pre-processing data analysis and correction processes. For example, compensation for missing data points may be used depending upon the computational algorithm chosen to perform the alignment. Furthermore, removal of an entire analyte may be used, if too many data points are missing or a nearest neighbor average may be employed, if cohort size is suitable.

For gene expression, the processing system may perform gene stability analysis and normalization. For example, a panel of genes may be compared against each other for stability within the set then a subset may be determined for sample normalization.

For protein expression, the processing system may normalize total sample protein concentration.

Further pre-processing by the processing system may include, analyzing fold change, significance, and false-detection rate of key variables for interpretation of single analyte dynamics.

The processing system, with the foregoing pre-processing, then identifies analytes (gene or protein expression) of interest, for example, via regularization or supervised discriminate analysis. Techniques that may be used include a Lasso or Elastic Net process and/or a Partial-Least Squares Discriminate Analysis (PLS-DA).

At a next stage, a reduction of the variables from the second stage is performed to determine a single metric, i.e., a compressed metric of the measured expression level data.

In exemplary embodiments, a process of decomposition matrix of gene expressions is performed and a gene expression score is attained. An example decomposition matrix is a singular value decomposition (SVD) process. In an example implementation, a single score was obtained by the processing system from the first left singular vector, which forms an orthonormal basis for the assay expression profiles. An examples decomposition matrix that may be used is a dynamic mode decomposition (DMD).

With a decomposition performed on the measured expression level data, the processing system may be further configured to employ a machine learning process to attain a prediction of disease state. An example, machine learning process is a Random forest (RF) generation or other ensemble/decision tree classification algorithm. In some examples, the machine learning process employs alogistic regression analysis. In some examples, the machine learning process employs a discriminant analysis (linear or quadratic). In some examples, the machine learning process employs a support vector machines analysis. In some examples, the machine learning process employs a nearest neighbor (fine-course, weighted) analysis.

FIGS. 9-12 illustrate example outputs from this third stage.

Figure 11:
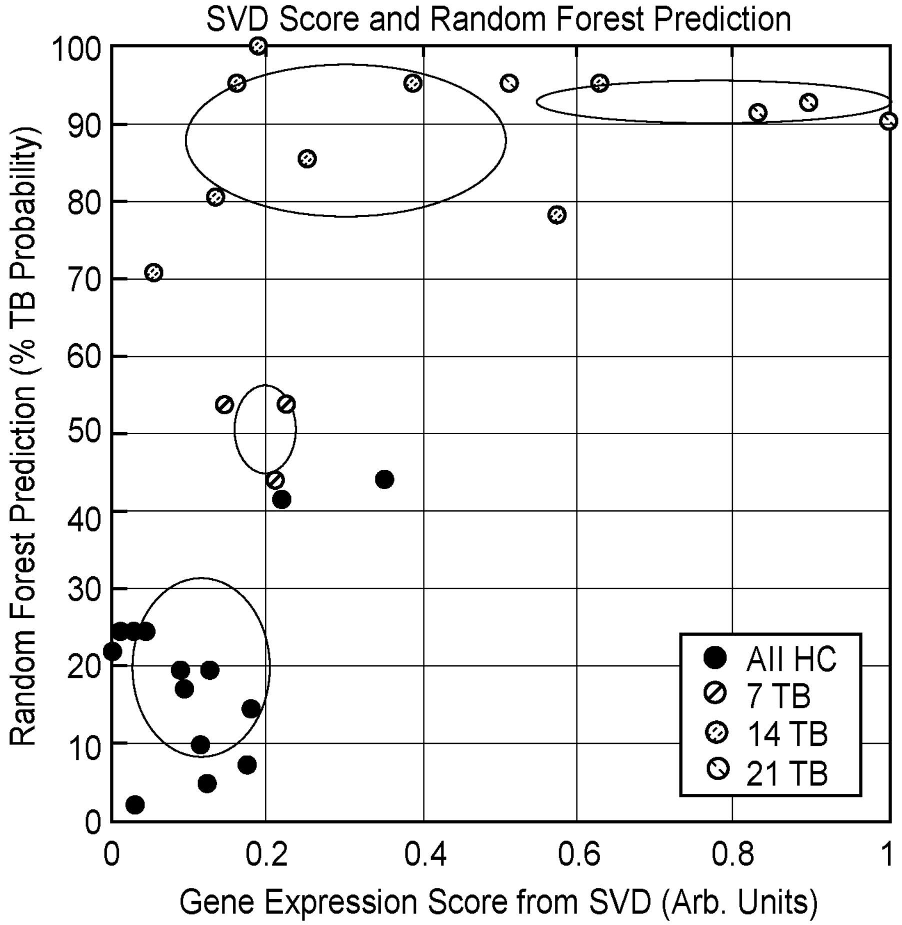
FIG. 11 is a graph of random forest prediction (% tumor bearing probability) vs. gene expression score from SVD.
Figure 12:
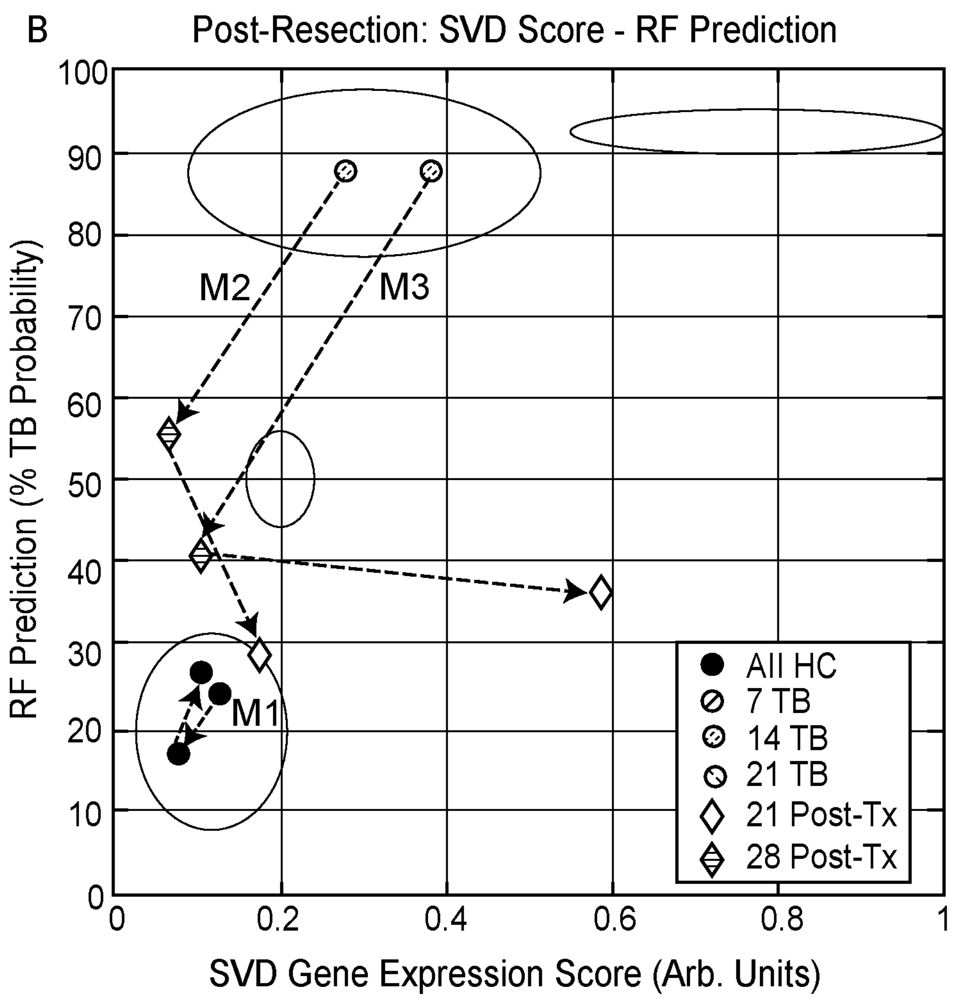
FIG. 12 is a graph of random forest prediction (% tumor bearing probability) vs. gene expression score from SVD for mice that were treated by surgical resection.

At a next stage, a combination is performed on multiple scores and a predicted metastatic potential is determined. In an exemplary embodiment, the SVD score and the Random Forest percentage prediction are combined to analyze the measured expression level data in a multidimensional process. For example, the SVD score and the Random Forest percentage prediction may be combined into an interrelation plot showing a multivariate analysis, such as a graphical output as in the example of FIGS. 11 and 12. In some examples, the two may be combined to form a numerical output. In either example, the multidimensional process may be used by the processing system to identify trends, correlations, and outliers and to assess pre metastasis. FIGS. 11 and 12 illustrate an example multivariate plot that may be generated and displayed by the processing system. The plot provides a visual indication of the outputs for correlation of the SVD and Random Forest values, including side by side box or bar plots for each algorithm or a combination of algorithms into a multidimensional output (e.g., scatter plot of SVD score and RF prediction).

In exemplary aspects, as described above, the measured levels of the genes, RNA, or proteins form a gene expression signature, an RNA signature, or a protein signature, respectively. In further aspects, the measurement of cell types in the sample form a cell signature. In exemplary instances, each of the signatures are processed into a single value.

Figure 16:
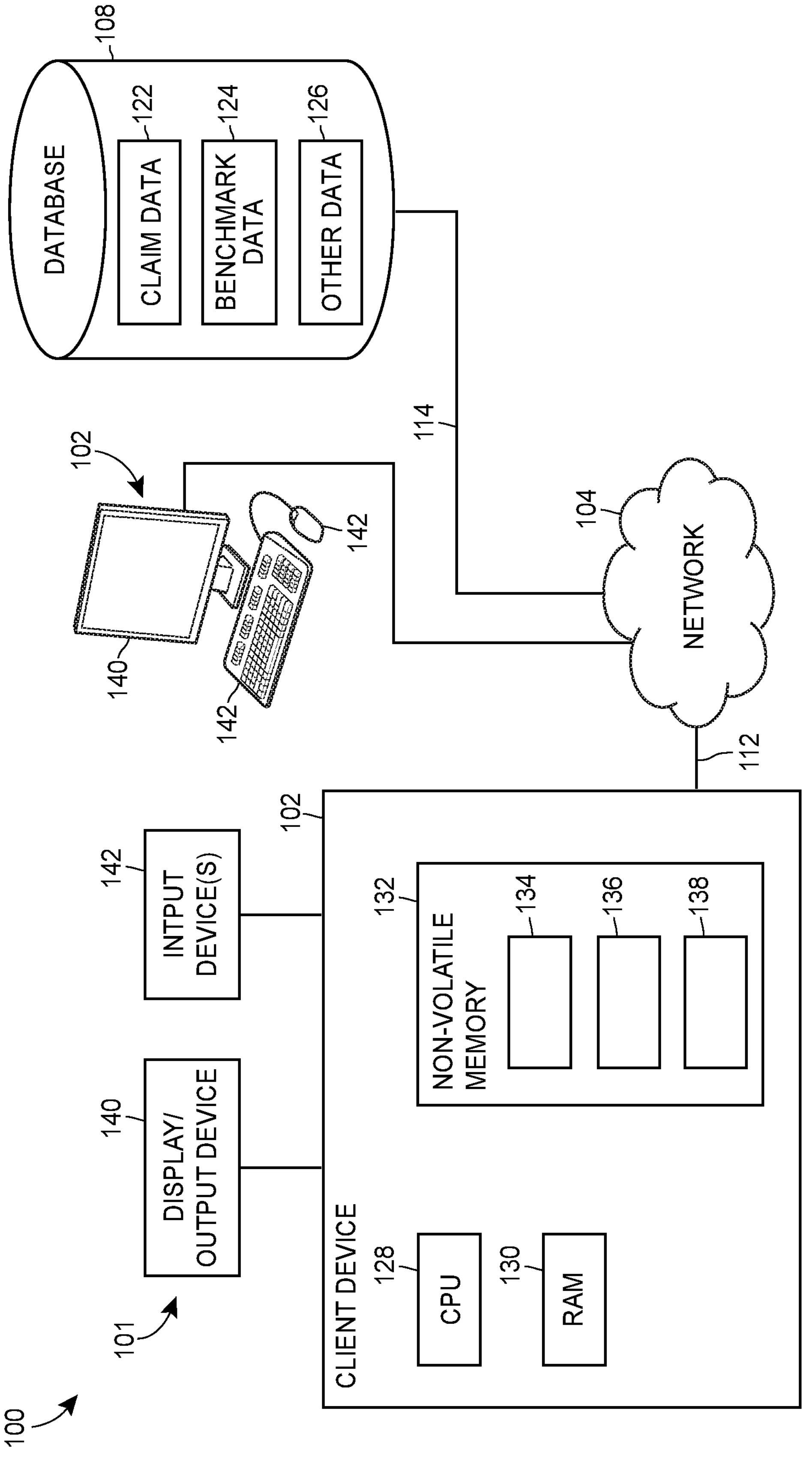
FIG. 16 is a system diagram of a processing system for performing the techniques described herein, including, assessing a subject's metastatic potential, in accordance with an example.

Systems, Computer-Readable Storage Media, and Methods Implemented by a Computer Processor FIG. 16 illustrates an exemplary embodiment 101 of a system 100 for assessing a subject's metastatic potential. Generally, the system 100 may include one or more client devices 102, a network 104, and a database 108. Each client device 102 may be communicatively coupled to the network 104 by one or more wired or wireless network connections 112, which may be, for example, a connection complying with a standard such as one of the IEEE 802.11 standards ("Wi-Fi"), the Ethernet standard, or any other appropriate network connection. Similarly, the database 108 may be communicatively coupled to the network 104 via one or more connections 114. (Of course, the database could alternatively be internal to one or more of the client devices 102.) The database 108 may store data related to the expression profiles for a variety of subjects, including, but not limited to, data of a sample obtained from a scaffold implanted in the subject, data of a sample obtained from a scaffold implanted in a control population, etc. In exemplary aspects, the control is a population of subjects known to not have a tumor or cancer. In exemplary aspects, the control is a population of subjects known to have a non-metastatic tumor or cancer. In exemplary aspects, the control is a population of subjects known to have metastatic cancer.

The data of the samples may be, for example, related to one or more of a level of expression of an S100A8 gene, RNA, or protein, a level of expression of an S100A9 gene, RNA, or protein, a level of expression of a gene, RNA, or protein of or encoded by one of: Ccl22, Cxcl2, Ccr7, Csf3, Bmp15, IL-23a, S100A9, Chi3I3, Pglryp1, S100A8, Ltf, Ela2, and Camp, etc., as described in greater detail below. The data of the samples may be, for example, related to one or more of a level of expression of an S100A8 gene, RNA, or protein, a level of expression of an S100A9 gene, RNA, or protein, a level of expression of a gene, RNA, or protein of or encoded by one of: Ccl22, Ccr7, Bmp15, S100A9, Chi3I3, Pglryp1, S100A8, Ltf, Ela2, and Camp.

As will be understood, the network 104 may be a local area network (LAN) or a wide-area network (WAN). That is, network 104 may include only local (e.g., intra-organization) connections or, alternatively, the network 104 may include connections extending beyond the organization and onto one or more public networks (e.g., the Internet). In some embodiments, for example, the client device 102 and the database 108 may be within the network operated by a single company (Company A). In other embodiments, for example, the client device(s) 102 may be on a network operated by Company A, while the database 108 may be on a network operated by a second company (Company B), and the networks of Company A and Company B may be coupled by a third network such as, for example, the Internet.

Referring still to FIG. 16, the client device 102 includes a processor 128 (CPU), a RAM 130, and a non-volatile memory 132. The non-volatile memory 132 may be any appropriate memory device including, by way of example and not limitation, a magnetic disk (e.g., a hard disk drive), a solid state drive (e.g., a flash memory), etc. Additionally, it will be understood that, at least with regard to FIG. 16, the database 108 need not be separate from the client device 102. Instead, in some embodiments, the database 108 is part of the non-volatile memory 132 and the data 122, 124, 126 may be stored as data within the memory 132. For example, the data 122 may be included as data in a spreadsheet file stored in the memory 132, instead of as data in the database 108. In addition to storing the records of the database 108 (in some embodiments), the memory 132 stores program data and other data necessary to analyze data of one or more sample and/or control populations, etc. For example, in an embodiment, the memory 132 stores a first routine 134, a second routine 136, and a third routine 138. The first routine 134 may receive data values related to a measured expression level of a gene, RNA, or protein of a sample obtained from a scaffold implanted in a test subject, and may process the data values received by the routine 134 through an algorithm to obtain a score. The second routine 136 may computer one or more statistical parameters of the data collected by the first routine 134, such as determining a mean value, a standard deviation value, etc. Additionally and/or alternatively, the second routine 136 may plot a score on a graphical or numerical output. Regardless, each of the routines is executable by the processor 128 and comprises a series of compiled or compilable machine-readable instructions stored in the memory 132. Additionally, the memory 132 may store generated reports or records of data output by one of the routines 134 or 136. Alternatively, the reports or records may be output to the database 108. One or more display/output devices 140 (e.g., printer, display, etc.) and one or more input devices 142 (e.g., mouse, keyboard, tablet, touch-sensitive interface, etc.) may also be coupled to the client device 102, as is generally known.

As will be understood, although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

For example, the network 104 may include but is not limited to any combination of a LAN, a MAN, a WAN, a mobile, a wired or wireless network, a private network, or a virtual private network. Moreover, while only two clients 102 are illustrated in FIG. 16 to simplify and clarify the description, it is understood that any number of client computers are supported and can be in communication with one or more servers (not shown).

Additionally, certain embodiments are described herein as including logic or a number of routines. Routines may constitute either software routines (e.g., code embodied on a machine-readable medium or in a transmission signal) or hardware routines. A hardware routine is tangible unit capable of performing certain operations and may be configured or arranged in a certain manner. In example embodiments, one or more computer systems (e.g., a standalone, client or server computer system) or one or more hardware routines of a computer system (e.g., a processor or a group of processors) may be configured by software (e.g., an application or application portion) as a hardware routine that operates to perform certain operations as described herein.

Similarly, the methods or routines described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments of a map editor system for purposes of illustration only. One skilled in the art will readily recognize from the following discussion that alternative embodiments of the structures and methods illustrated herein may be employed without departing from the principles described herein Upon reading this disclosure, those of skill in the art will appreciate still additional alternative structural and functional designs for a system and a process for identifying terminal road segments through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The present disclosure provides systems comprising: a processor; a memory device coupled to the processor, and machine readable instructions stored on the memory device. In exemplary embodiments, the machine readable instructions that, when executed by the processor, cause the processor to (i) receive a plurality of data values, each data value is a measured expression level of a different gene of a sample obtained from a synthetically-engineered pMN implanted in a test subject;

(ii) process the plurality of data values though (a) a decomposition algorithm to obtain a single score for gene expression for the test subject, (b) a machine learning algorithm to obtain a score of prediction of disease state for the test subject, or (c) a combination of (a) and (b) to obtain a combined score for the test subject;

(iii) plot the single score for gene expression for the test subject, the score of prediction of disease state for the test subject, or the combined score for the test subject on a graphical or numerical output, wherein the graphical or numerical output comprises an average single score for gene expression for a control, an average score of prediction of disease state for a control, or an average combined score for a control.

In exemplary aspects, the control is a population of subjects known to not have a tumor or cancer. In exemplary aspects, the control is a population of subjects known to have a non-metastatic tumor or cancer. In exemplary aspects, the control is a population of subjects known to have metastatic cancer. In exemplary aspects, the graphical or numerical output comprises the average score (single score for gene expression, score of prediction of disease state, or combined score) for multiple controls. In exemplary aspects, the graphical or numerical output comprises the average score (single score for gene expression, score of prediction of disease state, or combined score) for subjects known to have a non-metastatic tumor or cancer, the average score for subjects known to not have a tumor or cancer, and the average score for subjects known to have metastatic cancer.

In alternative or additional aspects, the system of the invention comprises machine readable instructions that, when executed by the processor, cause the processor to:

(i) receive a plurality of data values, each data value is a measured expression level of a different RNA of a sample obtained from a synthetically-engineered pMN implanted in a test subject;

(ii) process the plurality of data values though (a) a decomposition algorithm to obtain a single score for RNA expression for the test subject, (b) a machine learning algorithm to obtain a score of prediction of disease state for the test subject, or (c) a combination of (a) and (b) to obtain a combined score for the test subject;

(iii) plot the single score for RNA expression for the test subject, the score of prediction of disease state for the test subject, or the combined score for the test subject on a graphical or numerical output, wherein the graphical or numerical output comprises an average single score for RNA expression for a control, an average score of prediction of disease state for a control, or an average combined score for a control.

In exemplary aspects, the control is a population of subjects known to not have a tumor or cancer. In exemplary aspects, the control is a population of subjects known to have a non-metastatic tumor or cancer. In exemplary aspects, the control is a population of subjects known to have metastatic cancer. In exemplary aspects, the graphical or numerical output comprises the average score (single score for RNA expression, score of prediction of disease state, or combined score) for multiple controls. In exemplary aspects, the graphical or numerical output comprises the average score (single score for RNA expression, score of prediction of disease state, or combined score) for subjects known to have a non-metastatic tumor or cancer, the average score for subjects known to not have a tumor or cancer, and the average score for subjects known to have metastatic cancer.

In yet further alternative or additional aspects, the system of the invention comprises machine readable instructions that, when executed by the processor, cause the processor to:

(i) receive a plurality of data values, each data value is a measured expression level of a different protein of a sample obtained from a synthetically-engineered pMN implanted in a test subject;

(ii) process the plurality of data values though (a) a decomposition algorithm to obtain a single score for protein expression for the test subject, (b) a machine learning algorithm to obtain a score of prediction of disease state for the test subject, or (c) a combination of (a) and (b) to obtain a combined score for the test subject;

(iii) plot the single score for protein expression for the test subject, the score of prediction of disease state for the test subject, or the combined score for the test subject on a graphical or numerical output, wherein the graphical or numerical output comprises an average single score for protein expression for a control, an average score of prediction of disease state for a control, or an average combined score for a control.

In exemplary aspects, the control is a population of subjects known to not have a tumor or cancer. In exemplary aspects, the control is a population of subjects known to have a non-metastatic tumor or cancer. In exemplary aspects, the control is a population of subjects known to have metastatic cancer. In exemplary aspects, the graphical or numerical output comprises the average score (single score for protein expression, score of prediction of disease state, or combined score) for multiple controls. In exemplary aspects, the graphical or numerical output comprises the average score (single score for protein expression, score of prediction of disease state, or combined score) for subjects known to have a non-metastatic tumor or cancer, the average score for subjects known to not have a tumor or cancer, and the average score for subjects known to have metastatic cancer.

Also provided herein are computer-readable storage media having stored thereon machine-readable instructions executable by a processor. In exemplary embodiments, the instructions comprise:

(i) instructions for receiving a plurality of data values, each data value is a measured expression level of a different gene of a sample obtained from a synthetically-engineered pMN implanted in a test subject (ii) instructions for processing the plurality of data values though (a) a decomposition algorithm to obtain a single score for gene expression for the test subject, (b) a machine learning algorithm to obtain a score of prediction of disease state for the test subject, or (c) a combination of (a) and (b) to obtain a combined score for the test subject;

(iii) instructions for plotting the single score for gene expression for the test subject, the score of prediction of disease state for the test subject, or the combined score for the test subject on a graphical or numerical output, wherein the graphical or numerical output comprises an average single score for gene expression for a control, an average score of prediction of disease state for a control, or an average combined score for a control.

In alternative or additional embodiments, the instructions comprise:

(i) instructions for receiving a plurality of data values, each data value is a measured expression level of a different RNA of a sample obtained from a synthetically-engineered pMN implanted in a test subject (ii) instructions for processing the plurality of data values though (a) a decomposition algorithm to obtain a single score for RNA expression for the test subject, (b) a machine learning algorithm to obtain a score of prediction of disease state for the test subject, or (c) a combination of (a) and (b) to obtain a combined score for the test subject;

(iii) instructions for plotting the single score for RNA expression for the test subject, the score of prediction of disease state for the test subject, or the combined score for the test subject on a graphical or numerical output, wherein the graphical or numerical output comprises an average single score for RNA expression for a control, an average score of prediction of disease state for a control, or an average combined score for a control.

In yet further alternative or additional embodiments, the instructions comprise:

(i) instructions for receiving a plurality of data values, each data value is a measured expression level of a different protein of a sample obtained from a synthetically-engineered pMN implanted in a test subject (ii) instructions for processing the plurality of data values though (a) a decomposition algorithm to obtain a single score for protein expression for the test subject, (b) a machine learning algorithm to obtain a score of prediction of disease state for the test subject, or (c) a combination of (a) and (b) to obtain a combined score for the test subject;

(iii) instructions for plotting the single score for protein expression for the test subject, the score of prediction of disease state for the test subject, or the combined score for the test subject on a graphical or numerical output, wherein the graphical or numerical output comprises an average single score for protein expression for a control, an average score of prediction of disease state for a control, or an average combined score for a control.

The controls may be as those described above.

Further provided herein are methods implemented by a processor in a computer. In exemplary embodiments, the method comprises the steps of:

(i) receiving a plurality of data values, each data value is a measured expression level of a different gene of a sample obtained from a synthetically-engineered pMN implanted in a test subject;

(ii) processing the plurality of data values though (a) a decomposition algorithm to obtain a single score for gene expression for the test subject, (b) a machine learning algorithm to obtain a score of prediction of disease state for the test subject, or (c) a combination of (a) and (b) to obtain a combined score for the test subject;

(iii) plotting the single score for gene expression for the test subject, the score of prediction of disease state for the test subject, or the combined score for the test subject on a graphical or numerical output, wherein the graphical or numerical output comprises an average single score for gene expression for a control, an average score of prediction of disease state for a control, or an average combined score for a control.

In alternative or exemplary embodiments, the method comprises the steps of:

(i) receiving a plurality of data values, each data value is a measured expression level of a different RNA of a sample obtained from a synthetically-engineered pMN implanted in a test subject;

(ii) processing the plurality of data values though (a) a decomposition algorithm to obtain a single score for RNA expression for the test subject, (b) a machine learning algorithm to obtain a score of prediction of disease state for the test subject, or (c) a combination of (a) and (b) to obtain a combined score for the test subject;

(iii) plotting the single score for RNA expression for the test subject, the score of prediction of disease state for the test subject, or the combined score for the test subject on a graphical or numerical output, wherein the graphical or numerical output comprises an average single score for RNA expression for a control, an average score of prediction of disease state for a control, or an average combined score for a control.

In yet further alternative or exemplary aspects, the method comprises the steps of:

(i) receiving a plurality of data values, each data value is a measured expression level of a different protein of a sample obtained from a synthetically-engineered pMN implanted in a test subject;

(ii) processing the plurality of data values though (a) a decomposition algorithm to obtain a single score for protein expression for the test subject, (b) a machine learning algorithm to obtain a score of prediction of disease state for the test subject, or (c) a combination of (a) and (b) to obtain a combined score for the test subject;

(iii) plotting the single score for protein expression for the test subject, the score of prediction of disease state for the test subject, or the combined score for the test subject on a graphical or numerical output, wherein the graphical or numerical output comprises an average single score for protein expression for a control, an average score of prediction of disease state for a control, or an average combined score for a control.

The controls may be as those described above.

Anti-Cancer Therapy and Treatments

Therapy and treatments for cancer, e.g., metastatic cancer, are known in the art. In exemplary aspects, the anti-cancer therapy or treatment comprises administration of one or more chemotherapeutic agents.

Chemotherapeutic agents are known in the art and include, but not limited to, platinum coordination compounds, topoisomerase inhibitors, antibiotics, antimitotic alkaloids and difluoronucleosides, as described in U.S. Pat. No. 6,630,124.

In some embodiments, the chemotherapeutic agent is a platinum coordination compound. The term "platinum coordination compound" refers to any tumor cell growth inhibiting platinum coordination compound that provides the platinum in the form of an ion. In some embodiments, cisplatin is the platinum coordination compound employed in the compositions and methods of the present disclosure. In some embodiments, the chemotherapeutic agent is a topoisomerase inhibitor. In some aspects, the topoisomerase inhibitor is camptothecin or a camptothecin analog. In still yet other embodiments of the present disclosure, the chemotherapeutic agent is an antibiotic compound. Suitable antibiotic include, but are not limited to, doxorubicin, mitomycin, bleomycin, daunorubicin and streptozocin. In some embodiments, the chemotherapeutic agent is an antimitotic alkaloid. In general, antimitotic alkaloids can be extracted from *Cantharanthus roseus*, and have been shown to be efficacious as anticancer chemotherapy agents. In other embodiments of the present disclosure, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity.

More than a dozen monoclonal antibodies are currently approved by the U.S. Food and Drug Administration to treat cancers. Among these agents are alemtuzumab (Campath®), which is indicated for chronic lymphocytic leukemia (CLL), and trastuzumab (Herceptin®), which is used for treating breast cancer. Some antibodies are labeled with chemotherapeutic drugs, including, for example, brentuximab vedotin (Adcetris®) and Ado-trastuzumab emtansine (Kadcyla®). Others are described in Guo et al., Clin Oncol Cancer Res (2011) 8: 215-219. Andrew Simpson and Otavia Caballero, BMC Proceedings Monoclonal antibodies for the therapy of cancer, October 2014, 8:06.

EXEMPLARY EMBODIMENTS

In exemplary embodiments, the present disclosure provides the following:

1. A method of determining a subject's metastatic potential, comprising measuring a level of expression of a gene, an RNA, or a protein, or a combination thereof, in a sample obtained from a synthetically-engineered pMN implanted in the subject, wherein the measured expression level of the gene, RNA, or protein in the sample is compared to a control level.
2. A method of detecting metastatic disease, or a predisposition thereto, in a subject in need thereof, comprising measuring a level of expression of a gene, an RNA or a protein, in a sample obtained from an engineered pre-metastatic niche (pMN) implanted in the subject, wherein the measured expression level of the gene, RNA or protein in the sample is compared to a control level.

3. The method of embodiment 1 or 2, comprising measuring the expression level of at least two genes, RNA, or proteins in the sample, wherein the measured expression levels are compared to control levels.
4. The method of embodiment 3, comprising measuring the expression level of a plurality of genes, RNA, or proteins in the sample, wherein the measured expression levels are compared to control levels.
5. The method of any one of embodiments 1 to 4, wherein the control level(s) of the gene(s), RNA, or protein(s) is/are level(s) of a subject known to have metastatic disease.
6. The method of any one of embodiments 1 to 4, wherein the control level(s) of the gene(s), RNA, or protein(s) is/are level(s) of a subject known to not have metastatic disease.
7. The method of any one of the preceding embodiments, wherein the synthetically-engineered pMN is a biomaterial implant as described in PCT/US17/12556 which published on Jul. 13, 2017, as WO 2017/120486 or in U.S. patent application Ser. No. 13/838,800, which published on Mar. 13, 2014, as U.S. Patent Publication No. 2014/0072510.
8. The method of any one of the preceding embodiments, wherein the measured levels of the genes, RNA, or proteins form a pMN expression signature and the expression signature is processed through a decomposition algorithm to obtain a single score for gene expression and/or a machine learning algorithm to obtain a score of prediction of disease state.
9. The method of embodiment 8, wherein the decomposition algorithm is a singular value decomposition.
10. The method of embodiment 8, wherein the machine learning algorithm is a random forest generation.
11. The method of any one of embodiments 8-10, wherein the expression signature is processed through a decomposition algorithm to obtain a single score for gene expression and a machine learning algorithm to obtain a score of prediction of disease state.
12. The method of embodiment 11, wherein the single score for gene expression and the score of prediction of disease state are combined to provide a combined score of metastatic potential.
13. The method of any one of the preceding embodiments, wherein the control levels of the genes, RNA, or proteins form a control pMN expression signature indicative of metastatic disease.
14. The method of embodiment 13, wherein the control pMN expression signature indicative of metastatic disease is processed through a decomposition algorithm to obtain a single score for gene expression and/or a machine learning algorithm to obtain a score of prediction of disease state.
15. The method of embodiment 14, wherein the decomposition algorithm is a singular value decomposition.
16. The method of embodiment 14, wherein the machine learning algorithm is a random forest generation.
17. The method of any one of embodiments 14-16, wherein the control pMN expression signature is processed through a decomposition algorithm to obtain a single control score for gene expression and a machine learning algorithm to obtain a control score of prediction of disease state.
18. The method of embodiment 17, wherein the single control score for gene expression and the control score of prediction of disease state are combined to provide a combined control score of metastatic potential.
19. The method of embodiment 18, wherein the combined score of metastatic potential is compared to the combined control score of metastatic potential to determine the subject's metastatic potential.
20. The method of any one of the preceding embodiments, wherein the gene is S100A8 gene or the S100A9 gene.
21. The method of embodiment 20, comprising measuring a level of expression of both the S100A8 gene and the S100A9 gene.
22. The method of any one of the preceding embodiments, comprising measuring a level of expression of one or more of the following genes: Ccl22, Cxcl2, Ccr7, Csf3, Bmp15, IL-23a, S100A9, Chi3l3, Pglryp1, S100A8, Ltf, Ela2, and Camp.
23. The method of any one of the preceding embodiments, comprising measuring a level of expression of the RNA or protein encoded by the S100A8 gene or the S100A9 gene or both.
24. The method of any one of the preceding embodiments, comprising measuring a level of expression of the RNA or protein encoded by one or more of the following genes: Ccl22, Cxcl2, Ccr7, Csf3, Bmp15, IL-23a, S100A9, Chi3l3, Pglryp1, S100A8, Ltf, Ela2, and Camp.
25. The method of any one of the preceding embodiments, comprising measuring a level of expression of one or more of Csf3, IL-1a, IL-12p70, IL-6, Cxcl5, IL-15, Cxcl10, Ccl2, Cxcl9, and Ccl5 at the gene, RNA and/or protein level.
26. A method of monitoring a subject's metastatic potential or metastatic disease, comprising measuring a level of expression of a gene, an RNA, or a protein, or a combination thereof, in a sample obtained from a synthetically-engineered pMN implanted in the subject at a first time point and measuring the expression level of the gene, RNA, or protein in a sample obtained from the synthetically-engineered pMN at a second time point, wherein the expression level measured at the first time point is compared to the expression level measured at the second time point.
27. The method of embodiment 26, comprising measuring the expression level of at least two genes, RNA, or proteins in the sample, wherein the measured expression levels are compared to control levels.
28. The method of embodiment 27, comprising measuring the expression level of a plurality of genes, RNA, or proteins in the sample, wherein the measured expression levels are compared to control levels.
29. The method of any one of embodiments 26 to 28, wherein the control level(s) of the gene(s), RNA, or protein(s) is/are level(s) of a subject known to have metastatic disease.
30. The method of any one of embodiments 26 to 28, wherein the control level(s) of the gene(s), RNA, or protein(s) is/are level(s) of a subject known to not have metastatic disease.
31. The method of any one of embodiments 26 to 30, wherein the synthetically-engineered pMN is a biomaterial implant as described in PCT/US17/12556 which published on Jul. 13, 2017, as WO 2017/120486 or in U.S. patent application Ser. No. 13/838,800, which published on Mar. 13, 2014, as U.S. Patent Publication No. 2014/0072510.

32. The method of any one of embodiments 26 to 31, wherein the measured levels of the genes, RNA, or proteins form a pMN expression signature and the expression signature is processed through a decomposition algorithm to obtain a single score for gene expression and/or a machine learning algorithm to obtain a score of prediction of disease state.
33. The method of embodiment 32, wherein the decomposition algorithm is a singular value decomposition.
34. The method of embodiment 32, wherein the machine learning algorithm is a random forest generation.
35. The method of any one of embodiments 32-34, wherein the expression signature is processed through a decomposition algorithm to obtain a single score for gene expression and a machine learning algorithm to obtain a score of prediction of disease state.
36. The method of embodiment 35, wherein the single score for gene expression and the score of prediction of disease state are combined to provide a combined score of metastatic potential.
37. The method of any one of embodiments 26 to 36, wherein the control levels of the genes, RNA, or proteins form a control pMN expression signature indicative of metastatic disease.
38. The method of embodiment 37, wherein the control pMN expression signature indicative of metastatic disease is processed through a decomposition algorithm to obtain a single score for gene expression and/or a machine learning algorithm to obtain a score of prediction of disease state.
39. The method of embodiment 38, wherein the decomposition algorithm is a singular value decomposition.
40. The method of embodiment 38, wherein the machine learning algorithm is a random forest generation.
41. The method of any one of embodiments 38-40, wherein the control pMN expression signature is processed through a decomposition algorithm to obtain a single control score for gene expression and a machine learning algorithm to obtain a control score of prediction of disease state.
42. The method of embodiment 41, wherein the single control score for gene expression and the control score of prediction of disease state are combined to provide a combined control score of metastatic potential.
43. The method of embodiment 42, wherein the combined score of metastatic potential is compared to the combined control score of metastatic potential to determine the subject's metastatic potential.
44. The method of any one of embodiments 26 to 43, wherein the gene is S100A8 gene or the S100A9 gene.
45. The method of embodiment 44, comprising measuring a level of expression of both the S100A8 gene and the S100A9 gene.
46. The method of any one of embodiments 26 to 45, comprising measuring a level of expression of one or more of the following genes: Ccl22, Cxcl2, Ccr7, Csf3, Bmp15, IL-23a, S100A9, Chi3l3, Pglryp1, S100A8, Ltf, Ela2, and Camp.
47. The method of any one of embodiments 26 to 46, comprising measuring a level of expression of the RNA or protein encoded by the S100A8 gene or the S100A9 gene or both.
48. The method of any one of embodiments 26 to 47, comprising measuring a level of expression of the RNA or protein encoded by one or more of the following genes: Ccl22, Cxcl2, Ccr7, Csf3, Bmp15, IL-23a, S100A9, Chi3l3, Pglryp1, S100A8, Ltf, Ela2, and Camp.
49. The method of any one of embodiments 26 to 48, comprising measuring a level of expression of one or more of Csf3, IL-1a, IL-12p70, IL-6, Cxcl5, IL-15, Cxcl10, Ccl2, Cxcl9, and Ccl5 at the gene, RNA and/or protein level.
50. The method of any one of embodiments 26 to 49, wherein the first time point occurs before a treatment and the second time point occurs after a treatment and the method determines the efficacy of a treatment for metastatic disease.
51. A method of determining a treatment's efficacy for treating a metastatic disease, comprising monitoring the metastatic disease in a subject at a first time point and a second time point according to any one of embodiments 26-50, wherein the first time point occurs before treatment and the second time point occurs after treatment.
52. The method of embodiment 51, wherein the treatment is surgical removal of a tumor, radiation therapy, or administration of a compound.
53. The method of embodiment 52, wherein the compound is a small molecule compound or a molecule comprising a peptide, polypeptide, protein, DNA, or RNA, or an analog thereof.
54. A method of determining treatment for a subject with a tumor or cancer, comprising determining a subject's metastatic potential according to any one of embodiments 1 to 25 or.
55. A method for determining a subject's need for metastatic disease therapy comprising determining a subject's metastatic potential according to any one of embodiments 1 to 25.
56. A method of treating metastatic disease or delaying the onset of metastatic disease, comprising determining a subject's need for metastatic disease therapy according to embodiment 55 and providing the metastatic disease therapy based on the subject's metastatic potential.
57. The method of any one of the preceding embodiments, wherein the sample obtained from a synthetically-engineered pMN implanted in the subject comprises immune cells, stromal cells, or a combination thereof.
58. The method of embodiment 57, wherein the sample obtained from the synthetically-engineered pMN substantially lacks tumor cells or cancer cells.
59. The method of any one of the preceding embodiments, wherein the synthetically-engineered pMN is implanted in a lung, liver, brain, bone, peritoneum, omental fat, muscle, or lymph node of the subject.
60. The method of any one of the preceding embodiments, comprising measuring different cell populations in the sample and/or measuring tumor cell populations in the sample, in addition to or instead of measuring a level of expression of a gene, an RNA or a protein, in a sample obtained from a synthetically-engineered pre-metastatic niche (pMN) implanted in the subject.
61. A system comprising: a processor; a memory device coupled to the processor, and machine readable instructions stored on the memory device. In exemplary embodiments, the machine readable instructions that, when executed by the processor, cause the processor to
(i) receive a plurality of data values, each data value is a measured expression level of a different gene of a sample obtained from a synthetically-engineered pMN implanted in a test subject;

(ii) process the plurality of data values though (a) a decomposition algorithm to obtain a single score for gene expression for the test subject, (b) a machine learning algorithm to obtain a score of prediction of disease state for the test subject, or (c) a combination of (a) and (b) to obtain a combined score for the test subject;

(iii) plot the single score for gene expression for the test subject, the score of prediction of disease state for the test subject, or the combined score for the test subject on a graphical or numerical output, wherein the graphical or numerical output comprises an average single score for gene expression for a control, an average score of prediction of disease state for a control, or an average combined score for a control.

62. The system of embodiment 61, wherein the control is a population of subjects known to not have a tumor or cancer, a population of subjects known to have a non-metastatic tumor or cancer, or a population of subjects known to have metastatic cancer.

63. The method embodiment 62, wherein the graphical or numerical output comprises the average score (single score for gene expression, score of prediction of disease state, or combined score) for multiple controls.

64. The method of embodiment 63, wherein the graphical or numerical output comprises the average score (single score for gene expression, score of prediction of disease state, or combined score) for subjects known to have a non-metastatic tumor or cancer, the average score for subjects known to not have a tumor or cancer, and the average score for subjects known to have metastatic cancer.

65. A system comprising machine readable instructions that, when executed by the processor, cause the processor to:

(i) receive a plurality of data values, each data value is a measured expression level of a different RNA of a sample obtained from a synthetically-engineered pMN implanted in a test subject;

(ii) process the plurality of data values though (a) a decomposition algorithm to obtain a single score for RNA expression for the test subject, (b) a machine learning algorithm to obtain a score of prediction of disease state for the test subject, or (c) a combination of (a) and (b) to obtain a combined score for the test subject;

(iii) plot the single score for RNA expression for the test subject, the score of prediction of disease state for the test subject, or the combined score for the test subject on a graphical or numerical output, wherein the graphical or numerical output comprises an average single score for RNA expression for a control, an average score of prediction of disease state for a control, or an average combined score for a control.

66. The system of embodiment 65, wherein the control is a population of subjects known to not have a tumor or cancer, a population of subjects known to have a non-metastatic tumor or cancer, or a population of subjects known to have metastatic cancer.

67. The method embodiment 66, wherein the graphical or numerical output comprises the average score (single score for RNA expression, score of prediction of disease state, or combined score) for multiple controls.

68. The method of embodiment 67, wherein the graphical or numerical output comprises the average score (single score for RNA expression, score of prediction of disease state, or combined score) for subjects known to have a non-metastatic tumor or cancer, the average score for subjects known to not have a tumor or cancer, and the average score for subjects known to have metastatic cancer.

69. A system comprising machine readable instructions that, when executed by the processor, cause the processor to:

(i) receive a plurality of data values, each data value is a measured expression level of a different protein of a sample obtained from a synthetically-engineered pMN implanted in a test subject;

(ii) process the plurality of data values though (a) a decomposition algorithm to obtain a single score for protein expression for the test subject, (b) a machine learning algorithm to obtain a score of prediction of disease state for the test subject, or (c) a combination of (a) and (b) to obtain a combined score for the test subject;

(iii) plot the single score for protein expression for the test subject, the score of prediction of disease state for the test subject, or the combined score for the test subject on a graphical or numerical output, wherein the graphical or numerical output comprises an average single score for protein expression for a control, an average score of prediction of disease state for a control, or an average combined score for a control.

70. The system of embodiment 69, wherein the control is a population of subjects known to not have a tumor or cancer, a population of subjects known to have a non-metastatic tumor or cancer, or a population of subjects known to have metastatic cancer.

71. The method embodiment 70, wherein the graphical or numerical output comprises the average score (single score for protein expression, score of prediction of disease state, or combined score) for multiple controls.

72. The method of embodiment 71, wherein the graphical or numerical output comprises the average score (single score for protein expression, score of prediction of disease state, or combined score) for subjects known to have a non-metastatic tumor or cancer, the average score for subjects known to not have a tumor or cancer, and the average score for subjects known to have metastatic cancer.

73. A computer-readable storage media having stored thereon machine-readable instructions executable by a processor, wherein the instructions comprise:

(i) instructions for receiving a plurality of data values, each data value is a measured expression level of a different gene of a sample obtained from a synthetically-engineered pMN implanted in a test subject (ii) instructions for processing the plurality of data values though (a) a decomposition algorithm to obtain a single score for gene expression for the test subject, (b) a machine learning algorithm to obtain a score of prediction of disease state for the test subject, or (c) a combination of (a) and (b) to obtain a combined score for the test subject;

(iii) instructions for plotting the single score for gene expression for the test subject, the score of prediction of disease state for the test subject, or the combined score for the test subject on a graphical or numerical output, wherein the graphical or numerical output comprises an average single score for gene expression for a control, an average score of prediction of disease state for a control, or an average combined score for a control.

74. A computer-readable storage media having stored thereon machine-readable instructions executable by a processor, wherein the instructions comprise:
   (i) instructions for receiving a plurality of data values, each data value is a measured expression level of a different RNA of a sample obtained from a synthetically-engineered pMN implanted in a test subject
   (ii) instructions for processing the plurality of data values though (a) a decomposition algorithm to obtain a single score for RNA expression for the test subject, (b) a machine learning algorithm to obtain a score of prediction of disease state for the test subject, or (c) a combination of (a) and (b) to obtain a combined score for the test subject;
   (iii) instructions for plotting the single score for RNA expression for the test subject, the score of prediction of disease state for the test subject, or the combined score for the test subject on a graphical or numerical output, wherein the graphical or numerical output comprises an average single score for RNA expression for a control, an average score of prediction of disease state for a control, or an average combined score for a control.

75. A computer-readable storage media having stored thereon machine-readable instructions executable by a processor, wherein the instructions comprise:
   (i) instructions for receiving a plurality of data values, each data value is a measured expression level of a different protein of a sample obtained from a synthetically-engineered pMN implanted in a test subject
   (ii) instructions for processing the plurality of data values though (a) a decomposition algorithm to obtain a single score for protein expression for the test subject, (b) a machine learning algorithm to obtain a score of prediction of disease state for the test subject, or (c) a combination of (a) and (b) to obtain a combined score for the test subject;
   (iii) instructions for plotting the single score for protein expression for the test subject, the score of prediction of disease state for the test subject, or the combined score for the test subject on a graphical or numerical output, wherein the graphical or numerical output comprises an average single score for protein expression for a control, an average score of prediction of disease state for a control, or an average combined score for a control.

76. A method implemented by a processor in a computer, the method comprising the steps of:
   (i) receiving a plurality of data values, each data value is a measured expression level of a different gene of a sample obtained from a synthetically-engineered pMN implanted in a test subject;
   (ii) processing the plurality of data values though (a) a decomposition algorithm to obtain a single score for gene expression for the test subject, (b) a machine learning algorithm to obtain a score of prediction of disease state for the test subject, or (c) a combination of (a) and (b) to obtain a combined score for the test subject;
   (iii) plotting the single score for gene expression for the test subject, the score of prediction of disease state for the test subject, or the combined score for the test subject on a graphical or numerical output, wherein the graphical or numerical output comprises an average single score for gene expression for a control, an average score of prediction of disease state for a control, or an average combined score for a control.

77. A method implemented by a processor in a computer, the method comprising the steps of:
   (i) receiving a plurality of data values, each data value is a measured expression level of a different RNA of a sample obtained from a synthetically-engineered pMN implanted in a test subject;
   (ii) processing the plurality of data values though (a) a decomposition algorithm to obtain a single score for RNA expression for the test subject, (b) a machine learning algorithm to obtain a score of prediction of disease state for the test subject, or (c) a combination of (a) and (b) to obtain a combined score for the test subject;
   (iii) plotting the single score for RNA expression for the test subject, the score of prediction of disease state for the test subject, or the combined score for the test subject on a graphical or numerical output, wherein the graphical or numerical output comprises an average single score for RNA expression for a control, an average score of prediction of disease state for a control, or an average combined score for a control.

78. A method implemented by a processor in a computer, the method comprising the steps of:
   (i) receiving a plurality of data values, each data value is a measured expression level of a different protein of a sample obtained from a synthetically-engineered pMN implanted in a test subject;
   (ii) processing the plurality of data values though (a) a decomposition algorithm to obtain a single score for protein expression for the test subject, (b) a machine learning algorithm to obtain a score of prediction of disease state for the test subject, or (c) a combination of (a) and (b) to obtain a combined score for the test subject;
   (iii) plotting the single score for protein expression for the test subject, the score of prediction of disease state for the test subject, or the combined score for the test subject on a graphical or numerical output, wherein the graphical or numerical output comprises an average single score for protein expression for a control, an average score of prediction of disease state for a control, or an average combined score for a control.

In exemplary embodiments, the present disclosure provides a method of determining a subject's metastatic potential, determining a tumor's or cancer's metastatic stage, or detecting metastatic disease, or a predisposition thereto, in a subject in need thereof, comprising measuring a level of expression of a gene, an RNA or a protein, in a sample obtained from an engineered pre-metastatic niche (pMN) implanted in the subject, wherein the measured expression level of the gene, RNA or protein in the sample is compared to a control level. In exemplary aspects, the method comprises measuring the expression level of at least two genes, RNA, or proteins in the sample, optionally, comprising measuring the expression level of a plurality of genes, RNA, or proteins in the sample, wherein the measured expression levels are compared to control levels. In certain instances, the control levels of the genes, RNA, or proteins form a control pMN expression signature indicative of no metastatic disease. In various aspects, the control pMN expression signature indicative of no metastatic disease is processed through a decomposition algorithm (e.g., a singular value decomposition) to obtain a single score for gene expression and/or a machine learning algorithm (e.g., a random forest generation) to obtain a score of prediction of disease state. In various instances, the control pMN expression signature is processed through a decomposition algorithm to obtain a single control score for gene expression and a machine learning algorithm to obtain a control score of prediction of disease state, and, optionally, the single control score for gene expression and the control score of prediction of disease state are combined to provide a combined control score of no metastatic disease. In various aspects, the combined score of metastatic potential is compared to the combined control score of no metastatic disease to determine the subject's metastatic potential. In various aspects, when the combined score of metastatic potential is low, relative to the combined control score, the subject's metastatic potential is low and/or the subject is deemed healthy, when the combined score of metastatic potential is intermediate, relative to the combined control score, the subject's metastatic potential indicates an early stage of metastatic disease, and when the combined score of metastatic potential is high, relative to the combined control score, the subject's metastatic potential indicates metastatic disease. The presently disclosed method of determining a subject's metastatic potential, determining a tumor's or cancer's metastatic stage, or detecting metastatic disease, or a predisposition thereto, in a subject in need thereof, enables the determination of the appropriate treatment for a subject with a tumor or cancer and/or the determination of a subject's need for metastatic disease therapy. Accordingly, the present disclosure provides methods of determining treatment for a subject with a tumor or cancer and/or determining a subject's need for metastatic disease therapy, comprising determining a subject's metastatic potential, determining a tumor's or cancer's metastatic stage, or detecting metastatic disease, or a predisposition thereto, as described herein. In various aspects, when the combined score of metastatic potential is intermediate, relative to the combined control score, the subject's metastatic potential indicates an early stage of metastatic disease, and the subject is determined as needing a therapy that targets the immune cells at the metastatic niche, such as phosphodiesterase 5 (PDE-5) or COX-2 inhibitors that inhibit the functionality of myeloid derived suppressor cells.

The present disclosure further provides methods of treating metastatic disease or delaying the onset of metastatic disease, comprising determining a subject's need for metastatic disease therapy, as described herein, and providing the metastatic disease therapy based on the subject's metastatic potential. In various aspects, the present disclosure provides a method of treating a subject, comprising administering to the subject an anti-metastatic disease treatment, optionally, wherein the anti-metastatic disease treatment comprises a PARP inhibitor or Gemcitabine, when the subject exhibits a high combined score of metastatic potential, relative to the combined control score, or administering to the subject a therapy that targets the immune cells at the metastatic niche, such as phosphodiesterase 5 (PDE-5) or COX-2 inhibitors that inhibit the functionality of myeloid derived suppressor cells, when the subject exhibits an intermediate combined score of metastatic potential, relative to the combined control score.

The following examples are given merely to illustrate the present invention and not in any way to limit its scope.

EXAMPLES

Example 1

The following example demonstrates that gene expression profiles of cells caught in synthetic engineered pre-metastatic niche (pMN) scaffolds change over time after tumorigenesis and that the gene expression profiles of tumor-bearing animals differ from those of tumor-free animals.

Figure 4:
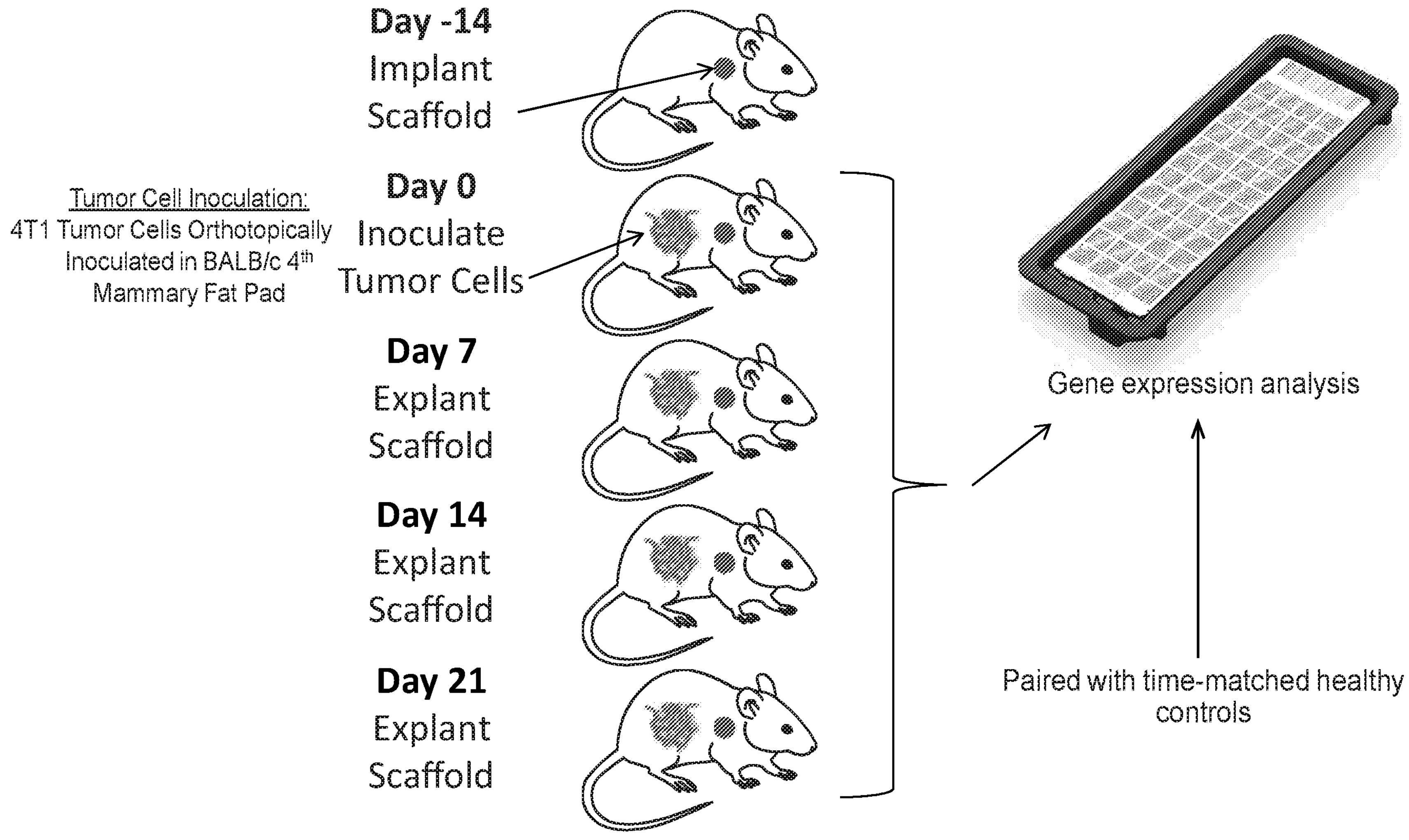
FIG. 4 is an outline of an experiment involving mice having an implanted scaffold and later inoculated with tumor cells. Gene expression of scaffold samples is analyzed at different time points after tumorigenesis.

A polymer scaffold comprising polycaprolactone (PCL) was implanted into the subcutaneous space of two groups of BALB/c mice. Fourteen days after scaffold implantation, 4T1 tumor cells (2E6 cells suspended in 50 μL of PBS) were orthotopically inoculated into the $4^{th}$ mammary fat pad of one group of mice. In the other group of mice, PCL scaffolds were implanted in the healthy mice but no inoculation was performed. This healthy, or control cohort, simulates the acquisition of an average gene expression from healthy patients. At Days 7, 14, and 21 following tumor cell inoculation, an explant was taken from the scaffold of each animal (of both the tumor-bearing and healthy control cohort) either through surgical resection or via use of a core needle biopsy. FIG. 4 shows an experimental outline of the above described steps.

To derive genomic content from the implanted scaffold, the explanted cells and polymer scaffold were homogenized with a mechanical dispersing instrument in Trizol reagent. RNA isolation was carried out via centrifugation filter kits that include a DNA enzymatic degradation. Quality and quantity of the RNA was assessed via a Bioanalyzer 2100 and Nanodrop 2000c, respectively. RNA was synthesized into cDNA via reverse transcription, following suggested preparation protocols for high-throughput qRT-PCR using OpenArray panels.

High-throughput qRT-PCR was carried out using a TaqMan® OpenArray® Mouse Inflammation Panel on a QuantStudio® 12K Flex. The OpenArray panel analyzes the expression of 635 genes that are associated with immunological pathways. Instrument parameters and quality control was managed by the University of Michigan DNA Sequencing Core. Additionally, single tube qRT-PCR was carried out on a subset of genes (determined from the OpenArray results) using Taqman probes to validate the results found using the high-throughput results as well as expand our tests. Gene expressions were normalized to a combination of 5 different housekeeping genes as determined by a house gene stability analysis of the 16 housekeeping genes included in the OpenArray panel.

Gene expression data were processed to generate a variety of graphical outputs. A volcano plot (a compilation of log-transform fold changes (x-axis) and log-transformed p-values (y-axis)) was generated to compare tumor-bearing cohorts and time-matched healthy controls. As shown in FIG. 5, the volcano plot illustrated the magnitude and significance of gene changes associated with metastatic conditioning by the primary tumor. From this plot, the dynamic nature of gene expression was evident.

Figure 6:
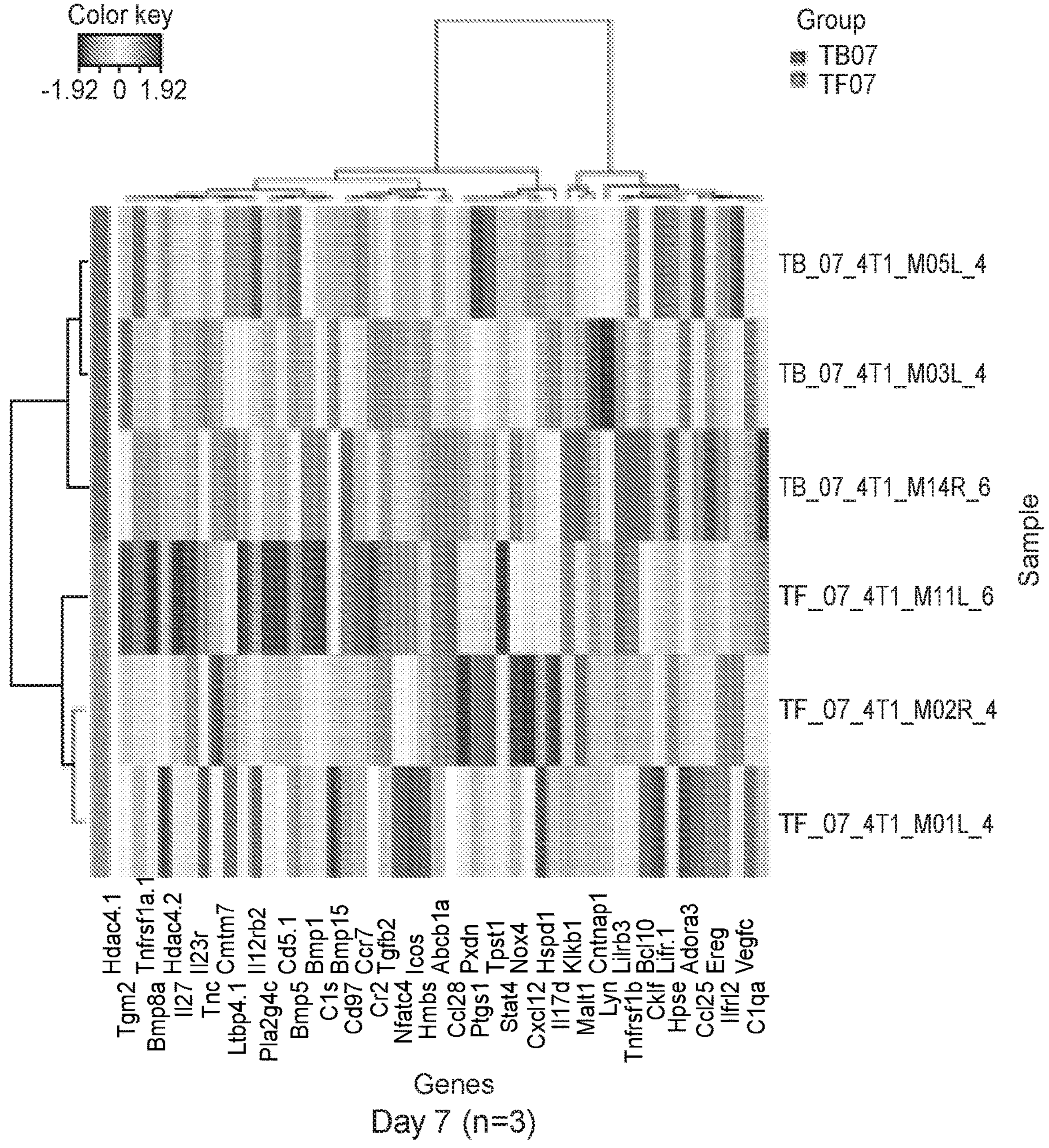
FIG. 6 is a pair of exemplary heat maps demonstrating PLS-DA classification and clustering base on scaffold gene expression in tumor-bearing (TB) or tumor-free (TF) mice 7 or 21 days post tumor inoculation.

Heatmaps generated through partial least squares discriminate analysis (PLS-DA), a supervised discriminate analysis algorithm, aided in the selection of features of most importance. Additionally, it clustered the samples based on selected features and conveyed the strength of relationships between different samples. Exemplary heat maps from explants obtained on Day 7 and Day 21 are shown in FIG. 6

Figure 7:
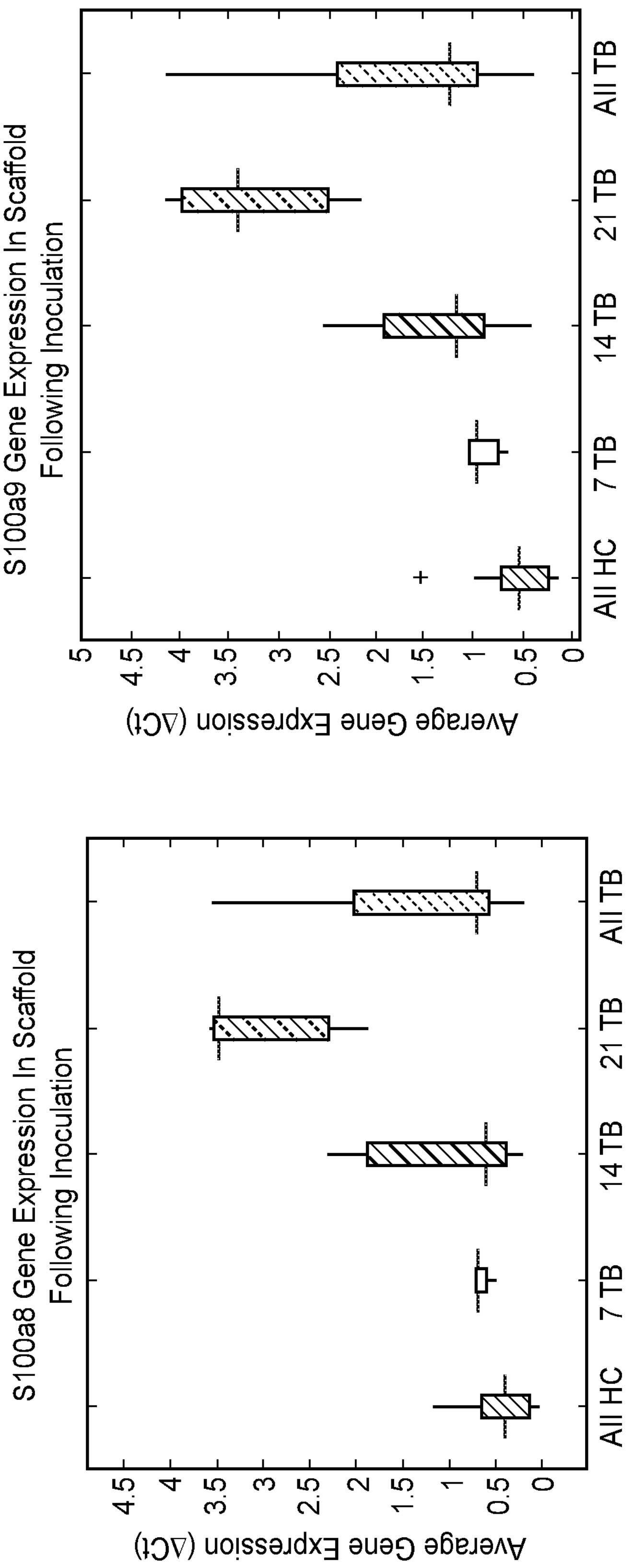
FIG. 7 is a pair of box plots demonstrating the change in average gene expression in tumor-bearing (TB) mice over time post tumor inoculation.

Box plots illustrated the progression of changes in the gene expression level of particular genes during metastatic conditioning. S100a8 and S100a9 have been indicated as fundamental to conditioning of the pMN and a microenvironment cytotoxic to T cells. The expression level of these two genes progressively changed between days 7, 14, and 21 (FIG. 7) during onset of metastatic disease. All healthy controls are grouped in the first column, time-point specific expression is indicated in columns 2-4 for days 7-14-21, all tumor-bearing controls are grouped in the last column.

Figure 8:
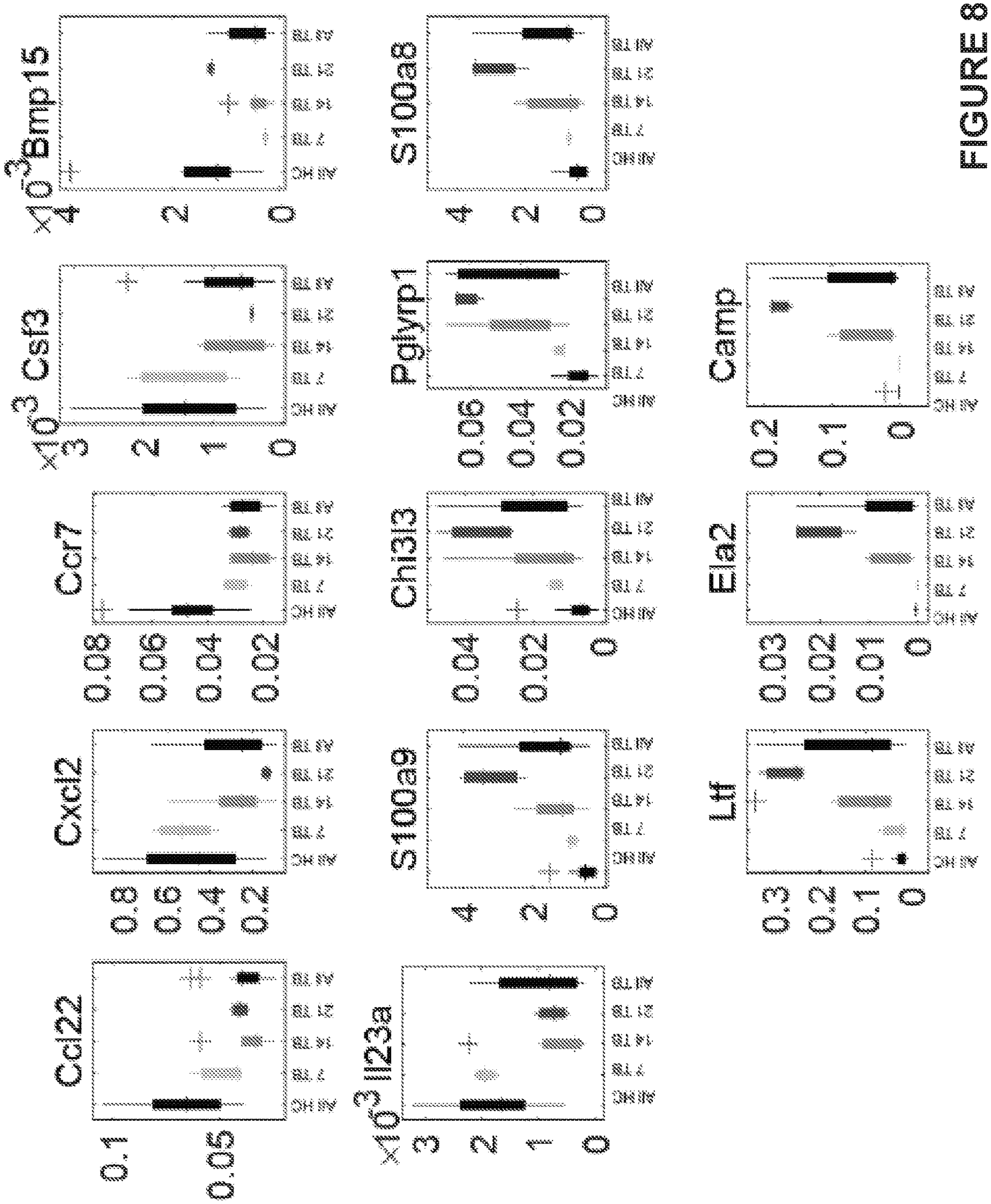
FIG. 8 is a set of box plots demonstrating the changes in average gene expression in tumor-bearing (TB) mice over time post tumor inoculation.

Similar to S100a8/a9, several other genes showed progressive alterations (increasing or decreasing) in expression over time as compared to time-matched healthy controls, with several of the upregulated being related to MDSC phenotype. These alterations are exemplified by the box plots shown in FIG. 8.

Example 2

This example demonstrates an exemplary method of processing of gene expression profiles from cells in the synthetic pMN into a single diagnostic metric.

Figure 9:
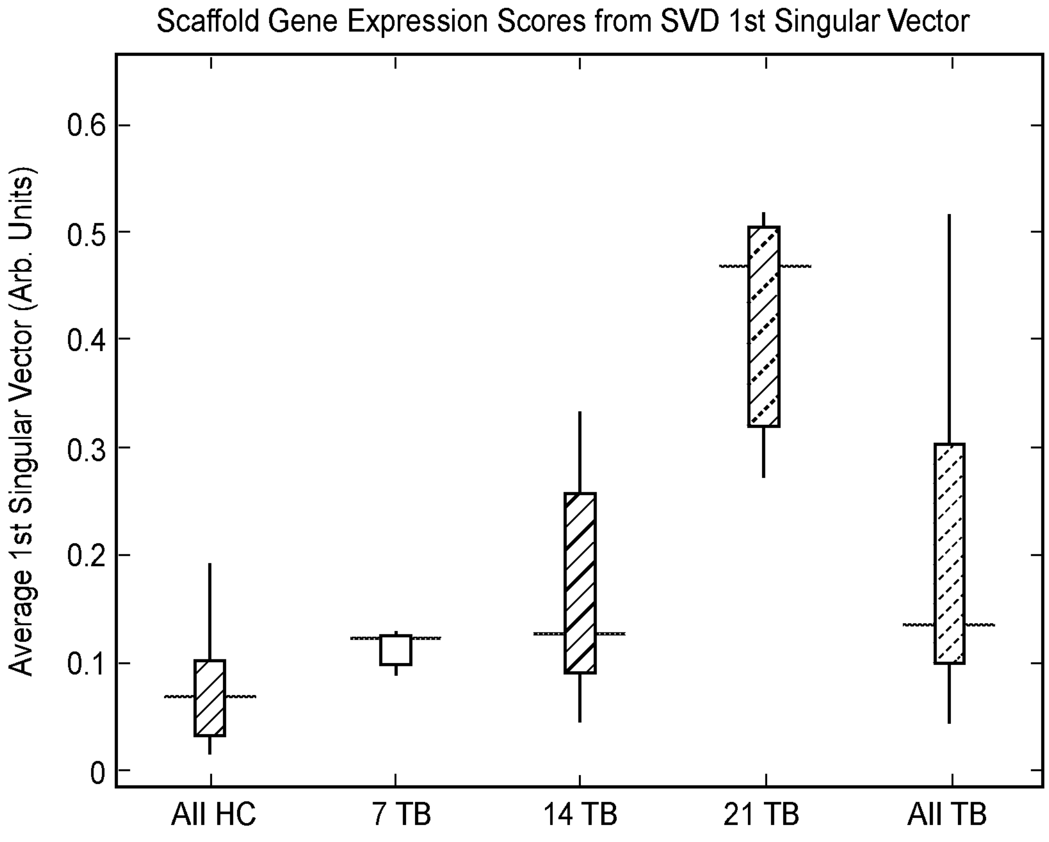
FIG. 9 is a box plot of gene expression scores from SVD 1$^{st}$ singular vector.

Following isolation of RNA and analysis of gene expression (as outlined in example 1), a multitude of alterations in the gene expression were combined into a single diagnostic metric through multiple dimensionality reduction and machine learning techniques. Results of these techniques are detailed below:

First, a method for reducing dimensionality of the data is the use of singular value decomposition (SVD) and extraction of the first left singular vector (an eigenvector) which provides a metric of the cumulative gene expression for each sample. This method serves to provide an unsupervised score for diagnosis of metastatic potential. The output of the SVD provides a score for each sample, when normalized the magnitude of the scores that were lowest are more closely associated with healthy mice on average, and the scores that are highest are more closely associated with tumor-bearing mice, with a progressive increase in score between days 7, 14, and 21. For illustration the averages for each cohort are shown in a box plot. FIG. 9. Thus, from this single metric, one could infer metastatic potential. Other methods that fill this role of dimensionality reduction for developing a pMN signature includes linear combination of select factors, dynamic mode decomposition (DMD), principle component analysis (PCA), or Fisher's linear discriminate.

Figure 10:
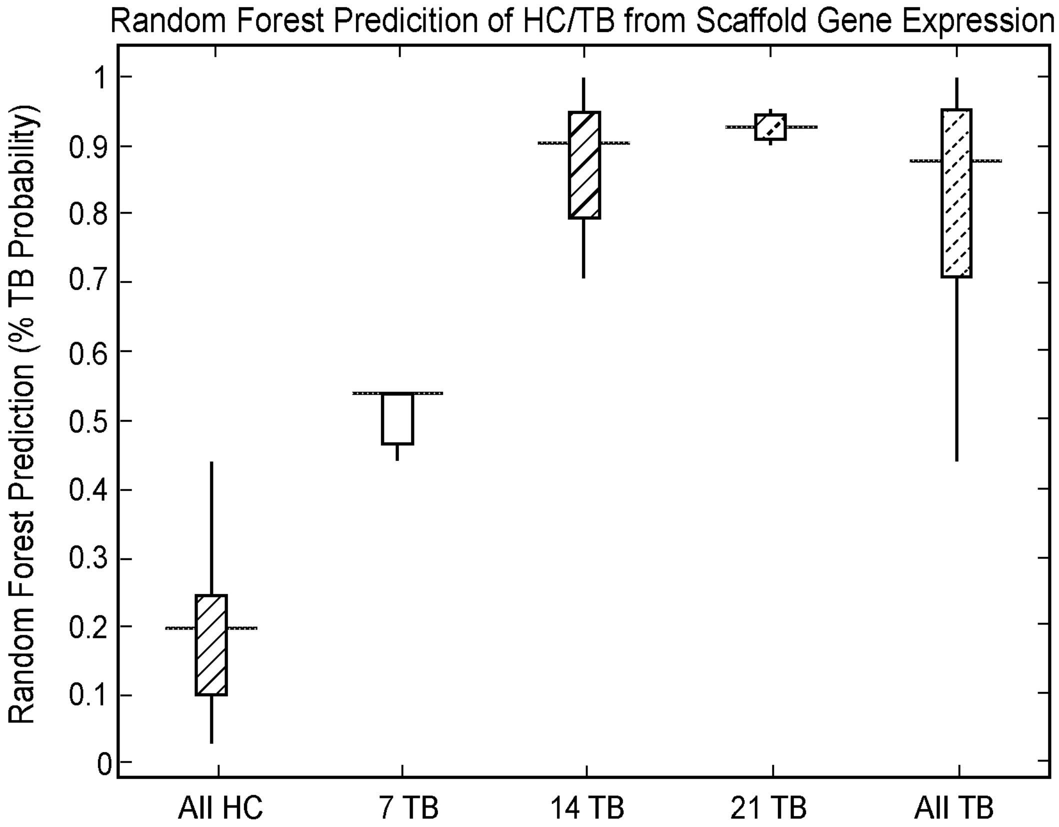
FIG. 10 is a box plot of random forest prediction of Healthy Control animals (HC) or tumor-bearing (TB) mice.

Second, a supervised, machine learning method for providing a prediction of metastatic potential (i.e. low or high likelihood that distal sites are primed for metastatic colonization) is the generation of random forest (RF) ensembles. This method aggregates a series of decision trees to provide a classification prediction. Probability of this prediction can be determined through cross validation. The output of the RF provides a probability for each sample, with the probabilities below 50% being predicted to be healthy mice on average, and the probabilities that are above 50% being more closely associated with tumor-bearing mice, with a progressive increase in probabilities between days 7, 14, and 21. For illustration the averages for each cohort are shown in a box plot. FIG. 10. Thus, from this single metric, one could infer metastatic potential. Logistic regression, partial least squares discriminate analysis, discriminate analysis (linear or quadratic), neural networks pattern recognition, support vector machines, nearest neighbor, and Bayesian networks.

Last, multiple metrics can be combined into either a numerical or visual output to convey a multivariate signature of the metastatic potential. In the FIG. 11, each sample from a healthy or tumor bearing mouse is plotted in the x-y plane. The x-axis correlates with SVD score and the y-axis correlates with the RF prediction. Average and first standard deviation of the SVD score and RF prediction for each cohort (all healthy control, days 7, 14, and 21 tumor bearing) are indicated by the larger faded ellipsoids in the background of the x-y plane. One can infer from the plot the clustering of the healthy cohorts, as well as the progressive increase in the multivariate signature of the tumor-bearing cohorts. It could additionally be inferred that any sample with a score/prediction outside of the healthy cohort average and standard deviation may warrant concern. Note that in general there is good agreement between the two metrics as there are no high scores with a low prediction, and few low scores with a high prediction. This demonstrates the benefit of combining multiple analytical approaches into a coherent output for diagnosis.

Example 3

This example demonstrates that the scaffold gene expression profiles and multivariate signature of cells caught in synthetic engineered pMN scaffolds change over time after treatment (surgical tumor resection) and that the gene expression profiles and multivariate signature of treated animals who remain healthy, differ from those who succumb to metastatic recurrence.

In the example, mice were implanted with scaffolds (as in Example 1), and a cohort of animals was inoculated with tumor cells (as in Example 1). One addition was that a series of 8 scaffolds were implanted into the subcutaneous space, which allow for more biopsies per mouse and thus enable the ability to longitudinally track each animal. While this presents a deviation from or previous approaches, it not expected to dramatically alter the diagnostic potential of the synthetic pMN.

At Day 14 (following tumor inoculation, as aligned with day 14 in Example 2), a single scaffold was explanted from each mouse. These scaffolds were processed for qRT-PCR, genes of interest were analyzed, and based on the algorithms in Example 2 they were assigned a score and prediction. The scaffold from a healthy mouse at Day 14 was located within the average and standard deviation for the healthy control multivariate signature (SVD-RF combination). The scaffolds from tumor-bearing mice were located within the average and standard deviation for the Day 14 tumor-bearing. Immediately following biopsy of the scaffolds, the tumors were resected from the tumor-bearing mice and the healthy mice was given a sham mammary fat pad resection to account for any surgically inducted alterations.

At Day 21, another scaffold was explanted from the same mice and similarly processed for gene expression and multivariate signature. The signature following resection of the primary tumor decreases in both score and prediction. Without the surgical resection it would have been expected to increase, and demonstrated in Example 2. For the healthy control that received a sham surgical resection there was very little change in the signature, and it was still located within the average and standard deviation for healthy.

At Day 28, another scaffold was explanted from the same mice and similarly processed from gene expression and multivariate signature. For one of the mice that originally had a tumor, the trend towards the healthy cohort continued. This mouse remained healthy and did not exhibit signs of metastatic disease. However, one of the mice showed a dramatic increase in the SVD score and the magnitude, or trajectory of its signature shift away from the healthy cohort. This mouse developed symptoms of metastatic disease and died at Day 34 due to lung and plural metastases. For the healthy control that received a sham surgical resection there was very little change in the signature, and it was still located within the average and standard deviation for healthy.

By plotting the results of each sample in the multivariate signature subspace, one can infer from the plots comparing SVD and RF the trajectory of metastatic potential for each mouse. For the healthy mouse (M1) there was little change in trajectory. For the mouse that underwent therapeutic resection of the primary tumor and remained healthy (M2), there was maintained decrease in the trajectory of its metastatic signature. For the mouse that underwent therapeutic resection of the primary tumor and then subsequently died due to metastatic disease (M3), there was an initial decrease in the trajectory of the metastatic potential, however, this trajectory was alter away from healthy. FIG. 12

Figure 13:
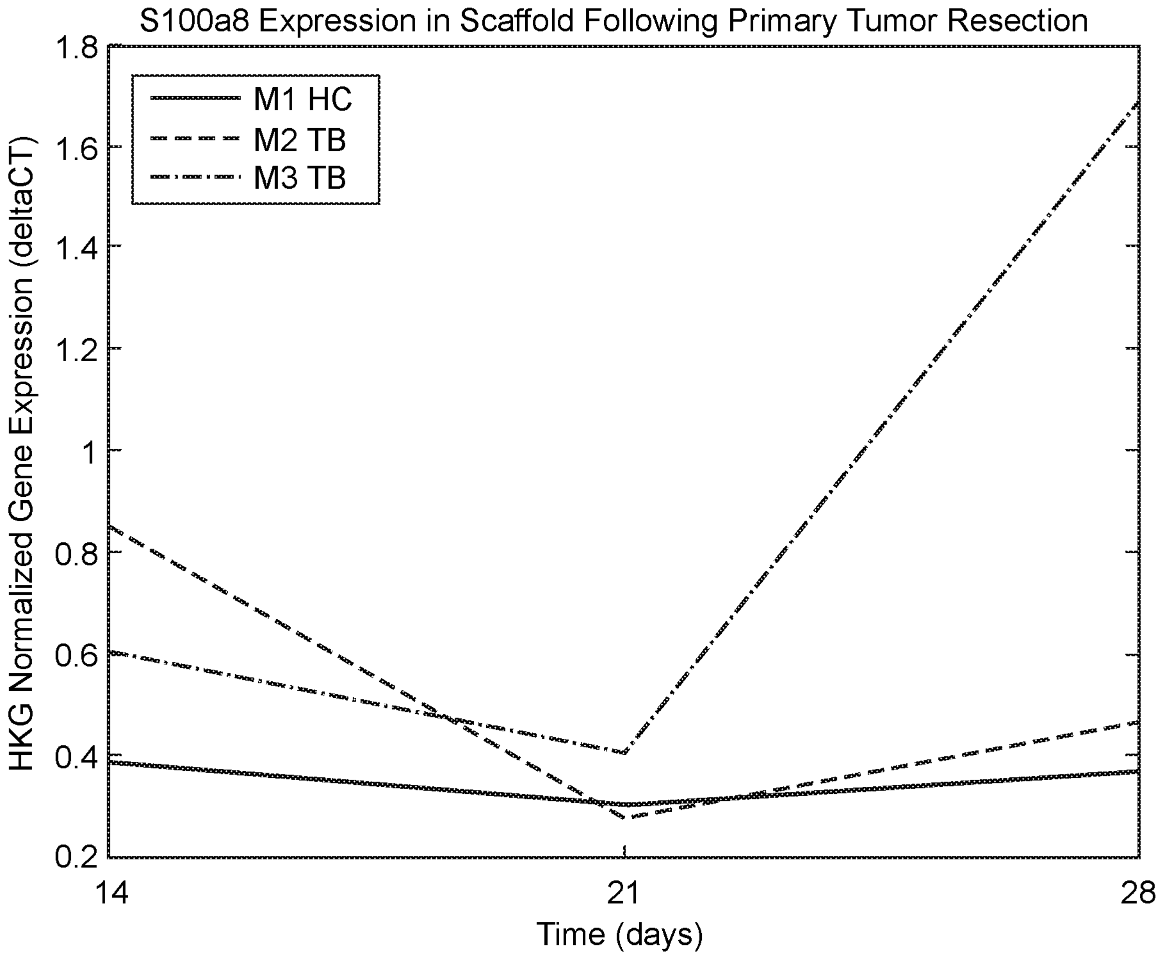
FIG. 13 is a graph of normalized S100A8 gene expression as a function of time.

Analysis of individual gene expressions following resection of the primary tumor showed a divergence between the mouse that remained healthy and the mouse that developed metastatic disease. For example, analysis of S100a8 shows that a healthy mouse (M1) has little change in its gene expression over time. Conversely, S100a8 goes down in both tumor-bearing mice (M2 and M3) following tumor resection. M2 remains similar to the healthy control at Day 28, and indeed this mouse did not develop symptoms of metastatic disease. Expression of S100a8 in M3 deviates from both M1 and M2 at day 28, which preceded the symptomatic onset of metastatic disease at Day 34. FIG. 13.

Example 4

This example demonstrates that the cytokine and chemokine expression profiles of immune cells caught in synthetic engineered pMN scaffolds change over time after tumorigenesis and that the cytokine and chemokine expression profiles of tumor-bearing animals differ from those of healthy, non-tumor-bearing animals.

Figure 14:
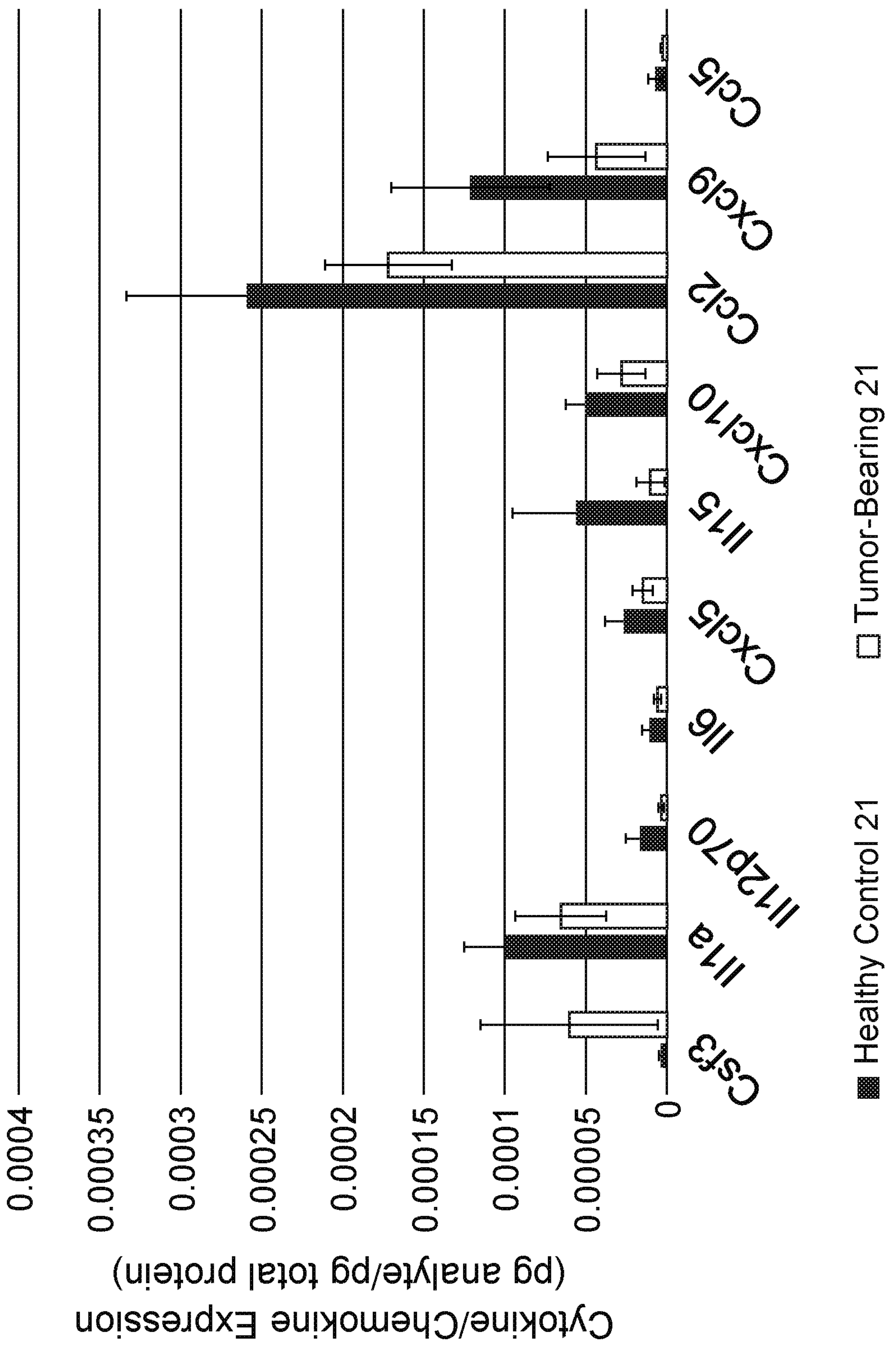
FIG. 14 is a graph of cytokine/chemokine expression for Healthy control animals and tumor-bearing animals.

Another potential input into the synthetic pMN multivariate signature is protein expression. Of interest are cytokines and chemokines that may direct cell-cell signaling. To determine how the expression changes in tumor-bearing mice, compared to healthy mice we implanted PCL scaffold and inoculated tumor cells (As in Example 1). Then at Day 21 we isolated proteins from the scaffolds of tumor-bearing and healthy mice by homogenizing in PBS. Homogenized solutions were then sequentially centrifuged and filtered to remove debris. To analyze the cytokine expression levels, we employed a bead-based multiplexed analysis (Mouse Cytokine/Chemokine Magnetic Bead Panel 32-plex) with analyzes 32 analytes per sample. Expression quantification was normalized to total protein concentration attained from a BCA assay. Several of the cytokines/chemokines showed a decrease in expression, which one (G-CSF) showed a dramatic upregulation in expression. FIG. 14

Figure 15:
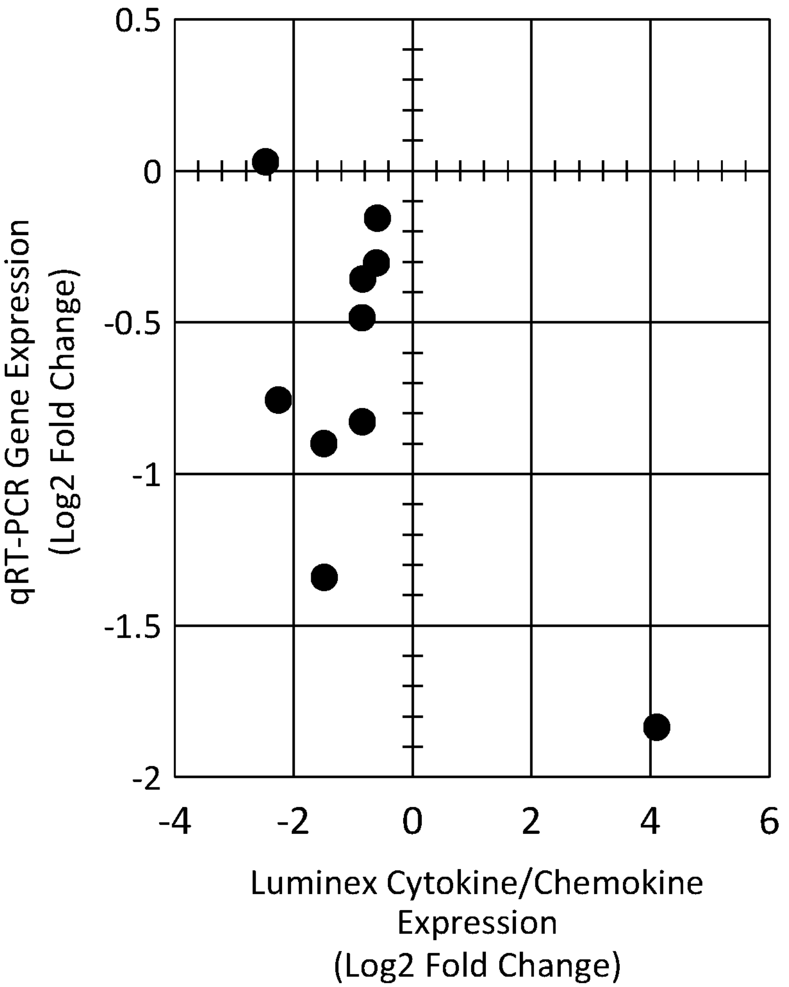
FIG. 15 is a graph of gene expression change relative to protein expression.

The drawing shows that many of the proteins that showed a decrease in expression also show a decrease in gene expression at Day 21 (as determined in Example 1). FIG. 15

Example 5

This example demonstrates that synthetic diagnostic sites reflect disease progression and predict therapeutic response.

Engineering tissues in vivo that signal the status of host biology can extend regenerative medicine beyond the classical concepts of replacing lost or damaged tissues, towards creating engineered sites that serve as diagnostics. In metastatic breast cancer, the tissues to signify are those distal to the primary tumor that are in solid organs and recruit metastatic cells based on aberrant inflammatory processes.[1-4] Herein, it is demonstrated that the aberrant inflammatory processes of metastasis are captured in the chronic foreign body response mounted against biomaterial implants. The data herein show that the inflammation within the microporous polymer implants is progressively altered by disease, with inflammation analogous to that in diseased lung. Following therapy, longitudinal tracking of implants in individual mice differentiated resistance versus response to therapy. These results demonstrate the potential for implanted materials to detect context-specific pathological states that can be used for early detection of disease or therapeutic monitoring.

The concept of engineering a synthetic diagnostic site (SynDx) is predicated on generating a tissue that integrates with the host, whose properties will be modified based on the development of disease.[5,6] Following implantation, a porous scaffold supports cell infiltration, vascularization, and a persistent inflammation as a consequence of the foreign body response (FBR)[7]. Herein, the inflammatory dynamics following the onset of disease are investigated as means to engineer a SynDx. It is hypothesized that the persistent inflammatory response at an implanted microporous polymer scaffold would acquire immunosuppressive trademarks in the context of metastatic cancer, thus mimicking those in disease-targeted organs.

Figure 22:
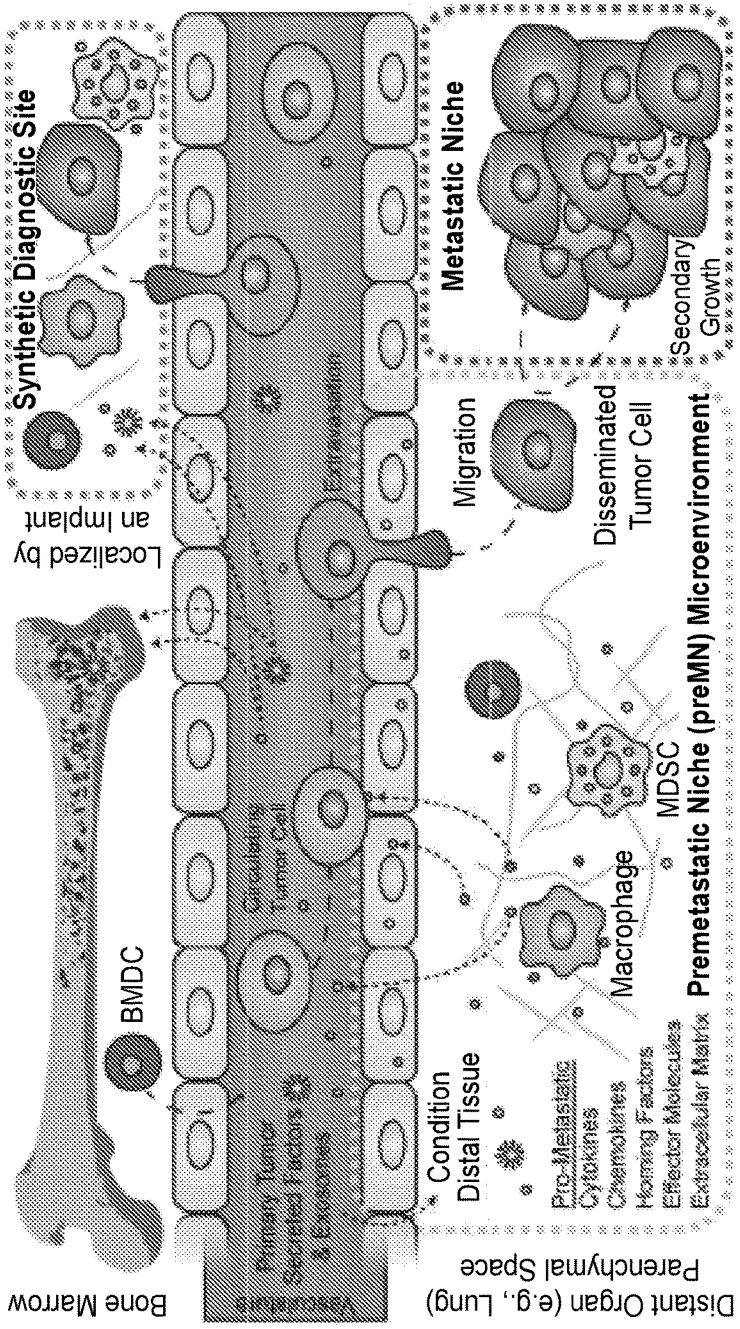
FIG. 22 demonstrates the development of the pre-metastatic niche (preMN), metastatic niche, and synthetic diagnostic site. Circulating tumor cells (CTCs) exhibit a tropism for specific distal microenvironments, thus indicating that metastasis is pre-determined. These primed distal microenvironments are denoted as the pre-metastatic niche (preMN) and facilitate homing then colonization of disseminated tumor cells (DTCs). Development of the preMN is driven by systemic conditioning from the primary tumor and secretion of factors and exosomes, which is amplified by simultaneous conditioning of the bone-marrow and alterations in bone-marrow derived cells (BMDCs). Given that the preMN contains a unique mixture of soluble factors, extracellular matrix, stromal and immune cells (e.g., cancer-associated fibroblasts and myeloid-derived suppressor cells, MDSCs), it is reasonable that preMN function could be synthesized through the recapitulation these unique factors at a synthetic site in vivo.

In cancer metastasis and therapy, SynDx would facilitate next-generation diagnostics by signaling the condition and susceptibility of metastatic colonization in vital organs. The biological premise for creating a SynDx is based on evidence that circulating acellular material from the primary tumor alters discrete sites, termed pre-metastatic niche (preMN), in distal organs that precede and aid metastatic tumor cells (FIG. 22), thus making its occurrence diagnostically valuable.[1] Unfortunately, the longitudinal monitoring of a physiologic preMN is complex due to their indistinct and difficult to access localization within distant vital organs, such as the lung and liver. Data from SynDx would complement gene expression platforms designed for primary tumor samples that have driven the description of cancer subtypes, facilitated prediction of risk for distant recurrence, and empowered molecular signatures that guide decisions about systemic therapy for cancer patients.[8] Unfortunately, the information obtained from the primary tumor is limited to a single measurement. Additionally, an understanding of distal tissue condition would complement liquid biopsies that face challenges in the relatively low numbers and phenotypic relevance as approximately 0.01% of circulating tumor cells will become metastatic foci.[9,10] Collectively, SynDx that signal the condition metastatically-susceptible organs would evolve personalized patient care from primary tumor-based prognostics to routine monitoring of synthetic, predetermined, modular, and predictable diagnostic sites.

Figure 17:
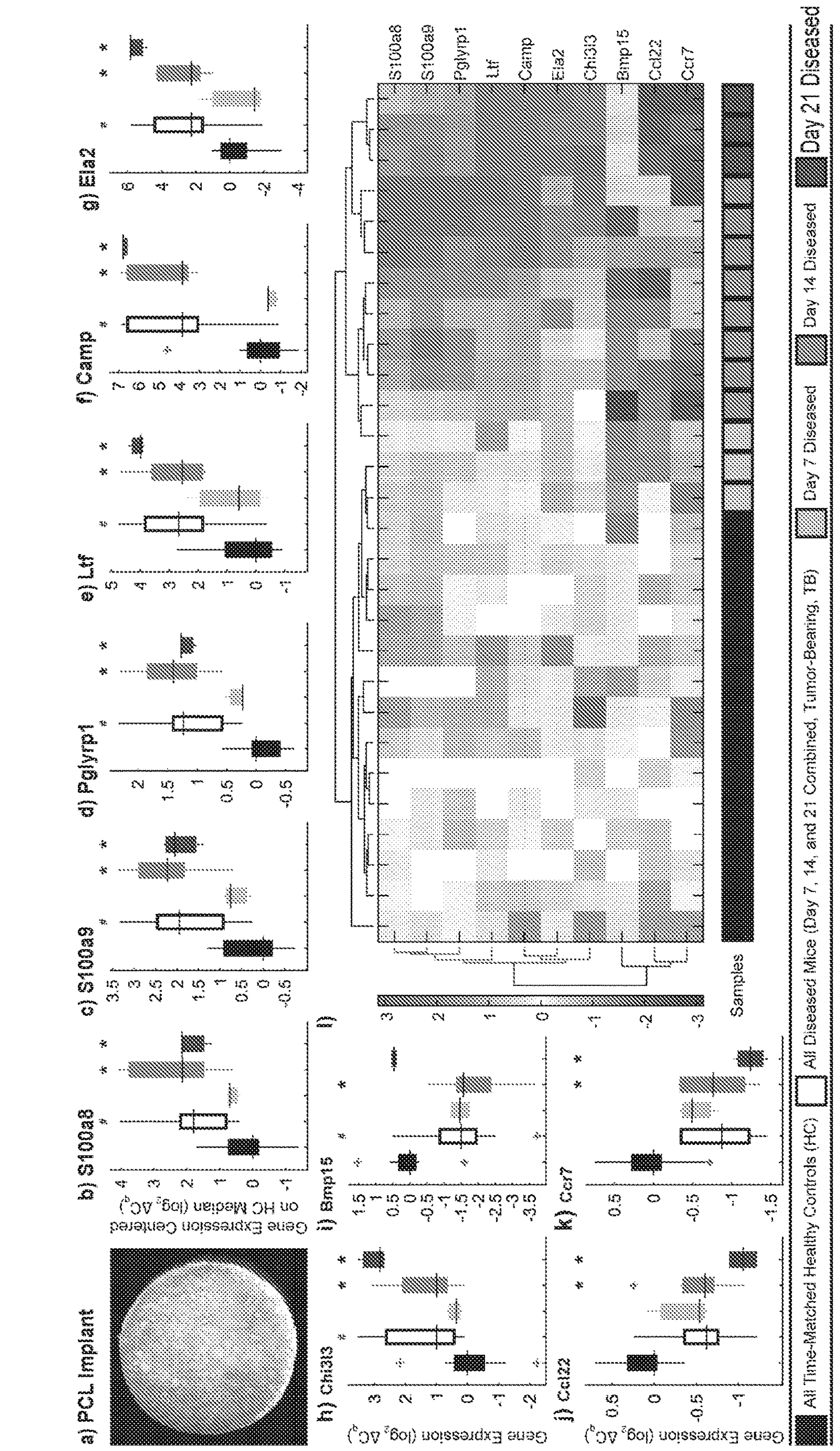
FIG. 17 demonstrates that progressive gene expression changes within implant-derived tissue during metastatic disease course. BALB/c mice were implanted with microporous polymer implants (Day −14) then inoculated with syngeneic 4T1 tumor cells at Day 0. Implants were biopsied at Days 7, 14, and 21 and tissue was analyzed with a high-throughput RT-qPCR platform (OpenArray™, 632 target and 16 reference genes). a) Microporous polymer (PCL) implant with a diameter of 5 mm, thickness of 2 mm, and interconnected 250-425 μm pores. b-k) Box plots for genes of interest show the median, 25th-75th percentiles and most extreme data points that were not considered outliers (outliers are visually indicated by red +). Diseased cohort expression is centered by the time-matched healthy cohort median. Scale depicts the log 2-transformed fold change. A two-way MANOVA showed a significant interaction effect between condition and time (Pillai's Trace=1.276, F(20, 28)=2.465, p=0.014). Post hoc univariate ANOVA showed significant differences within the diseased cohort over time (indicated by #, df=(2,22), p<0.05). Simple effects analysis showed significant differences between diseased and time-matched healthy controls (indicated by *, Šidák adjusted p<0.05 adjusted, see Data S5 for exact F and p values). l) Heatmap and unsupervised hierarchal clustering of 10 genes of interest with expression levels for each gene depicted as standardized data (n=14 per condition). Cohort size at Days 7 (n=3),14 (n=8), and 21 (n=3) represent biological replicates.
Figure 23:
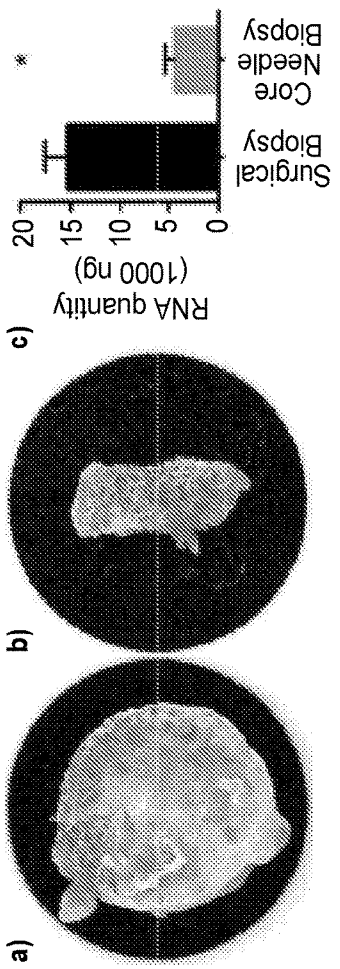
FIG. 23 demonstrates that implant microenvironment exhibits good tissue ingrowth and facilitates surgical and core-needle biopsies to acquire RNA for transcriptomic or gene expression analysis. a) A surgically-biopsied implant illustrating the intact, frozen condition prior to RNA isolation and RT-qPCR assessment. b) A sample derived from a scaffold using a core needle biopsy (CNB, Bard® Mission® Disposable Core Biopsy Instrument) which enables minimally invasive retrieval of samples, similar to clinical approaches for sampling suspicious tissue. In both samples tissue ingrowth into the microporous structure is evident but especially in the CNB as the cutting plane transected the inner core of the implant. Scaffolds as shown are in −80° C. frozen state. Diameter of the black background circle is 7.5 mm. c) Comparing the RNA isolated from the full surgically biopsied scaffold compared to the CNB sample, there is a significant −1.812 log-transformed fold change, but sufficient material for numerous gene expression assessments (RT-qPCR, RNAseq, etc.) with the CNB samples containing an average of 4376 ng of total RNA. * indicates differences between surgically biopsied and CNB samples from an unpaired t-test ($p<0.05$, $n=8$).
Figure 24:
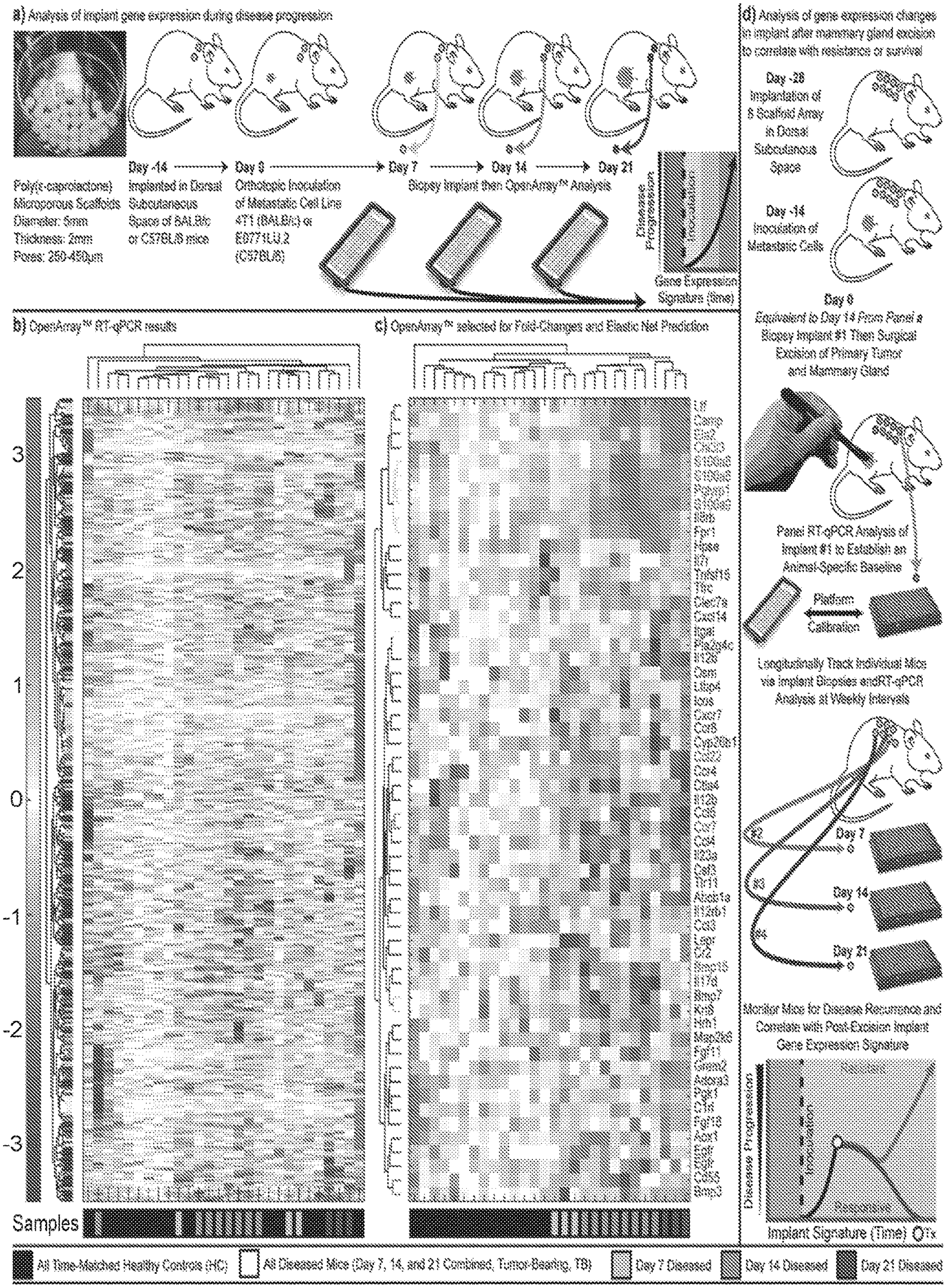
FIG. 24 demonstrates the experimental designs and OpenArray™ output for select genes with high fold-change and predictive value. a) Experimental outline for model training study including the fabrication of microporous PCL scaffolds, their implantation into mice. Mice were then inoculated with tumor cells and the resulting changes in implant gene expression were studied via OpenArray™ RT-qPCR. b) Results from OpenArray for tumor-bearing mice at Days 7 (n=3), 14 (n=8), and 21 (n=3) along with time-matched healthy control mice (n=14). c) Results from OpenArray selected for fold change and predictive value of TF or TB by a derivative of the LASSO algorithm (Elastic Net). For panels b-c mice are indicated on x-axis and genes are indicated on y-axis with clustering done via Euclidian distance and average linkage. Genes indicated in red text on the y-axis were selected for the smaller 10-gene panel analysis is subsequent studies. d) Experimental outline for model testing in a post-excision model including the implantation of scaffolds, tumor inoculation, isolation of pre-treatment implant, tumor and mammary gland excision, then weekly isolation of a synthetic niche for analysis.

Studies from this research group and others have demonstrated that metastatic tumor cells colonize microporous polymer implants and focused on their early arrival as a metric of efficacy.[11-14] These implants (FIGS. 17*a*, 23 & 24*a*) were composed of poly(ε-caprolactone) (PCL) polymer formed into a disc and designed with a microporous architecture (5 mm diameter, 2 mm thickness, interconnected 250-425 μm pores) to support cellular ingrowth of stromal, immune, and epithelial cells that vastly outnumber the colonizing tumor cells. Additionally, persistent inflammation and the FBR at the microporous PCL scaffolds shows little change following two weeks after implantation in healthy mice.[12] For the studies herein, a microporous PCL scaffold was implanted into the easily accessible dorsal subcutaneous space of healthy BALB/c mice (FIG. 23) to allow tissue ingrowth for two weeks. Mice were then orthotopically inoculated at Day 0 with triple-negative 4T1 tumor cells (FIG. 24*a*).

Figure 25:
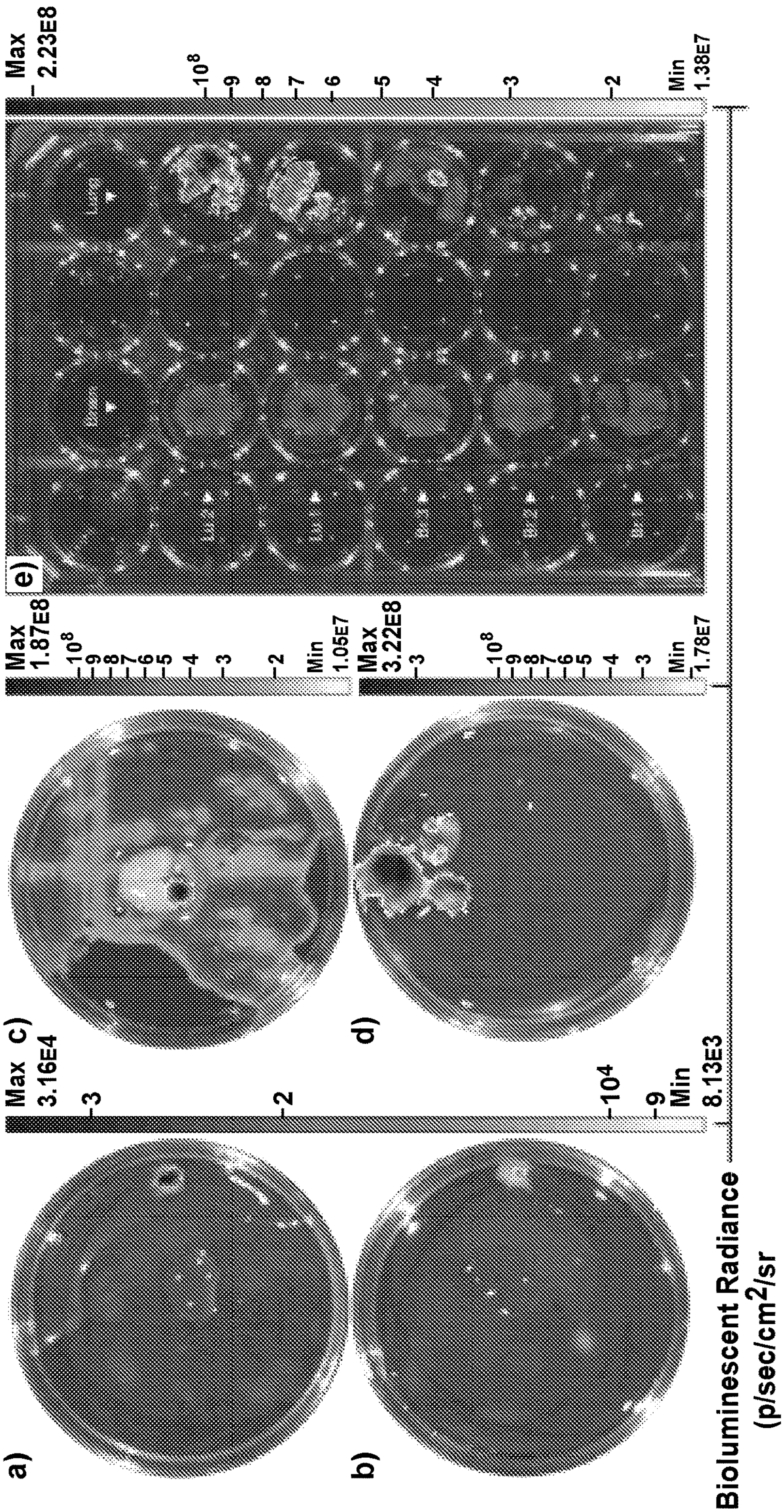
FIG. 25 demonstrates the development of E0771 metastatic variants. Scaffolds from a) left and b) right side of of a mouse inoculated with parental E0771 which developed a high metastatic burden which metastases present in the c) brain and d) lungs. Metastatic lines Br.1 and Lu.1 were derived from the tumor cells from these brain and lung metastases, respectively. Serial inoculation via intracardiac injection and isolation of developed metastases e) indicated a propensity for the lung derived metastases have an organotropic bias toward lung tissue. f) Confirmation of fluorescent tumor cells in the scaffolds from a-b was verified by fluorescent microscopy of scaffold tissue sections. g) In vivo imaging of Br.1 and Lu.1 line 11 days following intracardiac inoculation.
Figure 25:
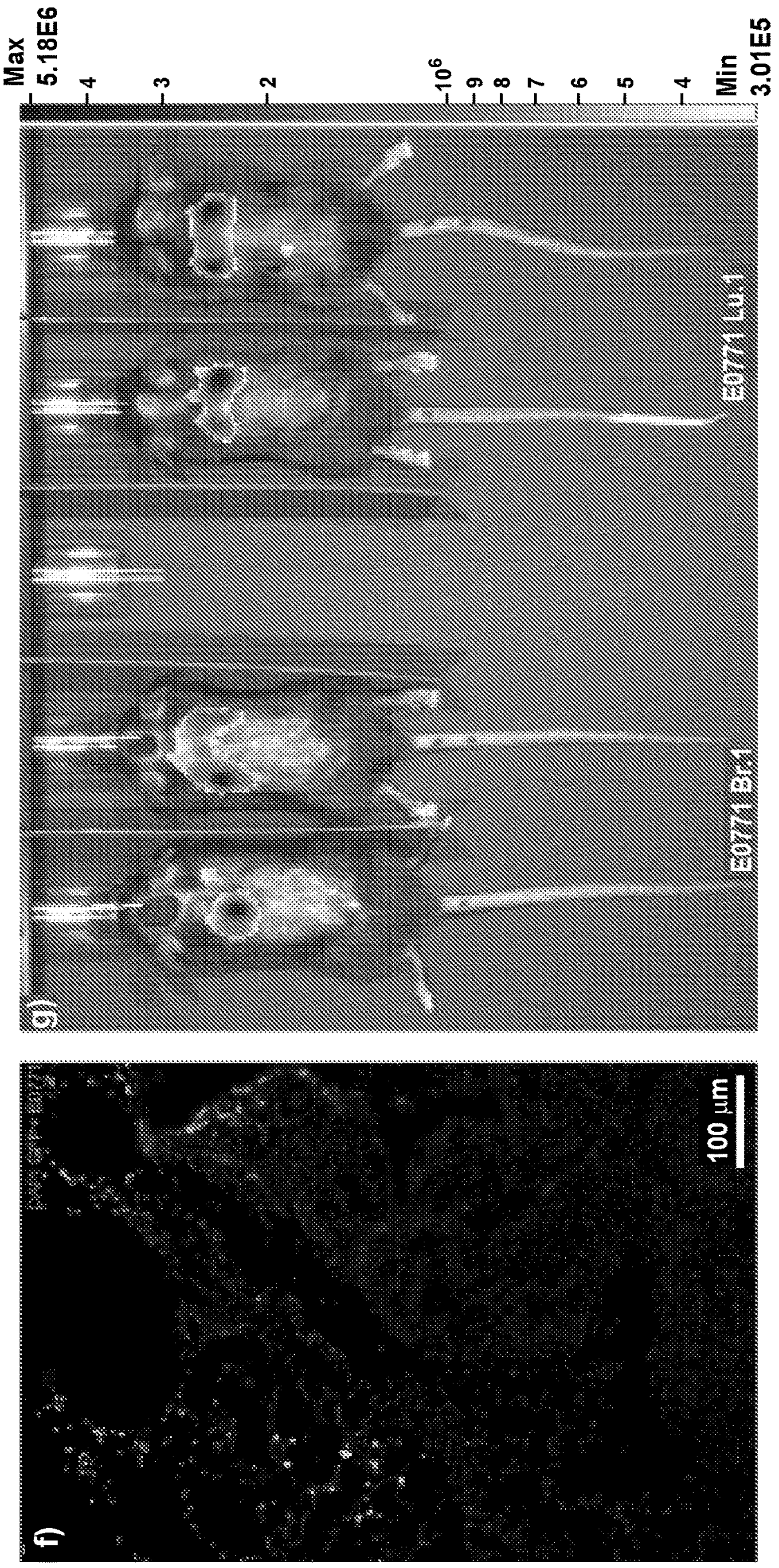
Figure 26:
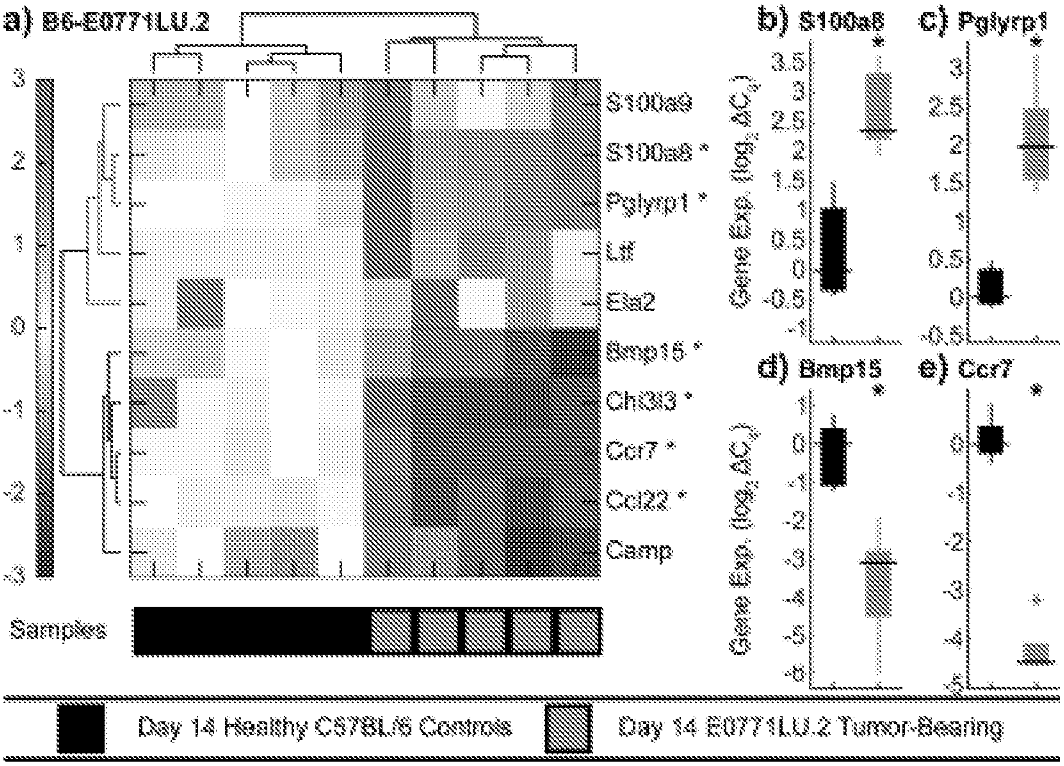
FIG. 26 demonstrates synthetic niche gene expression in C57BL/6 mice inoculated with metastatic tumor cells. C57BL/6 mice were implanted with microporous PCL scaffolds (Day −14) and then inoculated with a metastatic derivative (developed through serial inoculations of explanted lung metastases) of the E0771 syngeneic line (Day 0). At Day 14, scaffolds were biopsied from inoculated mice and healthy controls. a) Heatmap of gene expressions for a 10-gene panel normalized to reference genes, centered on the healthy control median, and standardized. Organization is based on unsupervised clustering of samples and genes. Significant alterations include the increases in b) S100a8 and c) Pglyrp1 alongside significant decreases in d) Bmp15 and e) Ccr7. * indicates significance (Dunn-Šidák corrected to $p<0.005$) from independent two-tailed t-tests comparing diseased to healthy (n=5 per condition). Data in b-e panels illustrate unstandardized, log 2-transformed fold-changes.

A large-scale gene expression analysis of the tissue in microporous polymer implants was performed following primary tumor inoculation to characterize inflammatory dynamics. Weekly (Days 7, 14, and 21) changes in gene expression were screened via a high-throughput RT-qPCR platform, OpenArray™, enabling parallel assessment of the expression of 632 target and 16 reference genes per sample (FIG. 24*b*). Altered expression was observed for 113 genes following tumor inoculation. A panel of genes of interest were defined based on their fold change, level of significance (false-discovery rate corrected), and expression stability. The 10 target genes (FIG. 17*b-k*, normalized to an average of 5 reference genes) included: S100 Calcium Binding Protein A8 (S100a8), S100 Calcium Binding Protein A9 (S100a9), Peptidoglycan Recognition Protein 1 (Pglyrp1), Lactotransferrin (Ltf), Cathelicidin Antimicrobial Peptide (Camp), Elastase 2 (Ela2), Chitinase (Chi3I3), Bone Morphogenetic Protein 15 (Bmp15), C-C Motif Chemokine Ligand 22 (Ccl22), C-C Motif Chemokine Receptor 7 (Ccr7). Unsupervised hierarchical clustering of these genes (FIG. 17*k*) based on Euclidean distance and average linkage produced a complete separation between healthy and diseased cohorts, with the gene expression in the tissue infiltrate of tumor-bearing mice progressing away from healthy controls as a function of time. This clustering identified distinct gene groups (i.e., S100a8/S100a9/Pglyrp1) that displayed similar expression profiles. Validation in C57BL/6 mice inoculated with a metastatic derivative of the E0771 line, denoted as Lu.2 (FIG. 25), showed similar gene expression changes and clustering, with 80% (8/10) of altered genes progressing in a similar direction (FIG. 26) as those in the BALB/c-4T1 model.

The changes in expression of specific genes within the implant-derived tissue suggest the adoption of an immunosuppressive and tumor cell hospitable environment, which is reflective of the natural preMN and supports its function as a SynDx. The increases in S100a8/9 are hallmarks of pre-metastatic and metastatic niche formation in metastasis-targeted organs (e.g., lungs) and myeloid-derived suppressor cell (MDSC) immunosuppressive functionality.[4] S100a8/9 expression leads to T cell inhibitory/cytotoxic byproducts (e.g., reactive oxygen species) and tumor cell proliferation.[15, 16] Unlike the increase in S100a8/9, the increase in Pglyrp1 has not yet been associated with the preMN, though its correlation with S100a8/9 was previously associated with bone-marrow derived granulocytic MDSCs and Th17 to regulatory T ($T_{REG}$) cell transdifferentiation.[17,18] Increases in Ela2, Camp, and Ltf were the greatest overall magnitude changes within this tissue at Day 21. Ltf and Camp are upregulated in granulocytic MDSCs as compared to neutrophils and increased levels of Ela2 and Camp have been identified as drivers of metastasis, with Ela2 associated with poor clinical outcomes and endocrine treatment failure.[19,20] C.hi3I3 expression progressively increased in the tissue infiltrate, which is supported by recent reports from chitinase knockout mice showing decreased metastasis.[21] A decrease in Ccr7 would limit the chemoattraction of T cells, which is reflective of the decrease in CD8+ and CD4+ T cells in tissue at Days 14 and 21, respectively.[12,22]Ccl22 expression can be upregulated in metastatic target organs and attracts $T_{REGS}$ in oncogenesis, thus this decrease in expression during disease progression was unexpected.[23]

Figure 18:
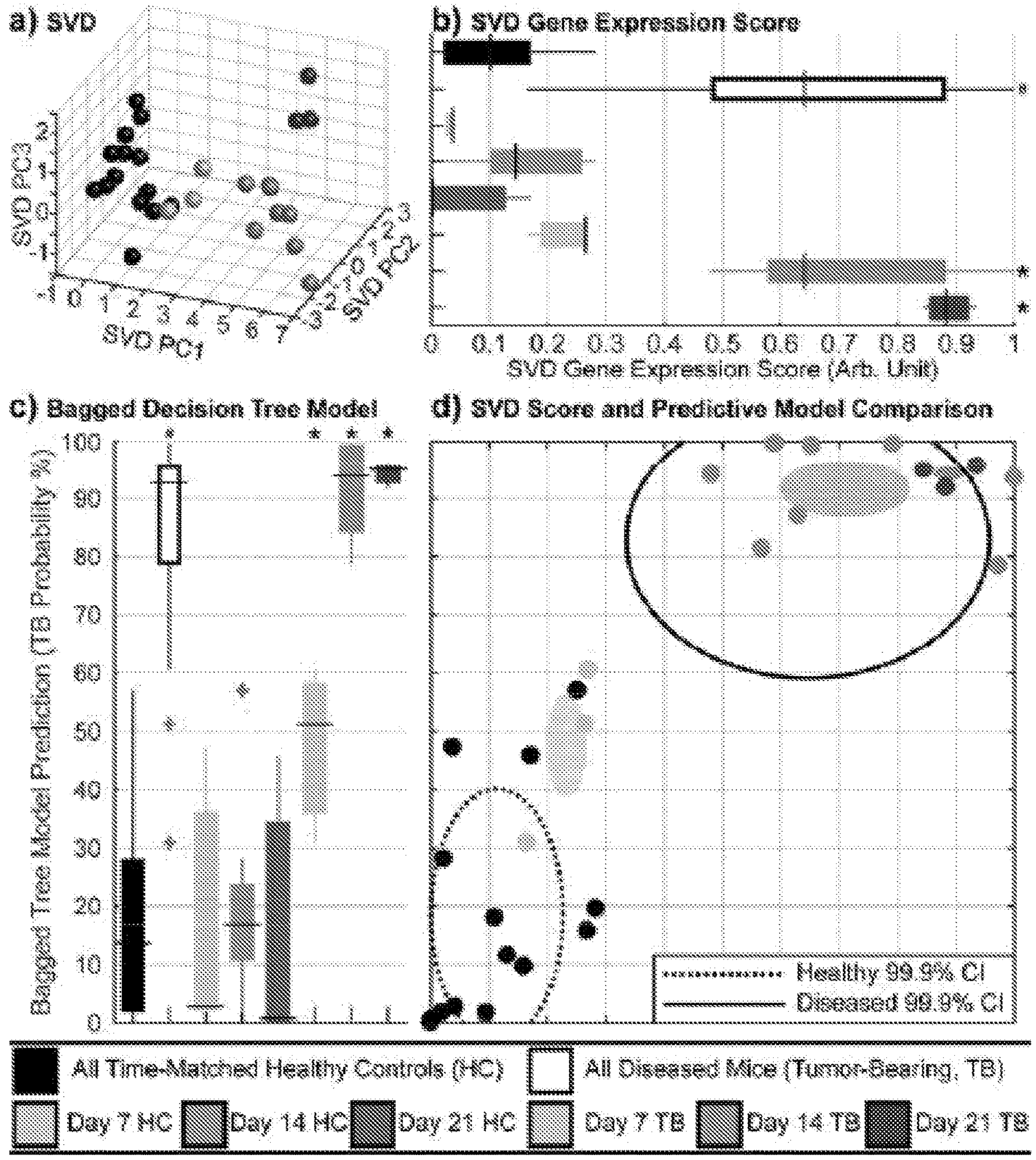
FIG. 18 demonstrates that signatures reduce gene expression to scoring metrics and diagnostic predictions. a) Gene expression from analysis of implant-derived tissue was reduced to an unsupervised scoring metric through singular value decomposition (SVD), which was converted to a score b) by calculating Euclidean distance from the healthy centroid to each sample. Scores were scaled between 0 and 1. c) In parallel, gene expression data was used to train a bootstrap aggregated (bagged) decision tree ensemble with leave-one-out cross validation to predict the likelihood that a mouse was tumor-bearing. d) Plot of the SVD score versus the bagged tree prediction. Dashed and solid line ellipses indicate the 99.9% confidence intervals for healthy (n=14) and diseased (n=14) cohorts, respectively. Filled ellipses indicate average and SEM of Days 7 (n=3), 14 (n=8), and 21 (n=3) diseased cohorts, illustrating the signature tracks with disease course. A two-way MANOVA showed a significant interaction effect between condition and time (Pillai's Trace=0.568, F(4,44)=4.361, p=0.005). Post hoc univariate ANOVA showed significant differences within the diseased cohort over time (indicated by #, df=(2,22), p<0.001). Simple effects analysis showed significant differences between diseased and time-matched healthy controls (indicated by *, Šidák adjusted p<0.05 adjusted, see Data S5 for exact F and p values).
Figure 28:
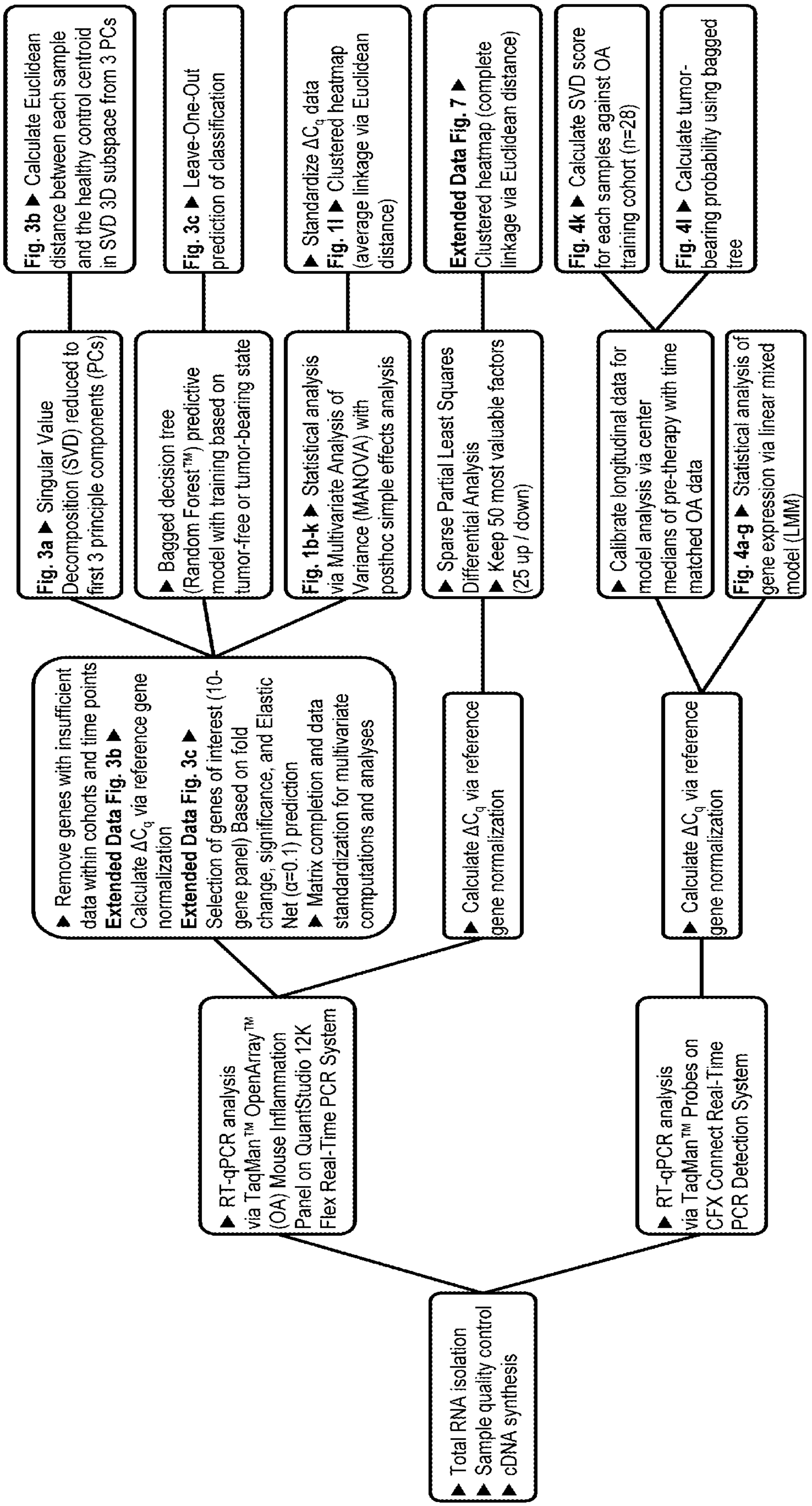
FIG. 28 demonstrates gene expression analysis and singular value decomposition, bagged decision tree, and sparse partial least squares discriminant analysis computational pipelines. Map of computational processes and the data outputs that are represented in the manuscript. For example, the calculation of the Euclidean distance from the first 3 principle components of the singular value decomposition (SVD) represented in FIG. 3*b* can be traced back through its processing steps to the total RNA isolation, quality control, and cDNA synthesis.
Figure 29:
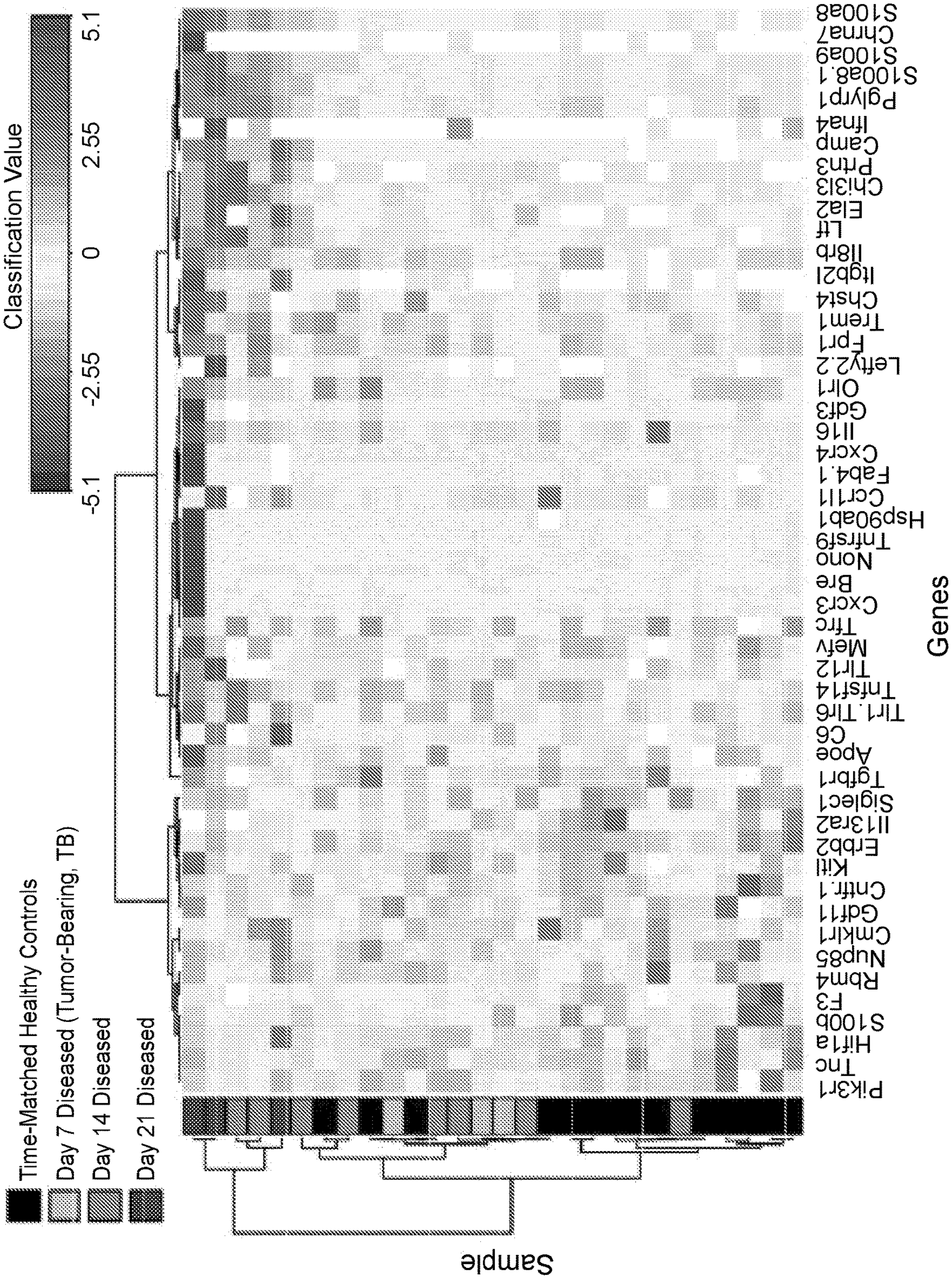
FIG. 29 demonstrates Sparse Partial Least Squares Discriminant Analysis (sPLS-DA) of the entire OpenArray™ RT-qPCR data limited to selection of the 25 most valuable factors that increased and decreased. Normalized OpenArray qRT-PCR data was analyzed with sparse partial least squares discriminant analysis (sPLS-DA) to identify the most discriminant factors for classification. Agreement in fold change magnitude, sPLS-DA discrimination, and an elastic net regularization were used to select for a subset of genes (expression changes listed below) for developing the signature and validation experiments that used SVD and bagged tree decision tree ensembles. Genes indicated in red text on the x-axis were included in the computational signatures.
Figure 30:
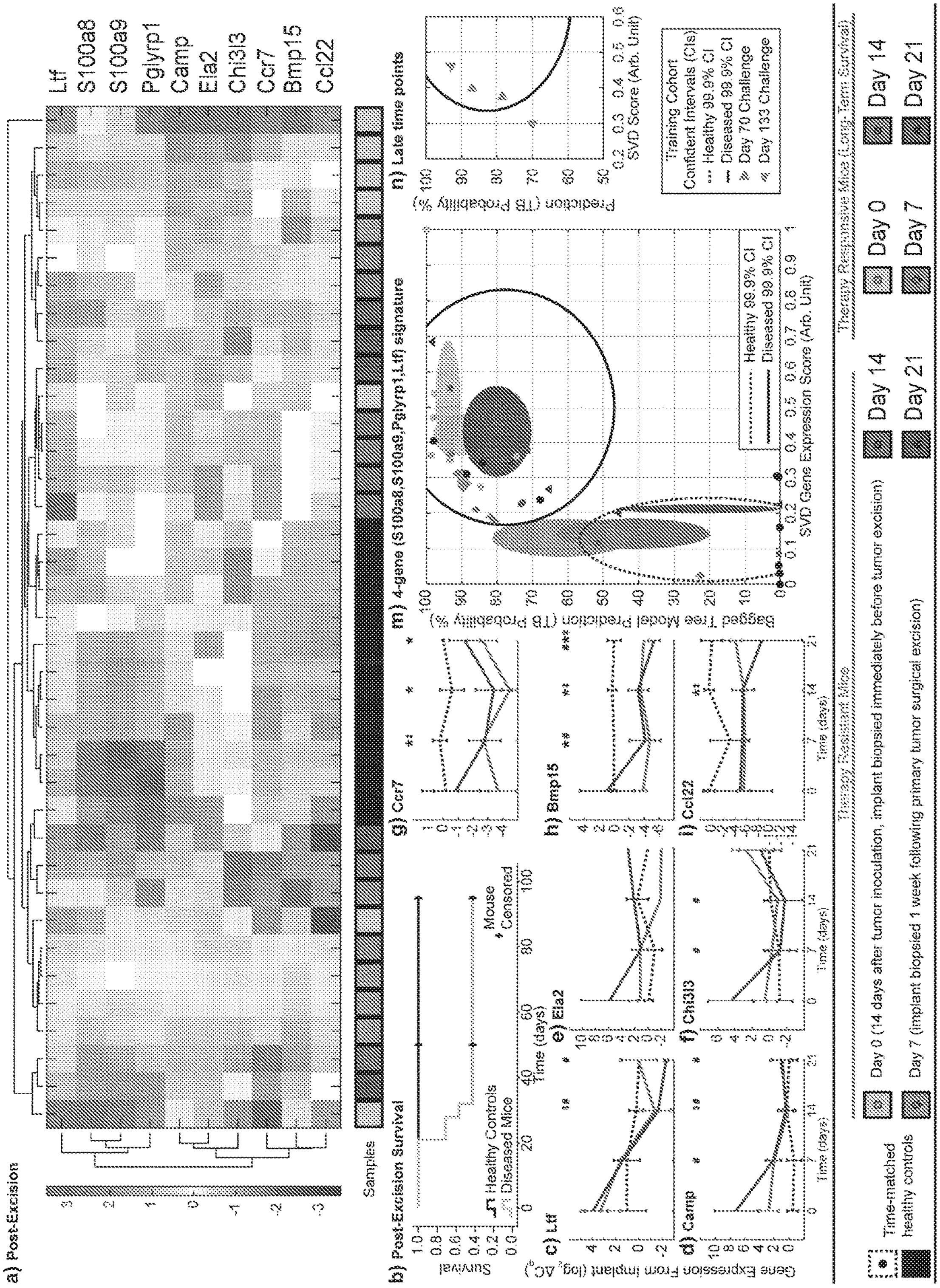
FIG. 30 demonstrates additional data from post-excision model including: heatmap to indicate full distribution of data, survival curve, gene expression and signature trajectories, and modified signature including only S100a8, S100a9, Pglyrp1, and Ltf. a) Heatmap gene expression ($C_q$) for a 10-gene panel normalized to reference genes. Genes indicated on the y-axis present in similar fashion to the gene expression from the OpenArray training data (e.g., the highest levels of S100a9 are present in pre-resection samples and cluster with S100a8 and Pglyrp1). Biopsied samples from pre-resection (Day 14) and post-resection (Days 21, 28, and 35) are indicated along the x-axis with unsupervised clustering showing a general aggregation of healthy samples with samples from specific mice moving towards healthy as a function of time. This time course, longitudinal analysis of gene expression trajectories as a function of survival b) is better conveyed as a line plot for c) Ltf, d) Camp, e) Ela2, f) Chi3I3, g) Ccr7, h) Bmp15, i) Ccl22. Error bars indicate SEM. m) Creation of a modified signature (SVD and bagged tree) from only S100a8, S100a9, Pglyrp1, and Ltf, which consistently cluster together across multiple models and in different tissues shows a stronger separation between mice that survived long-term and those that developed recurrence. n) To challenge the long-term dynamics in the synthetic niche, the healthy control mice (n=3) were inoculated at late time points (Day 56 and Day 119 after implantation) in their left 4$^{th}$ mammary fat pad (contralateral to right excision at day 0). Synthetic niche gene expression and signature alignment was analyzed at Days 70 and 133 (133 data points are from different niches in the same mouse). Dashed and solid lines indicate the 99.9% confidence intervals for healthy and diseased training cohorts, respectively. Error bars in line plots for gene expression and signature trajectory indicate SEM. The cohort size for each group is decreased by one at Day 21 due recurrence and animal censorship. For longitudinal data, statistics were performed via a linear mixed model. Post hoc simple effects analysis indicates significant differences (p<0.05) between (*) healthy and resistant, (‡) healthy and responsive, (&) resistant and responsive, (#) responsive and responsive Day 0 (pre-excision), and ($) resistant and resistant Day 0 (pre-excision) following significant (p<0.05) or trending (p<0.1) interactions in a two-way ANOVA.

A powerful use of multi-gene panels in medicine is the computational reduction to single metric scores and predictions, often referred to as signatures, which have guided clinical management in breast cancer patients using primary tumor tissue assays.[24] The 10-gene panel selected from the OpenArray™ RT-qPCR analysis (FIG. 17) was reduced to a single metric and predictive model for the probability that a mouse was either tumor-bearing (TB) or a healthy control (HC). Three computational techniques were investigated in parallel based on the knowledge that a spectrum of regression and modeling approaches provides more robust interpretations of data and biological networks (FIG. 28).[25] First, data dimensionality was reduced via an unsupervised matrix factorization (singular value decomposition, SVD, FIG. 18*a-b*)[26], which linearly transformed the data into eigengenes and eigenarrays that indicate gene significance and sample grouping, respectively. The SVD separation of the samples in three-dimensional (3D) subspace (FIG. 18*a*) established a scoring metric by setting a 3D reference point at the centroid of the healthy controls and calculating Euclidean distance to each sample data point (FIG. 18*b*, scores are scaled between 0 and 1). Second, supervised machine learning created a predictive model via a bootstrap aggregated (bagged) decision tree ensemble (i.e. Random Forest™)[27], which used a forest of decision trees (n=5000) based on a random selection of a gene from the 10-gene panel to predict a mouse status as healthy or diseased. For each sample a prediction score (FIG. 18*c*) was determined via leave-one-out analysis. Third, a supervised approach using sparse partial least squares discriminant analysis (sPLS-DA)[28], was employed using the entire OpenArray™ data set for assessment of variable selection and classification (FIG. 29), which showed that 7 of 10 genes from the 10-gene panel were highly valuable for the stratification of samples (FIG. 29). Collectively, the output from these computational pipelines showed consensus in prediction (FIG. 18*d*), with progression of disease evidenced by the significant changes identified from Day 7 through Day 21.

Figure 19:
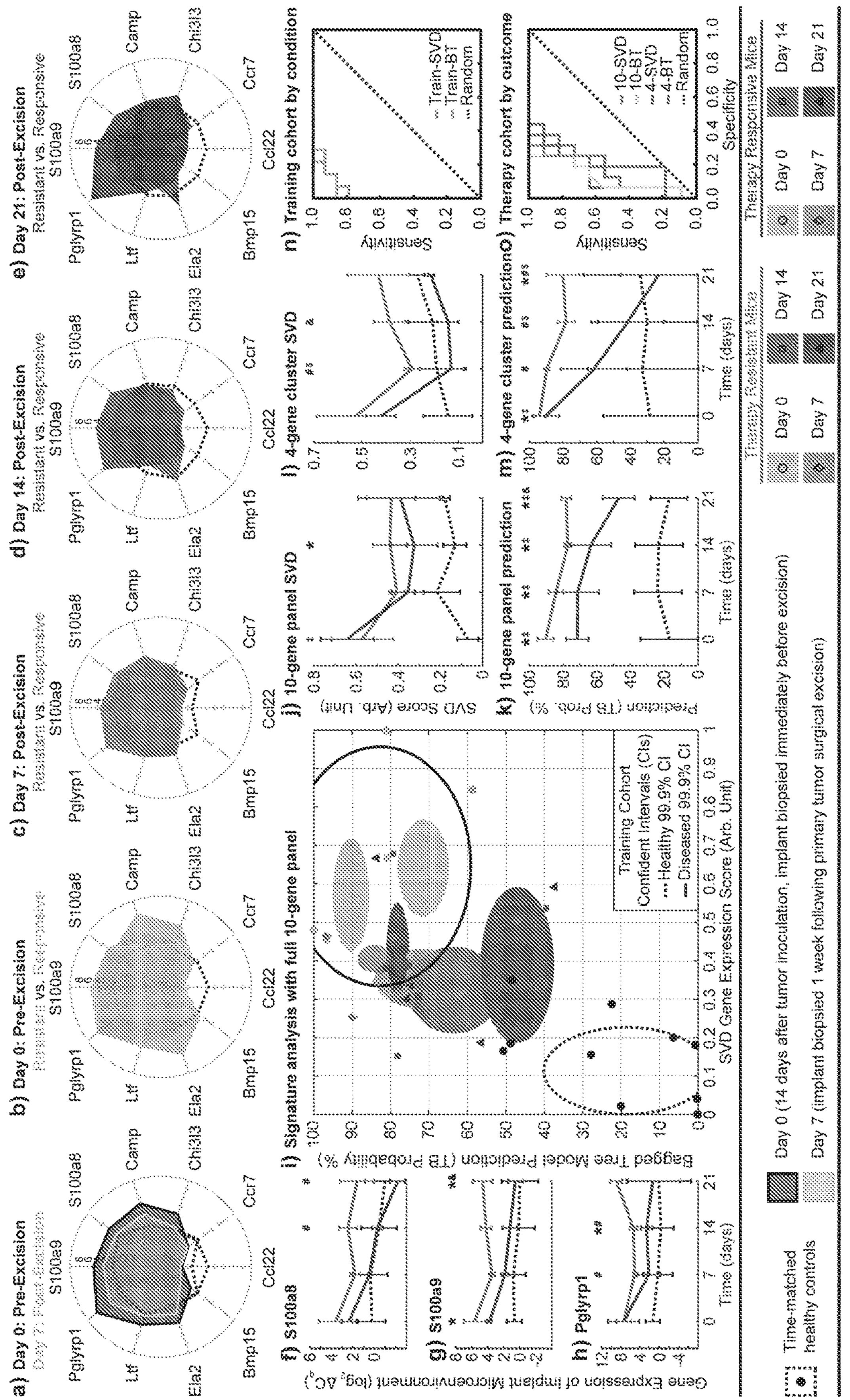
FIG. 19 demonstrates that primary tumor mastectomy redirects gene expression and signature trajectory, which predicts therapeutic efficacy. Mice with an array of implants (n=8 sites per mouse, n=10 mice) and a primary tumor in their 4th mammary fat pad (n=7 mice) had implant #1 surgically biopsied then immediately had their primary tumor resected along with the surrounding fat pad (Day 0, tumor-burden equivalent to Day 14 in FIG. 1&3). Healthy mice (n=3) received sham inoculation and a mammary gland excision. All mice where then monitored by weekly (Days 7, 14, 21) SynDx biopsy, RT-qPCR, and signature analysis. a) For the 7 genes that showed an increased expression in the metastatic onset model, there was an organized regression in expression 1-week after therapy. b-e) Longitudinal survival monitoring stratified diseased mice into therapeutic resistant (n=4) and therapeutic responsive (n=3) groups. While a significant decrease in expression was evident in several genes (FIG. 18), the divergence between the resistant and responsive was most evident in f-h) S100a8, S100a9, and Pglyrp1. i-k) Associated alterations in SVD score and a significant divergence in bagged tree model prediction was observed. Creation of a modified 4-gene 1) SVD and m) bagged tree signature from S100a8, S100a9, Pglyrp1, and Ltf. ROC curves of predicted performance for SVD and bagged tree models in the n) training cohort (n=28) for tumor-bearing and o) therapy cohort for resistance from Days 7 to 21. All area under the curve (AUC) calculations for the therapy cohort exceeded 0.8 with the 10-gene bagged tree (10-BT) having the highest AUC at 0.878 (95% CI, 0.743-1.000). Filled ellipses indicate the average and SEM of Day 0, 7, 14, and 21. Error bars in line plots for gene expression and signature trajectory indicate SEM. The cohort size for each group is decreased by one at Day 21 due recurrence and animal censorship. For longitudinal data, statistics were performed via a linear mixed model. Post hoc simple effects analysis indicates significant differences (p<0.05) between (*) healthy and resistant, ($) healthy and responsive, (&) resistant and responsive, and (#) responsive and responsive Day 0 (pre-excision) following significant (p<0.05) or trending (p<0.1) interactions in a two-way ANOVA (see Data S5 for exact F and p values for all genes).
Figure 31:
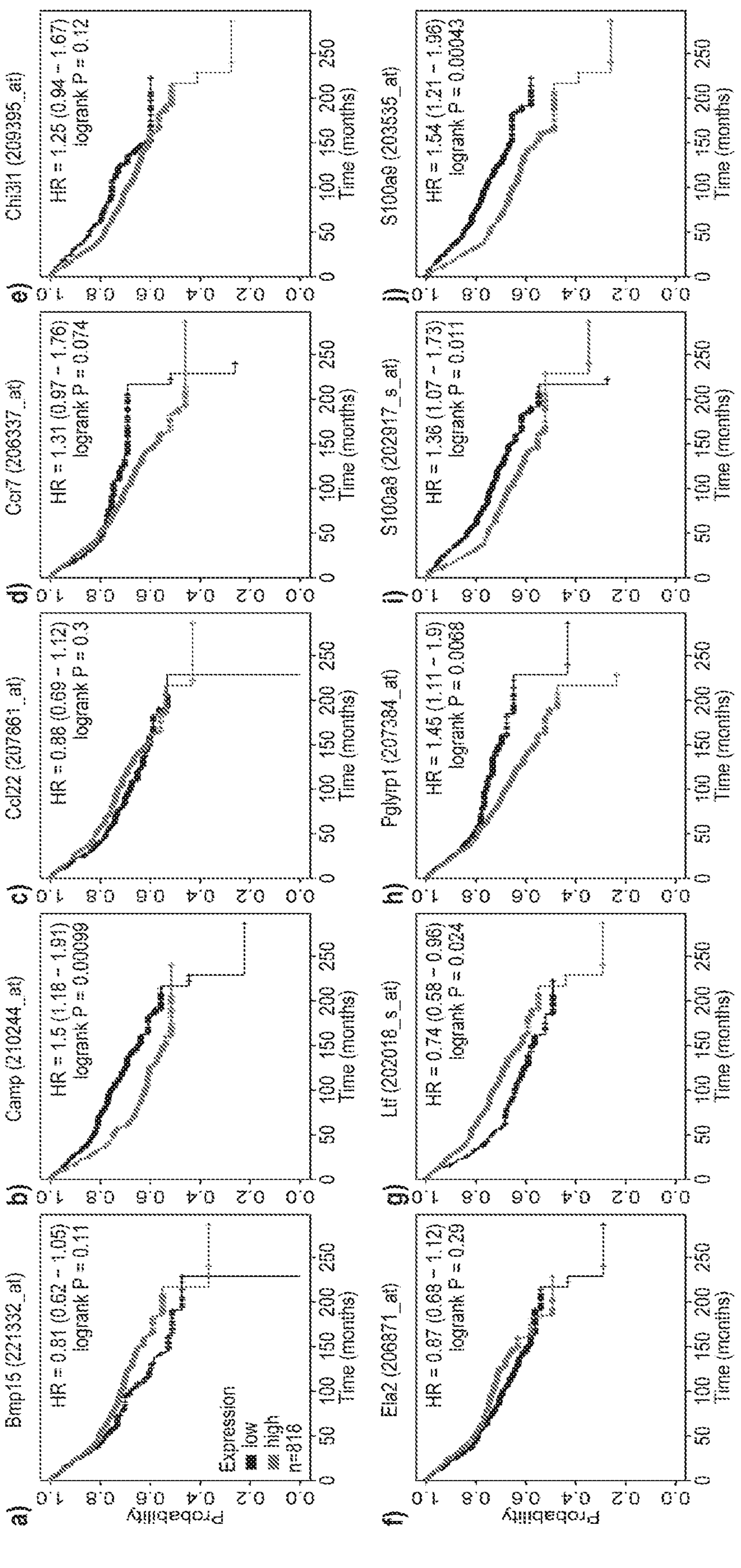
FIG. 31 demonstrates Kaplan-Meier survival curves correlated with high and low gene expression from breast cancer patient samples. Microarray (GEO via KMPlot) and prognosis data a-j) were queried for genes selected for the 10-gene panel from the synthetic niche to determine the expression level relevance in primary tumors on the clinical outcome of systemically untreated breast cancer patients (n=818). Kaplan-Meier plots indicate as separation of two profiles separating high and low gene expression that are automatically divided by the median expression of the genes for all samples. Plots indicate the Hazard Ratio (HR) which is highest for S100a9 and logrank significance comparing high and low expression as a function of recurrence-free survival. (*) FDR 10% corrected significance (p<0.011) and (**) FDR 5% corrected significance (p<0.00099).

The gene expression signatures were interrogated following therapy to test if the signature obtained from disease progression data (FIGS. 17 & 18) maintained utility in the context of a therapeutic response. We investigated the potential of the signatures to differentiate therapeutically responsive and resistant mice using a mouse model where the tumor-bearing mammary gland was excised, with tissue biopsied from SynDx before and after treatment. BALB/c mice were implanted with multiple implants (n=8 per mouse) in their subcutaneous space to facilitate individualized, longitudinal tracking (FIG. 24*d*) following 4T1 tumor inoculation. Fourteen days following inoculation, tissue from the implant was biopsied prior to removal of the mammary gland to align with the Day 14 data in FIGS. 17 & 18. Immediately following biopsy (identified as Day 0 in FIG. 19), the tumor-bearing mammary gland was completely excised. Additionally, in healthy control mice a control excision of the mammary gland was performed as indicated in FIG. 19. At weekly intervals following mammary gland excision (Days 7, 14, and 21 post-excision in FIG. 19) a single biopsy was retrieved per mouse. At Day 7, following tumor-bearing mammary gland excision (FIG. 19A), a regression towards healthy baseline of all the genes with increased expression (S100a8, S100a9, Pglyrp1, Camp, Ltf, Chi3I3, and Ela2) was observed, which was a striking shift in the implant gene expression relative to the untreated disease course (Day 21, FIG. 17). This regression towards healthy continued over the next two weeks (Days 14 and 21 post-surgery) for responsive mice that survived long-term with no signs of recurrence at the study end (survival >70 days following therapy). However, redirection of gene expressions towards diseased levels was observed for mice resistant to therapy (survival <32 days following therapy). Signature analysis for each animal (FIG. 19*i-k*) also showed a shift towards healthy 7 days after therapy for all mice, however, the average prediction remained significantly elevated above the healthy control baseline for mice that would develop a recurrence. The difference was most notable 21 days after mammary gland excision, where the trajectory for surviving mice continued a downward trend while the resistant mice increased. Lastly, to improve divergence between resistant and responsive mice a revised 4-gene (S100a8, S100a9, Pglyrp1, Ltf) signature was constructed to test separation (FIG. 19*l-m*). ROC curve analysis of the training and therapy cohorts indicated a capacity of all computational signatures to separate resistant from responsive and healthy control mice (FIG. 19*o*). Interestingly, patient primary tumor sample analysis matched with survival data (FIG. 31) revealed some conserved inflammatory mechanisms that were readily captured by SynDx and may identify the timing of recurrence that would not be possible through the analysis of primary tumors used by platforms like Oncotype DX and Mammaprint.[29,30]

Figure 20:
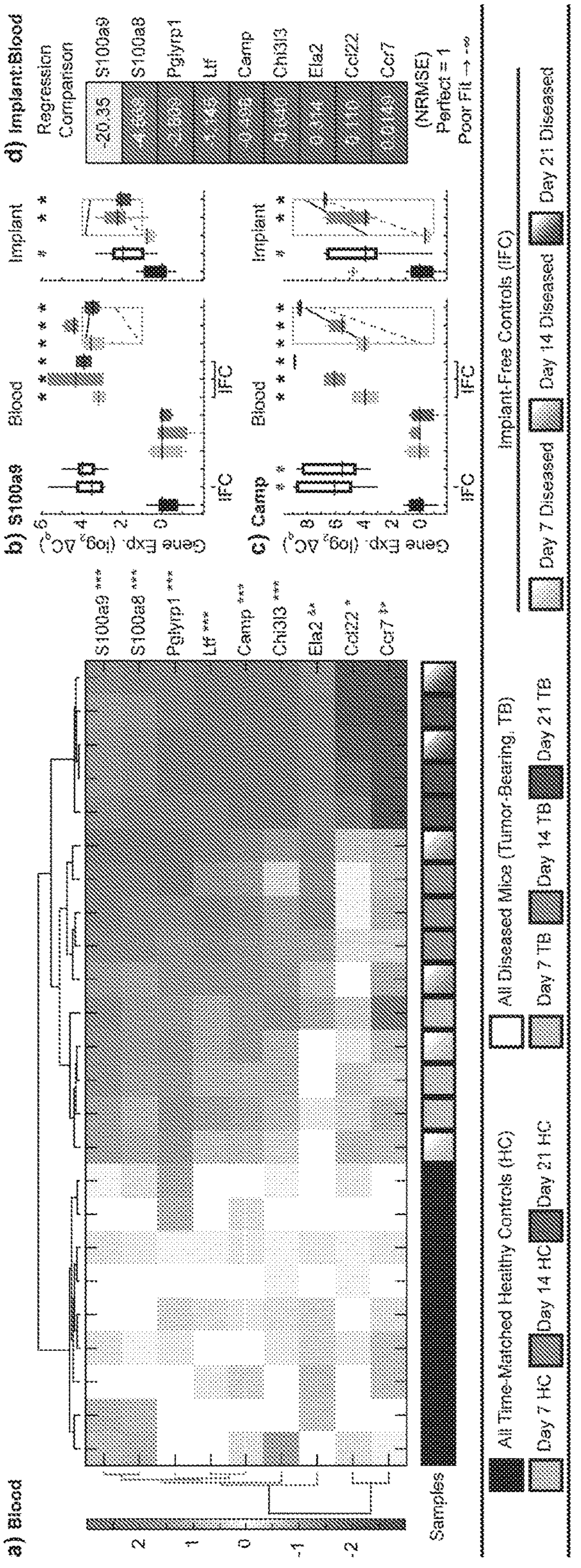
FIG. 20 demonstrates gene expression changes found in blood following tumor inoculation. a) Heatmap of blood leukocyte RT-qPCR data from BALB/c mice inoculated with 4T1 tumor cells shows unsupervised clustering based on samples and genes. Implant-free control (IFC) samples were also analyzed in the cohort as indicated in the data. A two-way MANOVA showed a significant interaction effect between condition and time (Pillai's Trace=2.527, F(36,40) =1.907, p=0.024). Post hoc univariate and simple effects analysis showed significant differences within the diseased cohort over time and when comparing diseased and IFCs to time-matched controls for (***) all time points, (*) Day 21, (‡*) Day 21 and diseased versus control at Day 7, (&*) Day 21 and diseased versus control at Day 14 (Šidák adjusted p<0.05 adjusted). Bmp15 was omitted due to a lack of detection. To compare gene expression dynamics between blood and synthetic niches, regression analyses (insets) were performed between Days 7, 14, and 21. To illustrate, b) blood S100a9 compared to implant-derived tissue S100a9 expression has a worse fit when compared to c) blood Camp and implanted-derived tissue expression as determined by d) Normalized Root Mean Squared Error (NRMSE). The S100a8, S100a9, and Pglyrp1 gene cluster had the worst fits when comparing blood to implant-derived tissue. Significant differences within blood expression indicated as #(df=(2, 15), p<0.001) and * indicates significant differences between diseased and time matched controls (Šidák adjusted p<0.05, see Data S5 for exact F and p values).
Figure 21:
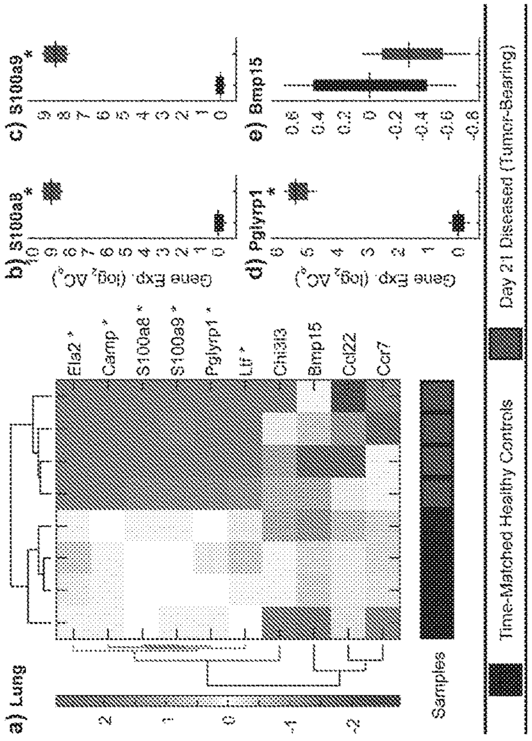
FIG. 21 demonstrates gene expression changes in lung at Day 21 following tumor inoculation. BALB/c mice inoculated with 4T1 tumor cells at Day 0, had lung tissue biopsies taken and RT-qPCR analyzed at Day 21 from tumor inoculated and healthy mice. a) Heatmap of gene expressions for 10-gene panel (reference gene normalized, centered on healthy median, and standardized). Organization was based on unsupervised clustering of samples and genes. Genes of interest with significant changes included an increase in b) S100a8, c) S100a9, and d) Pglyrp1. e) Unlike the blood, Bmp15 was detectable but not significant. * indicates significance (Dunn-Šidák corrected to p<0.005) from independent two-tailed t-tests comparing diseased to healthy controls (n=4 per condition). Data in b-e panels is unstandardized, log 2-transformed fold-changes.

To contextualize our findings, we analyzed the gene expression of blood leukocytes and lung biopsies. Liquid biopsies (FIG. 20) represent a relatively easy to access source for molecular analysis, while solid organ (e.g., lung) biopsies (FIG. 21) are arguably more valuable, yet acquisition poses greater patient risk. While 9 of the 10 genes from the panel were expressed at some level in blood, the pattern of expression differed from that of the implant-derived tissue. These dynamics were particularly evident for S100a8, S100a9, and Pglyrp1, which have a poor correlation to the disease stage and cannot distinguish disease progression in blood. Notably, these 3 factors (S100a8, S100a9, and Pglyrp1) in implant-derived tissue were most prominent in distinguishing therapy response and resistance (FIG. 19*f-h*). Importantly, the gene expression patterns in the lung at Day 21 closely mimicked that observed in the implant-derived tissue for all genes in the panel.

Herein the utility of SynDx developed through biopsy of tissue in microporous polymer implants during disease course in multiple pre-clinical models of metastatic breast cancer is demonstrated. Using SynDx as surrogates for metastatic sites in diseased vital organs, a high-throughput gene expression platform is implemented and signatures to track disease progression and enable longitudinal monitoring of individual mice before and after treatment are developed. Collectively, these data indicate that the tissue within implants is dynamic, with context-dependent profiles that reflect disease course and therapeutic response. Broadly, the concept of a synthesizing tissues and sites necessary for effective diagnostics may have substantial transdisciplinary potential when extended to other disorders with immunologically driven or affected components.

Example 6

This example describes the methods used for the experiments of Example 5.

Microporous PCL Scaffold Fabrication:

Preparation of microporous PCL scaffolds for implantation was performed as previously described in studies that included material characterization via mechanical testing, scanning electron microscopy, and porosity calculations. Briefly, PCL microspheres were prepared by emulsifying (homogenization at 10,000 rpm for 1 minute) a 6% (w/w) solution of PCL (Lactel Absorbable Polymers) in dichloromethane in a 10% poly(vinyl alcohol) solution, which was then stirred in DI water for 3 hours. Particles were collected by centrifugation, serially washed with MilliQ filtered water, then lyophilized. Salt porogen (NaCl) with a size range of 250-425 μm was selected through sieving. PCL microspheres and NaCl were then mixed in a 1:30 (w/w) ratio and pressed at 1,500 psi in a stainless-steel die (International Crystal Laboratories) for 45 seconds. The volume and die size used results in a PCL/NaCl disc that is 5 mm wide and 2 mm thick (FIG. 24*a*). PCL/NaCl discs were then heated on glass slides on a hot plate set to 135° C. for 5 minutes per side. NaCl was then removed via leaching in MilliQ water for 1.5 hours. The resulting microporous PCL scaffolds were disinfected in 70% ethanol then serially rinsed in sterile filtered MilliQ water. Scaffolds were dried on a sterile gauze and stored at −80° C. until time of implantation.

Animals and Scaffold Implantation:

Microporous PCL scaffolds were implanted in the subcutaneous space of female mice to facilitate synthetic niche development for subsequent isolation. All animal studies were performed in accordance with institutional guidelines and protocols approved by the University of Michigan Institutional Animal Care and Use Committee. Female mice of the BALB/c and C57BL/6 strains were purchased from Jackson Laboratories at an age of 8 weeks. For implantation, mice were administered the analgesic Carprofen (5 mg/kg) prior to and 24 hours after surgery. Mice were anesthetized under isoflurane (2.0-2.5%) and assessed by toe pinch reflex for level of sedation. The upper dorsal area above the scapula was then shaved and prepared using betadine and ethanol swabs. An incision (approximate 7-10 mm from anterior to posterior) was made in the upper dorsal area. A subcutaneous cutdown created a pocket in the lateral direction on the left and right sides of the mouse. A single scaffold was then inserted into each pocket. Two scaffolds were implanted for mice used to identify the initial gene expression changes and develop a signature. The incision line in these mice was closed with 7 mm stainless-steel wound clips (Roboz Surgical Instrument Co.). An array of eight scaffolds was implanted in mice used for longitudinal monitoring of disease course after therapy. Skin in these mice was closed with suture (MONOCRYL—poliglecaprone 25, Ethicon, Inc.).

Metastatic Tumor Cell Lines and Animal Inoculation:

Orthotopic inoculation of tumor cells was performed 2 weeks after scaffold implantation. 4T1-luc2-tdTomato cells were obtained from Perkin Elmer which had been authenticated previously via short tandem repeat (STR) and comparison with ATCC STR database. E0771 GFP+ cells were a kind gift from the Laboratory of Gary and Kathryn Luker at the University of Michigan Center for Molecular Imaging. To develop a more aggressive metastatic cell line, we employed a serial inoculation strategy that began when a C57BL/6 mouse inoculated with the parental line exhibited secondary metastatic growths at many sites including: lung, brain, mesentery, and diaphragm. Cells derived from the original lung (Lu.1) and brain (Br.1) metastases were then inoculated via intracardiac injection, which resulted in brain and lung metastases that were again isolated as Lu.2 and Br.2. Both Lu.1 and Lu.2 showed a stronger inclination for metastatic colonization of the lung (FIG. 25*e*), similar to reports on 4T1 phenotype. 4T1-uc2-tdTomato (BALB/c) or E0771 Lu.2 (C57BL/6) syngeneic tumor cells were orthotopically inoculated at a density of 40,000 cells/μL for a total of 800,000 in 20 μL of sterile Dulbecco's phosphate buffer saline (DPBS; Gibco). Inoculation was performed by making a small incision (5 mm dorsal to ventral) above the $4^{th}$ right mammary fat pad. The mammary fat pad was exposed, injected, then the skin was closed with tissue adhesive (3M Vetbond™). For healthy mice that were inoculated at late time points to study the dynamics at Day 70 and 133 the inoculation process was replicated with the inoculation being performed in the $4^{th}$ left mammary fat pad, as the right mammary fat pad had already been resected as a control.

Biopsies of Scaffold, Blood, and Lung Tissue:

Microporous scaffolds, blood leukocytes, and lung tissue were isolated to study gene expression changes due to disease progression. Microporous scaffolds that had been implanted for either 7, 14, or 21 days following inoculation of primary tumors (as indicated in figures) were surgically biopsied following isoflurane (2.0-2.5%) sedation by making an incision adjacent to the implant site and removing the implant without taking surrounding tissue. For core-needle biopsy (CNB) of the synthetic niche a disposable CNB tool (Bard® Mission® Disposable Core Biopsy Instrument) was inserted through the skin and used to isolate a portion of the synthetic niche (FIG. 23*b*), which enables minimally invasive retrieval of samples. Blood leukocytes were isolated via an intracardiac blood draw stabilized by EDTA. Erythrocyte lysis in EDTA-treated blood samples was performed with Ammonium-Chloride-Potassium (ACK) Lysing Buffer (Gibco) with serial washes in DPBS. Lung tissue from time-matched healthy control and tumor-bearing mice at Day 21 were isolated for endpoint comparative analysis following euthanasia.

Surgical Resection of Primary Tumor and Longitudinal Tracking:

To test the responsiveness of the synthetic niche to therapeutic treatment mammary gland removal was performed on the 4T1 primary tumor that had been inoculated in the $4^{th}$ right mammary fat pad of BALB/c mice. In this model, the primary tumor was resected 14 days after inoculation, which aligns with the time point for the initial set of experiments to study the progressive changes in the synthetic niche as a function of disease course. The skin above the primary tumor was prepared by swabbing with betadine and ethanol. A dermal incision was made adjacent to the primary tumor for the length of the primary tumor and mammary fat pad (approximately 1 cm). Large vessels surrounding the primary tumor were cauterized using a Gemini Cautery System (Roboz Surgical Instrument Co.). Iris scissors were used to cut connective tissue to separate the mammary fat pad and contained primary tumor from the superficial dermal and underlying body cavity wall. The dermal incision was closed using suture (MONOCRYL—poliglecaprone 25, Ethicon, Inc.). Following tumor resection and mammary gland removal, animal health was monitored daily for activity and responsiveness, including posture, mobility, body weight, grooming behavior, and respiratory conditions. Animals were euthanized if found in a moribund condition or when a primary tumor regrowth was positively identified.

RNA Isolation, Purity, Integrity, and cDNA Synthesis:

Total RNA was isolated from synthetic niches, lung, and blood leukocytes. Frozen (−80° C.), surgically biopsied scaffolds were immersed in monophasic solution of phenol and guanidine isothiocyanate (TRIzol® reagent, Thermo Fisher Scientific, Waltham, MA) at 4° C., then homogenized with a rotor stator homogenizer (T25, S25N-8G-ST dispersing element, IKA® Works, Inc.). Samples were then centrifuged at 10,000g to remove particulate, and the TRIzol® containing genomic content from the scaffold was then processed in a silica-based matrix spin column (Direct-zol™ RNA Miniprep Plus, Zymo Research Corp., Irvine, CA) with DNase I treatment to isolate total RNA. Concentration (modified Beer-Lambert at 260 nm) and purity (260 nm/280 nm absorbance ratio) of the RNA isolation was assessed by light absorbance via a NanoDrop 2000c (Thermo Fisher Scientific). Additionally, RNA integrity number (RIN) analysis was obtained through RNA fragment analysis (RNA 6000 Nano Kit on a 2100 Bioanalyzer, Agilent Technologies, Inc., Santa Clara, CA). RIN for samples used in high-throughput RT-qPCR ranged from 8.2-9.7. Generation of first strand cDNA was performed through reverse transcription (RT, SuperScript™ VILO™ cDNA Synthesis Kit, Thermo Fisher Scientific). For all RT-qPCR of synthetic niche, RT was performed with an RNA concentration of 200 ng/μL. cDNA was either used immediately for RT-qPCR or stored at −80° C. Frozen lung tissue biopsy RNA was isolated in similar fashion to synthetic niches with RT performed at an RNA concentration of 200 ng/μL. Blood leukocyte RNA was isolated by thoroughly mixing blood leukocytes following ACK lysis in TRIzol, then processing for RNA and performing RT at 100 ng/μL due to limited quantities of total RNA. RNA concentration was increased to 200 ng/μL (niches and lungs) or 100 ng/μL (blood) using a RNA clean-up kit (RNA Clean & Concentrator-5, Zymo Research Corp.) for samples below these thresholds.

OpenArray™ High-Throughput RT-qPCR:

Synthetic niche gene expression was analyzed with OpenArray® (OA), a high-throughput RT-qPCR platform that analyzes 648 genes per sample in parallel, in accordance with the standard OA protocol. All materials used in this section were purchased from Thermo Fisher Scientific. Briefly, the genes for this study were focused on the inflammatory pathways and included a panel of 16 reference (housekeeping) genes per sample (Applied Biosystems™ TaqMan™ OA Mouse Inflammation Panel, Cat. No. 4475393). cDNA from synthetic niches biopsied from tumor-free healthy controls (n=14 total healthy) and tumor-bearing mice (n=14 total diseased) across the three time points of 7 (n=3), 14 (n=8), and 21 (n=3) days were mixed with 2× TaqMan® OA Real-Time Master Mix then loaded onto the OA panels via a robotic OA AccuFill™ System in an order that staggered conditions and time points across the panels analyzed. The OA RT-qPCR run (QuantStudio 12K Flex Real-Time PCR System, ThermoFisher Scientific) and sample quality control were performed by the Affymetrix Group at the University of Michigan DNA Sequencing Core. In accordance with OA standard operating procedure, $C_q$ was calculated as $C_{rt}$, a curve-specific method. Complete matrices of raw data for non-normalized ($C_q$), reference gene normalized ($\Delta C_q$), and fold change calculations between tumor-bearing and healthy ($\Delta\Delta C_q$) at Days 7, 14, and 21 are available and organized according to the RT-PCR GEOarchive template.

Analysis of Gene Expression and Selection of Genes of Interest:

Gene expressions from OA was screened to identify genes of interest during disease course. First, genes with insufficient data within synthetic niche samples (missing greater than 4/14 per cohort or 2/3 per time-point) were dropped from the study, resulting in 559 genes for full analysis. Next the 16 reference genes were ranked according to their expression stability compared to each other and as a function of experimental design (NormFinder Algorithm), which led to the selection of Gapdh, Tbp, Ywhaz, Hmbs, and Ubc. $\Delta C_q$ values were calculated against the average of the reference genes, centered on median of time-matched healthy controls, then standardized for cluster and multivariate statistical analysis. From $\Delta C_q$ data fold change, significance (uncorrected p and false-discovery rate corrected q), at Days 7, 14, and 21 were calculated. For computational analysis $\Delta C_q$ values were $\log_2$ transformed and centered on the healthy-control time-matched median as reflected in the figure box plots, which show the median, 25th-75th percentiles and most extreme data points not considered outliers (outliers are visually indicated by +). Management of non-detects within the OA data was handled in two manners: for multivariate statistical analysis non-detects were interpolated based on the $\Delta C_q$ average across all cohorts and time points, and for signature construction non-detects were interpolated based on the $\Delta C_q$ average for a specific cohort at a specific time point.

10-gene panel RT-qPCR analysis in 96-well format: Experiments for signature validation, analysis of blood, lung and post-excision monitoring was performed by RT-qPCR analysis in a 96-well plate format using matched Taqman® probes from the OA platform. Like the OA RT-qPCR, samples were staged within plates alternating between healthy and diseased. The same 5 reference genes (Gapdh, Tbp, Ywhaz, Hmbs, Ubc) were run in parallel with the 10 target genes of interest (Bmp15, Camp, Ccl22, Ccr7, Chi3l3, Ela2, Ltf, Pglyrp1, S100a8, S100a9) for all studies in BALB/c mice. Ywhaz and Ubc were only used for the C57BL/6-E0771 analysis due to poor detection and poor stability in Gapdh, Tbp, and Hmbs reference genes. Analysis was performed on a CFX Connect™ Real-Time PCR Detection System (Bio-Rad Laboratories, Inc., Hercules, CA) with CFX Manager Software that calculated the $C_q$ values based on the regression analysis mode, which applies a multivariable, nonlinear regression model to each well trace. For signature computation and multivariate statistics, non-detects were interpolated based on $\Delta C_q$ average across all cohorts and time points to limit predictive bias, which could be exaggerated by use of a static, arbitrary $\Delta C_q$. Non-detects were left blank for univariate, multiple comparison, and linear mixed model analysis. Synthetic niche gene expression dynamics and blood gene expression dynamics were compared by goodness of fit using a normalized root mean square error cost function on a linear polynomial curve fit between Days 7, 14, and 21. Cohort centering was used to align the longitudinal data from the therapy study for subsequent signature analysis. The median of the therapy cohorts Day 0 pre-excision was centered on the OA Day 14 data median, which was experimentally equivalent. The calibration factor used for aligning therapy cohorts Day 0 to OA Day 7 was applied to all successive time points.

Figure 27:
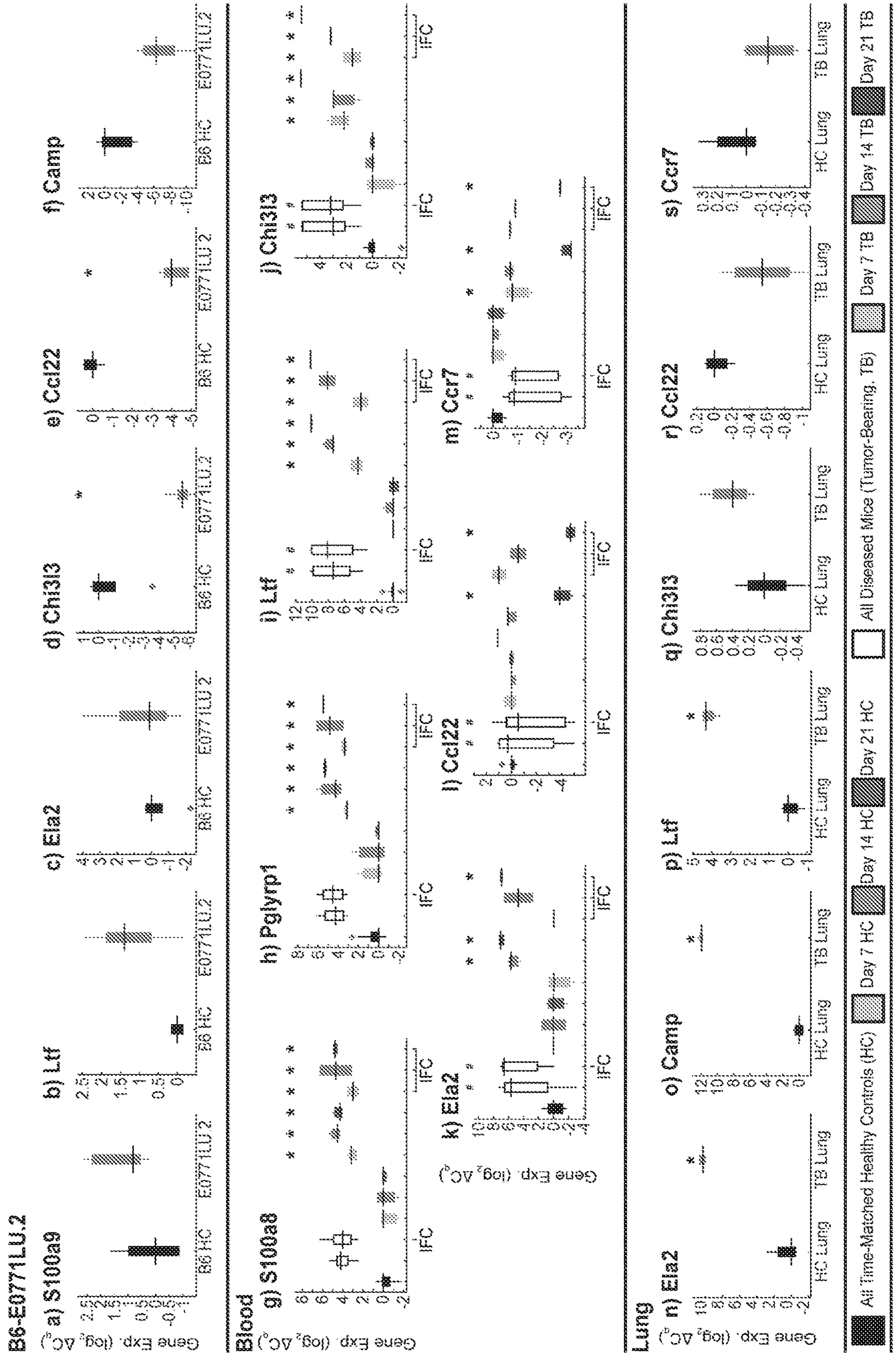
FIG. 27 demonstrates additional box plots for C57BL/6, blood and lung gene expression. a-f) box plots of gene expression to complete the data in the B6-E0771Lu.2 heatmap from FIG. 2. g-m) box plots of gene expression to complete the data in the Blood heatmap from FIG. 5. n-s) box plots of gene expression to complete the data in the Lung heatmap from FIG. 6. For the C57BL/6 model in a-f) * indicates significance (Dunn-Šidák corrected to $p<0.005$) from independent two-tailed t-tests comparing diseased to healthy (n=5 per condition). For blood data n-s) a two-way MANOVA showed a significant interaction effect between condition and time (Pillai's Trace=2.527, $F(36,40)=1.907$, $p=0.024$). Post hoc univariate and simple effects analysis showed significant differences within the diseased cohort over time as indicated as # (df=(2,15), $p<0.001$) and * indicates significant differences compared to time matched controls (Šidák adjusted $p<0.05$ adjusted. For the lung data in n-s) * indicates significance (Dunn-Šidák corrected to $p<0.005$) from independent two-tailed t-tests comparing diseased to healthy (n=4 per condition).

Gene Expression Dimensionality Reduction and Classification:

The source data and code for the computational pipeline (FIG. 27) within this section are publicly accessible as indicated in the Data and Code Availability sections. To screen for the genes of interest an Elastic Net regularization, a variation of the LASSO (least absolute shrinkage and selection operator) algorithm with an $\alpha$=0.1 and leave-one-out cross validation, was employed using the Matlab lasso function on the $\Delta C_q$ of the 559 genes with sufficient data. This data indicated the predictive nature of genes for tumor-bearing classification at specific time points (FIG. 24*b*). Clustering of samples was performed with the Matlab clustergram function on standardized $\Delta C_q$ data. Dendograms indicate clustered genes and samples, in which samples are indicated on the x-axis and genes expressed are indicated on the y-axis with a complete linkage and a display range of −3.5 to +3.5. Unsupervised dimensionality reduction was performed using singular value decomposition ($X=USV^T$) with the Matlab svds function on the 10-gene and 4-gene panels standardized $\Delta C_q$ values centered on the time-matched healthy controls. The first 3 principle components (PCs) were computed from the first 3 left singular vectors (columns of U, eigenassays) and singular values (diagonal matrix S). Unsupervised separation of the samples was visualized by plotting the PCs in 3D scatter, which was quantified by calculating the 3D Euclidean distance to each sample from the centroid of all the healthy-controls. Distance calculations were scaled between 0 and 1. A supervised machine learning algorithm, bootstrap aggregated (bagged) decision tree ensemble (i.e., Random Forest™), was used t construct a predictive model based on the 10-gene and 4-gene panels standardized $\Delta C_q$ values centered on the time-matched healthy controls. The model was constructed using the Matlab core fitcensemble function with the Bag method. Decision tree depth was limited by the number of splits to two times the number of input predictors (genes). The number of learning cycles for final model was set to 5000 cycles. A partitioned model and leave-one-out cross-validation was performed using the Matlab crossval and kfoldPredict functions, which returned the posterior probability for classification of each sample. A second supervised learning approach, Sparse Partial Least Squares Discriminant Analysis (sPLS-DA) was employed using the MixOmics package in R, to process the $\Delta C_q$ from 632 target genes at Days 7, 14, and 21. For this analysis $\Delta C_q$ was normalized to a combination of the 8 most stable reference genes (Hmbs, Gusb, Ubc, Ywhaz, Cdkn1a, Tbp, Gapdh, Hprt1), yet was not $\log_2$ transformed or centered. This reduction in processing was done to improve confidence in the selected genes of interest. For cluster analysis the 50 (25 positive and 25 negative) most valuable genes for classification were retained. For sample and gene clustering the R cim function was used. Receiver Operating Characteristic (ROC) curves were used to compute the true positive rate (sensitivity) against the false positive rate (specificity) to determine diagnostic cutoff points and model accuracy for training cohort (n=28) data with SVD and bagged tree as test variables and tumor-bearing designation as the state variable. The therapy cohort from post-excision Days 7 to 21 was analyzed by the 10-gene panel SVD, 10-gene panel bagged tree prediction, 4-gene (S100a8, S100a9, Pglyrp1, and Ltf) cluster SVD, 4-gene cluster bagged tree prediction as test conditions with the therapy resistance designation as the state variable. Area under the curve with confidence intervals are listed within the figure legend.

Statistics:

This section details the statistical tests used to evaluate the hypotheses. Error bars are defined within figure legends, with all line plots indicating standard error of the mean. The exact n for each test is detailed in the legends along with the methods for multiple comparisons corrections. All n throughout the manuscript indicate biological replicates from different mice. During the initial screen of the OA data and selection of genes of interest, a false-discovery rate corrected two-tailed t-test using a linear step-up procedure to account for all genes analyzed (559 total following elimination of genes that did not contain sufficient sample) contrasted samples from diseased mice and healthy time-matched controls. These tests were carried out in Matlab using the mattest and mafdr functions. All statistical indicators within the manuscript were computed using packages and syntax in the Statistical Package for the Social Sciences (SPSS, International Business Machines Co., Armonk, NY). Multiple comparisons analysis for comparisons with an individual time point were compared via an independent Student's two-tailed t-test with Dunn-Šidák correction for multiple comparisons resulting in a $p<0.0051$ being considered significant. Two-way multivariate analysis of variance (MANOVA) for genes of interest and reduced dependent variables (SVD score or bagged tree prediction) were performed within the generalized linear model (GLM) syntax package using the BY command for condition and time. First, Pillai's Trace statistic ($p<0.05$) was used to determine MANOVA significant interaction effects. Second, fixed-effects ANOVA was used to assess univariate interaction effects. Last, following determination of multivariate and univariate interaction effects, a post-hoc simple effects analysis was computed with Šidák correction from an initial $p<0.05$ for multiple comparisons to determine within groups over time and between groups at Days 7, 14, and 21. To analyze the differences within mice tracked longitudinally before and after a therapeutic tumor excision a Linear Mixed Model (LMM) was employed. The SPSS syntax for the LMM is available in the prepress repository. First, two-way ANOVA within the LMM was assessed for significant ($p<0.05$) or trending ($p<0.1$) interactions. Last, post hoc simple effects analysis indicated significant differences ($p<0.05$) within groups over time and between groups at Days 7, 14, and 21. Within the figures the focus for within group effects was how the gene expression, SVD, or bagged tree data changed from pre-excision (Day 0) to post-excision (Days 7, 14, and 21).

Breast Cancer Patient Microarray Kaplan-Meier Correlation:

A repository of human patient microarray data was analyzed for gene expressions correlations with high or low gene expression and patient recurrence free survival (RFS). Microarray data from Gene Expression Omnibus (GEO) via Kaplan-Meier Plotter (KMPlot, kmplot.com/analysis/) and prognosis data were queried for genes selected for the 10-gene panel from the synthetic niche to determine the expression level relevance in primary tumors on the clinical outcome of systemically untreated breast cancer patients. Separation of high and low gene expression profiles was automatically divided by the median expression of the genes for all samples (n=818). Redundant and outlier microarrays were excluded, and only breast cancer patients that were systemically untreated were included. Data outputs for Hazard Ratio (HR) and logrank significance are indicated in plots with multiple comparisons corrected using the KMPlotter tool for false-discovery rate (FDR) with FDR 10% corrected significance ($p<0.011$) and (**) FDR 5% corrected significance ($p<0.00099$).

Protocol Availability and Life Science Reporting Summary:

Many of the experimental protocols including scaffold fabrication, RNA isolation, and RT-qPCR follow previously published or manufacturer recommended guidelines and additional specifics may be located in the life science reporting summary.

Example 7

This example describes an exemplary method of treating a subject.

A polymer scaffold comprising PCL is implanted into a subject following the treatment of a primary tumor (e.g., a malignant growth in the breast) according to standard of therapy (surgery, chemotherapy, radiation). The polymer scaffold is implanted by either surgical insertion or through minimally-invasive placement via a trocar. After insertion, a tissue sample is obtained from the scaffold through a core-needle biopsy to establish a baseline result for the patient. The same core-needle biopsy approach is used at scheduled intervals (e.g., every 3 months) to generate a metastatic potential score and thereby monitor the patient for early-onset metastatic events. To attain the metastatic potential score, the cellular components of the implant are processed to extract total RNA through use of a standard Trizol extraction protocol and purification technique using a silica based filter and DNase. (Zymo Research Directzol and Qiagen RNeasy kits are both suitable options, though others exist.)

The purified RNA is processed via qRT-PCR for a panel of genes associated with disease progression (as detailed in the data) using TaqMan probes or SYBR-green, based detection. The expression of the genes in the panel is analyzed by an amplification curve regression analysis. Gene expression is normalized to a panel of housekeeping genes (e.g., Gapdh, Hmbs, Tbp, Ubc, Ywhaz) which is averaged for each sample (as demonstrated and common in clinical practice). Gene expression data is processed to generate a variety of graphical outputs, including a heatmap to graphically represent a patient's readout compared to healthy and diseased control groups, as well as the patient's previous readouts. Each is expressed as a comparison to healthy controls, thus providing insights on a patient's similarity or dissimilarity with healthy or matched diseased samples. The patient results are also classified as either pre-metastatic, early metastatic, or late metastatic through machine learning algorithms or linear regression (e.g., using singular value decomposition and bootstrap aggregated decision trees).

The sample analysis can provide a range of scores, with a low score indicating healthy, an intermediate score indicating an early stage of disease, such as pre-metastatic, and a high score indicating metastases. The observation of an intermediate score that is distinct from a healthy control leads to the application of therapies that target the immune cells at a metastatic niche, such as phosphodiesterase 5 (PDE-5) or COX-2 inhibitors that inhibit the functionality of myeloid derived suppressor cells. The observation of a high score or one that is distinct from a healthy control is indicative of high metastatic potential and disease conditioning, and thus, anti-metastatic disease therapy is warranted for the subject. If a high score or signature of metastatic disease is observed, the subject is determined as needing treatment targeting the metastatic cells, such as, for instance, PARP inhibitors (e.g., Olaparib) or alternative chemotherapies (e.g. Gemcitabine). Additionally, or alternatively, the subject may be treated with more specific drugs targeting metastatic pathways that are currently available for clinical use or are in the drug discovery pipeline. The implant environment is reassessed for metastatic potential following treatments to identify the efficacy of a specific approach in suppressing the metastasis promoting environment.

One to three months following treatment in response to a low (e.g., PDE-5) or high score (e.g., Olaparib), a biopsy from the scaffold is taken, the cells from the biopsy are processed, RNA is isolated, and gene expression analysis is performed as described above. The observation that the patient's readout is more concordant with a healthy control indicates that the treatment with the chosen drug is effective, whereas a readout indicating concordance with the disease state indicates that a different treatment strategy, e.g., treatment with eribulin mesylate, should be implemented. If the specific treatment plan for the patient does not result in a reduction in the metastatic potential score, ongoing readouts from the scaffold can serve to direct patient care towards alternative targeted management plans. Follow up analysis as described is performed regularly (e.g., every 3 months) until a patient's condition plateaus (e.g., patient experiences 9 months at a continuous readout, no progression of metastatic events) at a level consistent with disease remission or stability. The implant may remain in the patient for future tests as necessary.

REFERENCES

1 Kaplan et al., *Nature* 438, 820-827, doi:10.1038/nature04186 (2005).

2 Giles et al., *Cancer Res*, doi:10.1158/0008-5472.CAN-15-0204 (2015).

3 Hiratsuka et al., *Nat Cell Biol* 8, 1369-1375, doi:10.1038/ncb1507 (2006).

4 Sinha et al., *The Journal of Immunology* 181, 4666-4675, doi:10.4049/jimmunol.181.7.4666 (2008).

5 Oliva et al., *Sci Transl Med* 7, 272ra211, doi:10.1126/scitranslmed.aaa1616 (2015).

6 Socarras et al., *PLoS One* 9, e110945, doi:10.1371/journal.pone.0110945 (2014).

7 Vegas et al., *Nat Biotechnol*, doi:10.1038/nbt.3462 (2016).

8 Harris et al., *J Clin Oncol* 34, 1134-1150, doi:10.1200/JCO.2015.65.2289 (2016).

9 Minn et al., *J Clin Invest* 115, 44-55, doi:10.1172/JC122320 (2005).

10 Luzzi et al., *Am J Pathol* 153, 865-873, doi:10.1016/S0002-9440(10)65628-3 (1998).

11 Azarin et al., *Nat Commun* 6, 8094, doi:10.1038/ncomms9094 (2015).

12 Rao et al., *Cancer Research* 76, 5209-5218, doi:10.1158/0008-5472.Can-15-2106 (2016).

13 Aguado et al., *Acta Biomater* 33, 13-24, doi:10.1016/j.actbio.2016.01.043 (2016).

14 Bersani et al., *Cancer Res* 74, 7229-7238, doi:10.1158/0008-5472.CAN-14-1809 (2014).

15 Cheng et al., *J Exp Med* 205, 2235-2249, doi:10.1084/jem.20080132 (2008).

16 Hiratsuka et al. *Nat Cell Biol* 10, 1349-1355, doi:10.1038/ncb1794 (2008).

17 Ouzounova et al., *Nat Commun* 8, 14979, doi:10.1038/ncomms14979 (2017).

18 Downs-Canner et al., *Nat Commun* 8, 14649, doi:10.1038/ncomms14649 (2017).

19 Weber et al., *Breast Cancer Res* 11, R6, doi:10.1186/bcr2221 (2009).

20 Youn et al., *J Leukoc Biol* 91, 167-181, doi:10.1189/jlb.0311177 (2012).

21 Kim et al. *Nat Commun* 9, 503, doi:10.1038/s41467-017-02731-6 (2018).

22 Muller et al., *Nature* 410, 50-56, doi:10.1038/35065016 (2001).

23 Curiel et al., *Nat Med* 10, 942-949, doi:10.1038/nm1093 (2004).

24 Kwa et al., *Nat Rev Clin Oncol* 14, 595-610, doi:10.1038/nrclinonc.2017.74 (2017).

25 Janes et al., *Curr Opin Chem Biol* 10, 73-80, doi:10.1016/j.cbpa.2005.12.016 (2006).

26 Alter et al., *Proceedings of the National Academy of Sciences* 97, 10101-10106, doi:10.1073/pnas.97.18.10101 (2000).

27 Breiman, *Machine Learning* 45, 5-32, doi:10.1023/a:1010933404324 (2001).

28 Decker et al., *Biotechnol Bioeng* 114, 2085-2095, doi:10.1002/bit.26293 (2017).

29 Paik et al., *N Engl J Med* 351, 2817-2826, doi:10.1056/NEJMoa041588 (2004).

30 van de Vijver et al., *N Engl J Med* 347, 1999-2009, doi:10.1056/NEJMoa021967 (2002).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method comprising:

a) measuring a level of expression of a panel of genes, RNAs, or proteins, in a test sample obtained from a synthetically-engineered pre-metastatic niche (pMN) implanted in a subject having or suspected of having cancer, wherein the test sample comprises immune cells and stromal cells and wherein less than 10% of the cells in the test sample are tumor cells;

b) determining that the subject has an increased metastatic potential based upon the level of expression of the panel of genes, RNAs, or proteins in the test sample relative to a control level or a level of expression at an earlier time point; and c) administering an anti-metastatic disease treatment to the subject determined in b) to have an increased metastatic potential, to thereby treat the subject for metastasis, wherein the subject is a mammal, and wherein the panel of genes, RNAs, or proteins comprises two or more of the following: S100 Calcium Binding Protein A8 (S100a8), S100 Calcium Binding Protein A9 (S100a9), Peptidoglycan Recognition Protein 1 (Pglyrpl), Lactotransferrin (Ltf), Cathelicidin Antimicrobial Peptide (Camp), Elastase 2 (Ela2), Chitinase (Chi313), Bone Morphogenetic Protein 15 (Bmp15), C-C Motif Chemokine Ligand 22 (Cc122), C-C Motif Chemokine Receptor 7 (Ccr7), granulocyte colony stimulating factor (G-CSF), interleukin 1-alpha (IL-1a), interleukin-12p70 (IL-12p70), interleukin-6 (IL-6), C-X-C motif chemokine 5 (Cxc15), interleukin-15 (IL-15), C-X-C motif chemokine 10 (Cxcl10), C-C motif chemokine ligand 2 (Cc12), C-X-C motif chemokine 9 (Cxc19), and C-C motif chemokine ligand 5 (Cc15).

2. The method of claim 1, wherein the control levels of the panel of genes, RNAs, or proteins are levels of a subject known to have metastatic disease or known to not have metastatic disease.

3. The method of claim 1, wherein the measured levels of the panel of genes, RNAs, or proteins form a pMN expression signature and wherein determining the subject's metastatic potential comprises processing the pMN expression signature through a decomposition algorithm to obtain a single score for gene expression and/or a machine learning algorithm to obtain a score of prediction of disease state.

4. The method of claim 3, wherein the decomposition algorithm is a singular value decomposition.

5. The method of claim 3, wherein the machine learning algorithm is a decision tree ensemble.

6. The method of claim 3, wherein the expression signature is processed through a decomposition algorithm to obtain a single score for gene expression and a machine learning algorithm to obtain a score of prediction of disease state.

7. The method of claim 6, wherein the single score for gene expression and the score of prediction of disease state are combined to provide a combined score of metastatic potential.

8. The method of claim 1, wherein the control levels of the genes, RNA, or proteins form a control pMN expression signature indicative of metastatic disease and wherein determining the subject's metastatic potential comprises processing the control pMN expression signature through a decomposition algorithm to obtain a single control score for gene expression and/or a machine learning algorithm to obtain a control score of prediction of disease state.

9. The method of claim 8, wherein the decomposition algorithm is a singular value decomposition.

10. The method of claim 8, wherein the machine learning algorithm is a decision tree ensemble.

11. The method of claim 8, wherein the control pMN expression signature is processed through a decomposition algorithm to obtain a single control score for gene expression and a machine learning algorithm to obtain a control score of prediction of disease state.

12. The method of claim 11, wherein the single control score for gene expression and the control score of prediction of disease state are combined to provide a combined control score.

13. The method of claim 12, wherein the combined score of metastatic potential is compared to the combined control score to determine the subject's metastatic potential.

14. The method of claim 1, wherein the control levels of the genes, RNA, or proteins form a control pMN expression signature indicative of no metastatic disease, and wherein determining the subject's metastatic potential comprises processing the control pMN expression signature through a decomposition algorithm to obtain a single control score for gene expression and/or a machine learning algorithm to obtain a control score of prediction of disease state.

15. The method of claim 14, wherein the decomposition algorithm is a singular value decomposition.

16. The method of claim 14, wherein the machine learning algorithm is a decision tree ensemble.

17. The method of claim 14, wherein the control pMN expression signature is processed through a decomposition algorithm to obtain a single control score for gene expression and a machine learning algorithm to obtain a control score of prediction of disease state.

18. The method of claim 17, wherein the single control score for gene expression and the control score of prediction of disease state are combined to provide a combined control score of no metastatic disease.

19. The method of claim 18, wherein the combined score of metastatic potential is compared to the combined control score of no metastatic disease to determine the subject's metastatic potential.

20. The method of claim 5, wherein the anti-metastatic disease treatment is a reactive nitrogen species (RNS) inhibitor, a nitroaspirin, a triterpenoid, a very small size proteoliposome (VSSP), a phosphodiesterase-5 (PDE-5) inhibitor, an exosome formation inhibitor, gemcitabine, 5-fluorouracil, a cyclooxygenase-2 (COX-2) inhibitor, a prostaglandin E2 (PGE2) inhibitor, sunitinib, amino bisphosphonate, doxorubicin, a cyclophosphamide, vemurafenib, a CXCR2 antagonist, a CXCR4 antagonist, vitamin D3, an anti-G-CSF antibody, an anti-Bv8 antibody, an anti-CSF-1 antibody, an anti-CCL2 antibody, a taxane, an all trans-retinoic acid (ATRA), a TLR9 activator, curcumin, whole-glucan particles (WGP), or a combination thereof.

21. The method of claim 1, wherein the earlier sample is obtained before surgical removal of a tumor, radiation therapy, or administration of a compound to the subject for treatment of cancer.

22. The method of claim 1, wherein the subject has or is suspected of having breast cancer.

* * * * *

SEQUENCE LISTING

<160> NUMBER OF SEQ ID NOS: 90

<210> SEQ ID NO 1
<211> LENGTH: 2933
<212> TYPE: DNA

<213> ORGANISM: Homo sapiens
<300> PUBLICATION INFORMATION:
<308> DATABASE ACCESSION NUMBER: NCBI / NM_002990.4
<309> DATABASE ENTRY DATE: 2017-09-10
<313> RELEVANT RESIDUES IN SEQ ID NO: (1)..(2933)

<400> SEQUENCE: 1
gcagacacct gggctgagac atacaggaca gagcatggat cgcctacaga ctgcactcct 60
ggttgtcctc gtcctccttg ctgtggcgct tcaagcaact gaggcaggcc cctacggcgc 120
caacatggaa gacagcgtct gctgccgtga ttacgtccgt taccgtctgc ccctgcgcgt 180
ggtgaaacac ttctactgga cctcagactc ctgcccgagg cctggcgtgg tgttgctaac 240
cttcagggat aaggagatct gtgccgatcc cagagtgccc tgggtgaaga tgattctcaa 300
taagctgagc caatgaagag cctactctga tgaccgtggc cttggctcct ccaggaaggc 360
tcaggagccc tacctccctg ccattatagc tgctccccgc cagaagcctg tgccaactct 420
ctgcattccc tgatctccat ccctgtggct gtcacccttg gtcacctccg tgctgtcact 480
gccatctccc ccctgacccc tctaacccat cctctgcctc cctccctgca gtcagagggt 540
cctgttccca tcagcgattc ccctgcttaa acccttccat gactccccac tgccctaagc 600
tgaggtcagt ctcccaagcc tggcatgtgg ccctctggat ctgggttcca tctctgtctc 660
cagcctgccc acttcccttc atgaatgttg ggttctagct ccctgttctc caaacccata 720
ctacacatcc cacttctggg tctttgcctg ggatgttgct gacacccaga aagtcccacc 780
acctgcacat gtgtagcccc accagccctc caaggcattg ctcgcccaag cagctggtaa 840
ttccatttca tgtattagat gtcccctggc cctctgtccc ctcttaataa ccctagtcac 900
agtctccgca gattcttggg atttgggggt tttctccccc acctctccac tagttggacc 960
aaggtttcta gctaagttac tctagtctcc aagcctctag catagagcac tgcagacagg 1020
ccctggctca gaatcagagc ccagaaagtg gctgcagaca aaatcaataa aactaatgtc 1080
cctcccctct ccctgccaaa aggcagttac atatcaatac agagactcaa ggtcactaga 1140
aatgggccag ctgggtcaat gtgaagcccc aaatttgccc agattcacct ttcttccccc 1200
actccctttt tttttttttt tttgagatgg agtttcgctc ttgtcaccca cgctggagtg 1260
caatggtgtg gtcttggctt attgaagcct ctgcctcctg ggttcaagtg attctcttgc 1320
ctcagcctcc tgagtagctg ggattacagg ttcctgctac cacgcccagc taatttttgt 1380
atttttagta gagacgaggc ttcaccatgt tggccaggct ggtctcgaac tcctgtcctc 1440
aggtaatccg cccacctcag cctcccaaag tgctgggatt acaggcgtga gccacagtgc 1500
ctggcctctt ccctctcccc accccccccc caactttttt ttttttttat ggcagggtct 1560
cactctgtcg cccaggctgg agtgcagtgg cgtgatctcg gctcactaca acctcgacct 1620
cctgggttca agcgattctc ccaccccagc ctcccaagta gctgggatta caggtgtgtg 1680
ccactacggc tggctaattt ttgtattttt agtagagaca ggtttcacca tattggccag 1740
gctggtcttg aactcctgac ctcaagtgat ccaccttcct tgtgctccca aagtgctgag 1800
attacaggcg tgagctatca cacccagcct ccccctttt ttcctaatag gagactcctg 1860
tacctttctt cgttttacct atgtgtcgtg tctgcttaca tttccttctc ccctcaggct 1920
ttttttgggt ggtcctccaa cctccaatac ccaggcctgg cctcttcaga gtacccccca 1980
ttccactttc cctgcctcct tccttaaata gctgacaatc aaattcatgc tatggtgtga 2040
aagactacct ttgacttggt attataagct ggagttatat atgtatttga aaacagagta 2100
aatacttaag aggccaaata gatgaatgga agaattttag gaactgtgag agggggacaa 2160
ggtggagctt tcctggccct gggaggaagc tggctgtggt agcgtagcgc tctctctctc 2220
tgtctgtggc aggaggcaaa gagtagggtg taattgagtg aaggaatcct gggtagagac 2280
cattctcagg tggttgggcc aggctaaaga ctgggatttg ggtctatcta tgcctttctg 2340
gctgattttt gtagagacgg ggttttgcca tgttacccag gctggtctca aactcctggg 2400
ctcaagcgat cctcctggct cagcctccca aagtgctggg attacaggcg tgagtcactg 2460
cgcctggctt cctcttcctc ttgagaaata ttcttttcat acagcaagta tgggacagca 2520
gtgtcccagg taaaggacat aaatgttaca agtgtctggt cctttctgag ggaggctggt 2580
gccgctctgc agggtatttg aacctgtgga attggaggag gccatttcac tccctgaacc 2640
cagcctgaca aatcacagtg agaatgttca ccttataggc ttgctgtggg gctcaggttg 2700
aaagtgtggg gagtgacact gcctaggcat ccagctcagt gtcatccagg gcctgtgtcc 2760
ctcccgaacc cagggtcaac ctgcctacca caggcactag aaggacgaat ctgcctactg 2820
cccatgaacg gggccctcaa gcgtcctggg atctccttct ccctcctgtc ctgtccttgc 2880
ccctcaggac tgctggaaaa taaatccttt aaaatagtaa aaaaaaaaaa aaa 2933

<210> SEQ ID NO 2
<211> LENGTH: 93
<212> TYPE: PRT
<213> ORGANISM: Homo sapiens
<300> PUBLICATION INFORMATION:
<308> DATABASE ACCESSION NUMBER: NCBI / NP_002981.2
<309> DATABASE ENTRY DATE: 2017-09-10
<313> RELEVANT RESIDUES IN SEQ ID NO: (1)..(93)

<400> SEQUENCE: 2

Met Asp Arg Leu Gln Thr Ala Leu Leu Val Val Leu Val Leu Leu Ala
1 5 10 15

Val Ala Leu Gln Ala Thr Glu Ala Gly Pro Tyr Gly Ala Asn Met Glu
20 25 30

Asp Ser Val Cys Cys Arg Asp Tyr Val Arg Tyr Arg Leu Pro Leu Arg
35 40 45

Val Val Lys His Phe Tyr Trp Thr Ser Asp Ser Cys Pro Arg Pro Gly
50 55 60

Val Val Leu Leu Thr Phe Arg Asp Lys Glu Ile Cys Ala Asp Pro Arg
65 70 75 80

Val Pro Trp Val Lys Met Ile Leu Asn Lys Leu Ser Gln
85 90

<210> SEQ ID NO 3
<211> LENGTH: 1234
<212> TYPE: DNA
<213> ORGANISM: Homo sapiens
<300> PUBLICATION INFORMATION:
<308> DATABASE ACCESSION NUMBER: NCBI / NM_002089.3
<309> DATABASE ENTRY DATE: 2017-05-07
<313> RELEVANT RESIDUES IN SEQ ID NO: (1)..(1234)

<400> SEQUENCE: 3
gagctccggg aatttccctg gcccgggact ccgggctttc cagccccaac catgcataaa 60
aggggttcgc cgttctcgga gagccacaga gcccgggcca caggcagctc cttgccagct 120
ctcctcctcg cacagccgct cgaaccgcct gctgagcccc atggcccgcg ccacgctctc 180
cgccgccccc agcaatcccc ggctcctgcg ggtggcgctg ctgctcctgc tcctggtggc 240
cgccagccgg cgcgcagcag gagcgcccct ggccactgaa ctgcgctgcc agtgcttgca 300

```
gaccctgcag ggaattcacc tcaagaacat ccaaagtgtg aaggtgaagt cccccggacc    360

ccactgcgcc caaaccgaag tcatagccac actcaagaat gggcagaaag cttgtctcaa    420

ccccgcatcg cccatggtta agaaaatcat cgaaaagatg ctgaaaaatg gcaaatccaa    480

ctgaccagaa ggaaggagga agcttattgg tggctgttcc tgaaggaggc cctgccctta    540

caggaacaga agaggaaaga gagacacagc tgcagaggcc acctggattg cgcctaatgt    600

gtttgagcat cacttaggag aagtcttcta tttatttatt tatttattta tttgtttgtt    660

ttagaagatt ctatgttaat attttatgtg taaaataagg ttatgattga atctacttgc    720

acactctccc attatattta ttgtttattt taggtcaaac ccaagttagt tcaatcctga    780

ttcatattta atttgaagat agaaggtttg cagatattct ctagtcattt gttaatattt    840

cttcgtgatg acatatcaca tgtcagccac tgtgatagag gctgaggaat ccaagaaaat    900

ggccagtgag atcaatgtga cggcagggaa atgtatgtgt gtctattttg taactgtaaa    960

gatgaatgtc agttgttatt tattgaaatg atttcacagt gtgtggtcaa catttctcat   1020

gttgaagctt taagaactaa aatgttctaa atatcccttg gacattttat gtctttcttg   1080

taaggcatac tgccttgttt aatgttaatt atgcagtgtt tccctctgtg ttagagcaga   1140

gaggtttcga tatttattga tgttttcaca aagaacagga aaataaaata tttaaaaata   1200

taaaaaaaaa aaaaaaaaaa aaaaaaaaaa aaaa                               1234
```

```
<210> SEQ ID NO 4
<211> LENGTH: 107
<212> TYPE: PRT
<213> ORGANISM: Homo sapiens
<300> PUBLICATION INFORMATION:
<308> DATABASE ACCESSION NUMBER: NCBI / NP_002080.1
<309> DATABASE ENTRY DATE: 2017-05-07
<313> RELEVANT RESIDUES IN SEQ ID NO: (1)..(107)

<400> SEQUENCE: 4

Met Ala Arg Ala Thr Leu Ser Ala Ala Pro Ser Asn Pro Arg Leu Leu
1               5                   10                  15

Arg Val Ala Leu Leu Leu Leu Leu Leu Val Ala Ala Ser Arg Arg Ala
            20                  25                  30

Ala Gly Ala Pro Leu Ala Thr Glu Leu Arg Cys Gln Cys Leu Gln Thr
        35                  40                  45

Leu Gln Gly Ile His Leu Lys Asn Ile Gln Ser Val Lys Val Lys Ser
    50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105


<210> SEQ ID NO 5
<211> LENGTH: 2157
<212> TYPE: DNA
<213> ORGANISM: Homo sapiens
<300> PUBLICATION INFORMATION:
<308> DATABASE ACCESSION NUMBER: NCBI / NM_001301714.1
<309> DATABASE ENTRY DATE: 2017-09-11
<313> RELEVANT RESIDUES IN SEQ ID NO: (1)..(2157)

<400> SEQUENCE: 5

cacttcctcc ccagacaggg gtagtgcgag gccgggcaca gccttcctgt gtggttttac     60
```

-continued

```
cgcccagaga gcgtcatgga cctgggtatg cctgtgtcaa gatgaggtca cggacgatta    120
catcggagac aacaccacag tggactacac tttgttcgag tctttgtgct ccaagaagga    180
cgtgcggaac tttaaagcct ggttcctccc tatcatgtac tccatcattt gtttcgtggg    240
cctactgggc aatgggctgg tcgtgttgac ctatatctat ttcaagaggc tcaagaccat    300
gaccgatacc tacctgctca acctggcggt ggcagacatc ctcttcctcc tgacccttcc    360
cttctgggcc tacagcgcgg ccaagtcctg ggtcttcggt gtccactttt gcaagctcat    420
ctttgccatc tacaagatga gcttcttcag tggcatgctc ctacttcttt gcatcagcat    480
tgaccgctac gtggccatcg tccaggctgt ctcagctcac cgccaccgtg cccgcgtcct    540
tctcatcagc aagctgtcct gtgtgggcat ctggatacta gccacagtgc tctccatccc    600
agagctcctg tacagtgacc tccagaggag cagcagtgag caagcgatgc gatgctctct    660
catcacagag catgtggagg cctttatcac catccaggtg gcccagatgg tgatcggctt    720
tctggtcccc ctgctggcca tgagcttctg ttaccttgtc atcatccgca ccctgctcca    780
ggcacgcaac tttgagcgca acaaggccat caaggtgatc atcgctgtgg tcgtggtctt    840
catagtcttc cagctgccct acaatggggt ggtcctggcc cagacggtgg ccaacttcaa    900
catcaccagt agcacctgtg agctcagtaa gcaactcaac atcgcctacg acgtcaccta    960
cagcctggcc tgcgtccgct gctgcgtcaa ccctttcttg tacgccttca tcggcgtcaa   1020
gttccgcaac gatctcttca agctcttcaa ggacctgggc tgcctcagcc aggagcagct   1080
ccggcagtgg tcttcctgtc ggcacatccg gcgctcctcc atgagtgtgg aggccgagac   1140
caccaccacc ttctccccat aggcgactct tctgcctgga ctagagggac ctctcccagg   1200
gtccctgggg tggggatagg gagcagatgc aatgactcag gacatccccc cgccaaaagc   1260
tgctcaggga aaagcagctc tcccctcaga gtgcaagccc ctgctccaga agatagcttc   1320
accccaatcc cagctacctc aaccaatgcc aaaaaaagac agggctgata agctaacacc   1380
agacagacaa cactgggaaa cagaggctat tgtcccctaa accaaaaact gaaagtgaaa   1440
gtccagaaac tgttcccacc tgctggagtg aaggggccaa ggagggtgag tgcaaggggc   1500
gtgggagtgg cctgaagagt cctctgaatg aaccttctgg cctcccacag actcaaatgc   1560
tcagaccagc tcttccgaaa accaggcctt atctccaaga ccagagatag tggggagact   1620
tcttggcttg gtgaggaaaa gcggacatca gctggtcaaa caaactctct gaacccctcc   1680
ctccatcgtt ttcttcactg tcctccaagc cagcgggaat ggcagctgcc acgccgccct   1740
aaaagcacac tcatcccctc acttgccgcg tcgccctccc aggctctcaa caggggagag   1800
tgtggtgttt cctgcaggcc aggccagctg cctccgcgtg atcaaagcca cactctgggc   1860
tccagagtgg ggatgacatg cactcagctc ttggctccac tgggatggga ggagaggaca   1920
agggaaatgt caggggcggg gagggtgaca gtggccgccc aaggcccacg agcttgttct   1980
ttgttctttg tcacagggac tgaaaacctc tcctcatgtt ctgctttcga ttcgttaaga   2040
gagcaacatt ttacccacac acagataaag ttttcccttg aggaaacaac agctttaaaa   2100
gaaaaagaaa aaaaaagtct ttggtaaatg gcaaaaaaaa aaaaaaaaaa aaaaaaa      2157
```

<210> SEQ ID NO 6
<211> LENGTH: 315
<212> TYPE: PRT
<213> ORGANISM: Homo sapiens
<300> PUBLICATION INFORMATION:
<308> DATABASE ACCESSION NUMBER: NCBI / NP_001288643.1
<309> DATABASE ENTRY DATE: 2017-09-11
<313> RELEVANT RESIDUES IN SEQ ID NO: (1)..(315)

<400> SEQUENCE: 6

```
Met Tyr Ser Ile Ile Cys Phe Val Gly Leu Leu Gly Asn Gly Leu Val
1               5                   10                  15

Val Leu Thr Tyr Ile Tyr Phe Lys Arg Leu Lys Thr Met Thr Asp Thr
            20                  25                  30

Tyr Leu Leu Asn Leu Ala Val Ala Asp Ile Leu Phe Leu Leu Thr Leu
        35                  40                  45

Pro Phe Trp Ala Tyr Ser Ala Ala Lys Ser Trp Val Phe Gly Val His
    50                  55                  60

Phe Cys Lys Leu Ile Phe Ala Ile Tyr Lys Met Ser Phe Phe Ser Gly
65                  70                  75                  80

Met Leu Leu Leu Leu Cys Ile Ser Ile Asp Arg Tyr Val Ala Ile Val
                85                  90                  95

Gln Ala Val Ser Ala His Arg His Arg Ala Arg Val Leu Leu Ile Ser
            100                 105                 110

Lys Leu Ser Cys Val Gly Ile Trp Ile Leu Ala Thr Val Leu Ser Ile
        115                 120                 125

Pro Glu Leu Leu Tyr Ser Asp Leu Gln Arg Ser Ser Ser Glu Gln Ala
    130                 135                 140

Met Arg Cys Ser Leu Ile Thr Glu His Val Glu Ala Phe Ile Thr Ile
145                 150                 155                 160

Gln Val Ala Gln Met Val Ile Gly Phe Leu Val Pro Leu Leu Ala Met
                165                 170                 175

Ser Phe Cys Tyr Leu Val Ile Ile Arg Thr Leu Leu Gln Ala Arg Asn
            180                 185                 190

Phe Glu Arg Asn Lys Ala Ile Lys Val Ile Ile Ala Val Val Val Val
        195                 200                 205

Phe Ile Val Phe Gln Leu Pro Tyr Asn Gly Val Val Leu Ala Gln Thr
    210                 215                 220

Val Ala Asn Phe Asn Ile Thr Ser Ser Thr Cys Glu Leu Ser Lys Gln
225                 230                 235                 240

Leu Asn Ile Ala Tyr Asp Val Thr Tyr Ser Leu Ala Cys Val Arg Cys
                245                 250                 255

Cys Val Asn Pro Phe Leu Tyr Ala Phe Ile Gly Val Lys Phe Arg Asn
            260                 265                 270

Asp Leu Phe Lys Leu Phe Lys Asp Leu Gly Cys Leu Ser Gln Glu Gln
        275                 280                 285

Leu Arg Gln Trp Ser Ser Cys Arg His Ile Arg Arg Ser Ser Met Ser
    290                 295                 300

Val Glu Ala Glu Thr Thr Thr Thr Phe Ser Pro
305                 310                 315
```

<210> SEQ ID NO 7
<211> LENGTH: 2457
<212> TYPE: DNA
<213> ORGANISM: Homo sapiens
<300> PUBLICATION INFORMATION:
<308> DATABASE ACCESSION NUMBER: NCBI / NM_001301716.1
<309> DATABASE ENTRY DATE: 2017-09-11
<313> RELEVANT RESIDUES IN SEQ ID NO: (1)..(2457)

<400> SEQUENCE: 7

```
ctctagatga gtcagtggag ggcgggtgga gcgttgaacc gtgaagagtg tggttgggcg      60

taaacgtgga cttaaactca ggagctaagg ggtaattcag tgaaaaaggg gaatgagcgg     120
```

```
tggggagctc tgttgcaaca gggtccaatc gcagcaggac tacaaatgcc cgagcgcagg    180
ctgggaacga ggggacagcg gctgcctgtc cccagaatag aaaatgcagc taggaagccc    240
tctttgagtg gacagcggag gactggactg ccaggccaag catcaggggc ttcatcctca    300
gggccggtta gagcccctga ggatttagga ggaagggaaa ccaatgaaaa gcgtgctggt    360
ggtggctctc cttgtcattt tccaggtatg cctgtgtcaa gatgaggtca cggacgatta    420
catcggagac aacaccacag tggactacac tttgttcgag tctttgtgct ccaagaagga    480
cgtgcggaac tttaaagcct ggttcctccc tatcatgtac tccatcattt gtttcgtggg    540
cctactgggc aatgggctgg tcgtgttgac ctatatctat ttcaagaggc tcaagaccat    600
gaccgatacc tacctgctca acctggcggt ggcagacatc ctcttcctcc tgacccttcc    660
cttctgggcc tacagcgcgg ccaagtcctg ggtcttcggt gtccactttt gcaagctcat    720
ctttgccatc tacaagatga gcttcttcag tggcatgctc ctacttcttt gcatcagcat    780
tgaccgctac gtggccatcg tccaggctgt ctcagctcac cgccaccgtg cccgcgtcct    840
tctcatcagc aagctgtcct gtgtgggcat ctggatacta gccacagtgc tctccatccc    900
agagctcctg tacagtgacc tccagaggag cagcagtgag caagcgatgc gatgctctct    960
catcacagag catgtggagg cctttatcac catccaggtg gcccagatgg tgatcggctt   1020
tctggtcccc ctgctggcca tgagcttctg ttaccttgtc atcatccgca ccctgctcca   1080
ggcacgcaac tttgagcgca acaaggccat caaggtgatc atcgctgtgg tcgtggtctt   1140
catagtcttc cagctgccct acaatggggt ggtcctggcc cagacggtgg ccaacttcaa   1200
catcaccagt agcacctgtg agctcagtaa gcaactcaac atcgcctacg acgtcaccta   1260
cagcctggcc tgcgtccgct gctgcgtcaa ccctttcttg tacgccttca tcggcgtcaa   1320
gttccgcaac gatctcttca agctcttcaa ggacctgggc tgcctcagcc aggagcagct   1380
ccggcagtgg tcttcctgtc ggcacatccg gcgctcctcc atgagtgtgg aggccgagac   1440
caccaccacc ttctccccat aggcgactct tctgcctgga ctagagggac ctctcccagg   1500
gtccctgggg tggggatagg gagcagatgc aatgactcag gacatccccc cgccaaaagc   1560
tgctcaggga aaagcagctc tcccctcaga gtgcaagccc ctgctccaga agatagcttc   1620
accccaatcc cagctacctc aaccaatgcc aaaaaaagac agggctgata agctaacacc   1680
agacagacaa cactgggaaa cagaggctat tgtcccctaa accaaaaact gaaagtgaaa   1740
gtccagaaac tgttcccacc tgctggagtg aaggggccaa ggagggtgag tgcaaggggc   1800
gtgggagtgg cctgaagagt cctctgaatg aaccttctgg cctcccacag actcaaatgc   1860
tcagaccagc tcttccgaaa accaggcctt atctccaaga ccagagatag tggggagact   1920
tcttggcttg gtgaggaaaa gcggacatca gctggtcaaa caaactctct gaacccctcc   1980
ctccatcgtt ttcttcactg tcctccaagc cagcgggaat ggcagctgcc acgccgccct   2040
aaaagcacac tcatcccctc acttgccgcg tcgccctccc aggctctcaa caggggagag   2100
tgtggtgttt cctgcaggcc aggccagctg cctccgcgtg atcaaagcca cactctgggc   2160
tccagagtgg ggatgacatg cactcagctc ttggctccac tgggatggga ggagaggaca   2220
agggaaatgt caggggcggg gagggtgaca gtggccgccc aaggcccacg agcttgttct   2280
ttgttctttg tcacagggac tgaaaacctc tcctcatgtt ctgctttcga ttcgttaaga   2340
gagcaacatt ttacccacac acagataaag ttttcccttg aggaaacaac agctttaaaa   2400
gaaaaagaaa aaaaaagtct ttggtaaatg gcaaaaaaaa aaaaaaaaaa aaaaaaa      2457
```

<210> SEQ ID NO 8
<211> LENGTH: 372
<212> TYPE: PRT
<213> ORGANISM: Homo sapiens
<300> PUBLICATION INFORMATION:
<308> DATABASE ACCESSION NUMBER: NCBI / NP_001288645.1
<309> DATABASE ENTRY DATE: 2017-09-11
<313> RELEVANT RESIDUES IN SEQ ID NO: (1)..(372)

<400> SEQUENCE: 8

```
Met Lys Ser Val Leu Val Val Ala Leu Leu Val Ile Phe Gln Val Cys
1               5                   10                  15

Leu Cys Gln Asp Glu Val Thr Asp Asp Tyr Ile Gly Asp Asn Thr Thr
            20                  25                  30

Val Asp Tyr Thr Leu Phe Glu Ser Leu Cys Ser Lys Lys Asp Val Arg
        35                  40                  45

Asn Phe Lys Ala Trp Phe Leu Pro Ile Met Tyr Ser Ile Ile Cys Phe
    50                  55                  60

Val Gly Leu Leu Gly Asn Gly Leu Val Val Leu Thr Tyr Ile Tyr Phe
65                  70                  75                  80

Lys Arg Leu Lys Thr Met Thr Asp Thr Tyr Leu Leu Asn Leu Ala Val
                85                  90                  95

Ala Asp Ile Leu Phe Leu Leu Thr Leu Pro Phe Trp Ala Tyr Ser Ala
            100                 105                 110

Ala Lys Ser Trp Val Phe Gly Val His Phe Cys Lys Leu Ile Phe Ala
        115                 120                 125

Ile Tyr Lys Met Ser Phe Phe Ser Gly Met Leu Leu Leu Leu Cys Ile
    130                 135                 140

Ser Ile Asp Arg Tyr Val Ala Ile Val Gln Ala Val Ser Ala His Arg
145                 150                 155                 160

His Arg Ala Arg Val Leu Leu Ile Ser Lys Leu Ser Cys Val Gly Ile
                165                 170                 175

Trp Ile Leu Ala Thr Val Leu Ser Ile Pro Glu Leu Leu Tyr Ser Asp
            180                 185                 190

Leu Gln Arg Ser Ser Ser Glu Gln Ala Met Arg Cys Ser Leu Ile Thr
        195                 200                 205

Glu His Val Glu Ala Phe Ile Thr Ile Gln Val Ala Gln Met Val Ile
    210                 215                 220

Gly Phe Leu Val Pro Leu Leu Ala Met Ser Phe Cys Tyr Leu Val Ile
225                 230                 235                 240

Ile Arg Thr Leu Leu Gln Ala Arg Asn Phe Glu Arg Asn Lys Ala Ile
                245                 250                 255

Lys Val Ile Ile Ala Val Val Val Val Phe Ile Val Phe Gln Leu Pro
            260                 265                 270

Tyr Asn Gly Val Val Leu Ala Gln Thr Val Ala Asn Phe Asn Ile Thr
        275                 280                 285

Ser Ser Thr Cys Glu Leu Ser Lys Gln Leu Asn Ile Ala Tyr Asp Val
    290                 295                 300

Thr Tyr Ser Leu Ala Cys Val Arg Cys Cys Val Asn Pro Phe Leu Tyr
305                 310                 315                 320

Ala Phe Ile Gly Val Lys Phe Arg Asn Asp Leu Phe Lys Leu Phe Lys
                325                 330                 335

Asp Leu Gly Cys Leu Ser Gln Glu Gln Leu Arg Gln Trp Ser Ser Cys
            340                 345                 350

Arg His Ile Arg Arg Ser Ser Met Ser Val Glu Ala Glu Thr Thr Thr
        355                 360                 365
```

Thr Phe Ser Pro
370

<210> SEQ ID NO 9
<211> LENGTH: 2213
<212> TYPE: DNA
<213> ORGANISM: Homo sapiens
<300> PUBLICATION INFORMATION:
<308> DATABASE ACCESSION NUMBER: NCBI / NM_001301717.1
<309> DATABASE ENTRY DATE: 2017-09-11
<313> RELEVANT RESIDUES IN SEQ ID NO: (1)..(2213)

<400> SEQUENCE: 9
ctctagatga gtcagtggag ggcgggtgga gcgttgaacc gtgaagagtg tggttgggcg 60
taaacgtgga cttaaactca ggagctaagg gggaaaccaa tgaaaagcgt gctggtggtg 120
gctctccttg tcattttcca ggtatgcctg tgtcaagatg aggtcacgga cgattacatc 180
ggagacaaca ccacagtgga ctacactttg ttcgagtctt tgtgctccaa gaaggacgtg 240
cggaacttta aagcctggtt cctccctatc atgtactcca tcatttgttt cgtgggccta 300
ctgggcaatg ggctggtcgt gttgacctat atctatttca agaggctcaa gaccatgacc 360
gatacctacc tgctcaacct ggcggtggca gacatcctct tcctcctgac ccttcccttc 420
tgggcctaca gcgcggccaa gtcctgggtc ttcggtgtcc acttttgcaa gctcatcttt 480
gccatctaca agatgagctt cttcagtggc atgctcctac ttctttgcat cagcattgac 540
cgctacgtgg ccatcgtcca ggctgtctca gctcaccgcc accgtgcccg cgtccttctc 600
atcagcaagc tgtcctgtgt gggcatctgg atactagcca cagtgctctc catcccagag 660
ctcctgtaca gtgacctcca gaggagcagc agtgagcaag cgatgcgatg ctctctcatc 720
acagagcatg tggaggcctt tatcaccatc caggtggccc agatggtgat cggctttctg 780 gtcccccctgc tggccatgag cttctgttac cttgtcatca tccgcaccct gctccaggca 840
cgcaactttg agcgcaacaa ggccatcaag gtgatcatcg ctgtggtcgt ggtcttcata 900
gtcttccagc tgccctacaa tggggtggtc ctggcccaga cggtggccaa cttcaacatc 960
accagtagca cctgtgagct cagtaagcaa ctcaacatcg cctacgacgt cacctacagc 1020
ctggcctgcg tccgctgctg cgtcaaccct ttcttgtacg ccttcatcgg cgtcaagttc 1080
cgcaacgatc tcttcaagct cttcaaggac ctgggctgcc tcagccagga gcagctccgg 1140
cagtggtctt cctgtcggca catccggcgc tcctccatga gtgtggaggc cgagaccacc 1200
accaccttct ccccataggc gactcttctg cctggactag agggacctct cccagggtcc 1260
ctggggtggg gatagggagc agatgcaatg actcaggaca tcccccccgcc aaaagctgct 1320 cagggaaaag cagctctccc ctcagagtgc aagcccctgc tccagaagat agcttcaccc 1380
caatcccagc tacctcaacc aatgccaaaa aaagacaggg ctgataagct aacaccagac 1440
agacaacact gggaaacaga ggctattgtc ccctaaacca aaaactgaaa gtgaaagtcc 1500
agaaactgtt cccacctgct ggagtgaagg ggccaaggag ggtgagtgca aggggcgtgg 1560
gagtggcctg aagagtcctc tgaatgaacc ttctggcctc ccacagactc aaatgctcag 1620
accagctctt ccgaaaacca ggccttatct ccaagaccag agatagtggg gagacttctt 1680
ggcttggtga ggaaaagcgg acatcagctg gtcaaacaaa ctctctgaac ccctccctcc 1740
atcgttttct tcactgtcct ccaagccagc gggaatggca gctgccacgc cgccctaaaa 1800
gcacactcat cccctcactt gccgcgtcgc cctcccaggc tctcaacagg ggagagtgtg 1860
gtgtttcctg caggccaggc cagctgcctc cgcgtgatca aagccacact ctgggctcca 1920
gagtggggat gacatgcact cagctcttgg ctccactggg atgggaggag aggacaaggg 1980
aaatgtcagg ggcggggagg gtgacagtgg ccgccccaagg cccacgagct tgttctttgt 2040
tctttgtcac agggactgaa aacctctcct catgttctgc tttcgattcg ttaagagagc 2100
aacattttac ccacacacag ataaagtttt cccttgagga aacaacagct ttaaaagaaa 2160
aagaaaaaaa aagtctttgg taaatggcaa aaaaaaaaaa aaaaaaaaaa aaa 2213

<210> SEQ ID NO 10
<211> LENGTH: 372
<212> TYPE: PRT
<213> ORGANISM: Homo sapiens
<300> PUBLICATION INFORMATION:
<308> DATABASE ACCESSION NUMBER: NCBI / NP_001288646.1
<309> DATABASE ENTRY DATE: 2017-09-11
<313> RELEVANT RESIDUES IN SEQ ID NO: (1)..(372)

<400> SEQUENCE: 10

Met Lys Ser Val Leu Val Val Ala Leu Leu Val Ile Phe Gln Val Cys
1 5 10 15

Leu Cys Gln Asp Glu Val Thr Asp Asp Tyr Ile Gly Asp Asn Thr Thr
20 25 30

Val Asp Tyr Thr Leu Phe Glu Ser Leu Cys Ser Lys Lys Asp Val Arg
35 40 45

Asn Phe Lys Ala Trp Phe Leu Pro Ile Met Tyr Ser Ile Ile Cys Phe
50 55 60

Val Gly Leu Leu Gly Asn Gly Leu Val Val Leu Thr Tyr Ile Tyr Phe
65 70 75 80

Lys Arg Leu Lys Thr Met Thr Asp Thr Tyr Leu Leu Asn Leu Ala Val
85 90 95

Ala Asp Ile Leu Phe Leu Leu Thr Leu Pro Phe Trp Ala Tyr Ser Ala
100 105 110

Ala Lys Ser Trp Val Phe Gly Val His Phe Cys Lys Leu Ile Phe Ala
115 120 125

Ile Tyr Lys Met Ser Phe Phe Ser Gly Met Leu Leu Leu Leu Cys Ile
130 135 140

Ser Ile Asp Arg Tyr Val Ala Ile Val Gln Ala Val Ser Ala His Arg
145 150 155 160

His Arg Ala Arg Val Leu Leu Ile Ser Lys Leu Ser Cys Val Gly Ile
165 170 175

Trp Ile Leu Ala Thr Val Leu Ser Ile Pro Glu Leu Leu Tyr Ser Asp
180 185 190

Leu Gln Arg Ser Ser Ser Glu Gln Ala Met Arg Cys Ser Leu Ile Thr
195 200 205

Glu His Val Glu Ala Phe Ile Thr Ile Gln Val Ala Gln Met Val Ile
210 215 220

Gly Phe Leu Val Pro Leu Leu Ala Met Ser Phe Cys Tyr Leu Val Ile
225 230 235 240

Ile Arg Thr Leu Leu Gln Ala Arg Asn Phe Glu Arg Asn Lys Ala Ile
245 250 255

Lys Val Ile Ile Ala Val Val Val Val Phe Ile Val Phe Gln Leu Pro
260 265 270

Tyr Asn Gly Val Val Leu Ala Gln Thr Val Ala Asn Phe Asn Ile Thr
275 280 285

Ser Ser Thr Cys Glu Leu Ser Lys Gln Leu Asn Ile Ala Tyr Asp Val
290 295 300

```
Thr Tyr Ser Leu Ala Cys Val Arg Cys Cys Val Asn Pro Phe Leu Tyr
305                 310                 315                 320

Ala Phe Ile Gly Val Lys Phe Arg Asn Asp Leu Phe Lys Leu Phe Lys
                325                 330                 335

Asp Leu Gly Cys Leu Ser Gln Glu Gln Leu Arg Gln Trp Ser Ser Cys
            340                 345                 350

Arg His Ile Arg Arg Ser Ser Met Ser Val Glu Ala Glu Thr Thr Thr
        355                 360                 365

Thr Phe Ser Pro
    370


<210> SEQ ID NO 11
<211> LENGTH: 2303
<212> TYPE: DNA
<213> ORGANISM: Homo sapiens
<300> PUBLICATION INFORMATION:
<308> DATABASE ACCESSION NUMBER: NCBI / NM_001301718.1
<309> DATABASE ENTRY DATE: 2017-09-11
<313> RELEVANT RESIDUES IN SEQ ID NO: (1)..(2303)

<400> SEQUENCE: 11

aggagaaggt gccttaaaca ggttcccacg catttcctgg cgctattgag cttggagctg     60

ccaagggcct gccttcactt gtggcatcgc agttactgac tctccagtgg gccaggccct    120

acctagctgg gacctgaggg tcaggatacg ggaagagggc tactgccgcc ctgacttgta    180

gggaaaccaa tgaaaagcgt gctggtggtg gctctccttg tcattttcca ggtatgcctg    240

tgtcaagatg aggtcacgga cgattacatc ggagacaaca ccacagtgga ctacactttg    300

ttcgagtctt tgtgctccaa gaaggacgtg cggaacttta aagcctggtt cctccctatc    360

atgtactcca tcatttgttt cgtgggccta ctgggcaatg ggctggtcgt gttgacctat    420

atctatttca agaggctcaa gaccatgacc gatacctacc tgctcaacct ggcggtggca    480

gacatcctct tcctcctgac ccttcccttc tgggcctaca gcgcggccaa gtcctgggtc    540

ttcggtgtcc acttttgcaa gctcatcttt gccatctaca agatgagctt cttcagtggc    600

atgctcctac ttctttgcat cagcattgac cgctacgtgg ccatcgtcca ggctgtctca    660

gctcaccgcc accgtgcccg cgtccttctc atcagcaagc tgtcctgtgt gggcatctgg    720

atactagcca cagtgctctc catcccagag ctcctgtaca gtgacctcca gaggagcagc    780

agtgagcaag cgatgcgatg ctctctcatc acagagcatg tggaggcctt tatcaccatc    840

caggtggccc agatggtgat cggctttctg gtcccccctgc tggccatgag cttctgttac    900

cttgtcatca tccgcaccct gctccaggca cgcaactttg agcgcaacaa ggccatcaag    960

gtgatcatcg ctgtggtcgt ggtcttcata gtcttccagc tgccctacaa tggggtggtc   1020

ctggcccaga cggtggccaa cttcaacatc accagtagca cctgtgagct cagtaagcaa   1080

ctcaacatcg cctacgacgt cacctacagc ctggcctgcg tccgctgctg cgtcaaccct   1140

ttcttgtacg ccttcatcgg cgtcaagttc cgcaacgatc tcttcaagct cttcaaggac   1200

ctgggctgcc tcagccagga gcagctccgg cagtggtctt cctgtcggca catccggcgc   1260

tcctccatga gtgtggaggc cgagaccacc accaccttct ccccataggc gactcttctg   1320

cctggactag agggacctct cccagggtcc ctggggtggg gatagggagc agatgcaatg   1380

actcaggaca tccccccgcc aaaagctgct cagggaaaag cagctctccc ctcagagtgc   1440

aagcccctgc tccagaagat agcttcaccc caatcccagc tacctcaacc aatgccaaaa   1500

aaagacaggg ctgataagct aacaccagac agacaacact gggaaacaga ggctattgtc   1560
```

```
ccctaaacca aaaactgaaa gtgaaagtcc agaaactgtt cccacctgct ggagtgaagg   1620

ggccaaggag ggtgagtgca aggggcgtgg gagtggcctg aagagtcctc tgaatgaacc   1680

ttctggcctc ccacagactc aaatgctcag accagctctt ccgaaaacca ggccttatct   1740

ccaagaccag agatagtggg gagacttctt ggcttggtga ggaaaagcgg acatcagctg   1800

gtcaaacaaa ctctctgaac ccctccctcc atcgttttct tcactgtcct ccaagccagc   1860

gggaatggca gctgccacgc cgccctaaaa gcacactcat cccctcactt gccgcgtcgc   1920

cctcccaggc tctcaacagg ggagagtgtg gtgtttcctg caggccaggc cagctgcctc   1980

cgcgtgatca aagccacact ctgggctcca gagtggggat gacatgcact cagctcttgg   2040

ctccactggg atgggaggag aggacaaggg aaatgtcagg ggcggggagg gtgacagtgg   2100

ccgcccaagg cccacgagct tgttctttgt tctttgtcac agggactgaa aacctctcct   2160

catgttctgc tttcgattcg ttaagagagc aacattttac ccacacacag ataaagtttt   2220

cccttgagga aacaacagct ttaaaagaaa aagaaaaaaa aagtctttgg taaatggcaa   2280

aaaaaaaaaa aaaaaaaaaa aaa                                           2303
```

```
<210> SEQ ID NO 12
<211> LENGTH: 372
<212> TYPE: PRT
<213> ORGANISM: Homo sapiens
<300> PUBLICATION INFORMATION:
<308> DATABASE ACCESSION NUMBER: NCBI / NP_001288647.1
<309> DATABASE ENTRY DATE: 2017-09-11
<313> RELEVANT RESIDUES IN SEQ ID NO: (1)..(372)

<400> SEQUENCE: 12

Met Lys Ser Val Leu Val Val Ala Leu Leu Val Ile Phe Gln Val Cys
1               5                   10                  15

Leu Cys Gln Asp Glu Val Thr Asp Asp Tyr Ile Gly Asp Asn Thr Thr
            20                  25                  30

Val Asp Tyr Thr Leu Phe Glu Ser Leu Cys Ser Lys Lys Asp Val Arg
        35                  40                  45

Asn Phe Lys Ala Trp Phe Leu Pro Ile Met Tyr Ser Ile Ile Cys Phe
    50                  55                  60

Val Gly Leu Leu Gly Asn Gly Leu Val Val Leu Thr Tyr Ile Tyr Phe
65                  70                  75                  80

Lys Arg Leu Lys Thr Met Thr Asp Thr Tyr Leu Leu Asn Leu Ala Val
                85                  90                  95

Ala Asp Ile Leu Phe Leu Leu Thr Leu Pro Phe Trp Ala Tyr Ser Ala
            100                 105                 110

Ala Lys Ser Trp Val Phe Gly Val His Phe Cys Lys Leu Ile Phe Ala
        115                 120                 125

Ile Tyr Lys Met Ser Phe Phe Ser Gly Met Leu Leu Leu Leu Cys Ile
    130                 135                 140

Ser Ile Asp Arg Tyr Val Ala Ile Val Gln Ala Val Ser Ala His Arg
145                 150                 155                 160

His Arg Ala Arg Val Leu Leu Ile Ser Lys Leu Ser Cys Val Gly Ile
                165                 170                 175

Trp Ile Leu Ala Thr Val Leu Ser Ile Pro Glu Leu Leu Tyr Ser Asp
            180                 185                 190

Leu Gln Arg Ser Ser Ser Glu Gln Ala Met Arg Cys Ser Leu Ile Thr
        195                 200                 205

Glu His Val Glu Ala Phe Ile Thr Ile Gln Val Ala Gln Met Val Ile
```

```
    210                 215                 220

Gly Phe Leu Val Pro Leu Leu Ala Met Ser Phe Cys Tyr Leu Val Ile
225                 230                 235                 240

Ile Arg Thr Leu Leu Gln Ala Arg Asn Phe Glu Arg Asn Lys Ala Ile
                245                 250                 255

Lys Val Ile Ile Ala Val Val Val Val Phe Ile Val Phe Gln Leu Pro
            260                 265                 270

Tyr Asn Gly Val Val Leu Ala Gln Thr Val Ala Asn Phe Asn Ile Thr
        275                 280                 285

Ser Ser Thr Cys Glu Leu Ser Lys Gln Leu Asn Ile Ala Tyr Asp Val
    290                 295                 300

Thr Tyr Ser Leu Ala Cys Val Arg Cys Cys Val Asn Pro Phe Leu Tyr
305                 310                 315                 320

Ala Phe Ile Gly Val Lys Phe Arg Asn Asp Leu Phe Lys Leu Phe Lys
                325                 330                 335

Asp Leu Gly Cys Leu Ser Gln Glu Gln Leu Arg Gln Trp Ser Ser Cys
            340                 345                 350

Arg His Ile Arg Arg Ser Ser Met Ser Val Glu Ala Glu Thr Thr Thr
        355                 360                 365

Thr Phe Ser Pro
    370
```

<210> SEQ ID NO 13
<211> LENGTH: 2207
<212> TYPE: DNA
<213> ORGANISM: Homo sapiens
<300> PUBLICATION INFORMATION:
<308> DATABASE ACCESSION NUMBER: NCBI / NM_001838.3
<309> DATABASE ENTRY DATE: 2017-09-11
<313> RELEVANT RESIDUES IN SEQ ID NO: (1)..(2207)

<400> SEQUENCE: 13

```
cacttcctcc ccagacaggg gtagtgcgag gccgggcaca gccttcctgt gtggttttac     60

cgcccagaga gcgtcatgga cctggggaaa ccaatgaaaa gcgtgctggt ggtggctctc    120

cttgtcattt tccaggtatg cctgtgtcaa gatgaggtca cggacgatta catcggagac    180

aacaccacag tggactacac tttgttcgag tctttgtgct ccaagaagga cgtgcggaac    240

tttaaagcct ggttcctccc tatcatgtac tccatcattt gtttcgtggg cctactgggc    300

aatgggctgg tcgtgttgac ctatatctat ttcaagaggc tcaagaccat gaccgatacc    360

tacctgctca acctggcggt ggcagacatc ctcttcctcc tgacccttcc cttctgggcc    420

tacagcgcgg ccaagtcctg ggtcttcggt gtccactttt gcaagctcat ctttgccatc    480

tacaagatga gcttcttcag tggcatgctc ctacttcttt gcatcagcat tgaccgctac    540

gtggccatcg tccaggctgt ctcagctcac cgccaccgtg cccgcgtcct tctcatcagc    600

aagctgtcct gtgtgggcat ctggatacta gccacagtgc tctccatccc agagctcctg    660

tacagtgacc tccagaggag cagcagtgag caagcgatgc gatgctctct catcacagag    720

catgtggagg cctttatcac catccaggtg gcccagatgg tgatcggctt tctggtcccc    780

ctgctggcca tgagcttctg ttaccttgtc atcatccgca ccctgctcca ggcacgcaac    840

tttgagcgca acaaggccat caaggtgatc atcgctgtgg tcgtggtctt catagtcttc    900

cagctgccct acaatggggt ggtcctggcc cagacggtgg ccaacttcaa catcaccagt    960

agcacctgtg agctcagtaa gcaactcaac atcgcctacg acgtcaccta cagcctggcc   1020

tgcgtccgct gctgcgtcaa ccctttcttg tacgccttca tcggcgtcaa gttccgcaac   1080
```

```
gatctcttca agctcttcaa ggacctgggc tgcctcagcc aggagcagct ccggcagtgg   1140

tcttcctgtc ggcacatccg gcgctcctcc atgagtgtgg aggccgagac caccaccacc   1200

ttctccccat aggcgactct tctgcctgga ctagagggac ctctcccagg gtccctgggg   1260

tggggatagg gagcagatgc aatgactcag gacatccccc cgccaaaagc tgctcaggga   1320

aaagcagctc tcccctcaga gtgcaagccc ctgctccaga agatagcttc accccaatcc   1380

cagctacctc aaccaatgcc aaaaaaagac agggctgata agctaacacc agacagacaa   1440

cactgggaaa cagaggctat tgtcccctaa accaaaaact gaaagtgaaa gtccagaaac   1500

tgttcccacc tgctggagtg aaggggccaa ggagggtgag tgcaaggggc gtgggagtgg   1560

cctgaagagt cctctgaatg aaccttctgg cctcccacag actcaaatgc tcagaccagc   1620

tcttccgaaa accaggcctt atctccaaga ccagagatag tggggagact tcttggcttg   1680

gtgaggaaaa gcggacatca gctggtcaaa caaactctct gaacccctcc ctccatcgtt   1740

ttcttcactg tcctccaagc cagcgggaat ggcagctgcc acgccgccct aaaagcacac   1800

tcatcccctc acttgccgcg tcgccctccc aggctctcaa caggggagag tgtggtgttt   1860

cctgcaggcc aggccagctg cctccgcgtg atcaaagcca cactctgggc tccagagtgg   1920

ggatgacatg cactcagctc ttggctccac tgggatggga ggagaggaca agggaaatgt   1980

caggggcggg gagggtgaca gtggccgccc aaggcccacg agcttgttct ttgttctttg   2040

tcacagggac tgaaaacctc tcctcatgtt ctgctttcga ttcgttaaga gagcaacatt   2100

ttacccacac acagataaag ttttcccttg aggaaacaac agctttaaaa gaaaaagaaa   2160

aaaaaagtct ttggtaaatg gcaaaaaaaa aaaaaaaaaa aaaaaaa                 2207
```

<210> SEQ ID NO 14
<211> LENGTH: 378
<212> TYPE: PRT
<213> ORGANISM: Homo sapiens
<300> PUBLICATION INFORMATION:
<308> DATABASE ACCESSION NUMBER: NCBI / NP_001829.1
<309> DATABASE ENTRY DATE: 2017-09-11
<313> RELEVANT RESIDUES IN SEQ ID NO: (1)..(378)

<400> SEQUENCE: 14

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
```

```
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375
```

<210> SEQ ID NO 15
<211> LENGTH: 1602
<212> TYPE: DNA
<213> ORGANISM: Homo sapiens
<300> PUBLICATION INFORMATION:
<308> DATABASE ACCESSION NUMBER: NCBI / NM_000759.3
<309> DATABASE ENTRY DATE: 2017-09-10
<313> RELEVANT RESIDUES IN SEQ ID NO: (1)..(1602)

<400> SEQUENCE: 15

```
agtcgtggcc ccaggtaatt tcctcccagg cctccatggg gttatgtata aaggcccccc      60

tagagctggg ccccaaaaca gcccggagcc tgcagcccag ccccacccag acccatggct     120

ggacctgcca cccagagccc catgaagctg atggccctgc agctgctgct gtggcacagt     180

gcactctgga cagtgcagga agccaccccc ctgggccctg ccagctccct gccccagagc     240

ttcctgctca agtgcttaga gcaagtgagg aagatccagg gcgatggcgc agcgctccag     300

gagaagctgg tgagtgagtg tgccacctac aagctgtgcc accccgagga gctggtgctg     360

ctcggacact ctctgggcat cccctgggct cccctgagca gctgccccag ccaggccctg     420

cagctggcag gctgcttgag ccaactccat agcggccttt tcctctacca ggggctcctg     480

caggccctgg aagggatctc cccgagttg ggtcccacct tggacacact gcagctggac      540

gtcgccgact ttgccaccac catctggcag cagatggaag aactgggaat ggcccctgcc     600

ctgcagccca cccagggtgc catgccggcc ttcgcctctg ctttccagcg ccgggcagga     660

ggggtcctgg ttgcctccca tctgcagagc ttcctggagg tgtcgtaccg cgttctacgc     720
```

```
caccttgccc agccctgagc caagccctcc ccatcccatg tatttatctc tatttaatat    780

ttatgtctat ttaagcctca tatttaaaga cagggaagag cagaacggag ccccaggcct    840

ctgtgtcctt ccctgcattt ctgagtttca ttctcctgcc tgtagcagtg agaaaaagct    900

cctgtcctcc catcccctgg actgggaggt agataggtaa ataccaagta tttattacta    960

tgactgctcc ccagccctgg ctctgcaatg ggcactggga tgagccgctg tgagcccctg   1020

gtcctgaggg tccccacctg ggacccttga gagtatcagg tctcccacgt gggagacaag   1080

aaatccctgt ttaatattta aacagcagtg ttccccatct gggtccttgc acccctcact   1140

ctggcctcag ccgactgcac agcggcccct gcatcccctt ggctgtgagg cccctggaca   1200

agcagaggtg gccagagctg ggaggcatgg ccctggggtc ccacgaattt gctggggaat   1260

ctcgtttttc ttcttaagac ttttgggaca tggtttgact cccgaacatc accgacgcgt   1320

ctcctgtttt tctgggtggc ctcgggacac ctgccctgcc cccacgaggg tcaggactgt   1380

gactcttttt agggccaggc aggtgcctgg acatttgcct tgctggacgg ggactgggga   1440

tgtgggaggg agcagacagg aggaatcatg tcaggcctgt gtgtgaaagg aagctccact   1500

gtcaccctcc acctcttcac cccccactca ccagtgtccc ctccactgtc acattgtaac   1560

tgaacttcag gataataaag tgtttgcctc caaaaaaaaa aa                      1602
```

```
<210> SEQ ID NO 16
<211> LENGTH: 207
<212> TYPE: PRT
<213> ORGANISM: Homo sapiens
<300> PUBLICATION INFORMATION:
<308> DATABASE ACCESSION NUMBER: NCBI / NP_000750.1
<309> DATABASE ENTRY DATE: 2017-09-10
<313> RELEVANT RESIDUES IN SEQ ID NO: (1)..(207)

<400> SEQUENCE: 16

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190
```

Phe Leu Glu Val Ser Tyr Arg Val Leu Arg His Leu Ala Gln Pro
        195                 200                 205

<210> SEQ ID NO 17
<211> LENGTH: 1485
<212> TYPE: DNA
<213> ORGANISM: Homo sapiens
<300> PUBLICATION INFORMATION:
<308> DATABASE ACCESSION NUMBER: NCBI / NM_001178147.1
<309> DATABASE ENTRY DATE: 2017-09-10
<313> RELEVANT RESIDUES IN SEQ ID NO: (1)..(1485)

<400> SEQUENCE: 17
agtcgtggcc ccaggtaatt tcctcccagg cctccatggg gttatgtata aaggcccccc 60
tagagctggg ccccaaaaca gcccggagcc tgcagcccag ccccacccag acccatggct 120
ggacctgcca cccagagccc catgaagctg atggccctgc agctgctgct gtggcacagt 180
gcactctgga cagtgcagga agccaccccc ctgggccctg ccagctccct gccccagagc 240
ttcctgctca agtgcttaga gcaagtgagg aagatccagg gcgatggcgc agcgctccag 300
gagaagctgg caggctgctt gagccaactc catagcggcc ttttcctcta ccaggggctc 360
ctgcaggccc tggaagggat ctcccccgag ttgggtccca ccttggacac actgcagctg 420
gacgtcgccg actttgccac caccatctgg cagcagatgg aagaactggg aatggcccct 480
gccctgcagc ccacccaggg tgccatgccg gccttcgcct ctgctttcca gcgccgggca 540
ggaggggtcc tggttgcctc ccatctgcag agcttcctgg aggtgtcgta ccgcgttcta 600
cgccaccttg cccagccctg agccaagccc tccccatccc atgtatttat ctctatttaa 660
tatttatgtc tatttaagcc tcatatttaa agacagggaa gagcagaacg gagccccagg 720
cctctgtgtc cttccctgca tttctgagtt tcattctcct gcctgtagca gtgagaaaaa 780
gctcctgtcc tcccatcccc tggactggga ggtagatagg taaataccaa gtatttatta 840
ctatgactgc tccccagccc tggctctgca atgggcactg ggatgagccg ctgtgagccc 900
ctggtcctga gggtccccac ctgggaccct tgagagtatc aggtctccca cgtgggagac 960
aagaaatccc tgtttaatat ttaaacagca gtgttcccca tctgggtcct tgcacccctc 1020
actctggcct cagccgactg cacagcggcc cctgcatccc cttggctgtg aggcccctgg 1080
acaagcagag gtggccagag ctgggaggca tggccctggg gtcccacgaa tttgctgggg 1140
aatctcgttt ttcttcttaa gacttttggg acatggtttg actcccgaac atcaccgacg 1200
cgtctcctgt ttttctgggt ggcctcggga cacctgccct gcccccacga gggtcaggac 1260
tgtgactctt tttagggcca ggcaggtgcc tggacatttg ccttgctgga cggggactgg 1320
ggatgtggga gggagcagac aggaggaatc atgtcaggcc tgtgtgtgaa aggaagctcc 1380
actgtcaccc tccacctctt caccccccac tcaccagtgt cccctccact gtcacattgt 1440
aactgaactt caggataata aagtgtttgc ctccaaaaaa aaaaa 1485

<210> SEQ ID NO 18
<211> LENGTH: 168
<212> TYPE: PRT
<213> ORGANISM: Homo sapiens
<300> PUBLICATION INFORMATION:
<308> DATABASE ACCESSION NUMBER: NCBI / NP_001171618.1
<309> DATABASE ENTRY DATE: 2017-09-10
<313> RELEVANT RESIDUES IN SEQ ID NO: (1)..(168)

<400> SEQUENCE: 18

Met Ala Gly Pro Ala Thr Gln Ser Pro Met Lys Leu Met Ala Leu Gln
1               5                   10                  15

```
Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Ala Gly Cys Leu Ser Gln Leu His Ser Gly Leu Phe Leu Tyr Gln
65                  70                  75                  80

Gly Leu Leu Gln Ala Leu Glu Gly Ile Ser Pro Glu Leu Gly Pro Thr
                85                  90                  95

Leu Asp Thr Leu Gln Leu Asp Val Ala Asp Phe Ala Thr Thr Ile Trp
            100                 105                 110

Gln Gln Met Glu Glu Leu Gly Met Ala Pro Ala Leu Gln Pro Thr Gln
        115                 120                 125

Gly Ala Met Pro Ala Phe Ala Ser Ala Phe Gln Arg Arg Ala Gly Gly
    130                 135                 140

Val Leu Val Ala Ser His Leu Gln Ser Phe Leu Glu Val Ser Tyr Arg
145                 150                 155                 160

Val Leu Arg His Leu Ala Gln Pro
                165
```

<210> SEQ ID NO 19
<211> LENGTH: 1593
<212> TYPE: DNA
<213> ORGANISM: Homo sapiens
<300> PUBLICATION INFORMATION:
<308> DATABASE ACCESSION NUMBER: NCBI / NM_172219.2
<309> DATABASE ENTRY DATE: 2017-09-10
<313> RELEVANT RESIDUES IN SEQ ID NO: (1)..(1593)

<400> SEQUENCE: 19

```
agtcgtggcc ccaggtaatt tcctcccagg cctccatggg gttatgtata aaggcccccc     60

tagagctggg ccccaaaaca gcccggagcc tgcagcccag ccccacccag acccatggct    120

ggacctgcca cccagagccc catgaagctg atggccctgc agctgctgct gtggcacagt    180

gcactctgga cagtgcagga agccaccccc ctgggccctg ccagctccct gccccagagc    240

ttcctgctca agtgcttaga gcaagtgagg aagatccagg gcgatggcgc agcgctccag    300

gagaagctgt gtgccaccta caagctgtgc caccccgagg agctggtgct gctcggacac    360

tctctgggca tcccctgggc tcccctgagc agctgcccca gccaggccct gcagctggca    420

ggctgcttga gccaactcca tagcggcctt ttcctctacc aggggctcct gcaggccctg    480

gaagggatct cccccgagtt gggtcccacc ttggacacac tgcagctgga cgtcgccgac    540

tttgccacca ccatctggca gcagatggaa gaactgggaa tggcccctgc cctgcagccc    600

acccagggtg ccatgccggc cttcgcctct gctttccagc gccgggcagg aggggtcctg    660

gttgcctccc atctgcagag cttcctggag gtgtcgtacc gcgttctacg ccaccttgcc    720

cagccctgag ccaagccctc cccatcccat gtatttatct ctatttaata tttatgtcta    780

tttaagcctc atatttaaag acagggaaga gcagaacgga gccccaggcc tctgtgtcct    840

tccctgcatt tctgagtttc attctcctgc ctgtagcagt gagaaaaagc tcctgtcctc    900

ccatcccctg gactgggagg tagataggta aataccaagt atttattact atgactgctc    960

cccagccctg gctctgcaat gggcactggg atgagccgct gtgagcccct ggtcctgagg   1020

gtccccacct gggacccttg agagtatcag gtctcccacg tgggagacaa gaaatccctg   1080
```

```
tttaatattt aaacagcagt gttccccatc tgggtccttg cacccctcac tctggcctca   1140

gccgactgca cagcggcccc tgcatcccct tggctgtgag gcccctggac aagcagaggt   1200

ggccagagct gggaggcatg gccctggggt cccacgaatt tgctggggaa tctcgttttt   1260

cttcttaaga cttttgggac atggtttgac tcccgaacat caccgacgcg tctcctgttt   1320

ttctgggtgg cctcgggaca cctgccctgc ccccacgagg gtcaggactg tgactctttt   1380

tagggccagg caggtgcctg gacatttgcc ttgctggacg gggactgggg atgtgggagg   1440

gagcagacag gaggaatcat gtcaggcctg tgtgtgaaag gaagctccac tgtcaccctc   1500

cacctcttca ccccccactc accagtgtcc cctccactgt cacattgtaa ctgaacttca   1560

ggataataaa gtgtttgcct ccaaaaaaaa aaa                                1593
```

```
<210> SEQ ID NO 20
<211> LENGTH: 204
<212> TYPE: PRT
<213> ORGANISM: Homo sapiens
<300> PUBLICATION INFORMATION:
<308> DATABASE ACCESSION NUMBER: NCBI / NP_757373.1
<309> DATABASE ENTRY DATE: 2017-09-10
<313> RELEVANT RESIDUES IN SEQ ID NO: (1)..(204)

<400> SEQUENCE: 20

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200


<210> SEQ ID NO 21
<211> LENGTH: 1494
<212> TYPE: DNA
<213> ORGANISM: Homo sapiens
<300> PUBLICATION INFORMATION:
<308> DATABASE ACCESSION NUMBER: NCBI / NM_172220.2
<309> DATABASE ENTRY DATE: 2017-09-10
<313> RELEVANT RESIDUES IN SEQ ID NO: (1)..(1494)
```

<400> SEQUENCE: 21
agtcgtggcc ccaggtaatt tcctcccagg cctccatggg gttatgtata aaggcccccc 60
tagagctggg ccccaaaaca gcccggagcc tgcagcccag ccccacccag acccatggct 120
ggacctgcca cccagagccc catgaagctg atggccctgc agctgctgct gtggcacagt 180
gcactctgga cagtgcagga agccaccccc ctgggccctg ccagctccct gccccagagc 240
ttcctgctca agtgcttaga gcaagtgagg aagatccagg gcgatggcgc agcgctccag 300
gagaagctgg tgagtgaggc aggctgcttg agccaactcc atagcggcct tttcctctac 360
caggggctcc tgcaggccct ggaagggatc tcccccgagt tgggtcccac cttggacaca 420
ctgcagctgg acgtcgccga ctttgccacc accatctggc agcagatgga agaactggga 480
atggcccctg ccctgcagcc cacccagggt gccatgccgg ccttcgcctc tgctttccag 540
cgccgggcag gaggggtcct ggttgcctcc catctgcaga gcttcctgga ggtgtcgtac 600
cgcgttctac gccaccttgc ccagccctga gccaagccct ccccatccca tgtatttatc 660
tctatttaat atttatgtct atttaagcct catatttaaa gacagggaag agcagaacgg 720
agccccaggc ctctgtgtcc ttccctgcat ttctgagttt cattctcctg cctgtagcag 780
tgagaaaaag ctcctgtcct cccatcccct ggactgggag gtagataggt aaataccaag 840
tatttattac tatgactgct ccccagccct ggctctgcaa tgggcactgg gatgagccgc 900
tgtgagcccc tggtcctgag ggtccccacc tgggaccctt gagagtatca ggtctcccac 960
gtgggagaca agaaatccct gtttaatatt taaacagcag tgttccccat ctgggtcctt 1020
gcacccctca ctctggcctc agccgactgc acagcggccc ctgcatcccc ttggctgtga 1080
ggcccctgga caagcagagg tggccagagc tgggaggcat ggccctgggg tcccacgaat 1140
ttgctgggga atctcgtttt tcttcttaag acttttggga catggtttga ctcccgaaca 1200
tcaccgacgc gtctcctgtt tttctgggtg gcctcgggac acctgccctg cccccacgag 1260
ggtcaggact gtgactcttt ttagggccag gcaggtgcct ggacatttgc cttgctggac 1320
ggggactggg gatgtgggag ggagcagaca ggaggaatca tgtcaggcct gtgtgtgaaa 1380
ggaagctcca ctgtcaccct ccacctcttc acccccccact caccagtgtc ccctccactg 1440
tcacattgta actgaacttc aggataataa agtgtttgcc tccaaaaaaa aaaa 1494

<210> SEQ ID NO 22
<211> LENGTH: 171
<212> TYPE: PRT
<213> ORGANISM: Homo sapiens
<300> PUBLICATION INFORMATION:
<308> DATABASE ACCESSION NUMBER: NCBI / NP_757374.2
<309> DATABASE ENTRY DATE: 2017-09-10
<313> RELEVANT RESIDUES IN SEQ ID NO: (1)..(171)

<400> SEQUENCE: 22

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Ala Gly Cys Leu Ser Gln Leu His Ser Gly Leu Phe
65                  70                  75                  80
```

```
Leu Tyr Gln Gly Leu Leu Gln Ala Leu Glu Gly Ile Ser Pro Glu Leu
                85                  90                  95

Gly Pro Thr Leu Asp Thr Leu Gln Leu Asp Val Ala Asp Phe Ala Thr
            100                 105                 110

Thr Ile Trp Gln Gln Met Glu Glu Leu Gly Met Ala Pro Ala Leu Gln
        115                 120                 125

Pro Thr Gln Gly Ala Met Pro Ala Phe Ala Ser Ala Phe Gln Arg Arg
    130                 135                 140

Ala Gly Gly Val Leu Val Ala Ser His Leu Gln Ser Phe Leu Glu Val
145                 150                 155                 160

Ser Tyr Arg Val Leu Arg His Leu Ala Gln Pro
                165                 170


<210> SEQ ID NO 23
<211> LENGTH: 1262
<212> TYPE: DNA
<213> ORGANISM: Homo sapiens
<300> PUBLICATION INFORMATION:
<308> DATABASE ACCESSION NUMBER: NCBI / NM_005448.2
<309> DATABASE ENTRY DATE: 2017-10-02
<313> RELEVANT RESIDUES IN SEQ ID NO: (1)..(1262)

<400> SEQUENCE: 23

tcccttgggc ttgtgttggg gcctgttgtt gaacactaag cctttcaaga tggtcctcct     60

cagtattctt agaattcttt ttctttgtga actcgtgctt ttcatggaac acagggccca    120

aatggcagaa ggagggcagt cctctattgc ccttctggct gaggccccta ctttgcccct    180

gattgaggag ctgctagaag aatcccctgg cgaacagcca aggaagcccc ggctcctagg    240

gcattcactg cggtacatgc tggagttgta ccggcgttca gctgactcgc atgggcaccc    300

tagagagaac cgcaccattg gggccaccat ggtgaggctg gtgaagccct tgaccaatgt    360

ggcaaggcct cacagaggta cctggcatat acagatcctg ggctttcctc tcagaccaaa    420

ccgaggacta taccaactag ttagagccac tgtggtttac cgccatcatc tccaactaac    480

tcgcttcaat ctctcctgcc atgtggagcc ctgggtgcag aaaaacccaa ccaaccactt    540

cccttcctca gaaggagatt cctcaaaacc ttccctgatg tctaacgctt ggaaagagat    600

ggatatcaca caacttgttc agcaaaggtt ctggaataac aagggacaca ggatcctacg    660

actccgtttt atgtgtcagc agcaaaaaga tagtggtggt cttgagctct ggcatggcac    720

ttcatccttg gacattgcct tcttgttact ctatttcaat gatactcata aaagcattcg    780

gaaggctaaa tttcttccca ggggcatgga ggagttcatg gaaagggaat ctcttctccg    840

gagaacccga caagcagatg gtatctcagc tgaggttact gcctcttcct caaaacatag    900

cgggcctgaa aataaccagt gttccctcca ccctttccaa atcagcttcc gccagctggg    960

ttgggatcac tggatcattg ctcccccttt ctacacccca aactactgta aaggaacttg   1020

tctccgagta ctacgcgatg gtctcaattc ccccaatcac gccattattc agaaccttat   1080

caatcagttg gtggaccaga gtgtccccrg gccctcctgt gtcccgtata agtatgttcc   1140

aattagtgtc cttatgattg aggcaaatgg gagtattttg tacaaggagt atgagggtat   1200

gattgctgag tcttgtacat gcagatgaca gcaacagtac ggctagatca ggtttcccag   1260

ga                                                                  1262


<210> SEQ ID NO 24
<211> LENGTH: 392
<212> TYPE: PRT
<213> ORGANISM: Homo sapiens
```

<300> PUBLICATION INFORMATION:
<308> DATABASE ACCESSION NUMBER: NCBI / NP_005439.2
<309> DATABASE ENTRY DATE: 2017-10-02
<313> RELEVANT RESIDUES IN SEQ ID NO: (1)..(392)

<400> SEQUENCE: 24

```
Met Val Leu Leu Ser Ile Leu Arg Ile Leu Phe Leu Cys Glu Leu Val
1               5                   10                  15

Leu Phe Met Glu His Arg Ala Gln Met Ala Glu Gly Gly Gln Ser Ser
            20                  25                  30

Ile Ala Leu Leu Ala Glu Ala Pro Thr Leu Pro Leu Ile Glu Glu Leu
        35                  40                  45

Leu Glu Glu Ser Pro Gly Glu Gln Pro Arg Lys Pro Arg Leu Leu Gly
    50                  55                  60

His Ser Leu Arg Tyr Met Leu Glu Leu Tyr Arg Arg Ser Ala Asp Ser
65                  70                  75                  80

His Gly His Pro Arg Glu Asn Arg Thr Ile Gly Ala Thr Met Val Arg
                85                  90                  95

Leu Val Lys Pro Leu Thr Asn Val Ala Arg Pro His Arg Gly Thr Trp
            100                 105                 110

His Ile Gln Ile Leu Gly Phe Pro Leu Arg Pro Asn Arg Gly Leu Tyr
        115                 120                 125

Gln Leu Val Arg Ala Thr Val Val Tyr Arg His His Leu Gln Leu Thr
    130                 135                 140

Arg Phe Asn Leu Ser Cys His Val Glu Pro Trp Val Gln Lys Asn Pro
145                 150                 155                 160

Thr Asn His Phe Pro Ser Ser Glu Gly Asp Ser Ser Lys Pro Ser Leu
                165                 170                 175

Met Ser Asn Ala Trp Lys Glu Met Asp Ile Thr Gln Leu Val Gln Gln
            180                 185                 190

Arg Phe Trp Asn Asn Lys Gly His Arg Ile Leu Arg Leu Arg Phe Met
        195                 200                 205

Cys Gln Gln Gln Lys Asp Ser Gly Gly Leu Glu Leu Trp His Gly Thr
    210                 215                 220

Ser Ser Leu Asp Ile Ala Phe Leu Leu Leu Tyr Phe Asn Asp Thr His
225                 230                 235                 240

Lys Ser Ile Arg Lys Ala Lys Phe Leu Pro Arg Gly Met Glu Glu Phe
                245                 250                 255

Met Glu Arg Glu Ser Leu Leu Arg Arg Thr Arg Gln Ala Asp Gly Ile
            260                 265                 270

Ser Ala Glu Val Thr Ala Ser Ser Ser Lys His Ser Gly Pro Glu Asn
        275                 280                 285

Asn Gln Cys Ser Leu His Pro Phe Gln Ile Ser Phe Arg Gln Leu Gly
    290                 295                 300

Trp Asp His Trp Ile Ile Ala Pro Pro Phe Tyr Thr Pro Asn Tyr Cys
305                 310                 315                 320

Lys Gly Thr Cys Leu Arg Val Leu Arg Asp Gly Leu Asn Ser Pro Asn
                325                 330                 335

His Ala Ile Ile Gln Asn Leu Ile Asn Gln Leu Val Asp Gln Ser Val
            340                 345                 350

Pro Arg Pro Ser Cys Val Pro Tyr Lys Tyr Val Pro Ile Ser Val Leu
        355                 360                 365

Met Ile Glu Ala Asn Gly Ser Ile Leu Tyr Lys Glu Tyr Glu Gly Met
    370                 375                 380
```

```
Ile Ala Glu Ser Cys Thr Cys Arg
385                 390


<210> SEQ ID NO 25
<211> LENGTH: 1049
<212> TYPE: DNA
<213> ORGANISM: Homo sapiens
<300> PUBLICATION INFORMATION:
<308> DATABASE ACCESSION NUMBER: NCBI / NM_016584.2
<309> DATABASE ENTRY DATE: 2017-09-25
<313> RELEVANT RESIDUES IN SEQ ID NO: (1)..(1049)

<400> SEQUENCE: 25

aaaacaacag gaagcagctt acaaactcgg tgaacaactg agggaaccaa accagagacg      60

cgctgaacag agagaatcag gctcaaagca agtggaagtg ggcagagatt ccaccaggac     120

tggtgcaagg cgcagagcca gccagatttg agaagaaggc aaaaagatgc tggggagcag     180

agctgtaatg ctgctgttgc tgctgccctg gacagctcag ggcagagctg tgcctggggg     240

cagcagccct gcctggactc agtgccagca gctttcacag aagctctgca cactggcctg     300

gagtgcacat ccactagtgg gacacatgga tctaagagaa gagggagatg aagagactac     360

aaatgatgtt ccccatatcc agtgtggaga tggctgtgac cccaaggac tcagggacaa      420

cagtcagttc tgcttgcaaa ggatccacca gggtctgatt ttttatgaga agctgctagg     480

atcggatatt ttcacagggg agccttctct gctccctgat agccctgtgg gccagcttca     540

tgcctcccta ctgggcctca gccaactcct gcagcctgag ggtcaccact gggagactca     600

gcagattcca agcctcagtc ccagccagcc atggcagcgt ctccttctcc gcttcaaaat     660

ccttcgcagc ctccaggcct ttgtggctgt agccgcccgg gtctttgccc atggagcagc     720

aaccctgagt ccctaaaggc agcagctcaa ggatggcact cagatctcca tggcccagca     780

aggccaagat aaatctacca ccccaggcac ctgtgagcca acaggttaat tagtccatta     840

attttagtgg gacctgcata tgttgaaaat taccaatact gactgacatg tgatgctgac     900

ctatgataag gttgagtatt tattagatgg gaagggaaat ttggggatta tttatcctcc     960

tggggacagt ttggggagga ttatttattg tatttatatt gaattatgta cttttttcaa    1020

taaagtctta tttttgtggc taaaaaaaa                                      1049


<210> SEQ ID NO 26
<211> LENGTH: 189
<212> TYPE: PRT
<213> ORGANISM: Homo sapiens
<300> PUBLICATION INFORMATION:
<308> DATABASE ACCESSION NUMBER: NCBI / NP_057668.1
<309> DATABASE ENTRY DATE: 2017-09-25
<313> RELEVANT RESIDUES IN SEQ ID NO: (1)..(189)

<400> SEQUENCE: 26

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
```

```
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 27
<211> LENGTH: 586
<212> TYPE: DNA
<213> ORGANISM: Homo sapiens
<300> PUBLICATION INFORMATION:
<308> DATABASE ACCESSION NUMBER: NCBI / NM_002965.3
<309> DATABASE ENTRY DATE: 2017-10-09
<313> RELEVANT RESIDUES IN SEQ ID NO: (1)..(586)

<400> SEQUENCE: 27

```
aaacactctg tgtggctcct cggctttgac agagtgcaag acgatgactt gcaaaatgtc      60

gcagctggaa cgcaacatag agaccatcat caacaccttc caccaatact ctgtgaagct     120

ggggcaccca gacaccctga accaggggga attcaaagag ctggtgcgaa aagatctgca     180

aaatttctc aagaaggaga ataagaatga aaaggtcata gaacacatca tggaggacct      240

ggacacaaat gcagacaagc agctgagctt cgaggagttc atcatgctga tggcgaggct     300

aacctgggcc tcccacgaga agatgcacga gggtgacgag ggccctggcc accaccataa     360

gccaggcctc ggggagggca ccccctaaga ccacagtggc caagatcaca gtggccacgg     420

ccacggccac agtcatggtg gccacggcca cagccactaa tcaggaggcc aggccaccct     480

gcctctaccc aaccagggcc ccggggcctg ttatgtcaaa ctgtcttggc tgtggggcta     540

ggggctgggg ccaaataaag tctcttcctc caagtcaaaa aaaaaa                    586
```

<210> SEQ ID NO 28
<211> LENGTH: 114
<212> TYPE: PRT
<213> ORGANISM: Homo sapiens
<300> PUBLICATION INFORMATION:
<308> DATABASE ACCESSION NUMBER: NCBI / NP_002956.1
<309> DATABASE ENTRY DATE: 2017-10-09
<313> RELEVANT RESIDUES IN SEQ ID NO: (1)..(114)

<400> SEQUENCE: 28

```
Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80
```

```
Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro


<210> SEQ ID NO 29
<211> LENGTH: 1539
<212> TYPE: DNA
<213> ORGANISM: Mus musculus
<300> PUBLICATION INFORMATION:
<308> DATABASE ACCESSION NUMBER: NCBI / NM_009892.3
<309> DATABASE ENTRY DATE: 2017-10-03
<313> RELEVANT RESIDUES IN SEQ ID NO: (1)..(1539)

<400> SEQUENCE: 29

aaaaagccag cagaagctct ccagaagcaa tcctgaagac accatggcca agctcattct     60

tgtcacaggt ctggcaattc ttctgaacgt acagctggga tcttcctacc agctgatgtg    120

ctactatacc agttgggcta aggacaggcc aatagaaggg agtttcaaac ctggtaatat    180

tgacccctgc ctgtgtactc acctgatcta tgcctttgct ggaatgcaga ataatgagat    240

cacttacaca catgagcaag acttgcgtga ctatgaagca ttgaatggtc tgaaagacaa    300

gaacactgag ctaaaaactc tcctggccat tggaggatgg aagtttggac ctgccccgtt    360

cagtgccatg gtctctactc ctcagaaccg tcagatattc attcagtcag ttatcagatt    420

ccttcgtcaa tataactttg atggcctcaa cctggactgg cagtaccctg ggtctcgagg    480

aagccctcct aaggacaaac atctcttcag tgttctggtg aaggaaatgc gtaaagcttt    540

tgaggaagaa tctgtggaga aagacattcc aaggctgcta ctcacttcca caggagcagg    600

aatcattgac gtaatcaagt ctgggtacaa gatccctgaa ctgtctcagt ctcttgacta    660

tattcaggtc atgacatatg atctccatga tcctaaggat ggctacactg gagaaaatag    720

tcccctctat aaatctccat atgacattgg aaagagtgct gatctcaatg tggattcaat    780

catttcctac tggaaggacc atggagcagc ttctgagaag ctcattgtgg gatttccagc    840

atatgggcat acctttatcc tgagtgaccc ttctaagact ggaattggtg cccctacaat    900

tagtactggc ccaccaggaa agtacacaga tgaatcagga ctcctggctt actatgaggt    960

ttgtacattt ctgaatgaag gagccactga ggtctgggat gccccccagg aagtacccta   1020

tgcctatcag ggtaatgagt gggttggtta tgacaatgtc aggagcttca agttgaaggc   1080

tcagtggctc aaggacaaca atttaggagg tgccgtggtc tggcccctgg acatggatga   1140

cttcagtggt tctttctgtc accagagaca tttccctctg acatctactt taaagggaga   1200

tctcaatata cacagtgcaa gttgcaaggg cccttattga gaggagcttt acacaatgat   1260

ttgtccttga aactctcaga ataagatcaa gttcaacggt tttccacag tgcattctgc   1320

atcatgcttc catggagaat aatagaaata agtcatgaac tttcctaaat tgaatcccag   1380

agtagtacta agatggatgt cttgtctgct gtaccagctg ggaagaaaca aaaaatgctc   1440

ttcatctgtc agctttggct aagctctgaa catcttttgc ttcctgtaaa accaccatgc   1500

ttgtttcttg ctctcacaat aaattccaca ttcatagca                          1539


<210> SEQ ID NO 30
<211> LENGTH: 398
<212> TYPE: PRT
<213> ORGANISM: Mus musculus
<300> PUBLICATION INFORMATION:
<308> DATABASE ACCESSION NUMBER: NCBI / NP_034022.2
```

<309> DATABASE ENTRY DATE: 2017-10-03
<313> RELEVANT RESIDUES IN SEQ ID NO: (1)..(398)

<400> SEQUENCE: 30

```
Met Ala Lys Leu Ile Leu Val Thr Gly Leu Ala Ile Leu Leu Asn Val
1               5                   10                  15

Gln Leu Gly Ser Ser Tyr Gln Leu Met Cys Tyr Tyr Thr Ser Trp Ala
            20                  25                  30

Lys Asp Arg Pro Ile Glu Gly Ser Phe Lys Pro Gly Asn Ile Asp Pro
        35                  40                  45

Cys Leu Cys Thr His Leu Ile Tyr Ala Phe Ala Gly Met Gln Asn Asn
    50                  55                  60

Glu Ile Thr Tyr Thr His Glu Gln Asp Leu Arg Asp Tyr Glu Ala Leu
65                  70                  75                  80

Asn Gly Leu Lys Asp Lys Asn Thr Glu Leu Lys Thr Leu Leu Ala Ile
                85                  90                  95

Gly Gly Trp Lys Phe Gly Pro Ala Pro Phe Ser Ala Met Val Ser Thr
            100                 105                 110

Pro Gln Asn Arg Gln Ile Phe Ile Gln Ser Val Ile Arg Phe Leu Arg
        115                 120                 125

Gln Tyr Asn Phe Asp Gly Leu Asn Leu Asp Trp Gln Tyr Pro Gly Ser
    130                 135                 140

Arg Gly Ser Pro Pro Lys Asp Lys His Leu Phe Ser Val Leu Val Lys
145                 150                 155                 160

Glu Met Arg Lys Ala Phe Glu Glu Glu Ser Val Glu Lys Asp Ile Pro
                165                 170                 175

Arg Leu Leu Leu Thr Ser Thr Gly Ala Gly Ile Ile Asp Val Ile Lys
            180                 185                 190

Ser Gly Tyr Lys Ile Pro Glu Leu Ser Gln Ser Leu Asp Tyr Ile Gln
        195                 200                 205

Val Met Thr Tyr Asp Leu His Asp Pro Lys Asp Gly Tyr Thr Gly Glu
    210                 215                 220

Asn Ser Pro Leu Tyr Lys Ser Pro Tyr Asp Ile Gly Lys Ser Ala Asp
225                 230                 235                 240

Leu Asn Val Asp Ser Ile Ile Ser Tyr Trp Lys Asp His Gly Ala Ala
                245                 250                 255

Ser Glu Lys Leu Ile Val Gly Phe Pro Ala Tyr Gly His Thr Phe Ile
            260                 265                 270

Leu Ser Asp Pro Ser Lys Thr Gly Ile Gly Ala Pro Thr Ile Ser Thr
        275                 280                 285

Gly Pro Pro Gly Lys Tyr Thr Asp Glu Ser Gly Leu Leu Ala Tyr Tyr
    290                 295                 300

Glu Val Cys Thr Phe Leu Asn Glu Gly Ala Thr Glu Val Trp Asp Ala
305                 310                 315                 320

Pro Gln Glu Val Pro Tyr Ala Tyr Gln Gly Asn Glu Trp Val Gly Tyr
                325                 330                 335

Asp Asn Val Arg Ser Phe Lys Leu Lys Ala Gln Trp Leu Lys Asp Asn
            340                 345                 350

Asn Leu Gly Gly Ala Val Val Trp Pro Leu Asp Met Asp Asp Phe Ser
        355                 360                 365

Gly Ser Phe Cys His Gln Arg His Phe Pro Leu Thr Ser Thr Leu Lys
    370                 375                 380

Gly Asp Leu Asn Ile His Ser Ala Ser Cys Lys Gly Pro Tyr
385                 390                 395
```

<210> SEQ ID NO 31
<211> LENGTH: 549
<212> TYPE: DNA
<213> ORGANISM: Homo sapiens
<300> PUBLICATION INFORMATION:
<308> DATABASE ACCESSION NUMBER: NCBI / NM_001319196.1
<309> DATABASE ENTRY DATE: 2017-09-25
<313> RELEVANT RESIDUES IN SEQ ID NO: (1)..(549)

<400> SEQUENCE: 31
gagaaaccag agactgtagc aactctggca gggagaagct gtctctgatg gcctgaagct 60
gtgggcagct ggccaagcct aaccgctata aaaaggagct gcctctcagc cctgcatgtc 120
tcttgtcagc tgtctttcag aagacctgaa ggttctgttt ttcaggtggg gcaagtccgt 180
gggcatcatg ttgaccgagc tggagaaagc cttgaactct atcatcgacg tctaccacaa 240
gtactccctg ataaagggga atttccatgc cgtctacagg gatgacctga agaaattgct 300
agagaccgag tgtcctcagt atatcaggaa aaagggtgca gacgtctggt tcaaagagtt 360
ggatatcaac actgatggtg cagttaactt ccaggagttc ctcattctgg tgataaagat 420
gggcgtggca gcccacaaaa aaagccatga agaaagccac aaagagtagc tgagttactg 480
ggcccagagg ctgggcccct ggacatgtac ctgcagaata ataaagtcat caatacctca 540
aaaaaaaaa 549

<210> SEQ ID NO 32
<211> LENGTH: 117
<212> TYPE: PRT
<213> ORGANISM: Homo sapiens
<300> PUBLICATION INFORMATION:
<308> DATABASE ACCESSION NUMBER: NCBI / NP_001306125.1
<309> DATABASE ENTRY DATE: 2017-09-25
<313> RELEVANT RESIDUES IN SEQ ID NO: (1)..(117)

<400> SEQUENCE: 32

Met Ser Leu Val Ser Cys Leu Ser Glu Asp Leu Lys Val Leu Phe Phe
1 5 10 15

Arg Trp Gly Lys Ser Val Gly Ile Met Leu Thr Glu Leu Glu Lys Ala
20 25 30

Leu Asn Ser Ile Ile Asp Val Tyr His Lys Tyr Ser Leu Ile Lys Gly
35 40 45

Asn Phe His Ala Val Tyr Arg Asp Asp Leu Lys Lys Leu Leu Glu Thr
50 55 60

Glu Cys Pro Gln Tyr Ile Arg Lys Lys Gly Ala Asp Val Trp Phe Lys
65 70 75 80

Glu Leu Asp Ile Asn Thr Asp Gly Ala Val Asn Phe Gln Glu Phe Leu
85 90 95

Ile Leu Val Ile Lys Met Gly Val Ala Ala His Lys Lys Ser His Glu
100 105 110

Glu Ser His Lys Glu
115

<210> SEQ ID NO 33
<211> LENGTH: 546
<212> TYPE: DNA
<213> ORGANISM: Homo sapiens
<300> PUBLICATION INFORMATION:
<308> DATABASE ACCESSION NUMBER: NCBI / NM_001319197.1
<309> DATABASE ENTRY DATE: 2017-09-25
<313> RELEVANT RESIDUES IN SEQ ID NO: (1)..(546)

<400> SEQUENCE: 33
gagaaaccag agactgtagc aactctggca gggagaagct gtctctgatg gcctgaagct 60
gtgggcagct ggccaagcct aaccgctata aaaaggagct gcctctcagc cctgcatgtc 120
tcttgtcagc tgtctttcag aagacctggt tctgtttttc aggtggggca agtccgtggg 180
catcatgttg accgagctgg agaaagcctt gaactctatc atcgacgtct accacaagta 240
ctccctgata aaggggaatt tccatgccgt ctacagggat gacctgaaga aattgctaga 300
gaccgagtgt cctcagtata tcaggaaaaa gggtgcagac gtctggttca aagagttgga 360
tatcaacact gatggtgcag ttaacttcca ggagttcctc attctggtga taaagatggg 420
cgtggcagcc cacaaaaaaa gccatgaaga aagccacaaa gagtagctga gttactgggc 480
ccagaggctg ggcccctgga catgtacctg cagaataata aagtcatcaa tacctcaaaa 540
aaaaaa 546

<210> SEQ ID NO 34
<211> LENGTH: 116
<212> TYPE: PRT
<213> ORGANISM: Homo sapiens
<300> PUBLICATION INFORMATION:
<308> DATABASE ACCESSION NUMBER: NCBI / NP_001306126.1
<309> DATABASE ENTRY DATE: 2017-09-25
<313> RELEVANT RESIDUES IN SEQ ID NO: (1)..(116)

<400> SEQUENCE: 34

Met Ser Leu Val Ser Cys Leu Ser Glu Asp Leu Val Leu Phe Phe Arg
1 5 10 15

Trp Gly Lys Ser Val Gly Ile Met Leu Thr Glu Leu Glu Lys Ala Leu
20 25 30

Asn Ser Ile Ile Asp Val Tyr His Lys Tyr Ser Leu Ile Lys Gly Asn
35 40 45

Phe His Ala Val Tyr Arg Asp Asp Leu Lys Lys Leu Leu Glu Thr Glu
50 55 60

Cys Pro Gln Tyr Ile Arg Lys Lys Gly Ala Asp Val Trp Phe Lys Glu
65 70 75 80

Leu Asp Ile Asn Thr Asp Gly Ala Val Asn Phe Gln Glu Phe Leu Ile
85 90 95

Leu Val Ile Lys Met Gly Val Ala Ala His Lys Lys Ser His Glu Glu
100 105 110

Ser His Lys Glu
115

<210> SEQ ID NO 35
<211> LENGTH: 450
<212> TYPE: DNA
<213> ORGANISM: Homo sapiens
<300> PUBLICATION INFORMATION:
<308> DATABASE ACCESSION NUMBER: NCBI / NM_001319198.1
<309> DATABASE ENTRY DATE: 2017-09-25
<313> RELEVANT RESIDUES IN SEQ ID NO: (1)..(450)

<400> SEQUENCE: 35
tgttttgata tcagaatttc tggggaacat ttggatttcc agaatctctt tcacatcagc 60
tgtaatgtgg ggcaagtccg tgggcatcat gttgaccgag ctggagaaag ccttgaactc 120
tatcatcgac gtctaccaca agtactccct gataaagggg aatttccatg ccgtctacag 180
ggatgacctg aagaaattgc tagagaccga gtgtcctcag tatatcagga aaaagggtgc 240
agacgtctgg ttcaaagagt tggatatcaa cactgatggt gcagttaact tccaggagtt 300
cctcattctg gtgataaaga tgggcgtggc agcccacaaa aaaagccatg aagaaagcca 360
caaagagtag ctgagttact gggcccagag gctgggcccc tggacatgta cctgcagaat 420
aataaagtca tcaatacctc aaaaaaaaaa 450

<210> SEQ ID NO 36
<211> LENGTH: 101
<212> TYPE: PRT
<213> ORGANISM: Homo sapiens
<300> PUBLICATION INFORMATION:
<308> DATABASE ACCESSION NUMBER: NCBI / NP_001306127.1
<309> DATABASE ENTRY DATE: 2017-09-25
<313> RELEVANT RESIDUES IN SEQ ID NO: (1)..(101)

<400> SEQUENCE: 36

Met Trp Gly Lys Ser Val Gly Ile Met Leu Thr Glu Leu Glu Lys Ala
1 5 10 15

Leu Asn Ser Ile Ile Asp Val Tyr His Lys Tyr Ser Leu Ile Lys Gly
20 25 30

Asn Phe His Ala Val Tyr Arg Asp Asp Leu Lys Lys Leu Leu Glu Thr
35 40 45

Glu Cys Pro Gln Tyr Ile Arg Lys Lys Gly Ala Asp Val Trp Phe Lys
50 55 60

Glu Leu Asp Ile Asn Thr Asp Gly Ala Val Asn Phe Gln Glu Phe Leu
65 70 75 80

Ile Leu Val Ile Lys Met Gly Val Ala Ala His Lys Lys Ser His Glu
85 90 95

Glu Ser His Lys Glu
100

<210> SEQ ID NO 37
<211> LENGTH: 504
<212> TYPE: DNA
<213> ORGANISM: Homo sapiens
<300> PUBLICATION INFORMATION:
<308> DATABASE ACCESSION NUMBER: NCBI / NM_001319201.1
<309> DATABASE ENTRY DATE: 2017-09-25
<313> RELEVANT RESIDUES IN SEQ ID NO: (1)..(504)

<400> SEQUENCE: 37
gagcagcctt cctgagagag gagagagaaa gctcagggag gtctggagca aagatactcc 60
tggaggtggg gagtgaggca gggataagga aggagagtat cctccagcac cttccagtgg 120
gtggggcaag tccgtgggca tcatgttgac cgagctggag aaagccttga actctatcat 180
cgacgtctac cacaagtact ccctgataaa ggggaatttc catgccgtct acagggatga 240
cctgaagaaa ttgctagaga ccgagtgtcc tcagtatatc aggaaaaagg gtgcagacgt 300
ctggttcaaa gagttggata tcaacactga tggtgcagtt aacttccagg agttcctcat 360
tctggtgata aagatgggcg tggcagccca caaaaaaagc catgaagaaa gccacaaaga 420
gtagctgagt tactgggccc agaggctggg cccctggaca tgtacctgca gaataataaa 480
gtcatcaata cctcaaaaaa aaaa 504

<210> SEQ ID NO 38
<211> LENGTH: 93
<212> TYPE: PRT
<213> ORGANISM: Homo sapiens
<300> PUBLICATION INFORMATION:
<308> DATABASE ACCESSION NUMBER: NCBI / NP_001306130.1
<309> DATABASE ENTRY DATE: 2017-09-25
<313> RELEVANT RESIDUES IN SEQ ID NO: (1)..(93)

<400> SEQUENCE: 38

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 39
<211> LENGTH: 532
<212> TYPE: DNA
<213> ORGANISM: Homo sapiens
<300> PUBLICATION INFORMATION:
<308> DATABASE ACCESSION NUMBER: NCBI / NM_002964.4
<309> DATABASE ENTRY DATE: 2017-09-25
<313> RELEVANT RESIDUES IN SEQ ID NO: (1)..(532)

<400> SEQUENCE: 39
gagaaaccag agactgtagc aactctggca gggagaagct gtctctgatg gcctgaagct 60
gtgggcagct ggccaagcct aaccgctata aaaaggagct gcctctcagc cctgcatgtc 120
tcttgtcagc tgtctttcag aagacctggt ggggcaagtc cgtgggcatc atgttgaccg 180
agctggagaa agccttgaac tctatcatcg acgtctacca caagtactcc ctgataaagg 240
ggaatttcca tgccgtctac agggatgacc tgaagaaatt gctagagacc gagtgtcctc 300
agtatatcag gaaaaagggt gcagacgtct ggttcaaaga gttggatatc aacactgatg 360
gtgcagttaa cttccaggag ttcctcattc tggtgataaa gatgggcgtg gcagcccaca 420
aaaaaagcca tgaagaaagc cacaaagagt agctgagtta ctgggcccag aggctgggcc 480
cctggacatg tacctgcaga ataataaagt catcaatacc tcaaaaaaaa aa 532

<210> SEQ ID NO 40
<211> LENGTH: 93
<212> TYPE: PRT
<213> ORGANISM: Homo sapiens
<300> PUBLICATION INFORMATION:
<308> DATABASE ACCESSION NUMBER: NCBI / NP_002955.2
<309> DATABASE ENTRY DATE: 2017-09-25
<313> RELEVANT RESIDUES IN SEQ ID NO: (1)..(93)

<400> SEQUENCE: 40

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu 85 90

<210> SEQ ID NO 41
<211> LENGTH: 2537
<212> TYPE: DNA
<213> ORGANISM: Homo sapiens
<300> PUBLICATION INFORMATION:
<308> DATABASE ACCESSION NUMBER: NCBI / NM_001199149.1
<309> DATABASE ENTRY DATE: 2017-10-09
<313> RELEVANT RESIDUES IN SEQ ID NO: (1)..(2537)

<400> SEQUENCE: 41
gtccaggatt ctggctcaga gttgcaccac tgggttttat attcacttgg atctttagtt 60
gttttggcgc ctactgaggt ctgaagtttg aatcctgcag tcaattggga tggtggcttg 120
taccccaaag tgccattgca acccttgtcc ttcctgagga aagggtggca gttgccctgt 180
ggaattcctg ccctgctccc cgtgggtgtc caggctgaca gaagttggga ctgtgtctgg 240
ctggccgtag gaggagtgtt cagtggtgcg ccgtatccca acccgaggcc acaaaatgct 300
tccaatggca aaggaatatg agaaaagtgc gtggccctcc tgtcagctgc ataaagagag 360
actcccccat ccagtgtatc caggccattg cggaaaacag ggccgatgct gtgacccttg 420
atggtggttt catatacgag gcaggcctgg ccccctacaa actgcgacct gtagcggcgg 480
aagtctacgg gaccgaaaga cagccacgaa ctcactatta tgccgtggct gtggtgaaga 540
agggcggcag ctttcagctg aacgaactgc aaggtctgaa gtcctgccac acaggccttc 600
gcaggaccgc tggatggaat gtccctatag ggacacttcg tccattcttg aattggacgg 660
gtccacctga gcccattgag gcagctgtgg ccaggttctt ctcagccagc tgtgttcccg 720
gtgcagataa aggacagttc cccaacctgt gtcgcctgtg tgcggggaca ggggaaaaca 780
aatgtgcctt ctcctcccag gaaccgtact tcagctactc tggtgccttc aagtgtctga 840
gagacggggc tggagacgtg gcttttatca gagagagcac agtgtttgag gacctgtcag 900
acgaggctga aagggacgag tatgagttac tctgcccaga caacactcgg aagccagtgg 960
acaagttcaa agactgccat ctggcccggg tcccttctca tgccgttgtg gcacgaagtg 1020
tgaatggcaa ggaggatgcc atctggaatc ttctccgcca ggcacaggaa aagtttggaa 1080
aggacaagtc accgaaattc cagctctttg gctcccctag tgggcagaaa gatctgctgt 1140
tcaaggactc tgccattggg ttttcgaggg tgcccccgag gatagattct gggctgtacc 1200
ttggctccgg ctacttcact gccatccaga acttgaggaa aagtgaggag gaagtggctg 1260
cccggcgtgc gcgggtcgtg tggtgtgcgg tgggcgagca ggagctgcgc aagtgtaacc 1320
agtggagtgg cttgagcgaa ggcagcgtga cctgctcctc ggcctccacc acagaggact 1380
gcatcgccct ggtgctgaaa ggagaagctg atgccatgag tttggatgga ggatatgtgt 1440
acactgcagg caaatgtggt ttggtgcctg tcctggcaga gaactacaaa tcccaacaaa 1500
gcagtgaccc tgatcctaac tgtgtggata gacctgtgga aggatatctt gctgtggcgg 1560
tggttaggag atcagacact agccttacct ggaactctgt gaaaggcaag aagtcctgcc 1620
acaccgccgt ggacaggact gcaggctgga atatccccat gggcctgctc ttcaaccaga 1680
cgggctcctg caaatttgat gaatatttca gtcaaagctg tgcccctggg tctgacccga 1740
gatctaatct ctgtgctctg tgtattggcg acgagcaggg tgagaataag tgcgtgccca 1800
acagcaacga gagatactac ggctacactg gggctttccg gtgcctggct gagaatgctg 1860
gagacgttgc atttgtgaaa gatgtcactg tcttgcagaa cactgatgga aataacaatg 1920
aggcatgggc taaggatttg aagctggcag actttgcgct gctgtgcctc gatggcaaac 1980

```
ggaagcctgt gactgaggct agaagctgcc atcttgccat ggccccgaat catgccgtgg   2040

tgtctcggat ggataaggtg gaacgcctga aacaggtgtt gctccaccaa caggctaaat   2100

ttgggagaaa tggatctgac tgcccggaca agttttgctt attccagtct gaaaccaaaa   2160

accttctgtt caatgacaac actgagtgtc tggccagact ccatggcaaa acaacatatg   2220

aaaaatattt gggaccacag tatgtcgcag gcattactaa tctgaaaaag tgctcaacct   2280

ccccccctcct ggaagcctgt gaattcctca ggaagtaaaa ccgaagaaga tggcccagct   2340

ccccaagaaa gcctcagcca ttcactgccc ccagctcttc tccccaggtg tgttggggcc   2400

ttggcctccc ctgctgaagg tggggattgc ccatccatct gcttacaatt ccctgctgtc   2460

gtcttagcaa gaagtaaaat gagaaatttt gttgatattc tctccttaaa aaaaaaaaaa   2520

aaaaaaaaaa aaaaaaa                                                  2537
```

```
<210> SEQ ID NO 42
<211> LENGTH: 666
<212> TYPE: PRT
<213> ORGANISM: Homo sapiens
<300> PUBLICATION INFORMATION:
<308> DATABASE ACCESSION NUMBER: NCBI / NP_001186078.1
<309> DATABASE ENTRY DATE: 2017-10-09
<313> RELEVANT RESIDUES IN SEQ ID NO: (1)..(666)

<400> SEQUENCE: 42

Met Arg Lys Val Arg Gly Pro Pro Val Ser Cys Ile Lys Arg Asp Ser
1               5                   10                  15

Pro Ile Gln Cys Ile Gln Ala Ile Ala Glu Asn Arg Ala Asp Ala Val
            20                  25                  30

Thr Leu Asp Gly Gly Phe Ile Tyr Glu Ala Gly Leu Ala Pro Tyr Lys
        35                  40                  45

Leu Arg Pro Val Ala Ala Glu Val Tyr Gly Thr Glu Arg Gln Pro Arg
    50                  55                  60

Thr His Tyr Tyr Ala Val Ala Val Val Lys Lys Gly Gly Ser Phe Gln
65                  70                  75                  80

Leu Asn Glu Leu Gln Gly Leu Lys Ser Cys His Thr Gly Leu Arg Arg
                85                  90                  95

Thr Ala Gly Trp Asn Val Pro Ile Gly Thr Leu Arg Pro Phe Leu Asn
            100                 105                 110

Trp Thr Gly Pro Pro Glu Pro Ile Glu Ala Ala Val Ala Arg Phe Phe
        115                 120                 125

Ser Ala Ser Cys Val Pro Gly Ala Asp Lys Gly Gln Phe Pro Asn Leu
    130                 135                 140

Cys Arg Leu Cys Ala Gly Thr Gly Glu Asn Lys Cys Ala Phe Ser Ser
145                 150                 155                 160

Gln Glu Pro Tyr Phe Ser Tyr Ser Gly Ala Phe Lys Cys Leu Arg Asp
                165                 170                 175

Gly Ala Gly Asp Val Ala Phe Ile Arg Glu Ser Thr Val Phe Glu Asp
            180                 185                 190

Leu Ser Asp Glu Ala Glu Arg Asp Glu Tyr Glu Leu Leu Cys Pro Asp
        195                 200                 205

Asn Thr Arg Lys Pro Val Asp Lys Phe Lys Asp Cys His Leu Ala Arg
    210                 215                 220

Val Pro Ser His Ala Val Val Ala Arg Ser Val Asn Gly Lys Glu Asp
225                 230                 235                 240

Ala Ile Trp Asn Leu Leu Arg Gln Ala Gln Glu Lys Phe Gly Lys Asp
```

```
                245                 250                 255

Lys Ser Pro Lys Phe Gln Leu Phe Gly Ser Pro Ser Gly Gln Lys Asp
            260                 265                 270

Leu Leu Phe Lys Asp Ser Ala Ile Gly Phe Ser Arg Val Pro Pro Arg
        275                 280                 285

Ile Asp Ser Gly Leu Tyr Leu Gly Ser Gly Tyr Phe Thr Ala Ile Gln
    290                 295                 300

Asn Leu Arg Lys Ser Glu Glu Glu Val Ala Ala Arg Arg Ala Arg Val
305                 310                 315                 320

Val Trp Cys Ala Val Gly Glu Gln Glu Leu Arg Lys Cys Asn Gln Trp
                325                 330                 335

Ser Gly Leu Ser Glu Gly Ser Val Thr Cys Ser Ser Ala Ser Thr Thr
            340                 345                 350

Glu Asp Cys Ile Ala Leu Val Leu Lys Gly Glu Ala Asp Ala Met Ser
        355                 360                 365

Leu Asp Gly Gly Tyr Val Tyr Thr Ala Gly Lys Cys Gly Leu Val Pro
    370                 375                 380

Val Leu Ala Glu Asn Tyr Lys Ser Gln Gln Ser Ser Asp Pro Asp Pro
385                 390                 395                 400

Asn Cys Val Asp Arg Pro Val Glu Gly Tyr Leu Ala Val Ala Val Val
                405                 410                 415

Arg Arg Ser Asp Thr Ser Leu Thr Trp Asn Ser Val Lys Gly Lys Lys
            420                 425                 430

Ser Cys His Thr Ala Val Asp Arg Thr Ala Gly Trp Asn Ile Pro Met
        435                 440                 445

Gly Leu Leu Phe Asn Gln Thr Gly Ser Cys Lys Phe Asp Glu Tyr Phe
    450                 455                 460

Ser Gln Ser Cys Ala Pro Gly Ser Asp Pro Arg Ser Asn Leu Cys Ala
465                 470                 475                 480

Leu Cys Ile Gly Asp Glu Gln Gly Glu Asn Lys Cys Val Pro Asn Ser
                485                 490                 495

Asn Glu Arg Tyr Tyr Gly Tyr Thr Gly Ala Phe Arg Cys Leu Ala Glu
            500                 505                 510

Asn Ala Gly Asp Val Ala Phe Val Lys Asp Val Thr Val Leu Gln Asn
        515                 520                 525

Thr Asp Gly Asn Asn Asn Glu Ala Trp Ala Lys Asp Leu Lys Leu Ala
    530                 535                 540

Asp Phe Ala Leu Leu Cys Leu Asp Gly Lys Arg Lys Pro Val Thr Glu
545                 550                 555                 560

Ala Arg Ser Cys His Leu Ala Met Ala Pro Asn His Ala Val Val Ser
                565                 570                 575

Arg Met Asp Lys Val Glu Arg Leu Lys Gln Val Leu Leu His Gln Gln
            580                 585                 590

Ala Lys Phe Gly Arg Asn Gly Ser Asp Cys Pro Asp Lys Phe Cys Leu
        595                 600                 605

Phe Gln Ser Glu Thr Lys Asn Leu Leu Phe Asn Asp Asn Thr Glu Cys
    610                 615                 620

Leu Ala Arg Leu His Gly Lys Thr Thr Tyr Glu Lys Tyr Leu Gly Pro
625                 630                 635                 640

Gln Tyr Val Ala Gly Ile Thr Asn Leu Lys Lys Cys Ser Thr Ser Pro
                645                 650                 655

Leu Leu Glu Ala Cys Glu Phe Leu Arg Lys
            660                 665
```

<210> SEQ ID NO 43
<211> LENGTH: 2642
<212> TYPE: DNA
<213> ORGANISM: Homo sapiens
<300> PUBLICATION INFORMATION:
<308> DATABASE ACCESSION NUMBER: NCBI / NM_001321121.1
<309> DATABASE ENTRY DATE: 2017-10-09
<313> RELEVANT RESIDUES IN SEQ ID NO: (1)..(2642)

<400> SEQUENCE: 43
gactcctagg ggcttgcaga ctagtgggag agaaagaaca tcgcagcagc caggcagaac 60
caggacaggt gaggtgcagg ctggctttcc tctcgcagcg cggtgtggag tcctgtcctg 120
cctcagggct tttcggagcc tggatcctca aggaacaagt agacctggcc gcggggagtg 180
gggagggaag gggtgtctat tgggcaacag ggcggggcaa agccctgaat aaaggggcgc 240
agggcaggcg caagtggcag agccttcgtt tgccaagtcg cctccagacc gcagacatga 300
aacttgtctt cctcgtcctg ctgttcctcg ggcccctcgg actgtgtctg gctggccgta 360
ggaggagtgt tcagtggtgc gccgtatccc aacccgaggc cacaaaatgc ttccaatggc 420
aaaggaatat gagaaaagtg cgtggccctc ctgtcagctg cataaagaga gactccccca 480
tccagtgtat ccaggccatt gcggaaaaca gggccgatgc tgtgaccctt gatggtggtt 540
tcatatacga ggcaggcctg gccccctaca aactgcgacc tgtagcggcg gaagtctacg 600
ggaccgaaag acagccacga actcactatt atgccgtggc tgtggtgaag aagggcggca 660
gctttcagct gaacgaactg caaggtctga agtcctgcca cacaggcctt cgcaggaccg 720
ctggatggaa tgtccctata gggacacttc gtccattctt gaattggacg ggtccacctg 780
agcccattga ggcagctgtg gccaggttct tctcagccag ctgtgttccc ggtgcagata 840
aaggacagtt ccccaacctg tgtcgcctgt gtgcggggac aggggaaaac aaatgtgcct 900
tctcctccca ggaaccgtac ttcagctact ctggtgcctt caagtgtctg agagacgggg 960
ctggagacgt ggcttttatc agagagagca cagtgtttga ggacctgtca gacgaggctg 1020
aaagggacga gtatgagtta ctctgcccag acaacactcg gaagccagtg gacaagttca 1080
aagactgcca tctggcccgg gtcccttctc atgccgttgt ggcacgaagt gtgaatggca 1140
aggaggatgc catctggaat cttctccgcc aggcacagga aaagtttgga aaggacaagt 1200
caccgaaatt ccagctcttt ggctccccta gtgggcagaa agatctgctg ttcaaggact 1260
ctgccattgg gttttcgagg gtgcccccga ggatagattc tgggctgtac cttggctccg 1320
gctacttcac tgccatccag aacttgagga aaagtgagga ggaagtggct gcccggcgtg 1380
cgcgggtcgt gtggtgtgcg gtgggcgagc aggagctgcg caagtgtaac cagtggagtg 1440
gcttgagcga aggcagcgtg acctgctcct cggcctccac cacagaggac tgcatcgccc 1500
tgaaaggaga agctgatgcc atgagtttgg atggaggata tgtgtacact gcaggcaaat 1560
gtggtttggt gcctgtcctg gcagagaact acaaatccca acaaagcagt gaccctgatc 1620
ctaactgtgt ggatagacct gtggaaggat atcttgctgt ggcggtggtt aggagatcag 1680
acactagcct tacctggaac tctgtgaaag gcaagaagtc ctgccacacc gccgtggaca 1740
ggactgcagg ctggaatatc cccatgggcc tgctcttcaa ccagacgggc tcctgcaaat 1800
ttgatgaata tttcagtcaa agctgtgccc ctgggtctga cccgagatct aatctctgtg 1860
ctctgtgtat tggcgacgag cagggtgaga ataagtgcgt gcccaacagc aacgagagat 1920
actacggcta cactggggct ttccggtgcc tggctgagaa tgctggagac gttgcatttg 1980

-continued

```
tgaaagatgt cactgtcttg cagaacactg atggaaataa caatgaggca tgggctaagg   2040

atttgaagct ggcagacttt gcgctgctgt gcctcgatgg caaacggaag cctgtgactg   2100

aggctagaag ctgccatctt gccatggccc cgaatcatgc cgtggtgtct cggatggata   2160

aggtggaacg cctgaaacag gtgttgctcc accaacaggc taaatttggg agaaatggat   2220

ctgactgccc ggacaagttt tgcttattcc agtctgaaac caaaaacctt ctgttcaatg   2280

acaacactga gtgtctggcc agactccatg gcaaaacaac atatgaaaaa tatttgggac   2340

cacagtatgt cgcaggcatt actaatctga aaaagtgctc aacctccccc ctcctggaag   2400

cctgtgaatt cctcaggaag taaaaccgaa gaagatggcc cagctcccca agaaagcctc   2460

agccattcac tgcccccagc tcttctcccc aggtgtgttg gggccttggc ctcccctgct   2520

gaaggtgggg attgcccatc catctgctta caattccctg ctgtcgtctt agcaagaagt   2580

aaaatgagaa attttgttga tattctctcc ttaaaaaaaa aaaaaaaaaa aaaaaaaaaa   2640

aa                                                                  2642
```

```
<210> SEQ ID NO 44
<211> LENGTH: 708
<212> TYPE: PRT
<213> ORGANISM: Homo sapiens
<300> PUBLICATION INFORMATION:
<308> DATABASE ACCESSION NUMBER: NCBI / NP_001308050.1
<309> DATABASE ENTRY DATE: 2017-10-09
<313> RELEVANT RESIDUES IN SEQ ID NO: (1)..(708)

<400> SEQUENCE: 44

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser Gln
            20                  25                  30

Pro Glu Ala Thr Lys Cys Phe Gln Trp Gln Arg Asn Met Arg Lys Val
        35                  40                  45

Arg Gly Pro Pro Val Ser Cys Ile Lys Arg Asp Ser Pro Ile Gln Cys
    50                  55                  60

Ile Gln Ala Ile Ala Glu Asn Arg Ala Asp Ala Val Thr Leu Asp Gly
65                  70                  75                  80

Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
    130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205

Phe Ser Tyr Ser Gly Ala Phe Lys Cys Leu Arg Asp Gly Ala Gly Asp
    210                 215                 220

Val Ala Phe Ile Arg Glu Ser Thr Val Phe Glu Asp Leu Ser Asp Glu
```

```
225                 230                 235                 240

Ala Glu Arg Asp Glu Tyr Glu Leu Leu Cys Pro Asp Asn Thr Arg Lys
                245                 250                 255

Pro Val Asp Lys Phe Lys Asp Cys His Leu Ala Arg Val Pro Ser His
            260                 265                 270

Ala Val Val Ala Arg Ser Val Asn Gly Lys Glu Asp Ala Ile Trp Asn
        275                 280                 285

Leu Leu Arg Gln Ala Gln Glu Lys Phe Gly Lys Asp Lys Ser Pro Lys
    290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                325                 330                 335

Leu Tyr Leu Gly Ser Gly Tyr Phe Thr Ala Ile Gln Asn Leu Arg Lys
            340                 345                 350

Ser Glu Glu Glu Val Ala Ala Arg Arg Ala Arg Val Val Trp Cys Ala
        355                 360                 365

Val Gly Glu Gln Glu Leu Arg Lys Cys Asn Gln Trp Ser Gly Leu Ser
    370                 375                 380

Glu Gly Ser Val Thr Cys Ser Ser Ala Ser Thr Thr Glu Asp Cys Ile
385                 390                 395                 400

Ala Leu Lys Gly Glu Ala Asp Ala Met Ser Leu Asp Gly Gly Tyr Val
                405                 410                 415

Tyr Thr Ala Gly Lys Cys Gly Leu Val Pro Val Leu Ala Glu Asn Tyr
            420                 425                 430

Lys Ser Gln Gln Ser Ser Asp Pro Asp Pro Asn Cys Val Asp Arg Pro
        435                 440                 445

Val Glu Gly Tyr Leu Ala Val Ala Val Val Arg Arg Ser Asp Thr Ser
    450                 455                 460

Leu Thr Trp Asn Ser Val Lys Gly Lys Lys Ser Cys His Thr Ala Val
465                 470                 475                 480

Asp Arg Thr Ala Gly Trp Asn Ile Pro Met Gly Leu Leu Phe Asn Gln
                485                 490                 495

Thr Gly Ser Cys Lys Phe Asp Glu Tyr Phe Ser Gln Ser Cys Ala Pro
            500                 505                 510

Gly Ser Asp Pro Arg Ser Asn Leu Cys Ala Leu Cys Ile Gly Asp Glu
        515                 520                 525

Gln Gly Glu Asn Lys Cys Val Pro Asn Ser Asn Glu Arg Tyr Tyr Gly
    530                 535                 540

Tyr Thr Gly Ala Phe Arg Cys Leu Ala Glu Asn Ala Gly Asp Val Ala
545                 550                 555                 560

Phe Val Lys Asp Val Thr Val Leu Gln Asn Thr Asp Gly Asn Asn Asn
                565                 570                 575

Glu Ala Trp Ala Lys Asp Leu Lys Leu Ala Asp Phe Ala Leu Leu Cys
            580                 585                 590

Leu Asp Gly Lys Arg Lys Pro Val Thr Glu Ala Arg Ser Cys His Leu
        595                 600                 605

Ala Met Ala Pro Asn His Ala Val Val Ser Arg Met Asp Lys Val Glu
    610                 615                 620

Arg Leu Lys Gln Val Leu Leu His Gln Gln Ala Lys Phe Gly Arg Asn
625                 630                 635                 640

Gly Ser Asp Cys Pro Asp Lys Phe Cys Leu Phe Gln Ser Glu Thr Lys
                645                 650                 655
```

```
Asn Leu Leu Phe Asn Asp Asn Thr Glu Cys Leu Ala Arg Leu His Gly
            660                 665                 670

Lys Thr Thr Tyr Glu Lys Tyr Leu Gly Pro Gln Tyr Val Ala Gly Ile
        675                 680                 685

Thr Asn Leu Lys Lys Cys Ser Thr Ser Pro Leu Leu Glu Ala Cys Glu
    690                 695                 700

Phe Leu Arg Lys
705


<210> SEQ ID NO 45
<211> LENGTH: 2881
<212> TYPE: DNA
<213> ORGANISM: Homo sapiens
<300> PUBLICATION INFORMATION:
<308> DATABASE ACCESSION NUMBER: NCBI / NM_001321122.1
<309> DATABASE ENTRY DATE: 2017-10-09
<313> RELEVANT RESIDUES IN SEQ ID NO: (1)..(2881)

<400> SEQUENCE: 45

acgtggcctt cacagctggc ctgagtgagc acagcgggca ctgaggggaa caaagcgtgg     60

gggccctcca gcagccctta tcatcacctg ccagccacct gcctcaggct gggcaggctg    120

caccctgggc tttctgctat tggcttccca gatccctgga actccagctg gggccctggg    180

ctgtggtctg acttgatcca gaatttaatg agtagaagga atggaagaag gctcattccc    240

ccagccctgg acacagacag cagacacaga ggcctccagc acagtgaagc ctgtggagca    300

gtcccctcca gaatgcaacc ttgtaggagg gcagcaccat gggccagcaa ctcagggtga    360

tcagcaaata aatgatcaat actaagacac caaggcccta agaagtcact ggatggggtc    420

ccgggtggat ttctagctct actgtccact ggctgtgaga ccatgaacag ggtgcattgc    480

ccaagtccac tcagctggaa acaggctctt tgagatctga cccaactcct ggcacgttgg    540

agatgtccca tagaccagtg ttgaatgaat gggactgtgt ctggctggcc gtaggaggag    600

tgttcagtgg tgcgccgtat cccaacccga ggccacaaaa tgcttccaat ggcaaaggaa    660

tatgagaaaa gtgcgtggcc ctcctgtcag ctgcataaag agagactccc ccatccagtg    720

tatccaggcc attgcggaaa acagggccga tgctgtgacc cttgatggtg gtttcatata    780

cgaggcaggc ctggccccct acaaactgcg acctgtagcg gcggaagtct acgggaccga    840

aagacagcca cgaactcact attatgccgt ggctgtggtg aagaagggcg gcagctttca    900

gctgaacgaa ctgcaaggtc tgaagtcctg ccacacaggc cttcgcagga ccgctggatg    960

gaatgtccct atagggacac ttcgtccatt cttgaattgg acgggtccac ctgagcccat   1020

tgaggcagct gtggccaggt tcttctcagc cagctgtgtt cccggtgcag ataaaggaca   1080

gttccccaac ctgtgtcgcc tgtgtgcggg gacaggggaa aacaaatgtg ccttctcctc   1140

ccaggaaccg tacttcagct actctggtgc cttcaagtgt ctgagagacg gggctggaga   1200

cgtggctttt atcagagaga gcacagtgtt tgaggacctg tcagacgagg ctgaaaggga   1260

cgagtatgag ttactctgcc cagacaacac tcggaagcca gtggacaagt tcaaagactg   1320

ccatctggcc cgggtccctt ctcatgccgt tgtggcacga agtgtgaatg gcaaggagga   1380

tgccatctgg aatcttctcc gccaggcaca ggaaaagttt ggaaaggaca agtcaccgaa   1440

attccagctc tttggctccc ctagtgggca gaaagatctg ctgttcaagg actctgccat   1500

tgggttttcg agggtgcccc cgaggataga ttctgggctg taccttggct ccggctactt   1560

cactgccatc cagaacttga ggaaaagtga ggaggaagtg gctgcccggc gtgcgcgggt   1620
```

cgtgtggtgt gcggtgggcg agcaggagct gcgcaagtgt aaccagtgga gtggcttgag 1680
cgaaggcagc gtgacctgct cctcggcctc caccacagag gactgcatcg ccctggtgct 1740
gaaaggagaa gctgatgcca tgagtttgga tggaggatat gtgtacactg caggcaaatg 1800
tggtttggtg cctgtcctgg cagagaacta caaatcccaa caaagcagtg accctgatcc 1860
taactgtgtg gatagacctg tggaaggata tcttgctgtg gcggtggtta ggagatcaga 1920
cactagcctt acctggaact ctgtgaaagg caagaagtcc tgccacaccg ccgtggacag 1980
gactgcaggc tggaatatcc ccatgggcct gctcttcaac cagacgggct cctgcaaatt 2040
tgatgaatat ttcagtcaaa gctgtgcccc tgggtctgac ccgagatcta atctctgtgc 2100
tctgtgtatt ggcgacgagc agggtgagaa taagtgcgtg cccaacagca acgagagata 2160
ctacggctac actggggctt tccggtgcct ggctgagaat gctggagacg ttgcatttgt 2220
gaaagatgtc actgtcttgc agaacactga tggaaataac aatgaggcat gggctaagga 2280
tttgaagctg gcagactttg cgctgctgtg cctcgatggc aaacggaagc ctgtgactga 2340
ggctagaagc tgccatcttg ccatggcccc gaatcatgcc gtggtgtctc ggatggataa 2400
ggtggaacgc ctgaaacagg tgttgctcca ccaacaggct aaatttggga gaaatggatc 2460
tgactgcccg gacaagtttt gcttattcca gtctgaaacc aaaaaccttc tgttcaatga 2520
caacactgag tgtctggcca gactccatgg caaaacaaca tatgaaaaat atttgggacc 2580
acagtatgtc gcaggcatta ctaatctgaa aaagtgctca acctcccccc tcctggaagc 2640
ctgtgaattc ctcaggaagt aaaaccgaag aagatggccc agctccccaa gaaagcctca 2700
gccattcact gcccccagct cttctcccca ggtgtgttgg ggccttggcc tcccctgctg 2760
aaggtgggga ttgcccatcc atctgcttac aattccctgc tgtcgtctta gcaagaagta 2820
aaatgagaaa ttttgttgat attctctcct taaaaaaaaa aaaaaaaaaa aaaaaaaaaa 2880
a 2881

<210> SEQ ID NO 46
<211> LENGTH: 697
<212> TYPE: PRT
<213> ORGANISM: Homo sapiens
<300> PUBLICATION INFORMATION:
<308> DATABASE ACCESSION NUMBER: NCBI / NP_001308051.1
<309> DATABASE ENTRY DATE: 2017-10-09
<313> RELEVANT RESIDUES IN SEQ ID NO: (1)..(697)

<400> SEQUENCE: 46

Met Gly Leu Cys Leu Ala Gly Arg Arg Arg Ser Val Gln Trp Cys Ala
1 5 10 15

Val Ser Gln Pro Glu Ala Thr Lys Cys Phe Gln Trp Gln Arg Asn Met
20 25 30

Arg Lys Val Arg Gly Pro Pro Val Ser Cys Ile Lys Arg Asp Ser Pro
35 40 45

Ile Gln Cys Ile Gln Ala Ile Ala Glu Asn Arg Ala Asp Ala Val Thr
50 55 60

Leu Asp Gly Gly Phe Ile Tyr Glu Ala Gly Leu Ala Pro Tyr Lys Leu
65 70 75 80

Arg Pro Val Ala Ala Glu Val Tyr Gly Thr Glu Arg Gln Pro Arg Thr
85 90 95

His Tyr Tyr Ala Val Ala Val Val Lys Lys Gly Gly Ser Phe Gln Leu
100 105 110

Asn Glu Leu Gln Gly Leu Lys Ser Cys His Thr Gly Leu Arg Arg Thr
115 120 125

-continued

```
Ala Gly Trp Asn Val Pro Ile Gly Thr Leu Arg Pro Phe Leu Asn Trp
    130                 135                 140

Thr Gly Pro Pro Glu Pro Ile Glu Ala Ala Val Ala Arg Phe Phe Ser
145                 150                 155                 160

Ala Ser Cys Val Pro Gly Ala Asp Lys Gly Gln Phe Pro Asn Leu Cys
                165                 170                 175

Arg Leu Cys Ala Gly Thr Gly Glu Asn Lys Cys Ala Phe Ser Ser Gln
            180                 185                 190

Glu Pro Tyr Phe Ser Tyr Ser Gly Ala Phe Lys Cys Leu Arg Asp Gly
        195                 200                 205

Ala Gly Asp Val Ala Phe Ile Arg Glu Ser Thr Val Phe Glu Asp Leu
    210                 215                 220

Ser Asp Glu Ala Glu Arg Asp Glu Tyr Glu Leu Leu Cys Pro Asp Asn
225                 230                 235                 240

Thr Arg Lys Pro Val Asp Lys Phe Lys Asp Cys His Leu Ala Arg Val
                245                 250                 255

Pro Ser His Ala Val Val Ala Arg Ser Val Asn Gly Lys Glu Asp Ala
            260                 265                 270

Ile Trp Asn Leu Leu Arg Gln Ala Gln Glu Lys Phe Gly Lys Asp Lys
        275                 280                 285

Ser Pro Lys Phe Gln Leu Phe Gly Ser Pro Ser Gly Gln Lys Asp Leu
    290                 295                 300

Leu Phe Lys Asp Ser Ala Ile Gly Phe Ser Arg Val Pro Pro Arg Ile
305                 310                 315                 320

Asp Ser Gly Leu Tyr Leu Gly Ser Gly Tyr Phe Thr Ala Ile Gln Asn
                325                 330                 335

Leu Arg Lys Ser Glu Glu Glu Val Ala Ala Arg Arg Ala Arg Val Val
            340                 345                 350

Trp Cys Ala Val Gly Glu Gln Glu Leu Arg Lys Cys Asn Gln Trp Ser
        355                 360                 365

Gly Leu Ser Glu Gly Ser Val Thr Cys Ser Ser Ala Ser Thr Thr Glu
    370                 375                 380

Asp Cys Ile Ala Leu Val Leu Lys Gly Glu Ala Asp Ala Met Ser Leu
385                 390                 395                 400

Asp Gly Gly Tyr Val Tyr Thr Ala Gly Lys Cys Gly Leu Val Pro Val
                405                 410                 415

Leu Ala Glu Asn Tyr Lys Ser Gln Gln Ser Ser Asp Pro Asp Pro Asn
            420                 425                 430

Cys Val Asp Arg Pro Val Glu Gly Tyr Leu Ala Val Ala Val Val Arg
        435                 440                 445

Arg Ser Asp Thr Ser Leu Thr Trp Asn Ser Val Lys Gly Lys Lys Ser
    450                 455                 460

Cys His Thr Ala Val Asp Arg Thr Ala Gly Trp Asn Ile Pro Met Gly
465                 470                 475                 480

Leu Leu Phe Asn Gln Thr Gly Ser Cys Lys Phe Asp Glu Tyr Phe Ser
                485                 490                 495

Gln Ser Cys Ala Pro Gly Ser Asp Pro Arg Ser Asn Leu Cys Ala Leu
            500                 505                 510

Cys Ile Gly Asp Glu Gln Gly Glu Asn Lys Cys Val Pro Asn Ser Asn
        515                 520                 525

Glu Arg Tyr Tyr Gly Tyr Thr Gly Ala Phe Arg Cys Leu Ala Glu Asn
    530                 535                 540
```

Ala Gly Asp Val Ala Phe Val Lys Asp Val Thr Val Leu Gln Asn Thr
545 550 555 560

Asp Gly Asn Asn Asn Glu Ala Trp Ala Lys Asp Leu Lys Leu Ala Asp
565 570 575

Phe Ala Leu Leu Cys Leu Asp Gly Lys Arg Lys Pro Val Thr Glu Ala
580 585 590

Arg Ser Cys His Leu Ala Met Ala Pro Asn His Ala Val Val Ser Arg
595 600 605

Met Asp Lys Val Glu Arg Leu Lys Gln Val Leu Leu His Gln Gln Ala
610 615 620

Lys Phe Gly Arg Asn Gly Ser Asp Cys Pro Asp Lys Phe Cys Leu Phe
625 630 635 640

Gln Ser Glu Thr Lys Asn Leu Leu Phe Asn Asp Asn Thr Glu Cys Leu
645 650 655

Ala Arg Leu His Gly Lys Thr Thr Tyr Glu Lys Tyr Leu Gly Pro Gln
660 665 670

Tyr Val Ala Gly Ile Thr Asn Leu Lys Lys Cys Ser Thr Ser Pro Leu
675 680 685

Leu Glu Ala Cys Glu Phe Leu Arg Lys
690 695

<210> SEQ ID NO 47
<211> LENGTH: 2648
<212> TYPE: DNA
<213> ORGANISM: Homo sapiens
<300> PUBLICATION INFORMATION:
<308> DATABASE ACCESSION NUMBER: NCBI / NM_002343.5
<309> DATABASE ENTRY DATE: 2017-10-09
<313> RELEVANT RESIDUES IN SEQ ID NO: (1)..(2648)

<400> SEQUENCE: 47
gactcctagg ggcttgcaga ctagtgggag agaaagaaca tcgcagcagc caggcagaac 60
caggacaggt gaggtgcagg ctggctttcc tctcgcagcg cggtgtggag tcctgtcctg 120
cctcagggct tttcggagcc tggatcctca aggaacaagt agacctggcc gcggggagtg 180
gggagggaag ggtgtctat tgggcaacag ggcggggcaa agccctgaat aaaggggcgc 240
agggcaggcg caagtggcag agccttcgtt tgccaagtcg cctccagacc gcagacatga 300
aacttgtctt cctcgtcctg ctgttcctcg gggccctcgg actgtgtctg gctggccgta 360
ggaggagtgt tcagtggtgc gccgtatccc aacccgaggc cacaaaatgc ttccaatggc 420
aaaggaatat gagaaaagtg cgtggccctc ctgtcagctg cataaagaga gactccccca 480
tccagtgtat ccaggccatt gcggaaaaca gggccgatgc tgtgaccctt gatggtggtt 540
tcatatacga ggcaggcctg gccccctaca aactgcgacc tgtagcggcg gaagtctacg 600
ggaccgaaag acagccacga actcactatt atgccgtggc tgtggtgaag aagggcggca 660
gctttcagct gaacgaactg caaggtctga agtcctgcca cacaggcctt cgcaggaccg 720
ctggatggaa tgtccctata gggacacttc gtccattctt gaattggacg ggtccacctg 780
agcccattga ggcagctgtg gccaggttct tctcagccag ctgtgttccc ggtgcagata 840
aaggacagtt ccccaacctg tgtcgcctgt gtgcggggac aggggaaaac aaatgtgcct 900
tctcctccca ggaaccgtac ttcagctact ctggtgcctt caagtgtctg agagacgggg 960
ctggagacgt ggcttttatc agagagagca cagtgtttga ggacctgtca gacgaggctg 1020
aaagggacga gtatgagtta ctctgcccag acaacactcg gaagccagtg gacaagttca 1080
aagactgcca tctggcccgg gtcccttctc atgccgttgt ggcacgaagt gtgaatggca 1140

```
aggaggatgc catctggaat cttctccgcc aggcacagga aaagtttgga aaggacaagt   1200

caccgaaatt ccagctcttt ggctccccta gtgggcagaa agatctgctg ttcaaggact   1260

ctgccattgg gttttcgagg gtgcccccga ggatagattc tggctgtac cttggctccg    1320

gctacttcac tgccatccag aacttgagga aaagtgagga ggaagtggct gcccggcgtg   1380

cgcgggtcgt gtggtgtgcg gtgggcgagc aggagctgcg caagtgtaac cagtggagtg   1440

gcttgagcga aggcagcgtg acctgctcct cggcctccac cacagaggac tgcatcgccc   1500

tggtgctgaa aggagaagct gatgccatga gtttggatgg aggatatgtg tacactgcag   1560

gcaaatgtgg tttggtgcct gtcctggcag agaactacaa atcccaacaa agcagtgacc   1620

ctgatcctaa ctgtgtggat agacctgtgg aaggatatct tgctgtggcg gtggttagga   1680

gatcagacac tagccttacc tggaactctg tgaaaggcaa gaagtcctgc cacaccgccg   1740

tggacaggac tgcaggctgg aatatcccca tgggcctgct cttcaaccag acgggctcct   1800

gcaaatttga tgaatatttc agtcaaagct gtgcccctgg gtctgacccg agatctaatc   1860

tctgtgctct gtgtattggc gacgagcagg gtgagaataa gtgcgtgccc aacagcaacg   1920

agagatacta cggctacact ggggctttcc ggtgcctggc tgagaatgct ggagacgttg   1980

catttgtgaa agatgtcact gtcttgcaga acactgatgg aaataacaat gaggcatggg   2040

ctaaggattt gaagctggca gactttgcgc tgctgtgcct cgatggcaaa cggaagcctg   2100

tgactgaggc tagaagctgc catcttgcca tggccccgaa tcatgccgtg gtgtctcgga   2160

tggataaggt ggaacgcctg aaacaggtgt tgctccacca acaggctaaa tttgggagaa   2220

atggatctga ctgcccggac aagttttgct tattccagtc tgaaaccaaa aaccttctgt   2280

tcaatgacaa cactgagtgt ctggccagac tccatggcaa aacaacatat gaaaaatatt   2340

tgggaccaca gtatgtcgca ggcattacta atctgaaaaa gtgctcaacc tccccccctcc  2400

tggaagcctg tgaattcctc aggaagtaaa accgaagaag atggcccagc tccccaagaa   2460

agcctcagcc attcactgcc cccagctctt ctccccaggt gtgttggggc cttggcctcc   2520

cctgctgaag gtggggattg cccatccatc tgcttacaat tccctgctgt cgtcttagca   2580

agaagtaaaa tgagaaattt tgttgatatt ctctccttaa aaaaaaaaaa aaaaaaaaaa   2640

aaaaaaaa                                                            2648
```

<210> SEQ ID NO 48
<211> LENGTH: 710
<212> TYPE: PRT
<213> ORGANISM: Homo sapiens
<300> PUBLICATION INFORMATION:
<308> DATABASE ACCESSION NUMBER: NCBI / NP_002334.2
<309> DATABASE ENTRY DATE: 2017-10-09
<313> RELEVANT RESIDUES IN SEQ ID NO: (1)..(710)

<400> SEQUENCE: 48

```
Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser Gln
            20                  25                  30

Pro Glu Ala Thr Lys Cys Phe Gln Trp Gln Arg Asn Met Arg Lys Val
        35                  40                  45

Arg Gly Pro Pro Val Ser Cys Ile Lys Arg Asp Ser Pro Ile Gln Cys
    50                  55                  60

Ile Gln Ala Ile Ala Glu Asn Arg Ala Asp Ala Val Thr Leu Asp Gly
65                  70                  75                  80
```

```
Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
    130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205

Phe Ser Tyr Ser Gly Ala Phe Lys Cys Leu Arg Asp Gly Ala Gly Asp
    210                 215                 220

Val Ala Phe Ile Arg Glu Ser Thr Val Phe Glu Asp Leu Ser Asp Glu
225                 230                 235                 240

Ala Glu Arg Asp Glu Tyr Glu Leu Leu Cys Pro Asp Asn Thr Arg Lys
                245                 250                 255

Pro Val Asp Lys Phe Lys Asp Cys His Leu Ala Arg Val Pro Ser His
            260                 265                 270

Ala Val Val Ala Arg Ser Val Asn Gly Lys Glu Asp Ala Ile Trp Asn
        275                 280                 285

Leu Leu Arg Gln Ala Gln Glu Lys Phe Gly Lys Asp Lys Ser Pro Lys
    290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                325                 330                 335

Leu Tyr Leu Gly Ser Gly Tyr Phe Thr Ala Ile Gln Asn Leu Arg Lys
            340                 345                 350

Ser Glu Glu Glu Val Ala Ala Arg Arg Ala Arg Val Val Trp Cys Ala
        355                 360                 365

Val Gly Glu Gln Glu Leu Arg Lys Cys Asn Gln Trp Ser Gly Leu Ser
    370                 375                 380

Glu Gly Ser Val Thr Cys Ser Ser Ala Ser Thr Thr Glu Asp Cys Ile
385                 390                 395                 400

Ala Leu Val Leu Lys Gly Glu Ala Asp Ala Met Ser Leu Asp Gly Gly
                405                 410                 415

Tyr Val Tyr Thr Ala Gly Lys Cys Gly Leu Val Pro Val Leu Ala Glu
            420                 425                 430

Asn Tyr Lys Ser Gln Gln Ser Ser Asp Pro Asp Pro Asn Cys Val Asp
        435                 440                 445

Arg Pro Val Glu Gly Tyr Leu Ala Val Ala Val Val Arg Arg Ser Asp
    450                 455                 460

Thr Ser Leu Thr Trp Asn Ser Val Lys Gly Lys Lys Ser Cys His Thr
465                 470                 475                 480

Ala Val Asp Arg Thr Ala Gly Trp Asn Ile Pro Met Gly Leu Leu Phe
                485                 490                 495
```

```
Asn Gln Thr Gly Ser Cys Lys Phe Asp Glu Tyr Phe Ser Gln Ser Cys
            500                 505                 510

Ala Pro Gly Ser Asp Pro Arg Ser Asn Leu Cys Ala Leu Cys Ile Gly
        515                 520                 525

Asp Glu Gln Gly Glu Asn Lys Cys Val Pro Asn Ser Asn Glu Arg Tyr
    530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
                565                 570                 575

Asn Asn Glu Ala Trp Ala Lys Asp Leu Lys Leu Ala Asp Phe Ala Leu
            580                 585                 590

Leu Cys Leu Asp Gly Lys Arg Lys Pro Val Thr Glu Ala Arg Ser Cys
        595                 600                 605

His Leu Ala Met Ala Pro Asn His Ala Val Val Ser Arg Met Asp Lys
    610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu
                645                 650                 655

Thr Lys Asn Leu Leu Phe Asn Asp Asn Thr Glu Cys Leu Ala Arg Leu
            660                 665                 670

His Gly Lys Thr Thr Tyr Glu Lys Tyr Leu Gly Pro Gln Tyr Val Ala
        675                 680                 685

Gly Ile Thr Asn Leu Lys Lys Cys Ser Thr Ser Pro Leu Leu Glu Ala
    690                 695                 700

Cys Glu Phe Leu Arg Lys
705                 710
```

<210> SEQ ID NO 49
<211> LENGTH: 1020
<212> TYPE: DNA
<213> ORGANISM: Homo sapiens
<300> PUBLICATION INFORMATION:
<308> DATABASE ACCESSION NUMBER: NCBI / NM_001972.3
<309> DATABASE ENTRY DATE: 2017-10-03
<313> RELEVANT RESIDUES IN SEQ ID NO: (1)..(1020)

<400> SEQUENCE: 49

```
gggagaggaa gtggagggcg ctggccggcc gtggggcaat gcaacggcct cccagcacag      60

ggctataaga ggagccgggc gggcacggag gggcagagac cccggagccc cagccccacc     120

atgaccctcg gccgccgact cgcgtgtctt ttcctcgcct gtgtcctgcc ggccttgctg     180

ctgggggggca ccgcgctggc ctcggagatt gtgggggggcc ggcgagcgcg gccccacgcg     240

tggcccttca tggtgtccct gcagctgcgc ggaggccact tctgcggcgc caccctgatt     300

gcgcccaact tcgtcatgtc ggccgcgcac tgcgtggcga atgtaaacgt ccgcgcggtg     360

cgggtggtcc tgggagccca taacctctcg cggcgggagc ccacccggca ggtgttcgcc     420

gtgcagcgca tcttcgaaaa cggctacgac cccgtaaact tgctcaacga catcgtgatt     480

ctccagctca acgggtcggc caccatcaac gccaacgtgc aggtggccca gctgccggct     540

cagggacgcc gcctgggcaa cggggtgcag tgcctggcca tgggctgggg ccttctgggc     600

aggaaccgtg ggatcgccag cgtcctgcag gagctcaacg tgacggtggt gacgtccctc     660

tgccgtcgca gcaacgtctg cactctcgtg aggggccggc aggccggcgt ctgtttcggg     720

gactccggca gcccccttggt ctgcaacggg ctaatccacg gaattgcctc cttcgtccgg     780
```

```
ggaggctgcg cctcagggct ctaccccgat gcctttgccc cggtggcaca gtttgtaaac    840

tggatcgact ctatcatcca acgctccgag gacaacccct gtccccaccc ccgggacccg    900

gacccggcca gcaggaccca ctgagaaggg ctgcccgggt cacctcagct gcccacaccc    960

acactctcca gcatctggca caataaacat tctctgtttt gtagaaaaaa aaaaaaaaaa   1020
```

<210> SEQ ID NO 50
<211> LENGTH: 267
<212> TYPE: PRT
<213> ORGANISM: Homo sapiens
<300> PUBLICATION INFORMATION:
<308> DATABASE ACCESSION NUMBER: NCBI / NP_001963.1
<309> DATABASE ENTRY DATE: 2017-10-09
<313> RELEVANT RESIDUES IN SEQ ID NO: (1)..(267)

<400> SEQUENCE: 50

```
Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
        35                  40                  45

Leu Arg Gly Gly His Phe Cys Gly Ala Thr Leu Ile Ala Pro Asn Phe
    50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
        115                 120                 125

Ile Asn Ala Asn Val Gln Val Ala Gln Leu Pro Ala Gln Gly Arg Arg
    130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His
            260                 265
```

<210> SEQ ID NO 51
<211> LENGTH: 758
<212> TYPE: DNA
<213> ORGANISM: Homo sapiens
<300> PUBLICATION INFORMATION:
<308> DATABASE ACCESSION NUMBER: NCBI / NM_004345.4

<309> DATABASE ENTRY DATE: 2017-08-21
<313> RELEVANT RESIDUES IN SEQ ID NO: (1)..(758)

<400> SEQUENCE: 51

```
gtcctgtgaa gcaatagcca ggggctaaag caaaccccag cccacaccct ggcaggcagc     60

cagggatggg tggatcagga aggctcctgg ttgggctttt gcatcaggct caggctgggc    120

ataaaggagg ctcctgtggg ctagagggag gcagacatgg ggaccatgaa gacccaaagg    180

gatggccact ccctggggcg gtggtcactg gtgctcctgc tgctgggcct ggtgatgcct    240

ctggccatca ttgcccaggt cctcagctac aaggaagctg tgcttcgtgc tatagatggc    300

atcaaccagc ggtcctcgga tgctaacctc taccgcctcc tggacctgga ccccaggccc    360

acgatggatg gggacccaga cacgccaaag cctgtgagct tcacagtgaa ggagacagtg    420

tgccccagga cgacacagca gtcaccagag gattgtgact tcaagaagga cgggctggtg    480

aagcggtgta tggggacagt gaccctcaac caggccaggg gctcctttga catcagttgt    540

gataaggata acaagagatt tgccctgctg ggtgatttct tccggaaatc taaagagaag    600

attggcaaag agtttaaaag aattgtccag agaatcaagg atttttttgcg gaatcttgta    660

cccaggacag agtcctagtg tgtgccctac cctggctcag gcttctgggc tctgagaaat    720

aaactatgag agcaatttcc tcaggaaaaa aaaaaaaa                            758
```

<210> SEQ ID NO 52
<211> LENGTH: 173
<212> TYPE: PRT
<213> ORGANISM: Homo sapiens
<300> PUBLICATION INFORMATION:
<308> DATABASE ACCESSION NUMBER: NCBI / NP_004336.3
<309> DATABASE ENTRY DATE: 2017-08-21
<313> RELEVANT RESIDUES IN SEQ ID NO: (1)..(173)

<400> SEQUENCE: 52

```
Met Gly Thr Met Lys Thr Gln Arg Asp Gly His Ser Leu Gly Arg Trp
1               5                   10                  15

Ser Leu Val Leu Leu Leu Leu Gly Leu Val Met Pro Leu Ala Ile Ile
            20                  25                  30

Ala Gln Val Leu Ser Tyr Lys Glu Ala Val Leu Arg Ala Ile Asp Gly
        35                  40                  45

Ile Asn Gln Arg Ser Ser Asp Ala Asn Leu Tyr Arg Leu Leu Asp Leu
    50                  55                  60

Asp Pro Arg Pro Thr Met Asp Gly Asp Pro Asp Thr Pro Lys Pro Val
65                  70                  75                  80

Ser Phe Thr Val Lys Glu Thr Val Cys Pro Arg Thr Thr Gln Gln Ser
                85                  90                  95

Pro Glu Asp Cys Asp Phe Lys Lys Asp Gly Leu Val Lys Arg Cys Met
            100                 105                 110

Gly Thr Val Thr Leu Asn Gln Ala Arg Gly Ser Phe Asp Ile Ser Cys
        115                 120                 125

Asp Lys Asp Asn Lys Arg Phe Ala Leu Leu Gly Asp Phe Phe Arg Lys
    130                 135                 140

Ser Lys Glu Lys Ile Gly Lys Glu Phe Lys Arg Ile Val Gln Arg Ile
145                 150                 155                 160

Lys Asp Phe Leu Arg Asn Leu Val Pro Arg Thr Glu Ser
                165                 170
```

<210> SEQ ID NO 53
<211> LENGTH: 972

<212> TYPE: DNA
<213> ORGANISM: Homo sapiens
<300> PUBLICATION INFORMATION:
<308> DATABASE ACCESSION NUMBER: NCBI / NM_005091.2
<309> DATABASE ENTRY DATE: 2017-09-10
<313> RELEVANT RESIDUES IN SEQ ID NO: (1)..(972)

<400> SEQUENCE: 53

```
acggcggggc gaagcgccca ggggcctgtg cgtccctccc tgctgagcga gggggcctgt      60

cattgccgtg ggcgtgaccc agaccccaac cacagtgcat cccgccctgg cccagccaga     120

gaaggaagct gagtctgggg tctgctgggc cagcaggaag tcccagcagg gtgtgaagca     180

agactttccg ggccactcct ggaatccccc agcagataaa ggcggcccct ccaccgggcg     240

ctcctagcgg tctcccggac cctgccgccc tgccactatg tcccgccgct ctatgctgct     300

tgcctgggct ctccccagcc tccttcgact cggagcggct caggagacag aagacccggc     360

ctgctgcagc cccatagtgc cccggaacga gtggaaggcc ctggcatcag agtgcgccca     420

gcacctgagc ctgcccttac gctatgtggt ggtatcgcac acggcgggca gcagctgcaa     480

cacccccgcc tcgtgccagc agcaggcccg gaatgtgcag cactaccaca tgaagacact     540

gggctggtgc gacgtgggct acaacttcct gattggagaa gacgggctcg tatacgaggg     600

ccgtggctgg aacttcacgg gtgcccactc aggtcactta tggaacccca tgtccattgg     660

catcagcttc atgggcaact acatggatcg ggtgcccaca ccccaggcca tccgggcagc     720

ccagggtcta ctggcctgcg gtgtggctca gggagccctg aggtccaact atgtgctcaa     780

aggacaccgg gatgtgcagc gtacactctc tccaggcaac cagctctacc acctcatcca     840

gaattggcca cactaccgct ccccctgagg ccctgctgat ccgcacccca ttcctcccct     900

cccatggcca aaaaccccac tgtctccttc tccaataaag atgtagctca aaaaaaaaaa     960

aaaaaaaaaa aa                                                         972
```

<210> SEQ ID NO 54
<211> LENGTH: 196
<212> TYPE: PRT
<213> ORGANISM: Homo sapiens
<300> PUBLICATION INFORMATION:
<308> DATABASE ACCESSION NUMBER: NCBI / NP_005082.1
<309> DATABASE ENTRY DATE: 2017-09-10
<313> RELEVANT RESIDUES IN SEQ ID NO: (1)..(196)

<400> SEQUENCE: 54

```
Met Ser Arg Arg Ser Met Leu Leu Ala Trp Ala Leu Pro Ser Leu Leu
1               5                   10                  15

Arg Leu Gly Ala Ala Gln Glu Thr Glu Asp Pro Ala Cys Cys Ser Pro
            20                  25                  30

Ile Val Pro Arg Asn Glu Trp Lys Ala Leu Ala Ser Glu Cys Ala Gln
        35                  40                  45

His Leu Ser Leu Pro Leu Arg Tyr Val Val Val Ser His Thr Ala Gly
    50                  55                  60

Ser Ser Cys Asn Thr Pro Ala Ser Cys Gln Gln Gln Ala Arg Asn Val
65                  70                  75                  80

Gln His Tyr His Met Lys Thr Leu Gly Trp Cys Asp Val Gly Tyr Asn
                85                  90                  95

Phe Leu Ile Gly Glu Asp Gly Leu Val Tyr Glu Gly Arg Gly Trp Asn
            100                 105                 110

Phe Thr Gly Ala His Ser Gly His Leu Trp Asn Pro Met Ser Ile Gly
        115                 120                 125
```

```
Ile Ser Phe Met Gly Asn Tyr Met Asp Arg Val Pro Thr Pro Gln Ala
    130                 135                 140

Ile Arg Ala Ala Gln Gly Leu Leu Ala Cys Gly Val Ala Gln Gly Ala
145                 150                 155                 160

Leu Arg Ser Asn Tyr Val Leu Lys Gly His Arg Asp Val Gln Arg Thr
                165                 170                 175

Leu Ser Pro Gly Asn Gln Leu Tyr His Leu Ile Gln Asn Trp Pro His
            180                 185                 190

Tyr Arg Ser Pro
        195


<210> SEQ ID NO 55
<211> LENGTH: 1852
<212> TYPE: DNA
<213> ORGANISM: Homo sapiens
<300> PUBLICATION INFORMATION:
<308> DATABASE ACCESSION NUMBER: NCBI / NM_001101
<309> DATABASE ENTRY DATE: 2011-11-26
<313> RELEVANT RESIDUES IN SEQ ID NO: (1)..(1852)

<400> SEQUENCE: 55

accgccgaga ccgcgtccgc cccgcgagca cagagcctcg cctttgccga tccgccgccc      60

gtccacaccc gccgccagct caccatggat gatgatatcg ccgcgctcgt cgtcgacaac     120

ggctccggca tgtgcaaggc cggcttcgcg ggcgacgatg ccccccgggc cgtcttcccc     180

tccatcgtgg ggcgccccag gcaccagggc gtgatggtgg gcatgggtca gaaggattcc     240

tatgtgggcg acgaggccca gagcaagaga ggcatcctca ccctgaagta ccccatcgag     300

cacggcatcg tcaccaactg ggacgacatg gagaaaatct ggcaccacac cttctacaat     360

gagctgcgtg tggctcccga ggagcacccc gtgctgctga ccgaggcccc cctgaacccc     420

aaggccaacc gcgagaagat gacccagatc atgtttgaga ccttcaacac cccagccatg     480

tacgttgcta tccaggctgt gctatccctg tacgcctctg gccgtaccac tggcatcgtg     540

atggactccg gtgacggggt cacccacact gtgcccatct acgaggggta tgccctcccc     600

catgccatcc tgcgtctgga cctggctggc cgggacctga ctgactacct catgaagatc     660

ctcaccgagc gcggctacag cttcaccacc acggccgagc gggaaatcgt gcgtgacatt     720

aaggagaagc tgtgctacgt cgccctggac ttcgagcaag agatggccac ggctgcttcc     780

agctcctccc tggagaagag ctacgagctg cctgacggcc aggtcatcac cattggcaat     840

gagcggttcc gctgccctga ggcactcttc cagccttcct tcctgggcat ggagtcctgt     900

ggcatccacg aaactacctt caactccatc atgaagtgtg acgtggacat ccgcaaagac     960

ctgtacgcca acacagtgct gtctggcggc accaccatgt accctggcat tgccgacagg    1020

atgcagaagg agatcactgc cctggcaccc agcacaatga agatcaagat cattgctcct    1080

cctgagcgca agtactccgt gtggatcggc ggctccatcc tggcctcgct gtccaccttc    1140

cagcagatgt ggatcagcaa gcaggagtat gacgagtccg gcccctccat cgtccaccgc    1200

aaatgcttct aggcggacta tgacttagtt gcgttacacc ctttcttgac aaaacctaac    1260

ttgcgcagaa aacaagatga gattggcatg gctttatttg tttttttgt tttgttttgg    1320

ttttttttt tttttggct tgactcagga tttaaaaact ggaacggtga aggtgacagc    1380

agtcggttgg agcgagcatc ccccaaagtt cacaatgtgg ccgaggactt tgattgcaca    1440

ttgttgtttt tttaatagtc attccaaata tgagatgcgt tgttacagga agtcccttgc    1500

catcctaaaa gccaccccac ttctctctaa ggagaatggc ccagtcctct cccaagtcca    1560
```

cacaggggag gtgatagcat tgctttcgtg taaattatgt aatgcaaaat ttttttaatc 1620
ttcgccttaa tacttttta ttttgtttta ttttgaatga tgagccttcg tgcccccct 1680 tcccccttt ttgtccccca acttgagatg tatgaaggct tttggtctcc ctgggagtgg 1740
gtggaggcag ccagggctta cctgtacact gacttgagac cagttgaata aaagtgcaca 1800
ccttaaaaat gaaaaaaaaa aaaaaaaaaa aaaaaaaaaa aaaaaaaaaa aa 1852

<210> SEQ ID NO 56
<211> LENGTH: 2408
<212> TYPE: DNA
<213> ORGANISM: Homo sapiens
<300> PUBLICATION INFORMATION:
<308> DATABASE ACCESSION NUMBER: NCBI / NM_000043
<309> DATABASE ENTRY DATE: 2011-11-28
<313> RELEVANT RESIDUES IN SEQ ID NO: (1)..(2408)

<400> SEQUENCE: 56
aaacaccgct ctggtcacca tggcaacagc gggatgccgc gaacggcttc tgggcggggc 60
cggtccctcg gacgattgga cctagcttgg cgcggaatcc gtgaattgcc cgcggcccga 120
gggtgcagct cccggactga ctggctctgc ccttccccat ggacgcctcc tctagcccgt 180
ggaatccaac cccggctcct gtcagcagcc ctcccctgct gctccccatc cctgccatcg 240
tcttcatcgc tgtgggcatc tatttgttgc tgctgggtct agtcctgctg actaggaact 300
gcctgctggc ccagggctgc tgcgcggacg gtagctcccc ctgcaggaag caaggttcct 360
ccgggccccc agactgctgc tggacctgtg cagaagcctg caactttcct ctgcctagcc 420
cggcccactt cctggatgct tgctgccccc agcccaccag agctgactgg gcacctcgct 480
gcccccgctg ctgcccactc tgcgactgtg cctgtacgtg ccagctcccc gactgccaga 540
gcctcaactg tctctgcttc gagatcaagc tccgatgagg acccagggcc cctgccctct 600
ggggagcggc cagcccccag ggcccatgtg ccctcctccc tgaagagcct ttccccacgc 660
cactggaacc acagatggcc tgccgagcac ccaggcctgg gaactggaag tggcagcgca 720
gggcctggct ccctgcaggg caggactctt ggccggctgg acggcagctc ctctggaggg 780
ccagaaaaga gaggggctag tgctcgggca ggtgccctgg cttcccttcc cctccacacg 840
tcaacgattc tatttgaagt tgggcagggg ggtggcgctg ctcaccacac acaagtgtta 900
taggaggagt ctggcccttg agtaccgggt acgcaggggt gcctcaacca cactccgtcc 960
acggactctc cgttatttta ggaggtccct ggccaaagat ttatttctct tgacaaccaa 1020
gggcctccgt ctggatttcc aaggaagaat ttcctctgaa gcaccggaac ttgctactac 1080
cagcaccatg ccctaccaat atccagcact gaccccggag cagaagaagg agctgtctga 1140
catcgctcac cgcatcgtgg cacctggcaa gggcatcctg gctgcagatg agtccactgg 1200
gagcattgcc aagcggctgc agtccattgg caccgagaac accgaggaga accggcgctt 1260
ctaccgccag ctgctgctga cagctgacga ccgcgtgaac ccctgcattg ggggtgtcat 1320
cctcttccat gagacactct accagaaggc ggatgatggg cgtcccttcc cccaagttat 1380
caaatccaag ggcggtgttg tgggcatcaa ggtagacaag ggcgtggtcc ccctggcagg 1440
gacaaatggc gagactacca cccaagggtt ggatgggctg tctgagcgct gtgcccagta 1500
caagaaggac ggagctgact tcgccaagtg gcgttgtgtg ctgaagattg ggggaacacac 1560 cccctcagcc ctcgccatca tggaaaatgc caatgttctg gcccgttatg ccagtatctg 1620
ccagcagaat ggcattgtgc ccatcgtgga gcctgagatc ctccctgatg gggaccatga 1680
cttgaagcgc tgccagtatg tgaccgagaa ggtgctggct gctgtctaca aggctctgag 1740

```
tgaccaccac atctacctgg aaggcacctt gctgaagccc aacatggtca ccccaggcca   1800

tgcttgcact cagaagtttt ctcatgagga gattgccatg gcgaccgtca cagcgctgcg   1860

ccgcacagtg ccccccgctg tcactgggat caccttcctg tctggaggcc agagtgagga   1920

ggaggcgtcc atcaacctca atgccattaa caagtgcccc ctgctgaagc cctgggccct   1980

gaccttctcc tacggccgag ccctgcaggc ctctgccctg aaggcctggg gcgggaagaa   2040

ggagaacctg aaggctgcgc aggaggagta tgtcaagcga gccctggcca acagccttgc   2100

ctgtcaagga aagtacactc cgagcggtca ggctggggct gctgccagcg agtccctctt   2160

cgtctctaac cacgcctatt aagcggaggt gttcccaggc tgcccccaac actccaggcc   2220

ctgccccctc ccactcttga agaggaggcc gcctcctcgg ggctccaggc tggcttgccc   2280

gcgctctttc ttccctcgtg acagtggtgt gtggtgtcgt ctgtgaatgc taagtccatc   2340

accctttccg gcacactgcc aaataaacag ctatttaagg gggagtcggc aaaaaaaaaa   2400

aaaaaaaa                                                            2408
```

<210> SEQ ID NO 57
<211> LENGTH: 1310
<212> TYPE: DNA
<213> ORGANISM: Homo sapiens
<300> PUBLICATION INFORMATION:
<308> DATABASE ACCESSION NUMBER: NCBI / NM_002046
<309> DATABASE ENTRY DATE: 2011-11-21
<313> RELEVANT RESIDUES IN SEQ ID NO: (1)..(1310)

<400> SEQUENCE: 57

```
aaattgagcc cgcagcctcc cgcttcgctc tctgctcctc ctgttcgaca gtcagccgca     60

tcttcttttg cgtcgccagc cgagccacat cgctcagaca ccatggggaa ggtgaaggtc    120

ggagtcaacg gatttggtcg tattgggcgc ctggtcacca gggctgcttt taactctggt    180

aaagtggata ttgttgccat caatgacccc ttcattgacc tcaactacat ggtttacatg    240

ttccaatatg attccaccca tggcaaattc catggcaccg tcaaggctga gaacgggaag    300

cttgtcatca atggaaatcc catcaccatc ttccaggagc gagatccctc caaaatcaag    360

tggggcgatg ctggcgctga gtacgtcgtg gagtccactg gcgtcttcac caccatggag    420

aaggctgggg ctcatttgca ggggggagcc aaaagggtca tcatctctgc cccctctgct    480

gatgccccca tgttcgtcat gggtgtgaac catgagaagt atgacaacag cctcaagatc    540

atcagcaatg cctcctgcac caccaactgc ttagcacccc tggccaaggt catccatgac    600

aactttggta tcgtggaagg actcatgacc acagtccatg ccatcactgc cacccagaag    660

actgtggatg gcccctccgg gaaactgtgg cgtgatggcc gcggggctct ccagaacatc    720

atccctgcct ctactggcgc tgccaaggct gtgggcaagg tcatccctga gctgaacggg    780

aagctcactg gcatggcctt ccgtgtcccc actgccaacg tgtcagtggt ggacctgacc    840

tgccgtctag aaaaacctgc caaatatgat gacatcaaga aggtggtgaa gcaggcgtcg    900

gagggccccc tcaagggcat cctgggctac actgagcacc aggtggtctc ctctgacttc    960

aacagcgaca cccactcctc cacctttgac gctggggctg gcattgccct caacgaccac   1020

tttgtcaagc tcatttcctg gtatgacaac gaatttggct acagcaacag ggtggtggac   1080

ctcatggccc acatggcctc caaggagtaa gacccctgga ccaccagccc cagcaagagc   1140

acaagaggaa gagagagacc ctcactgctg gggagtccct gccacactca gtcccccacc   1200

acactgaatc tcccctcctc acagttgcca tgtagacccc ttgaagaggg gaggggccta   1260
```

gggagccgca ccttgtcatg taccatcaat aaagtaccct gtgctcaacc 1310

<210> SEQ ID NO 58
<211> LENGTH: 2439
<212> TYPE: DNA
<213> ORGANISM: Homo sapiens
<300> PUBLICATION INFORMATION:
<308> DATABASE ACCESSION NUMBER: NCBI / NM_000291
<309> DATABASE ENTRY DATE: 2011-11-26
<313> RELEVANT RESIDUES IN SEQ ID NO: (1)..(2439)

<400> SEQUENCE: 58
gagagcagcg gccgggaagg ggcggtgcgg gaggcggggt gtggggcggt agtgtgggcc 60
ctgttcctgc ccgcgcggtg ttccgcattc tgcaagcctc cggagcgcac gtcggcagtc 120
ggctccctcg ttgaccgaat caccgacctc tctccccagc tgtatttcca aaatgtcgct 180
ttctaacaag ctgacgctgg acaagctgga cgttaaaggg aagcgggtcg ttatgagagt 240
cgacttcaat gttcctatga agaacaacca gataacaaac aaccagagga ttaaggctgc 300
tgtcccaagc atcaaattct gcttggacaa tggagccaag tcggtagtcc ttatgagcca 360
cctaggccgg cctgatggtg tgcccatgcc tgacaagtac tccttagagc cagttgctgt 420
agaactcaaa tctctgctgg gcaaggatgt tctgttcttg aaggactgtg taggcccaga 480
agtggagaaa gcctgtgcca acccagctgc tgggtctgtc atcctgctgg agaacctccg 540
ctttcatgtg gaggaagaag ggaagggaaa agatgcttct gggaacaagg ttaaagccga 600
gccagccaaa atagaagctt tccgagcttc actttccaag ctaggggatg tctatgtcaa 660
tgatgctttt ggcactgctc acagagccca cagctccatg gtaggagtca atctgccaca 720
gaaggctggt gggtttttga tgaagaagga gctgaactac tttgcaaagg ccttggagag 780
cccagagcga cccttcctgg ccatcctggg cggagctaaa gttgcagaca agatccagct 840
catcaataat atgctggaca aagtcaatga gatgattatt ggtggtggaa tggcttttac 900
cttccttaag gtgctcaaca acatggagat tggcacttct ctgtttgatg aagagggagc 960
caagattgtc aaagacctaa tgtccaaagc tgagaagaat ggtgtgaaga ttaccttgcc 1020
tgttgacttt gtcactgctg acaagtttga tgagaatgcc aagactggcc aagccactgt 1080
ggcttctggc atacctgctg gctggatggg cttggactgt ggtcctgaaa gcagcaagaa 1140
gtatgctgag gctgtcactc gggctaagca gattgtgtgg aatggtcctg tgggggtatt 1200
tgaatgggaa gcttttgccc ggggaaccaa agctctcatg gatgaggtgg tgaaagccac 1260
ttctaggggc tgcatcacca tcataggtgg tggagacact gccacttgct gtgccaaatg 1320
gaacacggag gataaagtca gccatgtgag cactgggggt ggtgccagtt tggagctcct 1380
ggaaggtaaa gtccttcctg gggtggatgc tctcagcaat atttagtact ttcctgcctt 1440
ttagttcctg tgcacagccc ctaagtcaac ttagcatttt ctgcatctcc acttggcatt 1500
agctaaaacc ttccatgtca agattcagct agtggccaag agatgcagtg ccaggaaccc 1560
ttaaacagtt gcacagcatc tcagctcatc ttcactgcac cctggatttg catacattct 1620
tcaagatccc atttgaattt tttagtgact aaaccattgt gcattctaga gtgcatatat 1680
ttatattttg cctgttaaaa agaaagtgag cagtgttagc ttagttctct tttgatgtag 1740
gttattatga ttagctttgt cactgtttca ctactcagca tggaaacaag atgaaattcc 1800
atttgtaggt agtgagacaa aattgatgat ccattaagta aacaataaaa gtgtccattg 1860
aaaccgtgat tttttttttt ttcctgtcat actttgttag gaagggtgag aatagaatct 1920
tgaggaacgg atcagatgtc tatattgctg aatgcaagaa gtggggcagc agcagtggag 1980
agatgggaca attagataaa tgtccattct ttatcaaggg cctactttat ggcagacatt 2040
gtgctagtgc ttttattcta acttttattt ttatcagtta cacatgatca taatttaaaa 2100
agtcaaggct tataacaaaa aagccccagc ccattcctcc cattcaagat tcccactccc 2160
cagaggtgac cactttcaac tcttgagttt ttcaggtata tacctccatg tttctaagta 2220
atatgcttat attgttcact tcttttttt ttatttttta aagaaatcta tttcatacca 2280
tggaggaagg ctctgttcca catatatttc cacttcttca ttctctcggt atagttttgt 2340
cacaattata gattagatca aaagtctaca taactaatac agctgagcta tgtagtatgc 2400
tatgattaaa tttacttatg taaaaaaaaa aaaaaaaaa 2439

<210> SEQ ID NO 59
<211> LENGTH: 2226
<212> TYPE: DNA
<213> ORGANISM: Homo sapiens
<300> PUBLICATION INFORMATION:
<308> DATABASE ACCESSION NUMBER: NCBI / NM_005566
<309> DATABASE ENTRY DATE: 2011-12-25
<313> RELEVANT RESIDUES IN SEQ ID NO: (1)..(2226)

<400> SEQUENCE: 59
gtctgccggt cggttgtctg gctgcgcgcg ccacccgggc ctctccagtg ccccgcctgg 60
ctcggcatcc acccccagcc cgactcacac gtgggttccc gcacgtccgc cggccccccc 120
cgctgacgtc agcatagctg ttccacttaa ggcccctccc gcgcccagct cagagtgctg 180
cagccgctgc cgccgattcc ggatctcatt gccacgcgcc cccgacgacc gcccgacgtg 240
cattcccgat tccttttggt tccaagtcca atatggcaac tctaaaggat cagctgattt 300
ataatcttct aaaggaagaa cagaccccc agaataagat tacagttgtt ggggttggtg 360
ctgttggcat ggcctgtgcc atcagtatct taatgaagga cttggcagat gaacttgctc 420
ttgttgatgt catcgaagac aaattgaagg gagagatgat ggatctccaa catggcagcc 480
ttttccttag aacaccaaag attgtctctg gcaaagacta taatgtaact gcaaactcca 540
agctggtcat tatcacggct ggggcacgtc agcaagaggg agaaagccgt cttaatttgg 600
tccagcgtaa cgtgaacatc tttaaattca tcattcctaa tgttgtaaaa tacagcccga 660
actgcaagtt gcttattgtt tcaaatccag tggatatctt gacctacgtg gcttggaaga 720
taagtggttt tcccaaaaac cgtgttattg gaagcggttg caatctggat tcagcccgat 780
tccgttacct aatgggggaa aggctgggag ttcacccatt aagctgtcat gggtgggtcc 840
ttggggaaca tggagattcc agtgtgcctg tatggagtgg aatgaatgtt gctggtgtct 900
ctctgaagac tctgcaccca gatttaggga ctgataaaga taaggaacag tggaaagagg 960
ttcacaagca ggtggttgag agtgcttatg aggtgatcaa actcaaaggc tacacatcct 1020
gggctattgg actctctgta gcagatttgg cagagagtat aatgaagaat cttaggcggg 1080
tgcacccagt ttccaccatg attaagggtc tttacggaat aaaggatgat gtcttcctta 1140
gtgttccttg cattttggga cagaatggaa tctcagacct tgtgaaggtg actctgactt 1200
ctgaggaaga ggcccgtttg aagaagagtg cagatacact ttgggggatc caaaaggagc 1260
tgcaatttta aagtcttctg atgtcatatc atttcactgt ctaggctaca acaggattct 1320
aggtggaggt tgtgcatgtt gtcctttttta tctgatctgt gattaaagca gtaatatttt 1380
aagatggact gggaaaaaca tcaactcctg aagttagaaa taagaatggt ttgtaaaatc 1440
cacagctata tcctgatgct ggatggtatt aatcttgtgt agtcttcaac tggttagtgt 1500

```
gaaatagttc tgccacctct gacgcaccac tgccaatgct gtacgtactg catttgcccc   1560

ttgagccagg tggatgttta ccgtgtgtta tataacttcc tggctccttc actgaacatg   1620

cctagtccaa cattttttcc cagtgagtca catcctggga tccagtgtat aaatccaata   1680

tcatgtcttg tgcataattc ttccaaagga tcttattttg tgaactatat cagtagtgta   1740

cattaccata taatgtaaaa agatctacat acaaacaatg caaccaacta tccaagtgtt   1800

ataccaacta aaaccccccaa taaaccttga acagtgacta ctttggttaa ttcattatat   1860

taagatataa agtcataaag ctgctagtta ttatattaat ttggaaatat taggctattc   1920

ttgggcaacc ctgcaacgat tttttctaac agggatatta ttgactaata gcagaggatg   1980

taatagtcaa ctgagttgta ttggtaccac ttccattgta agtcccaaag tattatatat   2040

ttgataataa tgctaatcat aattggaaag taacattcta tatgtaaatg taaaatttat   2100

ttgccaactg aatataggca atgatagtgt gtcactatag ggaacacaga tttttgagat   2160

cttgtcctct ggaagctggt aacaattaaa aacaatctta aggcagggaa aaaaaaaaaa   2220

aaaaaa                                                              2226
```

<210> SEQ ID NO 60
<211> LENGTH: 1068
<212> TYPE: DNA
<213> ORGANISM: Homo sapiens
<300> PUBLICATION INFORMATION:
<308> DATABASE ACCESSION NUMBER: NCBI / NM_002954
<309> DATABASE ENTRY DATE: 2011-11-28
<313> RELEVANT RESIDUES IN SEQ ID NO: (1)..(1068)

<400> SEQUENCE: 60

```
ctcgacctcc ttttaaaaat tctcttagcc acgttgattg tacgggaaaa gcctttttaa     60

aacatctttt acgttgctta aacctacagt ttcgaaagca ttccgaaggc taaagtgaga    120

aataagccca ggctagggag aggagaaacg aagttcacgt cctagtctgg caccgggttg    180

gattgtcgct gggacggcag tcaggcattt ggtgtggtcg cctaaggggt gggtccttcg    240

gcgggagctc cgggaaaccc cgtgggcctg cgcggcgttc ttccttttcg atccgccatc    300

tgcggtggag ccgccaccaa aatgcagatt ttcgtgaaaa cccttacggg gaagaccatc    360

accctcgagg ttgaaccctc ggatacgata gaaaatgtaa aggccaagat ccaggataag    420

gaaggaattc ctcctgatca gcagagactg atctttgctg gcaagcagct ggaagatgga    480

cgtactttgt ctgactacaa tattcaaaag gagtctactc ttcatcttgt gttgagactt    540

cgtggtggtg ctaagaaaag gaagaagaag tcttacacca ctcccaagaa gaataagcac    600

aagagaaaga aggttaagct ggctgtcctg aaatattata aggtggatga gaatggcaaa    660

attagtcgcc ttcgtcgaga gtgcccttct gatgaatgtg gtgctggggt gtttatggca    720

agtcactttg acagacatta ttgtggcaaa tgttgtctga cttactgttt caacaaacca    780

gaagacaagt aactgtatga gttaataaaa gacatgaact aacatttatt gttgggtttt    840

attgcagtaa aaagaatggt ttttaagcac caaattgatg gtcacaccat ttcctttttag    900

tagtgctact gctatcgctg tgtgaatgtt gcctctgggg attatgtgac ccagtggttc    960

tgtatacctg ccaggtgcca accacttgta aaggtcttga tattttcaat tcttagacta   1020

cctatacttt ggcagaagtt atatttaatg taagttgtct aaatataa                1068
```

<210> SEQ ID NO 61
<211> LENGTH: 748
<212> TYPE: DNA
<213> ORGANISM: Homo sapiens <300> PUBLICATION INFORMATION:
<308> DATABASE ACCESSION NUMBER: NCBI / NM_000981
<309> DATABASE ENTRY DATE: 2011-12-17
<313> RELEVANT RESIDUES IN SEQ ID NO: (1)..(748)

<400> SEQUENCE: 61
gcagataatg ggaggagccg ggcccgagcg agctctttcc tttcgctgct gcggccgcag 60
ccatgagtat gctcaggctt cagaagaggc tcgcctctag tgtcctccgc tgtggcaaga 120
agaaggtctg gttagacccc aatgagacca atgaaatcgc caatgccaac tcccgtcagc 180
agatccggaa gctcatcaaa gatgggctga tcatccgcaa gcctgtgacg gtccattccc 240
gggctcgatg ccggaaaaac accttggccc gccggaaggg caggcacatg ggcataggta 300
agcggaaggg tacagccaat gcccgaatgc cagagaaggt cacatggatg aggagaatga 360
ggattttgcg ccggctgctc agaagatacc gtgaatctaa gaagatcgat cgccacatgt 420
atcacagcct gtacctgaag gtgaagggga atgtgttcaa aaacaagcgg attctcatgg 480
aacacatcca caagctgaag gcagacaagg cccgcaagaa gctcctggct gaccaggctg 540
aggcccgcag gtctaagacc aaggaagcac gcaagcgccg tgaagagcgc ctccaggcca 600
agaaggagga gatcatcaag actttatcca aggaggaaga gaccaagaaa taaaacctcc 660
cactttgtct gtacatactg gcctctgtga ttacatagat cagccattaa aataaaacaa 720
gccttaatct gcaaaaaaaa aaaaaaaa 748

<210> SEQ ID NO 62
<211> LENGTH: 644
<212> TYPE: DNA
<213> ORGANISM: Homo sapiens
<300> PUBLICATION INFORMATION:
<308> DATABASE ACCESSION NUMBER: NCBI / NM_000975
<309> DATABASE ENTRY DATE: 2011-12-19
<313> RELEVANT RESIDUES IN SEQ ID NO: (1)..(644)

<400> SEQUENCE: 62
aaggccctcg gccggaagct ccgctttctc ttcctgctct ccatcatggc gcaggatcaa 60
ggtgaaaagg agaaccccat gcgggaactt cgcatccgca aactctgtct caacatctgt 120
gttggggaga gtggagacag actgacgcga gcagccaagg tgttggagca gctcacaggg 180
cagacccctg tgttttccaa agctagatac actgtcagat cctttggcat ccggagaaat 240
gaaaagattg ctgtccactg cacagttcga ggggccaagg cagaagaaat cttggagaag 300
ggtctaaagg tgcgggagta tgagttaaga aaaaacaact tctcagatac tggaaacttt 360
ggttttggga tccaggaaca catcgatctg ggtatcaaat atgacccaag cattggtatc 420
tacggcctgg acttctatgt ggtgctgggt aggccaggtt tcagcatcgc agacaagaag 480
cgcaggacag gctgcattgg ggccaaacac agaatcagca aagaggaggc catgcgctgg 540
ttccagcaga agtatgatgg gatcatcctt cctggcaaat aaattcccgt ttctatccaa 600
aagagcaata aaaagttttc agtgaaatgt gcaaaaaaaa aaaa 644

<210> SEQ ID NO 63
<211> LENGTH: 3114
<212> TYPE: DNA
<213> ORGANISM: Homo sapiens
<300> PUBLICATION INFORMATION:
<308> DATABASE ACCESSION NUMBER: NCBI / NM_007363
<309> DATABASE ENTRY DATE: 2011-12-24
<313> RELEVANT RESIDUES IN SEQ ID NO: (1)..(3114)

<400> SEQUENCE: 63

-continued

```
caggcgcagt gcaggactgc tccgagcacg cctacgcgcg cattttctcc ccttcctctc     60
cctctttcca ctttcctctc ccttttttctc ctctcctttc cccctcccac cacttggtct   120
ttcagtcttt cagtcagttc gtttaggtct ctccttccga cccccacccc cagctcctct   180
ccctttcctt ttccccctcc ccctttcctt tcccgtctca cgcgccaggc cgcttgcaca   240
tgcgcattag gtacaaagcc tcgctctttg tccccatctg tcgttcacac gaactcaagc   300
ctttggcatt cggcagccaa tagaatctaa gaaatggcgg aaaaatgatt ccgcctcggg   360
agctaaacct tgattggcag tttagctaac caatcgagaa cgccattttg taccccttgg   420
caggcaccga gctccgtcgt ctcgtttccg gcggtcgcgc gctcttttct cgggacggga   480
gaggccgtgt agcgtcgccg ttactccgag gagataccag tcggtagagg agaagtcgag   540
gttagaggga actgggaggc actttgctgt ctgcaatcga agttgagggt gcaaaaatgc   600
agagtaataa aacttttaac ttggagaagc aaaaccatac tccaagaaag catcatcaac   660
atcaccacca gcagcagcac caccagcagc aacagcagca gccgccacca ccgccaatac   720
ctgcaaatgg gcaacaggcc agcagccaaa atgaaggctt gactattgac ctgaagaatt   780
ttagaaaacc aggagagaag accttcaccc aacgaagccg tctttttgtg ggaaatcttc   840
ctcccgacat cactgaggaa gaaatgagga aactatttga gaaatatgga aaggcaggcg   900
aagtcttcat tcataaggat aaaggatttg gctttatccg cttggaaacc cgaaccctag   960
cggagattgc caaagtggag ctggacaata tgccactccg tggaaagcag ctgcgtgtgc  1020
gctttgcctg ccatagtgca tcccttacag ttcgaaacct tcctcagtat gtgtccaacg  1080
aactgctgga agaagccttt tctgtgtttg gccaggtaga gagggctgta gtcattgtgg  1140
atgatcgagg aaggccctca ggaaaaggca ttgttgagtt ctcagggaag ccagctgctc  1200
ggaaagctct ggacagatgc agtgaaggct ccttcctgct aaccacattt cctcgtcctg  1260
tgactgtgga gcccatggac cagttagatg atgaagaggg acttccagag aagctggtta  1320
taaaaaacca gcaatttcac aaggaacgag agcagccacc cagatttgca cagcctggct  1380
cctttgagta tgaatatgcc atgcgctgga aggcactcat tgagatggag aagcagcagc  1440
aggaccaagt ggaccgcaac atcaaggagg ctcgtgagaa gctggagatg gagatggaag  1500
ctgcacgcca tgagcaccag gtcatgctaa tgagacagga tttgatgagg cgccaagaag  1560
aacttcggag gatggaagag ctgcacaacc aagaggtgca aaaacgaaag caactggagc  1620
tcaggcagga ggaagagcgc aggcgccgtg aagaagagat gcggcggcag caagaagaaa  1680
tgatgcggcg acagcaggaa ggattcaagg gaaccttccc tgatgcgaga gagcaggaga  1740
ttcggatggg tcagatggct atgggaggtg ctatgggcat aaacaacaga ggtgccatgc  1800
cccctgctcc tgtgccagct ggtaccccag ctcctccagg acctgccact atgatgccgg  1860
atggaacttt gggattgacc ccaccaacaa ctgaacgctt tggtcaggct gctacaatgg  1920
aaggaattgg ggcaattggt ggaactcctc ctgcattcaa ccgtgcagct cctggagctg  1980
aatttgcccc aaacaaacgt cgccgatact aataagttgc agtgtctagt ttctcaaaac  2040
ccttaaaaga aggacccttt ttggactagc cagaattcta ccctggaaaa gtgttaggga  2100
ttccttccaa tagttagatc taccctgcct gtactactct agggagtatg ctggaggcag  2160
agggcaaggg aggggtggta ttaaacaagt caattctgtg tggtatattg tttaatcagt  2220
tctgtgtggt gcattcctga agtctctaat gtgactgttg agggcctggg gaaaccatgg  2280
caaagtggat ccagttagag cccattaatc ttgatcattc cggttttttt tttttttgtc  2340
catcttgttt catttgcttg ccccgccccc gagacggagt cttactctgt cgcccaggct  2400
```

ggagtgtagt ggcatgatct cggctcactg caatctctgc ctcccgggtt caagcttgtc 2460
caggttgatc ttgaactcct gacctcgtga tctacccacc tcggcctccc aaaatgctgg 2520
gattacaggg gtgagccacc gtgcccaacc tcacttgctt cttatcctta cactccccca 2580
gccccagaga aactgccaca tacaccacaa aaaccaaaca tcccccaatg accttagccc 2640
cattgctcca ttcactccca ggtgagaatt caggcaaacg tccacaaagg tcacaggcag 2700
cgtacatacg gttctgttat accccatata ttaccccttc atgtcctaaa gaagacattt 2760
tctcttagag attttcattt tagtgtatct ttaaaaaaaa atcttgtgtt aacttgcctc 2820
catctttttc ttgggtgagg acacccagga atgacccttt tgtgtctatg atgttgctgt 2880
tcacagcttt tcttgatagg cctagtacaa tcttgggaac agggttactg tatactgaag 2940
gtctgacagt agctcttaga ctcgcctatc ttaggtagtc atgctgtgca tttttttttt 3000
cattggtgta ctgtgtttga tttgtctcat atatttggag tttttctgaa aaatggagca 3060
gtaatgcagc atcaacctat taaaatacat tttaagcctt ttaaaaaaaa aaaa 3114

<210> SEQ ID NO 64
<211> LENGTH: 1956
<212> TYPE: DNA
<213> ORGANISM: Homo sapiens
<300> PUBLICATION INFORMATION:
<308> DATABASE ACCESSION NUMBER: NCBI / NM_004309
<309> DATABASE ENTRY DATE: 2011-11-28
<313> RELEVANT RESIDUES IN SEQ ID NO: (1)..(1956)

<400> SEQUENCE: 64
gagcggaagt ctcgtgaccc cggaagtgac aggcagggcg ggcggggcgg ccgacgacgt 60
tcgtcattta gtgcgggagg gatcctgaac cgcgcggccg aaccctccgg tgtcccgacc 120
caggctaagc ttgagcatgg ctgagcagga gcccacagcc gagcagctgg cccagattgc 180
agcggagaac gaggaggatg agcactcggt caactacaag cccccggccc agaagagcat 240
ccaggagatc caggagctgg acaaggacga cgagagcctg cgaaagtaca aggaggccct 300
gctgggccgc gtggccgttt ccgcagaccc caacgtcccc aacgtcgtgg tgactggcct 360
gaccctggtg tgcagctcgg ccccgggccc cctggagctg gacctgacgg gcgacctgga 420
gagcttcaag aagcagtcgt ttgtgctgaa ggagggtgtg gagtaccgga taaaaatctc 480
tttccgggtt aaccgagaga tagtgtccgg catgaagtac atccagcata cgtacaggaa 540
aggcgtcaag attgacaaga ctgactacat ggtaggcagc tatgggcccc gggccgagga 600
gtacgagttc ctgacccccg tggaggaggc acccaagggt atgctggccc ggggcagcta 660
cagcatcaag tcccgcttca cagacgacga caagaccgac cacctgtcct gggagtggaa 720
tctcaccatc aagaaggact ggaaggactg agcccagcca gaggcgggca gggcagactg 780
acggacggac gacggacagg cggatgtgtc ccccccagcc cctcccctcc ccataccaaa 840
gtgctgacag gccctccgtg cccctcccac cctggtccgc ctccctggcc tggctcaacc 900
gagtgcctcc gacccccctc ctcagccctc ccccacccac aggcccagcc tcctcggtct 960
cctgtctcgt tgctgcttct gcctgtgctg tgggggagag aggccgcagc caggcctctg 1020
ctgccctttc tgtgcccccc aggttctatc tccccgtcac acccgaggcc tggcttcagg 1080
agggagcgga gcagccattc tccaggcccc gtggttgccc ctggacgtgt gcgtctgctg 1140
ctccggggtg gagctggggt gtgggatgca cggcctcgtg gggggccgggc cgtcctccag 1200 ccccgctgct ccctggccag cccccttgtc gctgtcggtc ccgtctaacc atgatgcctt 1260
aacatgtgga gtgtaccgtg ggcctcact agcctctaac tccctgtgtc tgcatgagca 1320
tgtggcctcc ccgtcccttc cccggtggcg aacccagtga cccagggaca cgtggggtgt 1380
gctgctgctg ctccccagcc caccagtgcc tggccagcct gccccccttcc ctggacaggg 1440 ctgtggagat ggctccggcg gcttggggaa agccaaattg ccaaaactca agtcacctca 1500
gtaccatcca ggaggctggg tattgtcctg cctctgcctt ttctgtctca gcgggcagtg 1560
cccagagccc acacccccccc aagagccctc gatggacagc ctcacccacc ccacctgggc 1620
ccagccagga gccccgcctg gccatcagta tttattgcct ccgtccgtgc cgtccctggg 1680
ccactggcct ggcgcctgtt cccccaggct ctcagtgcca ccacccccgg caggccttcc 1740
ctgacccagc caggaacaaa caagggacca agtgcacaca ttgctgagag ccgtctcctg 1800
tgcctccccc gccccatccc cggtcttcgt gttgtgtctg ccaggctcag gcagaggcgc 1860
ctgtccctgc ttcttttctg accgggaaat aaatgcccct gaaggaaaaa aaaaaaaaaa 1920
aaaaaaaaaa aaaaaaaaaa aaaaaaaaaa aaaaaa 1956

<210> SEQ ID NO 65
<211> LENGTH: 1668
<212> TYPE: DNA
<213> ORGANISM: Homo sapiens
<300> PUBLICATION INFORMATION:
<308> DATABASE ACCESSION NUMBER: NCBI / NM_000994
<309> DATABASE ENTRY DATE: 2011-11-28
<313> RELEVANT RESIDUES IN SEQ ID NO: (1)..(1668)

<400> SEQUENCE: 65
aggggttacg acccatcagc ccttgcgcgc caccgtccct tctctcttcc tcggcgctgc 60
ctacggaggt ggcagccatc tccttctcgg catcatggcc gccctcagac cccttgtgaa 120
gcccaagatc gtcaaaaaga gaaccaagaa gttcatccgg caccagtcag accgatatgt 180
caaaattaag cgtaactggc ggaaacccag aggcattgac aacagggttc gtagaagatt 240
caagggccag atcttgatgc ccaacattgg ttatggaagc aacaaaaaaa caaagcacat 300
gctgcccagt ggcttccgga agttcctggt ccacaacgtc aaggagctgg aagtgctgct 360
gatgtgcaac aaatcttact gtgccgagat cgctcacaat gtttcctcca agaaccgcaa 420
agccatcgtg gaaagagctg cccaactggc catcagagtc accaacccca atgccaggct 480
gcgcagtgaa gaaaatgagt aggcagctca tgtgcacgtt ttctgtttaa ataaatgtaa 540
aaactgccat ctggcatctt ccttccttga ttttaagtct tcagcttctt ggccaactta 600
gtttgccaca gagattgttc ttttgcttaa gcccctttgg aatctcccat ttggagggga 660
tttgtaaagg acactcagtc cttgaacagg ggaatgtggc ctcaagtgca cagactagcc 720
ttagtcatct ccagttgagg ctgggtatga ggggtacaga cttggccctc acaccaggta 780
ggttctgaga cacttgaaga agcttgtggc tcccaagcca caagtagtca ttcttagcct 840
tgcttttgta aagttaggtg acaagttatt ccatgtgatg cttgtgagaa ttgagaaaat 900
atgcatggaa atatccagat gaatttctta cacagattct tacgggatgc ctaaattgca 960
tcctgtaact tctgtccaaa aagaacagga tgatgtacaa attgctcttc caggtaatcc 1020
accacggtta actggaaaag cactttcagt ctcctataac cctcccacca gctgctgctt 1080
caggtataat gttacagcag tttgccaagg cggggaccta actggtgaca attgagcctc 1140
ttgactggta ctcagaattt agtgacacgt ggtcctgatt ttttttggag acggggtctt 1200
gctctcaccc aggctgggag tgcagtggca cactgactac agccttgacc tccccaggct 1260
caggtgatct tcccacctca gccttccaag tagctgggac tacagatgca cacctccaaa 1320

```
cctgggtagt ttttgaagtt tttttgtaga ggtggtctag ccatgttgcc taggctcccg   1380

aactcctgag ctcaagcaat cctgcttcag cctcccaaag tactgggatt acaggcatct   1440

tctgtagtat ataggtcatg agggatatgg gatgtggtac ttatgagaca gaaatgctta   1500

caggatgttt ttctgtaacc atcctggtca acttagcaga aatgctgcgc tgggtataat   1560

aaagcttttc tacttctagt ctagacagga atcttacaga ttgtctcctg ttcaaaacct   1620

agtcataaat atttataatg caaactggtc aaaaaaaaaa aaaaaaaa                1668


<210> SEQ ID NO 66
<211> LENGTH: 2594
<212> TYPE: DNA
<213> ORGANISM: Homo sapiens
<300> PUBLICATION INFORMATION:
<308> DATABASE ACCESSION NUMBER: NCBI / NM_021009
<309> DATABASE ENTRY DATE: 2011-12-24
<313> RELEVANT RESIDUES IN SEQ ID NO: (1)..(2594)

<400> SEQUENCE: 66

aggggccgcg gagccgcggc taaggaacgc gggccgccca cccgctcccg gtgcagcggc     60

ctccgcgccg ggttttggcg cctcccgcgg gcgccccccct cctcacggcg agcgctgcca   120

cgtcagacga agggcgcagc gagcgtcctg atccttccgc ccggacgctc aggacagcgg    180

cccgctgctc ataagactcg gccttagaac cccagtatca gcagaaggac attttaggac    240

gggacttggg tgactctagg gcactggttt tctttccaga gagcggaaca ggcgaggaaa    300

agtagtccct tctcggcgat tctgcggagg gatctccgtg gggcggtgaa cgccgatgat    360

tatataagga cgcgccgggt gtggcacagc tagttccgtc gcagccggga tttgggtcgc    420

agttcttgtt tgtggatcgc tgtgatcgtc acttgacaat gcagatcttc gtgaagactc    480

tgactggtaa gaccatcacc ctcgaggttg agcccagtga caccatcgag aatgtcaagg    540

caaagatcca agataaggaa ggcatccctc ctgaccagca gaggctgatc tttgctggaa    600

aacagctgga agatgggcgc accctgtctg actacaacat ccagaaagag tccaccctgc    660

acctggtgct ccgtctcaga ggtgggatgc aaatcttcgt gaagacactc actggcaaga    720

ccatcaccct tgaggtcgag cccagtgaca ccatcgagaa cgtcaaagca aagatccagg    780

acaaggaagg cattcctcct gaccagcaga ggttgatctt tgccggaaag cagctggaag    840

atgggcgcac cctgtctgac tacaacatcc agaaagagtc taccctgcac ctggtgctcc    900

gtctcagagg tgggatgcag atcttcgtga agaccctgac tggtaagacc atcaccctcg    960

aggtggagcc cagtgacacc atcgagaatg tcaaggcaaa gatccaagat aaggaaggca   1020

ttccttctga tcagcagagg ttgatctttg ccggaaaaca gctggaagat ggtcgtaccc   1080

tgtctgacta caacatccag aaagagtcca ccttgcacct ggtactccgt ctcagaggtg   1140

ggatgcaaat cttcgtgaag acactcactg gcaagaccat caccccttgag gtcgagccca  1200

gtgacactat cgagaacgtc aaagcaaaga tccaagacaa ggaaggcatt cctcctgacc   1260

agcagaggtt gatctttgcc ggaaagcagc tggaagatgg gcgcaccctg tctgactaca   1320

acatccagaa agagtctacc ctgcacctgg tgctccgtct cagaggtggg atgcagatct   1380

tcgtgaagac cctgactggt aagaccatca ctctcgaagt ggagccgagt gacaccattg   1440

agaatgtcaa ggcaaagatc caagacaagg aaggcatccc tcctgaccag cagaggttga   1500

tctttgccgg aaaacagctg gaagatggtc gtaccctgtc tgactacaac atccagaaag   1560

agtccacctt gcacctggtg ctccgtctca gaggtgggat gcagatcttc gtgaagaccc   1620
```

tgactggtaa gaccatcact ctcgaggtgg agccgagtga caccattgag aatgtcaagg 1680
caaagatcca agacaaggaa ggcatccctc ctgaccagca gaggttgatc tttgctggga 1740
aacagctgga agatggacgc accctgtctg actacaacat ccagaaagag tccaccctgc 1800
acctggtgct ccgtcttaga ggtgggatgc agatcttcgt gaagaccctg actggtaaga 1860
ccatcactct cgaagtggag ccgagtgaca ccattgagaa tgtcaaggca aagatccaag 1920
acaaggaagg catccctcct gaccagcaga ggttgatctt tgctgggaaa cagctggaag 1980
atggacgcac cctgtctgac tacaacatcc agaaagagtc caccctgcac ctggtgctcc 2040
gtcttagagg tgggatgcag atcttcgtga agaccctgac tggtaagacc atcactctcg 2100
aagtggagcc gagtgacacc attgagaatg tcaaggcaaa gatccaagac aaggaaggca 2160
tccctcctga ccagcagagg ttgatctttg ctgggaaaca gctggaagat ggacgcaccc 2220
tgtctgacta caacatccag aaagagtcca ccctgcacct ggtgctccgt ctcagaggtg 2280
ggatgcaaat cttcgtgaag accctgactg gtaagaccat caccctcgag gtggagccca 2340
gtgacaccat cgagaatgtc aaggcaaaga tccaagataa ggaaggcatc cctcctgatc 2400
agcagaggtt gatctttgct gggaaacagc tggaagatgg acgcaccctg tctgactaca 2460
acatccagaa agagtccact ctgcacttgg tcctgcgctt gaggggggt gtctaagttt 2520 ccccttttaa ggtttcaaca aatttcattg cactttcctt tcaataaagt tgttgcattc 2580
ccaaaaaaaa aaaa 2594

<210> SEQ ID NO 67
<211> LENGTH: 1526
<212> TYPE: DNA
<213> ORGANISM: Homo sapiens
<300> PUBLICATION INFORMATION:
<308> DATABASE ACCESSION NUMBER: NCBI / NM_000190.3
<309> DATABASE ENTRY DATE: 2017-10-01
<313> RELEVANT RESIDUES IN SEQ ID NO: (1)..(1526)

<400> SEQUENCE: 67
ccggaagtga cgcgaggctc tgcggagacc aggagtcaga ctgtaggacg acctcgggtc 60
ccacgtgtcc ccggtactcg ccggccggag cccccggctt cccggggccg ggggacctta 120
gcggcaccca cacacagcct actttccaag cggagccatg tctggtaacg gcaatgcggc 180
tgcaacggcg gaagaaaaca gcccaaagat gagagtgatt cgcgtgggta cccgcaagag 240
ccagcttgct cgcatacaga cggacagtgt ggtggcaaca ttgaaagcct cgtaccctgg 300
cctgcagttt gaaatcattg ctatgtccac cacaggggac aagattcttg atactgcact 360
ctctaagatt ggagagaaaa gcctgtttac caaggagctt gaacatgccc tggagaagaa 420
tgaagtggac ctggttgttc actccttgaa ggacctgccc actgtgcttc ctcctggctt 480
caccatcgga gccatctgca agcgggaaaa ccctcatgat gctgttgtct ttcacccaaa 540
atttgttggg aagaccctag aaaccctgcc agagaagagt gtggtgggaa ccagctccct 600
gcgaagagca gcccagctgc agagaaagtt cccgcatctg gagttcagga gtattcgggg 660
aaacctcaac acccggcttc ggaagctgga cgagcagcag gagttcagtg ccatcatcct 720
ggcaacagct ggcctgcagc gcatgggctg gcacaaccgg gtggggcaga tcctgcaccc 780
tgaggaatgc atgtatgctg tgggccaggg ggccttgggc gtggaagtgc gagccaagga 840
ccaggacatc ttggatctgg tgggtgtgct gcacgatccc gagactctgc ttcgctgcat 900
cgctgaaagg gccttcctga ggcacctgga aggaggctgc agtgtgccag tagccgtgca 960
tacagctatg aaggatgggc aactgtacct gactggagga gtctggagtc tagacggctc 1020
agatagcata caagagacca tgcaggctac catccatgtc cctgcccagc atgaagatgg 1080
ccctgaggat gacccacagt tggtaggcat cactgctcgt aacattccac gagggcccca 1140
gttggctgcc cagaacttgg gcatcagcct ggccaacttg ttgctgagca aaggagccaa 1200
aaacatcctg gatgttgcac ggcagcttaa cgatgcccat taactggttt gtggggcaca 1260
gatgcctggg ttgctgctgt ccagtgccta catcccgggc ctcagtgccc cattctcact 1320
gctatctggg gagtgattac cccgggagac tgaactgcag ggttcaagcc ttccagggat 1380
ttgcctcacc ttggggcctt gatgactgcc ttgcctcctc agtatgtggg ggcttcatct 1440
ctttagagaa gtccaagcaa cagcctttga atgtaaccaa tcctactaat aaaccagttc 1500
tgaaggtgta aaaaaaaaaa aaaaaa 1526

<210> SEQ ID NO 68
<211> LENGTH: 361
<212> TYPE: PRT
<213> ORGANISM: Homo sapiens
<300> PUBLICATION INFORMATION:
<308> DATABASE ACCESSION NUMBER: NCBI / NP_000181.2
<309> DATABASE ENTRY DATE: 2017-10-01
<313> RELEVANT RESIDUES IN SEQ ID NO: (1)..(361)

<400> SEQUENCE: 68

Met Ser Gly Asn Gly Asn Ala Ala Ala Thr Ala Glu Glu Asn Ser Pro
1 5 10 15

Lys Met Arg Val Ile Arg Val Gly Thr Arg Lys Ser Gln Leu Ala Arg
20 25 30

Ile Gln Thr Asp Ser Val Val Ala Thr Leu Lys Ala Ser Tyr Pro Gly
35 40 45

Leu Gln Phe Glu Ile Ile Ala Met Ser Thr Thr Gly Asp Lys Ile Leu
50 55 60

Asp Thr Ala Leu Ser Lys Ile Gly Glu Lys Ser Leu Phe Thr Lys Glu
65 70 75 80

Leu Glu His Ala Leu Glu Lys Asn Glu Val Asp Leu Val Val His Ser
85 90 95

Leu Lys Asp Leu Pro Thr Val Leu Pro Pro Gly Phe Thr Ile Gly Ala
100 105 110

Ile Cys Lys Arg Glu Asn Pro His Asp Ala Val Val Phe His Pro Lys
115 120 125

Phe Val Gly Lys Thr Leu Glu Thr Leu Pro Glu Lys Ser Val Val Gly
130 135 140

Thr Ser Ser Leu Arg Arg Ala Ala Gln Leu Gln Arg Lys Phe Pro His
145 150 155 160

Leu Glu Phe Arg Ser Ile Arg Gly Asn Leu Asn Thr Arg Leu Arg Lys
165 170 175

Leu Asp Glu Gln Gln Glu Phe Ser Ala Ile Ile Leu Ala Thr Ala Gly
180 185 190

Leu Gln Arg Met Gly Trp His Asn Arg Val Gly Gln Ile Leu His Pro
195 200 205

Glu Glu Cys Met Tyr Ala Val Gly Gln Gly Ala Leu Gly Val Glu Val
210 215 220

Arg Ala Lys Asp Gln Asp Ile Leu Asp Leu Val Gly Val Leu His Asp
225 230 235 240

Pro Glu Thr Leu Leu Arg Cys Ile Ala Glu Arg Ala Phe Leu Arg His
245 250 255

```
Leu Glu Gly Gly Cys Ser Val Pro Val Ala Val His Thr Ala Met Lys
            260                 265                 270

Asp Gly Gln Leu Tyr Leu Thr Gly Gly Val Trp Ser Leu Asp Gly Ser
        275                 280                 285

Asp Ser Ile Gln Glu Thr Met Gln Ala Thr Ile His Val Pro Ala Gln
    290                 295                 300

His Glu Asp Gly Pro Glu Asp Asp Pro Gln Leu Val Gly Ile Thr Ala
305                 310                 315                 320

Arg Asn Ile Pro Arg Gly Pro Gln Leu Ala Ala Gln Asn Leu Gly Ile
                325                 330                 335

Ser Leu Ala Asn Leu Leu Leu Ser Lys Gly Ala Lys Asn Ile Leu Asp
            340                 345                 350

Val Ala Arg Gln Leu Asn Asp Ala His
        355                 360


<210> SEQ ID NO 69
<211> LENGTH: 1428
<212> TYPE: DNA
<213> ORGANISM: Homo sapiens
<300> PUBLICATION INFORMATION:
<308> DATABASE ACCESSION NUMBER: NCBI / NM_001024382.1
<309> DATABASE ENTRY DATE: 2017-10-01
<313> RELEVANT RESIDUES IN SEQ ID NO: (1)..(1428)

<400> SEQUENCE: 69

agtgtcctgg ttactgcagc ggcagcaaca gcaggtccta ctatcgcctc cctctagtct     60

ctgcttctct ggatccctga ggagggcaga aggaagaaaa cagcccaaag atgagagtga    120

ttcgcgtggg tacccgcaag agccagcttg ctcgcataca gacggacagt gtggtggcaa    180

cattgaaagc ctcgtaccct ggcctgcagt ttgaaatcat tgctatgtcc accacagggg    240

acaagattct tgatactgca ctctctaaga ttggagagaa aagcctgttt accaaggagc    300

ttgaacatgc cctggagaag aatgaagtgg acctggttgt tcactccttg aaggacctgc    360

ccactgtgct tcctcctggc ttcaccatcg gagccatctg caagcgggaa aaccctcatg    420

atgctgttgt ctttcaccca aaatttgttg ggaagaccct agaaaccctg ccagagaaga    480

gtgtggtggg aaccagctcc ctgcgaagag cagcccagct gcagagaaag ttcccgcatc    540

tggagttcag gagtattcgg ggaaacctca acacccggct tcggaagctg gacgagcagc    600

aggagttcag tgccatcatc ctggcaacag ctggcctgca gcgcatgggc tggcacaacc    660

gggtggggca gatcctgcac cctgaggaat gcatgtatgc tgtgggccag ggggccttgg    720

gcgtggaagt gcgagccaag gaccaggaca tcttggatct ggtgggtgtg ctgcacgatc    780

ccgagactct gcttcgctgc atcgctgaaa gggccttcct gaggcacctg gaaggaggct    840

gcagtgtgcc agtagccgtg catacagcta tgaaggatgg gcaactgtac ctgactggag    900

gagtctggag tctagacggc tcagatagca tacaagagac catgcaggct accatccatg    960

tccctgccca gcatgaagat ggccctgagg atgacccaca gttggtaggc atcactgctc   1020

gtaacattcc acgagggccc cagttggctg cccagaactt gggcatcagc ctggccaact   1080

tgttgctgag caaaggagcc aaaaacatcc tggatgttgc acggcagctt aacgatgccc   1140

attaactggt ttgtggggca cagatgcctg ggttgctgct gtccagtgcc tacatcccgg   1200

gcctcagtgc ccattctca ctgctatctg gggagtgatt accccgggag actgaactgc   1260

agggttcaag ccttccaggg atttgcctca ccttggggcc ttgatgactg ccttgcctcc   1320

tcagtatgtg gggcttcat ctctttagag aagtccaagc aacagccttt gaatgtaacc   1380
```

aatcctacta ataaaccagt tctgaaggtg taaaaaaaaa aaaaaaaa 1428

<210> SEQ ID NO 70
<211> LENGTH: 344
<212> TYPE: PRT
<213> ORGANISM: Homo sapiens
<300> PUBLICATION INFORMATION:
<308> DATABASE ACCESSION NUMBER: NCBI / NP_001019553.1
<309> DATABASE ENTRY DATE: 2017-10-01
<313> RELEVANT RESIDUES IN SEQ ID NO: (1)..(344)

<400> SEQUENCE: 70

```
Met Arg Val Ile Arg Val Gly Thr Arg Lys Ser Gln Leu Ala Arg Ile
1               5                   10                  15

Gln Thr Asp Ser Val Val Ala Thr Leu Lys Ala Ser Tyr Pro Gly Leu
            20                  25                  30

Gln Phe Glu Ile Ile Ala Met Ser Thr Thr Gly Asp Lys Ile Leu Asp
        35                  40                  45

Thr Ala Leu Ser Lys Ile Gly Glu Lys Ser Leu Phe Thr Lys Glu Leu
    50                  55                  60

Glu His Ala Leu Glu Lys Asn Glu Val Asp Leu Val Val His Ser Leu
65                  70                  75                  80

Lys Asp Leu Pro Thr Val Leu Pro Pro Gly Phe Thr Ile Gly Ala Ile
                85                  90                  95

Cys Lys Arg Glu Asn Pro His Asp Ala Val Val Phe His Pro Lys Phe
            100                 105                 110

Val Gly Lys Thr Leu Glu Thr Leu Pro Glu Lys Ser Val Val Gly Thr
        115                 120                 125

Ser Ser Leu Arg Arg Ala Ala Gln Leu Gln Arg Lys Phe Pro His Leu
    130                 135                 140

Glu Phe Arg Ser Ile Arg Gly Asn Leu Asn Thr Arg Leu Arg Lys Leu
145                 150                 155                 160

Asp Glu Gln Gln Glu Phe Ser Ala Ile Ile Leu Ala Thr Ala Gly Leu
                165                 170                 175

Gln Arg Met Gly Trp His Asn Arg Val Gly Gln Ile Leu His Pro Glu
            180                 185                 190

Glu Cys Met Tyr Ala Val Gly Gln Gly Ala Leu Gly Val Glu Val Arg
        195                 200                 205

Ala Lys Asp Gln Asp Ile Leu Asp Leu Val Gly Val Leu His Asp Pro
    210                 215                 220

Glu Thr Leu Leu Arg Cys Ile Ala Glu Arg Ala Phe Leu Arg His Leu
225                 230                 235                 240

Glu Gly Gly Cys Ser Val Pro Val Ala Val His Thr Ala Met Lys Asp
                245                 250                 255

Gly Gln Leu Tyr Leu Thr Gly Gly Val Trp Ser Leu Asp Gly Ser Asp
            260                 265                 270

Ser Ile Gln Glu Thr Met Gln Ala Thr Ile His Val Pro Ala Gln His
        275                 280                 285

Glu Asp Gly Pro Glu Asp Asp Pro Gln Leu Val Gly Ile Thr Ala Arg
    290                 295                 300

Asn Ile Pro Arg Gly Pro Gln Leu Ala Ala Gln Asn Leu Gly Ile Ser
305                 310                 315                 320

Leu Ala Asn Leu Leu Leu Ser Lys Gly Ala Lys Asn Ile Leu Asp Val
                325                 330                 335

Ala Arg Gln Leu Asn Asp Ala His
            340
```

<210> SEQ ID NO 71
<211> LENGTH: 1406
<212> TYPE: DNA
<213> ORGANISM: Homo sapiens
<300> PUBLICATION INFORMATION:
<308> DATABASE ACCESSION NUMBER: NCBI / NM_001258208.1
<309> DATABASE ENTRY DATE: 2017-10-03
<313> RELEVANT RESIDUES IN SEQ ID NO: (1)..(1406)

<400> SEQUENCE: 71

```
ccggaagtga cgcgaggctc tgcggagacc aggagtcaga ctgtaggacg acctcgggtc     60

ccacgtgtcc ccggtactcg ccggccggag cccccggctt cccggggccg ggggacctta    120

gcggcaccca cacacagcct actttccaag cggagccatg tctggtaacg gcaatgcggc    180

tgcaacggcg gaagaaaaca gcccaaagat gagagtgatt cgcgtgggta cccgcaagag    240

ccagcttgct cgcatacaga cggacagtgt ggtggcaaca ttgaaagcct cgtaccctgg    300

cctgcagttt gaaatcattg ctatgtccac cacaggggac aagattcttg atactgcact    360

ctctaagatt ggagagaaaa gcctgtttac caaggagctt gaacatgccc tggagaagaa    420

tgaagtggac ctggttgttc actccttgaa ggacctgccc actgtgcttc ctcctggctt    480

caccatcgga gccatctgca agcgggaaaa ccctcatgat gctgttgtct ttcacccaaa    540

atttgttggg aagaccctag aaaccctgcc agagaagagt gtggtgggaa ccagctccct    600

gcgaagagca gcccagctgc agagaaagtt cccgcatctg gagttcagga gtattcgggg    660

aaacctcaac acccggcttc ggaagctgga cgagcagcag gagttcagtg ccatcatcct    720

ggcaacagct ggcctgcagc gcatgggctg gcacaaccgg gtggggcaga tcctgcaccc    780

tgaggaatgc atgtatgctg tgggccagga aggaggctgc agtgtgccag tagccgtgca    840

tacagctatg aaggatgggc aactgtacct gactggagga gtctggagtc tagacggctc    900

agatagcata caagagacca tgcaggctac catccatgtc cctgcccagc atgaagatgg    960

ccctgaggat gacccacagt tggtaggcat cactgctcgt aacattccac gagggcccca   1020

gttggctgcc cagaacttgg gcatcagcct ggccaacttg ttgctgagca aaggagccaa   1080

aaacatcctg gatgttgcac ggcagcttaa cgatgcccat taactggttt gtggggcaca   1140

gatgcctggg ttgctgctgt ccagtgccta catcccgggc ctcagtgccc cattctcact   1200

gctatctggg gagtgattac cccgggagac tgaactgcag ggttcaagcc ttccagggat   1260

ttgcctcacc ttggggcctt gatgactgcc ttgcctcctc agtatgtggg ggcttcatct   1320

ctttagagaa gtccaagcaa cagcctttga atgtaaccaa tcctactaat aaaccagttc   1380

tgaaggtgta aaaaaaaaaa aaaaaa                                        1406
```

<210> SEQ ID NO 72
<211> LENGTH: 321
<212> TYPE: PRT
<213> ORGANISM: Homo sapiens
<300> PUBLICATION INFORMATION:
<308> DATABASE ACCESSION NUMBER: NCBI / NP_001245137.1
<309> DATABASE ENTRY DATE: 2017-10-03
<313> RELEVANT RESIDUES IN SEQ ID NO: (1)..(321)

<400> SEQUENCE: 72

```
Met Ser Gly Asn Gly Asn Ala Ala Ala Thr Ala Glu Glu Asn Ser Pro
1               5                   10                  15

Lys Met Arg Val Ile Arg Val Gly Thr Arg Lys Ser Gln Leu Ala Arg
            20                  25                  30
```

Ile Gln Thr Asp Ser Val Val Ala Thr Leu Lys Ala Ser Tyr Pro Gly
35 40 45

Leu Gln Phe Glu Ile Ile Ala Met Ser Thr Thr Gly Asp Lys Ile Leu
50 55 60

Asp Thr Ala Leu Ser Lys Ile Gly Glu Lys Ser Leu Phe Thr Lys Glu
65 70 75 80

Leu Glu His Ala Leu Glu Lys Asn Glu Val Asp Leu Val Val His Ser
85 90 95

Leu Lys Asp Leu Pro Thr Val Leu Pro Pro Gly Phe Thr Ile Gly Ala
100 105 110

Ile Cys Lys Arg Glu Asn Pro His Asp Ala Val Val Phe His Pro Lys
115 120 125

Phe Val Gly Lys Thr Leu Glu Thr Leu Pro Glu Lys Ser Val Val Gly
130 135 140

Thr Ser Ser Leu Arg Arg Ala Ala Gln Leu Gln Arg Lys Phe Pro His
145 150 155 160

Leu Glu Phe Arg Ser Ile Arg Gly Asn Leu Asn Thr Arg Leu Arg Lys
165 170 175

Leu Asp Glu Gln Gln Glu Phe Ser Ala Ile Ile Leu Ala Thr Ala Gly
180 185 190

Leu Gln Arg Met Gly Trp His Asn Arg Val Gly Gln Ile Leu His Pro
195 200 205

Glu Glu Cys Met Tyr Ala Val Gly Gln Glu Gly Gly Cys Ser Val Pro
210 215 220

Val Ala Val His Thr Ala Met Lys Asp Gly Gln Leu Tyr Leu Thr Gly
225 230 235 240

Gly Val Trp Ser Leu Asp Gly Ser Asp Ser Ile Gln Glu Thr Met Gln
245 250 255

Ala Thr Ile His Val Pro Ala Gln His Glu Asp Gly Pro Glu Asp Asp
260 265 270

Pro Gln Leu Val Gly Ile Thr Ala Arg Asn Ile Pro Arg Gly Pro Gln
275 280 285

Leu Ala Ala Gln Asn Leu Gly Ile Ser Leu Ala Asn Leu Leu Leu Ser
290 295 300

Lys Gly Ala Lys Asn Ile Leu Asp Val Ala Arg Gln Leu Asn Asp Ala
305 310 315 320

His

<210> SEQ ID NO 73
<211> LENGTH: 1497
<212> TYPE: DNA
<213> ORGANISM: Homo sapiens
<300> PUBLICATION INFORMATION:
<308> DATABASE ACCESSION NUMBER: NCBI / NM_001258209.1
<309> DATABASE ENTRY DATE: 2017-10-03
<313> RELEVANT RESIDUES IN SEQ ID NO: (1)..(1497)

<400> SEQUENCE: 73
ccggaagtga cgcgaggctc tgcggagacc aggagtcaga ctgtaggacg acctcgggtc 60
ccacgtgtcc ccggtactcg ccggccggag cccccggctt cccggggccg ggggacctta 120
gcggcaccca cacacagcct actttccaag cggagccatg tctggtaacg gcaatgcggc 180
tgcaacggcg gtgagtgctg agccggtgac cagcacactt tgggcttctg gacgagccgt 240
gcagcgattg gccccaggtt gccatcctca gtcgtctatt ggaagaaaac agcccaaaga 300
tgagagtgat tcgcgtgggt acccgcaaga gccagcttgc tcgcatacag acggacagtg 360

```
tggtggcaac attgaaagcc tcgtaccctg gcctgcagtt tgaaatcatt gctatgtcca    420

ccacagggga caagattctt gatactgcac tctctaagat tggagagaaa agcctgttta    480

ccaaggagct tgaacatgcc ctggagaaga atgaagtgga cctggttgtt cactccttga    540

aggacctgcc cactgtgctt cctcctggct tcaccatcgg agccatctgc aagcgggaaa    600

accctcatga tgctgttgtc tttcacccaa aatttgttgg gaagacccta gaaaccctgc    660

cagagaagag tgtggtggga accagctccc tgcgaagagc agcccagctg cagagaaagt    720

tcccgcatct ggagttcagg agtattcggg gaaacctcaa cacccggctt cggaagctgg    780

acgagcagca ggagttcagt gccatcatcc tggcaacagc tggcctgcag cgcatgggct    840

ggcacaaccg ggtggggcag atcctgcacc ctgaggaatg catgtatgct gtgggccagg    900

aaggaggctg cagtgtgcca gtagccgtgc atacagctat gaaggatggg caactgtacc    960

tgactggagg agtctggagt ctagacggct cagatagcat acaagagacc atgcaggcta   1020

ccatccatgt ccctgcccag catgaagatg gccctgagga tgacccacag ttggtaggca   1080

tcactgctcg taacattcca cgagggcccc agttggctgc ccagaacttg ggcatcagcc   1140

tggccaactt gttgctgagc aaaggagcca aaaacatcct ggatgttgca cggcagctta   1200

acgatgccca ttaactggtt tgtggggcac agatgcctgg gttgctgctg tccagtgcct   1260

acatcccggg cctcagtgcc ccattctcac tgctatctgg ggagtgatta ccccgggaga   1320

ctgaactgca gggttcaagc cttccaggga tttgcctcac cttggggcct tgatgactgc   1380

cttgcctcct cagtatgtgg gggcttcatc tctttagaga agtccaagca acagcctttg   1440

aatgtaacca atcctactaa taaaccagtt ctgaaggtgt aaaaaaaaaa aaaaaaa      1497
```

```
<210> SEQ ID NO 74
<211> LENGTH: 304
<212> TYPE: PRT
<213> ORGANISM: Homo sapiens
<300> PUBLICATION INFORMATION:
<308> DATABASE ACCESSION NUMBER: NCBI / NP_001245138.1
<309> DATABASE ENTRY DATE: 2017-10-03
<313> RELEVANT RESIDUES IN SEQ ID NO: (1)..(304)

<400> SEQUENCE: 74

Met Arg Val Ile Arg Val Gly Thr Arg Lys Ser Gln Leu Ala Arg Ile
1               5                   10                  15

Gln Thr Asp Ser Val Val Ala Thr Leu Lys Ala Ser Tyr Pro Gly Leu
            20                  25                  30

Gln Phe Glu Ile Ile Ala Met Ser Thr Thr Gly Asp Lys Ile Leu Asp
        35                  40                  45

Thr Ala Leu Ser Lys Ile Gly Glu Lys Ser Leu Phe Thr Lys Glu Leu
    50                  55                  60

Glu His Ala Leu Glu Lys Asn Glu Val Asp Leu Val Val His Ser Leu
65                  70                  75                  80

Lys Asp Leu Pro Thr Val Leu Pro Pro Gly Phe Thr Ile Gly Ala Ile
                85                  90                  95

Cys Lys Arg Glu Asn Pro His Asp Ala Val Val Phe His Pro Lys Phe
            100                 105                 110

Val Gly Lys Thr Leu Glu Thr Leu Pro Glu Lys Ser Val Val Gly Thr
        115                 120                 125

Ser Ser Leu Arg Arg Ala Ala Gln Leu Gln Arg Lys Phe Pro His Leu
    130                 135                 140

Glu Phe Arg Ser Ile Arg Gly Asn Leu Asn Thr Arg Leu Arg Lys Leu
```

-continued

```
145                 150                 155                 160

Asp Glu Gln Gln Glu Phe Ser Ala Ile Ile Leu Ala Thr Ala Gly Leu
                165                 170                 175

Gln Arg Met Gly Trp His Asn Arg Val Gly Gln Ile Leu His Pro Glu
            180                 185                 190

Glu Cys Met Tyr Ala Val Gly Gln Glu Gly Gly Cys Ser Val Pro Val
        195                 200                 205

Ala Val His Thr Ala Met Lys Asp Gly Gln Leu Tyr Leu Thr Gly Gly
    210                 215                 220

Val Trp Ser Leu Asp Gly Ser Asp Ser Ile Gln Glu Thr Met Gln Ala
225                 230                 235                 240

Thr Ile His Val Pro Ala Gln His Glu Asp Gly Pro Glu Asp Asp Pro
                245                 250                 255

Gln Leu Val Gly Ile Thr Ala Arg Asn Ile Pro Arg Gly Pro Gln Leu
            260                 265                 270

Ala Ala Gln Asn Leu Gly Ile Ser Leu Ala Asn Leu Leu Leu Ser Lys
        275                 280                 285

Gly Ala Lys Asn Ile Leu Asp Val Ala Arg Gln Leu Asn Asp Ala His
    290                 295                 300


<210> SEQ ID NO 75
<211> LENGTH: 1719
<212> TYPE: DNA
<213> ORGANISM: Homo sapiens
<300> PUBLICATION INFORMATION:
<308> DATABASE ACCESSION NUMBER: NCBI / NM_001172085.1
<309> DATABASE ENTRY DATE: 2017-10-02
<313> RELEVANT RESIDUES IN SEQ ID NO: (1)..(1719)

<400> SEQUENCE: 75

ggcggaagtg acattatcaa cgcgcgccag gggttcagtg aggtcgggca ggttcgctgt     60

ggcgggcgcc tgggccgccg gctgtttaac ttcgcttccg ctggcccata gtgatctttg    120

cagtgaccca gggtgccatg actcccggaa tccctatctt tagtccaatg atgccttatg    180

gcactggact gaccccacag cctattcaga acaccaatag tctgtctatt ttggaagagc    240

aacaaaggca gcagcagcaa caacaacagc agcagcagca gcagcagcag caacagcaac    300

agcagcagca gcagcagcag cagcagcagc agcagcagca gcagcagcag cagcagcaac    360

aggcagtggc agctgcagcc gttcagcagt caacgtccca gcaggcaaca cagggaacct    420

caggccaggc accacagctc ttccactcac agactctcac aactgcaccc ttgccgggca    480

ccactccact gtatccctcc cccatgactc ccatgacccc catcactcct gccacgccag    540

cttcggagag ttctgggatt gtaccgcagc tgcaaaatat tgtatccaca gtgaatcttg    600

gttgtaaact tgacctaaag accattgcac ttcgtgcccg aaacgccgaa tataatccca    660

agcggtttgc tgcggtaatc atgaggataa gagagccacg aaccacggca ctgattttca    720

gttctgggaa aatggtgtgc acaggagcca agagtgaaga acagtccaga ctggcagcaa    780

gaaaatatgc tagagttgta cagaagttgg gttttccagc taagttcttg gacttcaaga    840

ttcagaatat ggtggggagc tgtgatgtga agtttcctat aaggttagaa ggccttgtgc    900

tcacccacca acaatttagt agttatgagc cagagttatt tcctggttta atctacagaa    960

tgatcaaacc cagaattgtt ctccttattt ttgtttctgg aaaagttgta ttaacaggtg   1020

ctaaagtcag agcagaaatt tatgaagcat ttgaaaacat ctaccctatt ctaaagggat   1080

tcaggaagac gacgtaatgg ctctcatgta cccttgcctc ccccaccccc ttcttttttt   1140
```

```
tttttaaac aaatcagttt gttttggtac ctttaaatgg tggtgttgtg agaagatgga   1200

tgttgagttg cagggtgtgg caccaggtga tgcccttctg taagtgccca ccgcgggatg   1260

ccgggaaggg gcattatttg tgcactgaga acaccgcgca gcgtgactgt gagttgctca   1320

taccgtgctg ctatctgggc agcgctgccc atttatttat atgtagattt taaacactgc   1380

tgttgacaag ttggtttgag ggagaaaact ttaagtgtta aagccacctc tataattgat   1440

tggacttttt aattttaatg tttttcccca tgaaccacag tttttatatt tctaccagaa   1500

aagtaaaaat ctttttttaaa agtgttgttt ttctaattta taactcctag gggttatttc   1560

tgtgccagac acattccacc tctccagtat tgcaggacag aatatatgtg ttaatgaaaa   1620

tgaatggctg tacatatttt tttctttctt cagagtactc tgtacaataa atgcagttta   1680

taaaagtgtt agattgttgt taaaaaaaaa aaaaaaaaa                          1719
```

<210> SEQ ID NO 76
<211> LENGTH: 319
<212> TYPE: PRT
<213> ORGANISM: Homo sapiens
<300> PUBLICATION INFORMATION:
<308> DATABASE ACCESSION NUMBER: NCBI / NP_001165556.1
<309> DATABASE ENTRY DATE: 2017-10-02
<313> RELEVANT RESIDUES IN SEQ ID NO: (1)..(319)

<400> SEQUENCE: 76

```
Met Thr Pro Gly Ile Pro Ile Phe Ser Pro Met Met Pro Tyr Gly Thr
1               5                   10                  15

Gly Leu Thr Pro Gln Pro Ile Gln Asn Thr Asn Ser Leu Ser Ile Leu
            20                  25                  30

Glu Glu Gln Gln Arg Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Gln Gln Gln Ala Val Ala Ala Ala
65                  70                  75                  80

Ala Val Gln Gln Ser Thr Ser Gln Gln Ala Thr Gln Gly Thr Ser Gly
                85                  90                  95

Gln Ala Pro Gln Leu Phe His Ser Gln Thr Leu Thr Thr Ala Pro Leu
            100                 105                 110

Pro Gly Thr Thr Pro Leu Tyr Pro Ser Pro Met Thr Pro Met Thr Pro
        115                 120                 125

Ile Thr Pro Ala Thr Pro Ala Ser Glu Ser Ser Gly Ile Val Pro Gln
    130                 135                 140

Leu Gln Asn Ile Val Ser Thr Val Asn Leu Gly Cys Lys Leu Asp Leu
145                 150                 155                 160

Lys Thr Ile Ala Leu Arg Ala Arg Asn Ala Glu Tyr Asn Pro Lys Arg
                165                 170                 175

Phe Ala Ala Val Ile Met Arg Ile Arg Glu Pro Arg Thr Thr Ala Leu
            180                 185                 190

Ile Phe Ser Ser Gly Lys Met Val Cys Thr Gly Ala Lys Ser Glu Glu
        195                 200                 205

Gln Ser Arg Leu Ala Ala Arg Lys Tyr Ala Arg Val Val Gln Lys Leu
    210                 215                 220

Gly Phe Pro Ala Lys Phe Leu Asp Phe Lys Ile Gln Asn Met Val Gly
225                 230                 235                 240

Ser Cys Asp Val Lys Phe Pro Ile Arg Leu Glu Gly Leu Val Leu Thr
                245                 250                 255
```

His Gln Gln Phe Ser Ser Tyr Glu Pro Glu Leu Phe Pro Gly Leu Ile
260 265 270

Tyr Arg Met Ile Lys Pro Arg Ile Val Leu Leu Ile Phe Val Ser Gly
275 280 285

Lys Val Val Leu Thr Gly Ala Lys Val Arg Ala Glu Ile Tyr Glu Ala
290 295 300

Phe Glu Asn Ile Tyr Pro Ile Leu Lys Gly Phe Arg Lys Thr Thr
305 310 315

<210> SEQ ID NO 77
<211> LENGTH: 1921
<212> TYPE: DNA
<213> ORGANISM: Homo sapiens
<300> PUBLICATION INFORMATION:
<308> DATABASE ACCESSION NUMBER: NCBI / NM_003194.4
<309> DATABASE ENTRY DATE: 2017-10-02
<313> RELEVANT RESIDUES IN SEQ ID NO: (1)..(1921)

<400> SEQUENCE: 77
ggcggaagtg acattatcaa cgcgcgccag gggttcagtg aggtcgggca ggttcgctgt 60
ggcgggcgcc tgggccgccg gctgtttaac ttcgcttccg ctggcccata gtgatctttg 120
cagtgaccca gcatcactgt ttcttggcgt gtgaagataa cccaaggaat tgaggaagtt 180
gctgagaaga gtgtgctgga gatgctctag gaaaaaattg aatagtgaga cgagttccag 240
cgcaagggtt tctggtttgc caagaagaaa gtgaacatca tggatcagaa caacagcctg 300
ccaccttacg ctcagggctt ggcctcccct cagggtgcca tgactcccgg aatccctatc 360
tttagtccaa tgatgcctta tggcactgga ctgaccccac agcctattca gaacaccaat 420
agtctgtcta ttttggaaga gcaacaaagg cagcagcagc aacaacaaca gcagcagcag 480
cagcagcagc agcaacagca acagcagcag cagcagcagc agcagcagca gcagcagcag 540
cagcagcagc agcagcagca acaggcagtg gcagctgcag ccgttcagca gtcaacgtcc 600
cagcaggcaa cacagggaac ctcaggccag gcaccacagc tcttccactc acagactctc 660
acaactgcac ccttgccggg caccactcca ctgtatccct cccccatgac tcccatgacc 720
cccatcactc ctgccacgcc agcttcggag agttctggga ttgtaccgca gctgcaaaat 780
attgtatcca cagtgaatct tggttgtaaa cttgacctaa agaccattgc acttcgtgcc 840
cgaaacgccg aatataatcc caagcggttt gctgcggtaa tcatgaggat aagagagcca 900
cgaaccacgg cactgatttt cagttctggg aaaatggtgt gcacaggagc caagagtgaa 960
gaacagtcca gactggcagc aagaaaatat gctagagttg tacagaagtt gggttttcca 1020
gctaagttct tggacttcaa gattcagaat atggtgggga gctgtgatgt gaagtttcct 1080
ataaggttag aaggccttgt gctcacccac caacaattta gtagttatga gccagagtta 1140
tttcctggtt taatctacag aatgatcaaa cccagaattg ttctccttat ttttgtttct 1200
ggaaaagttg tattaacagg tgctaaagtc agagcagaaa tttatgaagc atttgaaaac 1260
atctacccta ttctaaaggg attcaggaag acgacgtaat ggctctcatg taccettgcc 1320 tcccccaccc ccttcttttt ttttttttaa acaaatcagt ttgttttggt acctttaaat 1380
ggtggtgttg tgagaagatg gatgttgagt tgcagggtgt ggcaccaggt gatgcccttc 1440
tgtaagtgcc caccgcggga tgccgggaag ggcattattt tgtgcactga gaacaccgcg 1500
cagcgtgact gtgagttgct cataccgtgc tgctatctgg gcagcgctgc ccatttattt 1560
atatgtagat tttaaacact gctgttgaca agttggtttg agggagaaaa ctttaagtgt 1620

```
taaagccacc tctataattg attggacttt ttaattttaa tgtttttccc catgaaccac   1680

agtttttata tttctaccag aaaagtaaaa atcttttttta aaagtgttgt ttttctaatt   1740

tataactcct aggggttatt tctgtgccag acacattcca cctctccagt attgcaggac   1800

agaatatatg tgttaatgaa aatgaatggc tgtacatatt tttttctttc ttcagagtac   1860

tctgtacaat aaatgcagtt tataaaagtg ttagattgtt gttaaaaaaa aaaaaaaaaa   1920

a                                                                     1921


<210> SEQ ID NO 78
<211> LENGTH: 339
<212> TYPE: PRT
<213> ORGANISM: Homo sapiens
<300> PUBLICATION INFORMATION:
<308> DATABASE ACCESSION NUMBER: NCBI / NP_003185.1
<309> DATABASE ENTRY DATE: 2017-10-02
<313> RELEVANT RESIDUES IN SEQ ID NO: (1)..(339)

<400> SEQUENCE: 78

Met Asp Gln Asn Asn Ser Leu Pro Pro Tyr Ala Gln Gly Leu Ala Ser
1               5                   10                  15

Pro Gln Gly Ala Met Thr Pro Gly Ile Pro Ile Phe Ser Pro Met Met
            20                  25                  30

Pro Tyr Gly Thr Gly Leu Thr Pro Gln Pro Ile Gln Asn Thr Asn Ser
        35                  40                  45

Leu Ser Ile Leu Glu Glu Gln Gln Arg Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln Ala
                85                  90                  95

Val Ala Ala Ala Ala Val Gln Gln Ser Thr Ser Gln Gln Ala Thr Gln
            100                 105                 110

Gly Thr Ser Gly Gln Ala Pro Gln Leu Phe His Ser Gln Thr Leu Thr
        115                 120                 125

Thr Ala Pro Leu Pro Gly Thr Thr Pro Leu Tyr Pro Ser Pro Met Thr
    130                 135                 140

Pro Met Thr Pro Ile Thr Pro Ala Thr Pro Ala Ser Glu Ser Ser Gly
145                 150                 155                 160

Ile Val Pro Gln Leu Gln Asn Ile Val Ser Thr Val Asn Leu Gly Cys
                165                 170                 175

Lys Leu Asp Leu Lys Thr Ile Ala Leu Arg Ala Arg Asn Ala Glu Tyr
            180                 185                 190

Asn Pro Lys Arg Phe Ala Ala Val Ile Met Arg Ile Arg Glu Pro Arg
        195                 200                 205

Thr Thr Ala Leu Ile Phe Ser Ser Gly Lys Met Val Cys Thr Gly Ala
    210                 215                 220

Lys Ser Glu Glu Gln Ser Arg Leu Ala Ala Arg Lys Tyr Ala Arg Val
225                 230                 235                 240

Val Gln Lys Leu Gly Phe Pro Ala Lys Phe Leu Asp Phe Lys Ile Gln
                245                 250                 255

Asn Met Val Gly Ser Cys Asp Val Lys Phe Pro Ile Arg Leu Glu Gly
            260                 265                 270

Leu Val Leu Thr His Gln Gln Phe Ser Ser Tyr Glu Pro Glu Leu Phe
        275                 280                 285

Pro Gly Leu Ile Tyr Arg Met Ile Lys Pro Arg Ile Val Leu Leu Ile
```

-continued 290 295 300

Phe Val Ser Gly Lys Val Val Leu Thr Gly Ala Lys Val Arg Ala Glu
305 310 315 320

Ile Tyr Glu Ala Phe Glu Asn Ile Tyr Pro Ile Leu Lys Gly Phe Arg
325 330 335

Lys Thr Thr

<210> SEQ ID NO 79
<211> LENGTH: 3020
<212> TYPE: DNA
<213> ORGANISM: Homo sapiens
<300> PUBLICATION INFORMATION:
<308> DATABASE ACCESSION NUMBER: NCBI / NM_001135699.1
<309> DATABASE ENTRY DATE: 2017-10-09
<313> RELEVANT RESIDUES IN SEQ ID NO: (1)..(3020)

<400> SEQUENCE: 79
tgtcccctcg cgcagtcacc gagcgcagat cccgcgctct cgattggaac gcctccccat 60
cactcagcca cactcagggg ctggacgcct cactcccgtt tccgagccat aaaaggtcta 120
ggaccgcttc ccccgagcca gcagaacatc cagtcatgga taaaaatgag ctggttcaga 180
aggccaaact ggccgagcag gctgagcgat atgatgacat ggcagcctgc atgaagtctg 240
taactgagca aggagctgaa ttatccaatg aggagaggaa tcttctctca gttgcttata 300
aaaatgttgt aggagcccgt aggtcatctt ggagggtcgt ctcaagtatt gaacaaaaga 360
cggaaggtgc tgagaaaaaa cagcagatgg ctcgagaata cagagagaaa attgagacgg 420
agctaagaga tatctgcaat gatgtactgt ctcttttgga aaagttcttg atccccaatg 480
cttcacaagc agagagcaaa gtcttctatt tgaaaatgaa aggagattac taccgttact 540
tggctgaggt tgccgctggt gatgacaaga aagggattgt cgatcagtca caacaagcat 600
accaagaagc ttttgaaatc agcaaaaagg aaatgcaacc aacacatcct atcagactgg 660
gtctggccct taacttctct gtgttctatt atgagattct gaactcccca gagaaagcct 720
gctctcttgc aaagacagct tttgatgaag ccattgctga acttgataca ttaagtgaag 780
agtcatacaa agacagcacg ctaataatgc aattactgag agacaacttg acattgtgga 840
catcggatac ccaaggagac gaagctgaag caggagaagg aggggaaaat taaccggcct 900
tccaactttt gtctgcctca ttctaaaatt tacacagtag accatttgtc atccatgctg 960
tcccacaaat agtttttttgt ttacgattta tgacaggttt atgttacttc tatttgaatt 1020
tctatatttc ccatgtggtt tttatgttta atattagggg agtagagcca gttaacattt 1080
agggagttat ctgttttcat cttgaggtgg ccaatatggg gatgtggaat ttttatacaa 1140
gttataagtg tttggcatag tacttttggt acattgtggc ttcaaaaggg ccagtgtaaa 1200
actgcttcca tgtctaagca aagaaaactg cctacatact ggtttgtcct ggcggggaat 1260
aaaagggatc attggttcca gtcacaggtg tagtaattgt gggtacttta aggtttggag 1320
cacttacaag gctgtggtag aatcataccc catggatacc acatattaaa ccatgtatat 1380
ctgtggaata ctcaatgtgt acacctttga ctacagctgc agaagtgttc ctttagacaa 1440
agttgtgacc cattttactc tggataaggg cagaaacggt tcacattcca ttatttgtaa 1500
agttacctgc tgttagcttt cattattttt gctacactca ttttatttgt atttaaatgt 1560
tttaggcaac ctaagaacaa atgtaaaagt aaagatgcag gaaaaatgaa ttgcttggta 1620
ttcattactt catgtatatc aagcacagca gtaaaacaaa aacccatgta tttaactttt 1680
ttttaggatt tttgcttttg tgattttttt tttttgata cttgcctaac atgcatgtgc 1740

```
tgtaaaaata gttaacaggg aaataacttg agatgatggc tagctttgtt taatgtctta   1800

tgaaattttc atgaacaatc caagcataat tgttaagaac acgtgtatta aattcatgta   1860

agtggaataa aagttttatg aatggacttt tcaactactt tctctacagc ttttcatgta   1920

aattagtctt ggttctgaaa cttctctaaa ggaaattgta catttttttga aatttattcc   1980

ttattccctc ttggcagcta atgggctctt accaagttta aacacaaaat ttatcataac   2040

aaaaatacta ctaatataac tactgtttcc atgtcccatg atcccctctc ttcctcccca   2100

ccctgaaaaa aatgagttcc tattttttct gggagagggg gggattgatt agaaaaaaat   2160

gtagtgtgtt ccatttaaaa ttttggcata tggcattttc taacttagga agccacaatg   2220

ttcttggccc atcatgacat tgggtagcat taactgtaag ttttgtgctt ccaaatcact   2280

ttttggtttt taagaatttc ttgatactct tatagcctgc cttcaatttt gatcctttat   2340

tctttctatt tgtcaggtgc acaagattac cttcctgttt tagccttctg tcttgtcacc   2400

aaccattctt acttggtggc catgtacttg gaaaaaggcc gcatgatctt tctggctcca   2460

ctcagtgtct aaggcaccct gcttcctttg cttgcatccc acagactatt tccctcatcc   2520

tatttactgc agcaaatctc tccttagttg atgagactgt gtttatctcc ctttaaaacc   2580

ctacctatcc tgaatggtct gtcattgtct gcctttaaaa tccttcctct ttcttcctcc   2640

tctattctct aaataatgat ggggctaagt tatacccaaa gctcacttta caaaatattt   2700

cctcagtact ttgcagaaaa caccaaacaa aaatgccatt ttaaaaaagg tgtatttttt   2760

cttttagaat gtaagctcct caagagcagg gacaatgttt tctgtatgtt ctattgtgcc   2820

tagtacactg taaatgctca ataaatattg atgatgggag gcagtgagtc ttgatgataa   2880

gggtgagaaa ctgaaatccc aaacactgtt ttgttgcttg ttttattatg acctcagatt   2940

aaattgggaa atattggccc ttttgaataa ttgtcccaaa tattacattc aaataaaagt   3000

gcaatggaga aaaaaaaaaa                                              3020
```

<210> SEQ ID NO 80
<211> LENGTH: 245
<212> TYPE: PRT
<213> ORGANISM: Homo sapiens
<300> PUBLICATION INFORMATION:
<308> DATABASE ACCESSION NUMBER: NCBI / NP_001129171.1
<309> DATABASE ENTRY DATE: 2017-10-09
<313> RELEVANT RESIDUES IN SEQ ID NO: (1)..(245)

<400> SEQUENCE: 80

```
Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
```

```
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245


<210> SEQ ID NO 81
<211> LENGTH: 2974
<212> TYPE: DNA
<213> ORGANISM: Homo sapiens
<300> PUBLICATION INFORMATION:
<308> DATABASE ACCESSION NUMBER: NCBI / NM_001135700.1
<309> DATABASE ENTRY DATE: 2017-10-09
<313> RELEVANT RESIDUES IN SEQ ID NO: (1)..(2974)

<400> SEQUENCE: 81

ggcggggagg ggccgggggc ctcggggacc caagcgcgag ggaaaggcct ggccgagagc     60

gggccggagc ccaggcctgg cgcggcggcg cccgccagaa catccagtca tggataaaaa    120

tgagctggtt cagaaggcca aactggccga gcaggctgag cgatatgatg acatggcagc    180

ctgcatgaag tctgtaactg agcaaggagc tgaattatcc aatgaggaga ggaatcttct    240

ctcagttgct tataaaaatg ttgtaggagc ccgtaggtca tcttggaggg tcgtctcaag    300

tattgaacaa aagacggaag gtgctgagaa aaaacagcag atggctcgag aatacagaga    360

gaaaattgag acggagctaa gagatatctg caatgatgta ctgtctcttt tggaaaagtt    420

cttgatcccc aatgcttcac aagcagagag caaagtcttc tatttgaaaa tgaaaggaga    480

ttactaccgt tacttggctg aggttgccgc tggtgatgac aagaaaggga ttgtcgatca    540

gtcacaacaa gcataccaag aagcttttga aatcagcaaa aaggaaatgc aaccaacaca    600

tcctatcaga ctgggtctgg cccttaactt ctctgtgttc tattatgaga ttctgaactc    660

cccagagaaa gcctgctctc ttgcaaagac agcttttgat gaagccattg ctgaacttga    720

tacattaagt gaagagtcat acaaagacag cacgctaata atgcaattac tgagagacaa    780

cttgacattg tggacatcgg atacccaagg agacgaagct gaagcaggag aaggaggggga    840

aaattaaccg gccttccaac ttttgtctgc ctcattctaa aatttacaca gtagaccatt    900

tgtcatccat gctgtcccac aaatagtttt ttgtttacga tttatgacag gtttatgtta    960

cttctatttg aatttctata tttcccatgt ggtttttatg tttaatatta ggggagtaga   1020

gccagttaac atttagggag ttatctgttt tcatcttgag gtggccaata tggggatgtg   1080

gaatttttat acaagttata agtgtttggc atagtacttt tggtacattg tggcttcaaa   1140

agggccagtg taaaactgct tccatgtcta agcaaagaaa actgcctaca tactggtttg   1200

tcctggcggg gaataaaagg gatcattggt tccagtcaca ggtgtagtaa ttgtgggtac   1260
```

```
tttaaggttt ggagcactta caaggctgtg gtagaatcat accccatgga taccacatat   1320

taaaccatgt atatctgtgg aatactcaat gtgtacacct ttgactacag ctgcagaagt   1380

gttcctttag acaaagttgt gacccatttt actctggata agggcagaaa cggttcacat   1440

tccattattt gtaaagttac ctgctgttag ctttcattat ttttgctaca ctcattttat   1500

ttgtatttaa atgttttagg caacctaaga acaaatgtaa aagtaaagat gcaggaaaaa   1560

tgaattgctt ggtattcatt acttcatgta tatcaagcac agcagtaaaa caaaaaccca   1620

tgtatttaac ttttttttag gatttttgct tttgtgattt tttttttttt gatacttgcc   1680

taacatgcat gtgctgtaaa aatagttaac agggaaataa cttgagatga tggctagctt   1740

tgtttaatgt cttatgaaat tttcatgaac aatccaagca taattgttaa gaacacgtgt   1800

attaaattca tgtaagtgga ataaaagttt tatgaatgga cttttcaact actttctcta   1860

cagcttttca tgtaaattag tcttggttct gaaacttctc taaaggaaat tgtacatttt   1920

ttgaaattta ttccttattc cctcttggca gctaatgggc tcttaccaag tttaaacaca   1980

aaatttatca taacaaaaat actactaata taactactgt ttccatgtcc catgatcccc   2040

tctcttcctc cccaccctga aaaaaatgag ttcctatttt ttctgggaga ggggggggatt   2100

gattagaaaa aaatgtagtg tgttccattt aaaattttgg catatggcat tttctaactt   2160

aggaagccac aatgttcttg gcccatcatg acattgggta gcattaactg taagttttgt   2220

gcttccaaat cactttttgg tttttaagaa tttcttgata ctcttatagc ctgccttcaa   2280

ttttgatcct ttattctttc tatttgtcag gtgcacaaga ttaccttcct gttttagcct   2340

tctgtcttgt caccaaccat tcttacttgg tggccatgta cttggaaaaa ggccgcatga   2400

tctttctggc tccactcagt gtctaaggca ccctgcttcc tttgcttgca tcccacagac   2460

tatttccctc atcctattta ctgcagcaaa tctctcctta gttgatgaga ctgtgtttat   2520

ctccctttaa aaccctacct atcctgaatg gtctgtcatt gtctgccttt aaaatccttc   2580

ctctttcttc ctcctctatt ctctaaataa tgatggggct aagttatacc caaagctcac   2640

tttacaaaat atttcctcag tactttgcag aaaacaccaa acaaaaaatgc cattttaaaa   2700

aaggtgtatt ttttctttta gaatgtaagc tcctcaagag cagggacaat gttttctgta   2760

tgttctattg tgcctagtac actgtaaatg ctcaataaat attgatgatg ggaggcagtg   2820

agtcttgatg ataagggtga gaaactgaaa tcccaaacac tgttttgttg cttgttttat   2880

tatgacctca gattaaattg ggaaatattg gcccttttga ataattgtcc caaatattac   2940

attcaaataa aagtgcaatg gagaaaaaaa aaaa                               2974
```

<210> SEQ ID NO 82
<211> LENGTH: 245
<212> TYPE: PRT
<213> ORGANISM: Homo sapiens
<300> PUBLICATION INFORMATION:
<308> DATABASE ACCESSION NUMBER: NCBI / NP_001129172.1
<309> DATABASE ENTRY DATE: 2017-10-09
<313> RELEVANT RESIDUES IN SEQ ID NO: (1)..(245)

<400> SEQUENCE: 82

```
Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45
```

```
Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245
```

<210> SEQ ID NO 83
<211> LENGTH: 3023
<212> TYPE: DNA
<213> ORGANISM: Homo sapiens
<300> PUBLICATION INFORMATION:
<308> DATABASE ACCESSION NUMBER: NCBI / NM_001135701.1
<309> DATABASE ENTRY DATE: 2017-10-09
<313> RELEVANT RESIDUES IN SEQ ID NO: (1)..(3023)

<400> SEQUENCE: 83

```
ggcggggagg ggccgggggc ctcggggacc caagcgcgag ggaaaggcct ggccgagagc     60

gggccggagc ccaggcctgg cgcggcggcg cccgccaggt agaccggggc gaggctgcgc    120

gccggcggga ggggagtcca ctgcgggaac atccagtcat ggataaaaat gagctggttc    180

agaaggccaa actggccgag caggctgagc gatatgatga catggcagcc tgcatgaagt    240

ctgtaactga gcaaggagct gaattatcca atgaggagag gaatcttctc tcagttgctt    300

ataaaaatgt tgtaggagcc cgtaggtcat cttggagggt cgtctcaagt attgaacaaa    360

agacggaagg tgctgagaaa aaacagcaga tggctcgaga atacagagag aaaattgaga    420

cggagctaag agatatctgc aatgatgtac tgtctctttt ggaaaagttc ttgatcccca    480

atgcttcaca agcagagagc aaagtcttct atttgaaaat gaaaggagat tactaccgtt    540

acttggctga ggttgccgct ggtgatgaca agaaagggat tgtcgatcag tcacaacaag    600

cataccaaga agcttttgaa atcagcaaaa aggaaatgca accaacacat cctatcagac    660

tgggtctggc ccttaacttc tctgtgttct attatgagat tctgaactcc ccagagaaag    720

cctgctctct tgcaaagaca gcttttgatg aagccattgc tgaacttgat acattaagtg    780

aagagtcata caaagacagc acgctaataa tgcaattact gagagacaac ttgacattgt    840
```

```
ggacatcgga tacccaagga gacgaagctg aagcaggaga aggaggggaa aattaaccgg    900
ccttccaact tttgtctgcc tcattctaaa atttacacag tagaccattt gtcatccatg    960
ctgtcccaca aatagttttt tgtttacgat ttatgacagg tttatgttac ttctatttga   1020
atttctatat ttcccatgtg gtttttatgt ttaatattag gggagtagag ccagttaaca   1080
tttagggagt tatctgtttt catcttgagg tggccaatat ggggatgtgg aatttttata   1140
caagttataa gtgtttggca tagtactttt ggtacattgt ggcttcaaaa gggccagtgt   1200
aaaactgctt ccatgtctaa gcaaagaaaa ctgcctacat actggtttgt cctggcgggg   1260
aataaaaggg atcattggtt ccagtcacag gtgtagtaat tgtgggtact ttaaggtttg   1320
gagcacttac aaggctgtgg tagaatcata ccccatggat accacatatt aaaccatgta   1380
tatctgtgga atactcaatg tgtacacctt tgactacagc tgcagaagtg ttcctttaga   1440
caaagttgtg acccatttta ctctggataa gggcagaaac ggttcacatt ccattatttg   1500
taaagttacc tgctgttagc tttcattatt tttgctacac tcattttatt tgtatttaaa   1560
tgttttaggc aacctaagaa caaatgtaaa agtaaagatg caggaaaaat gaattgcttg   1620
gtattcatta cttcatgtat atcaagcaca gcagtaaaac aaaaacccat gtatttaact   1680
ttttttagg atttttgctt ttgtgatttt ttttttttg atacttgcct aacatgcatg    1740
tgctgtaaaa atagttaaca gggaaataac ttgagatgat ggctagcttt gtttaatgtc   1800
ttatgaaatt ttcatgaaca atccaagcat aattgttaag aacacgtgta ttaaattcat   1860
gtaagtggaa taaaagtttt atgaatggac ttttcaacta ctttctctac agcttttcat   1920
gtaaattagt cttggttctg aaacttctct aaaggaaatt gtacattttt tgaaatttat   1980
tccttattcc ctcttggcag ctaatgggct cttaccaagt ttaaacacaa aatttatcat   2040
aacaaaaata ctactaatat aactactgtt tccatgtccc atgatcccct ctcttcctcc   2100
ccaccctgaa aaaaatgagt tcctattttt tctgggagag ggggggattg attagaaaaa   2160
aatgtagtgt gttccattta aaattttggc atatggcatt ttctaactta ggaagccaca   2220
atgttcttgg cccatcatga cattgggtag cattaactgt aagttttgtg cttccaaatc   2280
actttttggt ttttaagaat ttcttgatac tcttatagcc tgccttcaat tttgatcctt   2340
tattctttct atttgtcagg tgcacaagat taccttcctg ttttagcctt ctgtcttgtc   2400
accaaccatt cttacttggt ggccatgtac ttggaaaaag gccgcatgat ctttctggct   2460
ccactcagtg tctaaggcac cctgcttcct ttgcttgcat cccacagact atttccctca   2520
tcctatttac tgcagcaaat ctctccttag ttgatgagac tgtgtttatc tccctttaaa   2580
accctaccta tcctgaatgg tctgtcattg tctgccttta aaatccttcc tctttcttcc   2640
tcctctattc tctaaataat gatggggcta agttataccc aaagctcact ttacaaaata   2700
tttcctcagt actttgcaga aaacaccaaa caaaaatgcc attttaaaaa aggtgtattt   2760
tttcttttag aatgtaagct cctcaagagc agggacaatg ttttctgtat gttctattgt   2820
gcctagtaca ctgtaaatgc tcaataaata ttgatgatgg gaggcagtga gtcttgatga   2880
taagggtgag aaactgaaat cccaaacact gttttgttgc ttgttttatt atgacctcag   2940
attaaattgg gaaatattgg cccttttgaa taattgtccc aaatattaca ttcaaataaa   3000
agtgcaatgg agaaaaaaaa aaa                                           3023
```

<210> SEQ ID NO 84
<211> LENGTH: 245
<212> TYPE: PRT

<213> ORGANISM: Homo sapiens
<300> PUBLICATION INFORMATION:
<308> DATABASE ACCESSION NUMBER: NCBI / NP_001129173.1
<309> DATABASE ENTRY DATE: 2017-10-09
<313> RELEVANT RESIDUES IN SEQ ID NO: (1)..(245)

<400> SEQUENCE: 84

Met Asp Lys Asn Glu Leu Val Gln Lys Ala Lys Leu Ala Glu Gln Ala
1 5 10 15

Glu Arg Tyr Asp Asp Met Ala Ala Cys Met Lys Ser Val Thr Glu Gln
20 25 30

Gly Ala Glu Leu Ser Asn Glu Glu Arg Asn Leu Leu Ser Val Ala Tyr
35 40 45

Lys Asn Val Val Gly Ala Arg Arg Ser Ser Trp Arg Val Val Ser Ser
50 55 60

Ile Glu Gln Lys Thr Glu Gly Ala Glu Lys Lys Gln Gln Met Ala Arg
65 70 75 80

Glu Tyr Arg Glu Lys Ile Glu Thr Glu Leu Arg Asp Ile Cys Asn Asp
85 90 95

Val Leu Ser Leu Leu Glu Lys Phe Leu Ile Pro Asn Ala Ser Gln Ala
100 105 110

Glu Ser Lys Val Phe Tyr Leu Lys Met Lys Gly Asp Tyr Tyr Arg Tyr
115 120 125

Leu Ala Glu Val Ala Ala Gly Asp Asp Lys Lys Gly Ile Val Asp Gln
130 135 140

Ser Gln Gln Ala Tyr Gln Glu Ala Phe Glu Ile Ser Lys Lys Glu Met
145 150 155 160

Gln Pro Thr His Pro Ile Arg Leu Gly Leu Ala Leu Asn Phe Ser Val
165 170 175

Phe Tyr Tyr Glu Ile Leu Asn Ser Pro Glu Lys Ala Cys Ser Leu Ala
180 185 190

Lys Thr Ala Phe Asp Glu Ala Ile Ala Glu Leu Asp Thr Leu Ser Glu
195 200 205

Glu Ser Tyr Lys Asp Ser Thr Leu Ile Met Gln Leu Leu Arg Asp Asn
210 215 220

Leu Thr Leu Trp Thr Ser Asp Thr Gln Gly Asp Glu Ala Glu Ala Gly
225 230 235 240

Glu Gly Gly Glu Asn
245

<210> SEQ ID NO 85
<211> LENGTH: 3042
<212> TYPE: DNA
<213> ORGANISM: Homo sapiens
<300> PUBLICATION INFORMATION:
<308> DATABASE ACCESSION NUMBER: NCBI / NM_001135702.1
<309> DATABASE ENTRY DATE: 2017-10-09
<313> RELEVANT RESIDUES IN SEQ ID NO: (1)..(3042)

<400> SEQUENCE: 85
gacacagatc cgccatgaca aaggaggaga gtcggggact tgagccgtgg ctccgacttg 60
ggcggagcct ggagggggt ggttgcgata cgcggaccgg agaatttgca ctttaaagtc 120
cgggtctgcc cgttttcgtt tcacagtaac cgacgtctca agtcagaaca tccagtcatg 180
gataaaaatg agctggttca gaaggccaaa ctggccgagc aggctgagcg atatgatgac 240
atggcagcct gcatgaagtc tgtaactgag caaggagctg aattatccaa tgaggagagg 300
aatcttctct cagttgctta taaaaatgtt gtaggagccc gtaggtcatc ttggagggtc 360

```
gtctcaagta ttgaacaaaa gacggaaggt gctgagaaaa aacagcagat ggctcgagaa    420
tacagagaga aaattgagac ggagctaaga gatatctgca atgatgtact gtctcttttg    480
gaaaagttct tgatccccaa tgcttcacaa gcagagagca aagtcttcta tttgaaaatg    540
aaaggagatt actaccgtta cttggctgag gttgccgctg gtgatgacaa gaaagggatt    600
gtcgatcagt cacaacaagc ataccaagaa gcttttgaaa tcagcaaaaa ggaaatgcaa    660
ccaacacatc ctatcagact gggtctggcc cttaacttct ctgtgttcta ttatgagatt    720
ctgaactccc cagagaaagc ctgctctctt gcaaagacag cttttgatga agccattgct    780
gaacttgata cattaagtga agagtcatac aaagacagca cgctaataat gcaattactg    840
agagacaact tgacattgtg gacatcggat acccaaggag acgaagctga agcaggagaa    900
ggaggggaaa attaaccggc cttccaactt ttgtctgcct cattctaaaa tttacacagt    960
agaccatttg tcatccatgc tgtcccacaa atagtttttt gtttacgatt tatgacaggt   1020
ttatgttact tctatttgaa tttctatatt tcccatgtgg tttttatgtt taatattagg   1080
ggagtagagc cagttaacat ttagggagtt atctgttttc atcttgaggt ggccaatatg   1140
gggatgtgga atttttatac aagttataag tgtttggcat agtacttttg gtacattgtg   1200
gcttcaaaag ggccagtgta aaactgcttc catgtctaag caaagaaaac tgcctacata   1260
ctggtttgtc ctggcgggga ataaaaggga tcattggttc cagtcacagg tgtagtaatt   1320
gtgggtactt taaggtttgg agcacttaca aggctgtggt agaatcatac cccatggata   1380
ccacatatta aaccatgtat atctgtggaa tactcaatgt gtacaccttt gactacagct   1440
gcagaagtgt tcctttagac aaagttgtga cccattttac tctggataag ggcagaaacg   1500
gttcacattc cattatttgt aaagttacct gctgttagct ttcattattt ttgctacact   1560
cattttattt gtatttaaat gttttaggca acctaagaac aaatgtaaaa gtaaagatgc   1620
aggaaaaatg aattgcttgg tattcattac ttcatgtata tcaagcacag cagtaaaaca   1680
aaaacccatg tatttaactt ttttttagga tttttgcttt tgtgattttt ttttttttga   1740
tacttgccta acatgcatgt gctgtaaaaa tagttaacag ggaaataact tgagatgatg   1800
gctagctttg tttaatgtct tatgaaattt tcatgaacaa tccaagcata attgttaaga   1860
acacgtgtat taaattcatg taagtggaat aaaagtttta tgaatggact tttcaactac   1920
tttctctaca gcttttcatg taaattagtc ttggttctga aacttctcta aaggaaattg   1980
tacatttttt gaaatttatt ccttattccc tcttggcagc taatgggctc ttaccaagtt   2040
taaacacaaa atttatcata acaaaaatac tactaatata actactgttt ccatgtccca   2100
tgatcccctc tcttcctccc caccctgaaa aaaatgagtt cctatttttt ctgggagagg   2160
gggggattga ttagaaaaaa atgtagtgtg ttccatttaa aattttggca tatggcattt   2220
tctaacttag gaagccacaa tgttcttggc ccatcatgac attgggtagc attaactgta   2280
agttttgtgc ttccaaatca ctttttggtt tttaagaatt tcttgatact cttatagcct   2340
gccttcaatt ttgatccttt attctttcta tttgtcaggt gcacaagatt accttcctgt   2400
tttagccttc tgtcttgtca ccaaccattc ttacttggtg gccatgtact tggaaaaagg   2460
ccgcatgatc tttctggctc cactcagtgt ctaaggcacc ctgcttcctt tgcttgcatc   2520
ccacagacta tttccctcat cctatttact gcagcaaatc tctccttagt tgatgagact   2580
gtgtttatct ccctttaaaa ccctacctat cctgaatggt ctgtcattgt ctgcctttaa   2640
aatccttcct ctttcttcct cctctattct ctaaataatg atggggctaa gttataccca   2700
```

```
aagctcactt tacaaaatat ttcctcagta ctttgcagaa aacaccaaac aaaaatgcca   2760

ttttaaaaaa ggtgtatttt ttcttttaga atgtaagctc ctcaagagca gggacaatgt   2820

tttctgtatg ttctattgtg cctagtacac tgtaaatgct caataaatat tgatgatggg   2880

aggcagtgag tcttgatgat aagggtgaga aactgaaatc ccaaacactg ttttgttgct   2940

tgttttatta tgacctcaga ttaaattggg aaatattggc ccttttgaat aattgtccca   3000

aatattacat tcaaataaaa gtgcaatgga gaaaaaaaaa aa                      3042
```

```
<210> SEQ ID NO 86
<211> LENGTH: 245
<212> TYPE: PRT
<213> ORGANISM: Homo sapiens
<300> PUBLICATION INFORMATION:
<308> DATABASE ACCESSION NUMBER: NCBI / NP_001129174.1
<309> DATABASE ENTRY DATE: 2017-10-09
<313> RELEVANT RESIDUES IN SEQ ID NO: (1)..(245)

<400> SEQUENCE: 86

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245


<210> SEQ ID NO 87
<211> LENGTH: 3003
<212> TYPE: DNA
<213> ORGANISM: Homo sapiens
<300> PUBLICATION INFORMATION:
<308> DATABASE ACCESSION NUMBER: NCBI / NM_003406.3
```

<309> DATABASE ENTRY DATE: 2017-10-09
<313> RELEVANT RESIDUES IN SEQ ID NO: (1)..(3003)

<400> SEQUENCE: 87

```
ctttctcctt ccccttcttc cgggctcccg tcccggctca tcacccggcc tgtggcccac     60

tcccaccgcc agctggaacc ctggggacta cgacgtccct caaaccttgc ttctaggaga    120

taaaaagaac atccagtcat ggataaaaat gagctggttc agaaggccaa actggccgag    180

caggctgagc gatatgatga catggcagcc tgcatgaagt ctgtaactga gcaaggagct    240

gaattatcca atgaggagag gaatcttctc tcagttgctt ataaaaatgt tgtaggagcc    300

cgtaggtcat cttggagggt cgtctcaagt attgaacaaa agacggaagg tgctgagaaa    360

aaacagcaga tggctcgaga atacagagag aaaattgaga cggagctaag agatatctgc    420

aatgatgtac tgtctctttt ggaaaagttc ttgatcccca atgcttcaca agcagagagc    480

aaagtcttct atttgaaaat gaaaggagat tactaccgtt acttggctga ggttgccgct    540

ggtgatgaca agaaagggat tgtcgatcag tcacaacaag cataccaaga agcttttgaa    600

atcagcaaaa aggaaatgca accaacacat cctatcagac tgggtctggc ccttaacttc    660

tctgtgttct attatgagat tctgaactcc ccagagaaag cctgctctct tgcaaagaca    720

gcttttgatg aagccattgc tgaacttgat acattaagtg aagagtcata caaagacagc    780

acgctaataa tgcaattact gagagacaac ttgacattgt ggacatcgga tacccaagga    840

gacgaagctg aagcaggaga aggaggggaa aattaaccgg ccttccaact tttgtctgcc    900

tcattctaaa atttacacag tagaccattt gtcatccatg ctgtcccaca aatagttttt    960

tgtttacgat ttatgacagg tttatgttac ttctatttga atttctatat ttcccatgtg   1020

gtttttatgt ttaatattag gggagtagag ccagttaaca tttagggagt tatctgtttt   1080

catcttgagg tggccaatat ggggatgtgg aatttttata caagttataa gtgtttggca   1140

tagtactttt ggtacattgt ggcttcaaaa gggccagtgt aaaactgctt ccatgtctaa   1200

gcaaagaaaa ctgcctacat actggtttgt cctggcgggg aataaaaggg atcattggtt   1260

ccagtcacag gtgtagtaat tgtgggtact ttaaggtttg gagcacttac aaggctgtgg   1320

tagaatcata ccccatggat accacatatt aaaccatgta tatctgtgga atactcaatg   1380

tgtacacctt tgactacagc tgcagaagtg ttcctttaga caaagttgtg acccatttta   1440

ctctggataa gggcagaaac ggttcacatt ccattatttg taaagttacc tgctgttagc   1500

tttcattatt tttgctacac tcattttatt tgtatttaaa tgttttaggc aacctaagaa   1560

caaatgtaaa agtaaagatg caggaaaaat gaattgcttg gtattcatta cttcatgtat   1620

atcaagcaca gcagtaaaac aaaaacccat gtatttaact ttttttagg atttttgctt   1680

ttgtgatttt tttttttttg atacttgcct aacatgcatg tgctgtaaaa atagttaaca   1740

gggaaataac ttgagatgat ggctagcttt gtttaatgtc ttatgaaatt ttcatgaaca   1800

atccaagcat aattgttaag aacacgtgta ttaaattcat gtaagtggaa taaaagtttt   1860

atgaatggac ttttcaacta ctttctctac agcttttcat gtaaattagt cttggttctg   1920

aaacttctct aaaggaaatt gtacattttt tgaaatttat tccttattcc ctcttggcag   1980

ctaatgggct cttaccaagt ttaaacacaa aatttatcat aacaaaaata ctactaatat   2040

aactactgtt tccatgtccc atgatcccct ctcttcctcc ccaccctgaa aaaaatgagt   2100

tcctattttt tctgggagag ggggggattg attagaaaaa aatgtagtgt gttccattta   2160

aaattttggc atatggcatt ttctaactta ggaagccaca atgttcttgg cccatcatga   2220
```

```
cattgggtag cattaactgt aagttttgtg cttccaaatc actttttggt ttttaagaat   2280

ttcttgatac tcttatagcc tgccttcaat tttgatcctt tattctttct atttgtcagg   2340

tgcacaagat taccttcctg ttttagcctt ctgtcttgtc accaaccatt cttacttggt   2400

ggccatgtac ttggaaaaag gccgcatgat ctttctggct ccactcagtg tctaaggcac   2460

cctgcttcct ttgcttgcat cccacagact atttccctca tcctatttac tgcagcaaat   2520

ctctccttag ttgatgagac tgtgtttatc tccctttaaa accctaccta tcctgaatgg   2580

tctgtcattg tctgccttta aaatccttcc tctttcttcc tcctctattc tctaaataat   2640

gatggggcta agttataccc aaagctcact ttacaaaata tttcctcagt actttgcaga   2700

aaacaccaaa caaaaatgcc attttaaaaa aggtgtattt tttcttttag aatgtaagct   2760

cctcaagagc agggacaatg ttttctgtat gttctattgt gcctagtaca ctgtaaatgc   2820

tcaataaata ttgatgatgg gaggcagtga gtcttgatga taagggtgag aaactgaaat   2880

cccaaacact gttttgttgc ttgttttatt atgacctcag attaaattgg gaaatattgg   2940

ccctttgaa taattgtccc aaatattaca ttcaaataaa agtgcaatgg agaaaaaaaa   3000

aaa                                                                  3003
```

<210> SEQ ID NO 88
<211> LENGTH: 245
<212> TYPE: PRT
<213> ORGANISM: Homo sapiens
<300> PUBLICATION INFORMATION:
<308> DATABASE ACCESSION NUMBER: NCBI / NP_003397.1
<309> DATABASE ENTRY DATE: 2017-10-09
<313> RELEVANT RESIDUES IN SEQ ID NO: (1)..(245)

<400> SEQUENCE: 88

```
Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205
```

```
Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245
```

<210> SEQ ID NO 89
<211> LENGTH: 3077
<212> TYPE: DNA
<213> ORGANISM: Homo sapiens
<300> PUBLICATION INFORMATION:
<308> DATABASE ACCESSION NUMBER: NCBI / NM_145690.2
<309> DATABASE ENTRY DATE: 2017-10-09
<313> RELEVANT RESIDUES IN SEQ ID NO: (1)..(3077)

<400> SEQUENCE: 89

```
gcagcgtttg acgtcatcgt gcgtgtggtg cccctgctgc cggggctggt gattggagga     60

aaccccgtgt ctgcggagcg gctgtagcct gtgagcagcg agatccaggg acagagtctc    120

agcctcgccg ctgctgccgc cgccgccgcc cagagactgc tgagcccgtc cgtccgccgc    180

caccacccac tccggacaca gaacatccag tcatggataa aaatgagctg gttcagaagg    240

ccaaactggc cgagcaggct gagcgatatg atgacatggc agcctgcatg aagtctgtaa    300

ctgagcaagg agctgaatta tccaatgagg agaggaatct tctctcagtt gcttataaaa    360

atgttgtagg agcccgtagg tcatcttgga gggtcgtctc aagtattgaa caaaagacgg    420

aaggtgctga gaaaaaacag cagatggctc gagaatacag agagaaaatt gagacggagc    480

taagagatat ctgcaatgat gtactgtctc ttttggaaaa gttcttgatc cccaatgctt    540

cacaagcaga gagcaaagtc ttctatttga aaatgaaagg agattactac cgttacttgg    600

ctgaggttgc cgctggtgat gacaagaaag ggattgtcga tcagtcacaa caagcatacc    660

aagaagcttt tgaaatcagc aaaaaggaaa tgcaaccaac acatcctatc agactgggtc    720

tggcccttaa cttctctgtg ttctattatg agattctgaa ctccccagag aaagcctgct    780

ctcttgcaaa gacagctttt gatgaagcca ttgctgaact tgatacatta agtgaagagt    840

catacaaaga cagcacgcta ataatgcaat tactgagaga caacttgaca ttgtggacat    900

cggataccca aggagacgaa gctgaagcag gagaaggagg ggaaaattaa ccggccttcc    960

aacttttgtc tgcctcattc taaaatttac acagtagacc atttgtcatc catgctgtcc   1020

cacaaatagt tttttgttta cgatttatga caggtttatg ttacttctat ttgaatttct   1080

atatttccca tgtggttttt atgtttaata ttaggggagt agagccagtt aacatttagg   1140

gagttatctg ttttcatctt gaggtggcca atatggggat gtggaatttt tatacaagtt   1200

ataagtgttt ggcatagtac ttttggtaca ttgtggcttc aaaagggcca gtgtaaaact   1260

gcttccatgt ctaagcaaag aaaactgcct acatactggt ttgtcctggc ggggaataaa   1320

agggatcatt ggttccagtc acaggtgtag taattgtggg tactttaagg tttggagcac   1380

ttacaaggct gtggtagaat cataccccat ggataccaca tattaaacca tgtatatctg   1440

tggaatactc aatgtgtaca cctttgacta cagctgcaga agtgttcctt tagacaaagt   1500

tgtgacccat tttactctgg ataagggcag aaacggttca cattccatta tttgtaaagt   1560

tacctgctgt tagctttcat tatttttgct acactcattt tatttgtatt taaatgtttt   1620

aggcaaccta agaacaaatg taaaagtaaa gatgcaggaa aaatgaattg cttggtattc   1680

attacttcat gtatatcaag cacagcagta aaacaaaaac ccatgtattt aacttttttt   1740
```

```
taggatttttt gcttttgtga ttttttttt tttgatactt gcctaacatg catgtgctgt   1800

aaaaatagtt aacagggaaa taacttgaga tgatggctag ctttgtttaa tgtcttatga   1860

aattttcatg aacaatccaa gcataattgt taagaacacg tgtattaaat tcatgtaagt   1920

ggaataaaag ttttatgaat ggacttttca actactttct ctacagcttt tcatgtaaat   1980

tagtcttggt tctgaaactt ctctaaagga aattgtacat tttttgaaat ttattcctta   2040

ttccctcttg gcagctaatg ggctcttacc aagtttaaac acaaaattta tcataacaaa   2100

aatactacta atataactac tgtttccatg tcccatgatc ccctctcttc ctccccaccc   2160

tgaaaaaaat gagttcctat tttttctggg agaggggggg attgattaga aaaaaatgta   2220

gtgtgttcca tttaaaattt tggcatatgg cattttctaa cttaggaagc cacaatgttc   2280

ttggcccatc atgacattgg gtagcattaa ctgtaagttt tgtgcttcca aatcactttt   2340

tggtttttaa gaatttcttg atactcttat agcctgcctt caattttgat cctttattct   2400

ttctatttgt caggtgcaca agattacctt cctgttttag ccttctgtct tgtcaccaac   2460

cattcttact tggtggccat gtacttggaa aaaggccgca tgatctttct ggctccactc   2520

agtgtctaag gcaccctgct tcctttgctt gcatccccaca gactatttcc ctcatcctat   2580

ttactgcagc aaatctctcc ttagttgatg agactgtgtt tatctccctt taaaacccta   2640

cctatcctga atggtctgtc attgtctgcc tttaaaatcc ttcctctttc ttcctcctct   2700

attctctaaa taatgatggg gctaagttat acccaaagct cactttacaa aatatttcct   2760

cagtactttg cagaaaacac caaacaaaaa tgccatttta aaaaaggtgt atttttttctt   2820

ttagaatgta agctcctcaa gagcagggac aatgttttct gtatgttcta ttgtgcctag   2880

tacactgtaa atgctcaata aatattgatg atgggaggca gtgagtcttg atgataaggg   2940

tgagaaactg aaatcccaaa cactgttttg ttgcttgttt tattatgacc tcagattaaa   3000

ttgggaaata ttggcccttt tgaataattg tcccaaatat tacattcaaa taaaagtgca   3060

atggagaaaa aaaaaaa                                                   3077
```

<210> SEQ ID NO 90
<211> LENGTH: 245
<212> TYPE: PRT
<213> ORGANISM: Homo sapiens
<300> PUBLICATION INFORMATION:
<308> DATABASE ACCESSION NUMBER: NCBI / NP_663723.1
<309> DATABASE ENTRY DATE: 2017-10-09
<313> RELEVANT RESIDUES IN SEQ ID NO: (1)..(245)

<400> SEQUENCE: 90

```
Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110
```

-continued

```
Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245
```